US007161018B2

(12) United States Patent
Zhao et al.

(10) Patent No.: US 7,161,018 B2
(45) Date of Patent: *Jan. 9, 2007

(54) SOLUBLE LATE TRANSITION METAL CATALYSTS FOR OLEFIN OLIGOMERIZATIONS II

(75) Inventors: Baiyi Zhao, Kingwood, TX (US); Enock Berluche, Phillipsburg, NJ (US); Smita Kacker, Houston, TX (US); Jo Ann Marie Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 486 days.

This patent is subject to a terminal disclaimer.

(21) Appl. No.: 10/449,273

(22) Filed: May 30, 2003

(65) Prior Publication Data

US 2004/0039238 A1 Feb. 26, 2004

Related U.S. Application Data

(60) Provisional application No. 60/396,370, filed on Jul. 17, 2002, provisional application No. 60/384,289, filed on May 30, 2002.

(51) Int. Cl.
*C07F 15/00* (2006.01)
*B01J 31/00* (2006.01)
*C07C 2/24* (2006.01)

(52) U.S. Cl. ............... 556/32; 585/512; 585/513; 502/150; 502/167

(58) Field of Classification Search ............ 556/32; 502/150, 167; 585/512, 513
See application file for complete search history.

(56) References Cited

U.S. PATENT DOCUMENTS

| 4,913,846 | A | * | 4/1990 | Suzuki et al. ............ 252/587 |
| 5,571,881 | A | | 11/1996 | Goodall et al. ............ 526/171 |
| 5,677,405 | A | | 10/1997 | Goodall et al. ............ 526/281 |
| 5,741,869 | A | | 4/1998 | Goodall et al. ............ 526/171 |
| 5,866,663 | A | | 2/1999 | Brookhart et al. .......... 526/170 |
| 5,880,323 | A | | 3/1999 | Brookhart, III et al. .... 585/527 |
| 6,303,724 | B1 | | 10/2001 | Goodall et al. ............ 526/266 |
| 6,545,108 | B1 | | 4/2003 | Moody et al. ............. 526/161 |
| 6,790,579 | B1 | | 9/2004 | Goodall et al. ............ 430/170 |
| 2004/0044150 | A1 | | 3/2004 | Zhao et al. .................. 526/90 |
| 2004/0186010 | A1 | | 9/2004 | Zhao et al. ................ 502/171 |

FOREIGN PATENT DOCUMENTS

| DE | 199 44 993 | 3/2001 |
| EP | 0924223 | 12/1998 |
| JP | 63039389 | 2/1988 |
| WO | 00/10945 | 3/2000 |
| WO | 00/50470 | 8/2000 |
| WO | 01/21586 | 3/2001 |
| WO | 01/83571 | 11/2001 |
| WO | 04/007509 | 1/2004 |

OTHER PUBLICATIONS

Zhong et al., "C—H Bond Activation by Cationic Platinum(II) Complexes: Ligand Electronic and Steric Effects", J. Am. Chem. Soc., vol. 124, No. 7, 2002, pp. 1378-1399.
Bähr, "Über Schwermetallkomplexe bifunktioneller Schiffscher Basen", Z. Anorg. Allg. Chem. Band, 267, (1951), pp. 137-160.
Drent et al., "Palladium Catalyzed Alternating Copolymerization of Alkenes and Carbon Monoxide", Chem.. Rev. (1996), pp. 663-681.
B. Elvers, et al., Ed. *Ullmann's Encyclopedia of Industrial Chemistry*, Hydrocarbons, vol. A 13, VCH Verlagsgesellschaft mbH, Weinheim, 1989, pp. 243-247 and 275-276.
B. Cornils, et al., Ed., "Applied Homogeneous Catalysis with Organometallic Compounds", *A Comprehensive Handbook*, vol. 1, VCH Verlagsgesellschaft mbH, Weinheim, 1996, pp. 245-258.
C. Killian, et al., "Preparation of Linear α-Olefins Using Cationic Nickel(II) α-Diimine", *Organometallics*, 1997, 16, pp. 2005-2007.
S. Svejda, et al., "Ethylene Oligomerization and Propylene Dimerization Using Cationic (α-Diimine)nickel(II) Catalysts", *Organometallics*, 1999, 18, pp. 65-74.
Abakumov et al., "Bis(1, 4-di-*tert*-butyl-1, 4-diazabutadiene)copper(I)[(3,6-di-*tert*-butyl-*o*-benzosemiquinono)(3,6-di-*tert*-butylcatecholato)cuprate(II)]. The molecular structure and intramolecular electron transfer", *Russian Chemical Bulletin*, International Edition, vol. 50, No. 11, Nov. 2001, pp. 2193-2199/-*.
Kannan, et al., "Dinuclear diimine palladium (II) and platinum (ii) hydroxo and amido complexes : synthesis and X-ray crystal structures", *Polyhedron* 19 (2000) pp. 155-163.
McCord, et al, "$^{13}$C and 2D NMR Analysis of Propylene Polymers Made with α-Diimine Late Metal Catalysts", *Macromolecules*, 2001, 34, pp. 362-371.
Pappalardo, et al., "Some Evidence of a Dual Stereodifferentation Mechanism in the Polymerization of Propene by α-Diimine Nickel Catalysts", *Macromolecules*, 2000, 33, pp. 9483-9487.
Yang, et al. "Unsymmetrical 1,4-Diazabutadiene Complexes of Platinum (II)", *Organometallics*, 1997, 16, pp. 5234-5243.
Yang, et al. "Dimethyl and Cationic 1,4-Diazabutadiene Complexes of Platinum (II)", *Organometallics*, 1998, 17, pp. 5102-5113.
Benedix, et al. "Electronic Structure and Spectroscopic Properties of Copper Catecholate Complexes with Interligand Charge Transfer Behavior", *Inorganica Chimica Acta*, 1993, 204, pp. 189-193.
Wenzel, et al., "New Indigoid Compounds by Reduction of *Bis*-Imidoylchlorides of Oxalic Acid—A Further Evidence for Dimeric Isocyanides?", *Monatshefte fur Chemie*, 130, 1999, pp. 1373-1382.

(Continued)

*Primary Examiner*—Porfirio Nazario-Gonzalez
(74) *Attorney, Agent, or Firm*—Catherine L. Bell

(57) ABSTRACT

A series of soluble α-diimine late transition metal catalysts has been invented. The catalysts demonstrate high activity and selectivity for linear α-olefins. As such, these catalysts conveniently oligomerize ethylene. Typical activators as known to those of ordinary skill in the art are used to activate these transition metal catalyst. These catalysts can be used in a supported or unsupported form.

57 Claims, No Drawings

OTHER PUBLICATIONS

Wood, et al., "Synthesis of Polystyrene by Dispersion Polymerization in 1,1,1,2-Tetrafluoroethane (R134a) Using Inexpensive Hydrocarbon Macromonomer Stabilizers", *Macromolecules*, 2003, 36 pp. 7534-7542.

Boussie, et al., "Parallel Solid-Phase Synthesis, Screening, and Encloding Strategies for Olefin-Polymerization Catalysts", *Tetrahedron*, 55, 1999, pp. 11699-11710.

ACS Registry Number 117869-99-5.

* cited by examiner

SOLUBLE LATE TRANSITION METAL CATALYSTS FOR OLEFIN OLIGOMERIZATIONS II

This application claims priority to U.S. Provisional Patent Application No. 60/384,289, filed May 30, 2002 and U.S. Provisional Patent Application No. 60/396,370, filed Jul. 17, 2002. This application also claims priority from USSN PCT/US03/16942.

FIELD OF INVENTION

This document relates to late transition metal catalysts for olefin oligomerizations and to methods for making and using these catalysts.

BACKGROUND

Alpha-olefins, especially those containing 6 to 20 carbon atoms, are important items of commerce. They are used as intermediates in the manufacture of detergents, as monomers (especially in linear low-density polyethylene), and as intermediates for many other types of products. As a consequence, improved methods of making these compounds are desired.

Most commercially produced α-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245–258. The major types of commercially used catalysts are alkylaluminum compounds, certain nickel-phosphine complexes, and a titanium halide with a Lewis acid such as $AlCl_3$. In all of these processes, significant amounts of branched and/or internal olefins and/or diolefins are produced. Since in most instances these are undesirable and often difficult to separate, these by-products are avoided commercially.

Recently, a series of cationic (α-diimine) nickel (II) catalysts for ethylene oligomerization and propylene dimerization were reported. (Organometallics 1999, 18, 65–74; Organometallics 1997, 16, 2005–2007; WO 00/10945; U.S. Pat. No. 5,880,323). These catalysts are highly active. But the corresponding pre-catalysts have low organic-solvent solubility. Therefore, their characterization and application is highly restricted. Catalyst solubility is desired for continuous solution reactors and for supporting the catalysts for use in a slurry phase reactor or fixed-bed reactor. Additionally, a soluble pre-catalyst is easier to completely activate to its catalytic form, and often provides a catalyst with significantly higher catalyst activity. In view of the difficulty and practical limitations in using insoluble or poorly soluble catalysts, soluble, α-olefin-producing catalyst systems need to be developed.

SUMMARY

Invention catalyst systems comprise nickel or palladium components (pre-catalyst or catalyst precursor) and an activator (cocatalyst)) that can produce α-olefins in a solution- or a slurry-phase oligomerization procedure. For purposes of this disclosure, "α-olefins" includes ethylene. The soluble oligomerization catalyst precursors of this invention are represented by the general formula

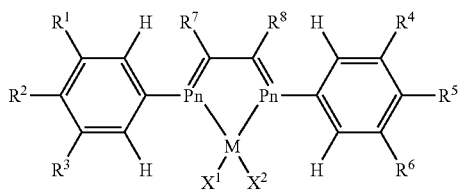

where
M is nickel or palladium;
Pn is a Group 15 element preferably nitrogen;
H is hydrogen;
$R^7$ and $R^8$ are independently
　hydrogen or
　$C_1$–$C_{30}$ hydrocarbyl radicals that may optionally join to form an aromatic or non-aromatic cyclic ring structure;
$R^1$, $R^2$, $R^3$, $R^4$, $R^5$, and $R^6$ are independently
　hydrogen or
　$C_1$–$C_{30}$ hydrocarbyl radicals
　provided that
　at least one $R^1$, $R^2$ or $R^3$ and
　at least one $R^4$, $R^5$ and $R^6$ is a $C_3$–$C_{30}$ hydrocarbyl radical. For purposes of this disclosure, this $C_3$–$C_{30}$ hydrocarbyl radical is sometimes referred to as a solubility handle. Optionally, one or more aromatic or non-aromatic structures may be formed by independently joining two or more adjacent
　non-hydrogen $R^1$, $R^2$ or $R^3$; or
　non-hydrogen $R^4$, $R^5$ or $R^6$,
X is independently
　a hydride radical,
　a hydrocarbyl radical,
　a halocarbyl radical, or
　a hydrocarbyl-substituted organometalloid radical; or
two X's join and bind to the metal atom to form a metallacycle ring containing from 2–30 carbon atoms.

Additionally, X may independently be selected from halogen, alkoxide, aryloxide, amide, phosphide, or other anionic ligand when non-sulfur-containing Lewis-acid activators (such as methylalumoxane, aluminum alkyls, alkylaluminum alkoxides) or alkylaluminum halides (capable of donating an X ligand, as described above, to the transition metal component) are used, or when an ionic activator is capable of extracting X, provided that the resulting activated catalyst contains as least one M—H or M—C bond into which an olefin can insert. Note that one or more X may optionally bridge to one another, as well.

Some invention embodiments relate to compositions comprising:
(a) at least one metal selected from nickel or palladium;
(b) at least one ancillary ligand system connected to the metal where the ancillary ligand system comprises
　(i) a backbone comprising:
　　a 1,4-diazabutadiene; and
　　backbone substituents connected to the 2 and 3 positions of the diazabutadiene;
　(ii) phenyl rings connected to the 1 and 4 positions of the diazabutadiene where
　　the phenyl rings are independently substituted with at least one side group at the phenyl-ring 3, 4, or 5 positions; and at least one side group of each phenyl ring is a solubility handle; and (iii) at least one abstractable ligand.

In another embodiment, this invention relates to a composition comprising:

(1) a metal selected from nickel or palladium connected to a ligand comprising 1,4-diazabutadiene:

(a) having a phenyl ring connected to the 1 position of the diazabutadiene where the phenyl ring is connected at the 3, 4 or 5 position to at least one hydrocarbyl group having at least three carbon atoms, and (b) having a phenyl ring connected to the 4 position of the diazabutadiene where the phenyl ring is connected at the 3, 4 or 5 position to at least one hydrocarbyl group having at least three carbon atoms, and (c) where the 2 and 6 positions of both phenyl rings are connected to hydrogen radicals, and (d) where the 2 and 3 positions of the diazabutadiene are, each independently, connected to hydrogen or a hydrocarbyl group; and (2) an abstractable ligand connected to the metal.

The compositions can be activated with cocatalyst activators, as are known in the art. Accordingly, invention embodiments also include such activated compositions. These activated compositions react with ethylene to form ethylene oligomers.

Methods of producing these compositions are outlined in this document. Because of this, invention embodiments include methods of producing these compositions, as well.

Definitions

The term "hydrocarbyl radical" is sometimes used interchangeably with "hydrocarbyl" throughout this document. For purposes of this disclosure, "hydrocarbyl radical" encompasses $C_1$–$C_{50}$ radicals. These radicals can be linear, branched, or cyclic, and when cyclic, aromatic or non-aromatic. Thus, the term "hydrocarbyl radical", in addition to unsubstituted hydrocarbyl radicals, encompasses substituted hydrocarbyl radicals, halocarbyl radicals, and substituted halocarbyl radicals, as these terms are defined below.

Substituted hydrocarbyl radicals are radicals in which at least one hydrogen atom has been substituted with at least one functional group such as NR"$_2$, OR", PR"$_2$, SR", BR"$_2$, SiR"$_3$, GeR"$_3$ and the like or where at least one non-hydrocarbon atom or group has been inserted within the hydrocarbyl radical, such as O, S, NR", PR", BR", SiR"$_2$, GeR"$_2$, and the like, where R" is independently a hydrocarbyl or halocarbyl radical.

Halocarbyl radicals are radicals in which one or more hydrocarbyl hydrogen atoms have been substituted with at least one halogen or halogen-containing group (e.g. F, Cl, Br, I).

Substituted halocarbyl radicals are radicals in which at least one hydrocarbyl hydrogen or halogen atom has been substituted with at least one functional group such as NR"$_2$, OR", PR"$_2$, SR", BR"$_2$, SiR"$_3$, GeR"$_3$ and the like or where at least one non-carbon atom or group has been inserted within the halocarbyl radical such as O, S, NR", PR", BR", SiR"$_2$, GeR"$_2$, and the like where R" is independently a hydrocarbyl or halocarbyl radical provided that at least one halogen atom remains on the original halocarbyl radical.

In some embodiments, the hydrocarbyl radical is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. The radical may then be subjected to the types of substitutions described above.

The nickel or palladium component can also be described as comprising at least one ancillary ligand that stabilizes the oxidation state of the transition metal. Ancillary ligands serve to enforce the geometry around the metal center. In this disclosure, ancillary ligands have a backbone that comprises 1,4-diazabutadiene to which backbone substituents are connected at the 2 and 3 positions of the diazabutadiene. Moreover, the backbone comprises phenyl rings connected at the 1 and 4 positions of the diazabutadiene.

A backbone substituent is independently hydrogen or a hydrocarbyl radical. In some embodiments, a backbone substituent is independently hydrogen or a $C_1$–$C_{30}$ hydrocarbyl radical. In these or other embodiments, two backbone substituents link to form a ring structure comprising one or more, aromatic or non-aromatic rings.

The phenyl-rings connected to the backbone (at the phenyl-ring 1 position) are independently substituted with at least one side group at the phenyl-ring 3, 4, or 5 position. At least one of these side groups is a solubility handle. A side group is independently hydrogen or a hydrocarbyl radical. In some embodiments, a side group is independently hydrogen or a $C_1$–$C_{30}$ hydrocarbyl radical.

For purposes of this disclosure, a solubility handle is a $C_3$ or greater hydrocarbyl radical. A solubility handle is a substituent on a given phenyl-ring 3, 4, or 5 position that causes the solubility of a catalyst or catalyst precursor comprising it to be greater than that of a corresponding catalyst or catalyst precursor that has a hydrogen or methyl group on that given phenyl-ring position. In some embodiments, the solubility handle is a $C_3$ or greater hydrocarbyl. In some embodiments, the solubility handle is a $C_1$–$C_{30}$ hydrocarbyl.

An "abstractable ligand" is a ligand that can be abstracted from the metal center by a cocatalyst leaving behind an activated catalyst. For purposes of this disclosure, an "abstractable ligand" does not contain sulfur atoms; i.e. all abstractable ligands are non-sulfur-containing ligands.

For purposes of this disclosure oligomers include molecules with from 2–75 mer units.

Without wishing to be bound by theory, the nitrogen atoms of the ancillary ligand are believed to coordinate to the nickel or palladium central atom. "Coordination" is "[t]he formation of a covalent bond, the two shared electrons of which have come from only one of the two parts of the molecular entity linked by it . . . . The synonym 'dative bond' is obsolete. (The origin of the bonding electrons has by itself no bearing on the character of the bond formed . . . ) . . . ." *Compendium of Chemical Terminology: IUPAC Recommendations*, Second edition, International Union of Pure and Applied Chemistry, published by Blackwell Science, 1997. In some structures throughout this specification, this coordination is sometimes indicated by drawing the ligand-metal connection with an arrow indicating that the electrons for the bond originally came from the ligand. At other times, this coordination is indicated by drawing a solid line showing the bond's covalent nature. One of ordinary skill in the art recognizes that these depictions are interchangeable.

DETAILED DESCRIPTION

Due to the addition of non-hydrogen $R^1$–$R^6$ substituents to the complex, the catalyst becomes more soluble in most organic solvents such as hexane, toluene, methylene chloride, and the like. Thus, as discussed before, this non-hydrogen $R^1$–$R^6$ group receives the name solubility handle because it functions to increase solubility.

In one invention embodiment, $R^2$ and $R^5$ are independently $C_3$–$C_{20}$ hydrocarbyl radicals, especially a $C_4$–$C_{12}$ hydrocarbyl radicals. Some embodiments independently select $R^2$ and $R^5$ to be $C_5$–$C_{10}$ hydrocarbyl radicals. Some embodiments select $R^2$ and $R^5$ to be n-butyl.

Examples of specific invention catalyst precursors take the following formula where some components are listed in Table 1. When alkyl, alkenyl and alkynyl radicals are disclosed in this application the term includes all isomers and all substitution types, as described above, unless otherwise stated. For example, butyl includes n-butyl, isobutyl, and tert-butyl; pentyl includes n-pentyl, 1-methylbutyl, 2-methylbutyl, 3-methylbutyl, 1-ethylpropyl, 2-ethylpropyl, and neopentyl; butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl. To illustrate members of the transition metal component, select any combination of the species listed in Table 1. For example, choosing the components in the first row, yields [1,4-bis(3,4,5-tributylphenyl)-1,4-diaza-1,3-butadiene] nickel dichloride. Any combination of components may be selected. The column labeled $R^{19}$ $R^{20}$ shows some examples of substituents that can serve as $R^{19}$ and $R^{20}$. Of course, selecting a particular substituent for $R^{19}$ is independent of the selection for $R^{20}$. In other words, the invention allows $R^{19}$=$R^{20}$, but does not demand it. The same goes for $R^7$ and $R^8$; the same goes for $X^1$ and $X^2$.

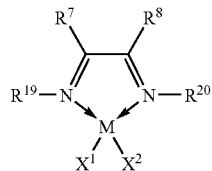

| $R^{19}$ $R^{20}$ | $R^7$ $R^8$ | $X^1$ $X^2$ | M |
|---|---|---|---|
| 3,4,5-tributylphenyl | hydrogen | chloride | nickel |
| 3,4,5-tridecylphenyl | methyl | bromide | palladium |
| 3,4,5-tridodecylphenyl | ethyl | iodide | |
| 3,4,5-triheptylphenyl | propyl | methyl | |
| 3,4,5-trihexylphenyl | butyl | ethyl | |
| 3,4,5-trinonylphenyl | pentyl | propyl | |
| 3,4,5-trioctylphenyl | hexyl | butyl | |
| 3,4,5-tripentylphenyl | heptyl | pentyl | |
| 3,4,5-tripropylphenyl | octyl | hexyl | |
| 3,4,5-tripropylphenyl | nonyl | heptyl | |
| 3,4,5-triundecylphenyl | decyl | octyl | |
| 3,4-dibutylphenyl | undecyl | nonyl | |
| 3,4-didecylphenyl | dodecyl | decyl | |
| 3,4-didodecylphenyl | tridecyl | undecyl | |
| 3,4-diheptylphenyl | tetradecyl | dodecyl | |

-continued

| $R^{19}$ $R^{20}$ | $R^7$ $R^8$ | $X^1$ $X^2$ | M |
|---|---|---|---|
| 3,4-dihexylphenyl | octacosyl | tridecyl | |
| 3,4-dinonylphenyl | nonacosyl | tetradecyl | |
| 3,4-dioctylphenyl | triacontyl | pentadecyl | |
| 3,4-dipentylphenyl | cyclohexyl | hexadecyl | |
| 3,4-dipropylphenyl | cyclopentyl | heptadecyl | |
| 3,4-dipropylphenyl | cycloheptyl | octadecyl | |
| 3,4-diundecylphenyl | cyclooctyl | nonadecyl | |
| 3,5-dibutylphenyl | cyclodecyl | eicosyl | |
| 3,5-dibutylphenyl | cyclododecyl | heneicosyl | |
| 3,5-didecylphenyl | napthyl | docosyl | |
| 3,5-didodecylphenyl | phenyl | tricosyl | |
| 3,5-diheptylphenyl | tolyl | tetracosyl | |
| 4-undecylphenyl | benzyl | pentacosyl | |
| 3,5-dihexylphenyl | phenethyl | hexacosyl | |
| 3,5-dinonylphenyl | $R^7$ joined to $R^8$ | heptacosyl | |
| 3,5-dioctylphenyl | 1,8-naphthalene | octacosyl | |
| 3,5-dipentylphenyl | 2,2'-biphenyl | nonacosyl | |
| 3,5-dipropylphenyl | | triacontyl | |
| 3,5-diundecylphenyl | | hydride | |
| 3-butylphenyl | | phenyl | |
| 3-decylphenyl | | benzyl | |
| 3-dodecylphenyl | | phenethyl | |
| 3-heptylphenyl | | tolyl | |
| 3-hexylphenyl | | methoxy | |
| 3-nonylphenyl | | ethoxy | |
| 3-octylphenyl | | propoxy | |
| 3-pentylphenyl | | butoxy | |
| 3-propylphenyl | | dimethylamido | |
| 3-propylphenyl | | diethylamido | |
| 3-undecylphenyl | | methylethylamido | |
| 4-butylphenyl | | phenoxy | |
| 4-decylphenyl | | benzoxy | |
| 4-dodecylphenyl | | allyl | |
| 4-heptylphenyl | | | |
| 4-hexylphenyl | | | |
| 4-nonylphenyl | | | |
| 4-octylphenyl | | | |
| 4-pentylphenyl | | | |
| 4-propylphenyl | | | |

The following structure illustrates an invention embodiment where $R^7$ is joined to $R^8$:

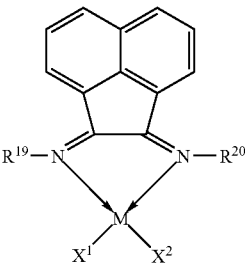

Of course, the naphthalenic ring structure can be hydrocarbyl-substituted, as well.

$R^{19}$ and $R^{20}$ can further independently be defined as the following substituent:

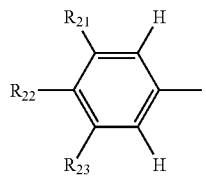

where $R^{21}$, $R^{22}$, and $R^{23}$ are independently hydrogen or hydrocarbyl radicals. Some invention embodiments select $R^{21}$, $R^{22}$ and $R^{23}$ from radicals comprising: methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl provided that at least one $R^{21}$, $R^{22}$, or $R^{23}$ is a $C_3$ or higher hydrocarbyl radical—a solubility handle. In some embodiments $R^{21}$ and $R^{22}$ or $R^{22}$ and $R^{23}$ join together to form a ring structure. In such embodiments, this additional ring structure serves as the $C_3$ or higher hydrocarbyl radical.

Invention catalyst systems can additionally be prepared by combining, in any order, the bidentate ligand,

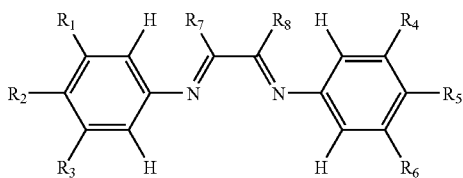

(where N, H, $R^1$, $R^2$, $R^3$, $R^4$, $R^5$, $R^6$, $R^7$ and $R^8$ are as previously defined except that N may be replaced by any Group 15 atom) with a nickel or palladium halide salt, which may optionally be coordinated by solvent (for example $NiX_2$ or $NiX_2$—$MeOCH_2CH_2OMe$ where X=Cl, Br, or I), in an activator solution (for example, methylalumoxane dissolved in toluene). All reactants may be added in any order, or even essentially simultaneously.

For purposes of this disclosure, the term activator is used interchangeably with cocatalyst. The activator functions to remove an abstractable ligand X from the transition metal. After activation the transition metal is left with an empty coordination site at which incoming α-olefin can coordinate before it is incorporated into the oligomer or polymer. Any reagent that can so function without destroying the commercial viability of the oligomerization or polymerization process is suitable for use as an activator or cocatalyst in this invention. Exemplary cocatalysts are discussed below.

Common activators well known in the literature including alumoxanes such as methylalumoxane, modified methylalumoxane, ethylalumoxane and the like; aluminum alkyls such as trimethyl aluminum, triethyl aluminum, triisopropyl aluminum and the like; alkyl aluminum halides such as diethyl aluminum chloride and the like, and alkylaluminum alkoxides are useful in the practice of this invention.

The alumoxane component useful as an activator typically is an oligomeric aluminum compound represented by the general formula $(R''-Al-O)_n$, which is a cyclic compound, or $R''(R''-Al-O)_n AlR''_2$, which is a linear compound. In the general alumoxane formula, $R''$ is independently a $C_1-C_{20}$ alkyl radical, for example, methyl, ethyl, propyl, butyl, pentyl, isomers thereof, and the like, and "n" is an integer from 1–50. Most preferably, $R''$ is methyl and "n" is at least 4. Methylalumoxane and modified methylalumoxanes are most preferred. For further descriptions see, EP 279586, EP 561476, WO94/10180 and U.S. Pat. Nos. 4,665,208, 4,908,463, 4,924,018, 4,952,540, 4,968,827, 5,041,584, 5,103,031, 5,157,137, 5,235,081, 5,248,801, 5,329,032, 5,391,793, and 5,416,229.

The aluminum alkyl component useful as an activator is represented by the general formula $R''AlZ_2$ where $R''$ is defined above, and each Z is independently $R''$ or a different univalent anionic ligand such as halogen (Cl, Br, I), alkoxide (OR'') and the like. Most preferred aluminum alkyls include triethylaluminum, diethylaluminum chloride, triisobutylaluminum, tri-n-octylaluminum and the like.

When alumoxane or aluminum alkyl activators are used, the catalyst-precursor-to-activator molar ratio is from about 1:1000 to 10:1; alternatively, 1:500 to 1:1; or 1:300 to 1:10.

Additionally, if both X are hydride or hydrocarbyl, discrete ionic activators such as $[Me_2PhNH][B(C_6F_5)_4]$, $[Bu_3NH][BF_4]$, $[NH_4][PF_6]$, $[NH_4][SbF_6]$, $[NH][AsF_6]$, $[NH_4][B(C_6H_5)_4]$ or Lewis acidic activators such as $B(C_6F_5)_3$ or $B(C_6H_5)_3$ can be used. These types of activators may also be used when X is not hydrocarbyl if they are used in conjunction with a compound capable of alkylating the metal such as an alumoxane or aluminum alkyl. Discrete ionic activators provide for an activated catalyst site and a relatively non-coordinating (or weakly coordinating) anion. Activators of this type are well known in the literature, see for instance W. Beck., et al., Chem. Rev., vol. 88, p. 1405–1421 (1988); S. H. Strauss, Chem. Rev., vol. 93, p. 927–942 (1993); U.S. Pat. Nos. 5,198,401, 5,278,119, 5,387,568, 5,763,549, 5,807,939, 6,262,202, and WO93/14132, WO99/45042 WO01/30785 and WO01/42249.

When a discrete ionic activator is used, the catalyst-precursor-toactivator molar ratio is from 10:1 to 1:10; 5:1 to 1:5; 2:1 to 1:2; or 1.2:1 to 1:1.

The solubility of invention catalyst precursors allows for the ready preparation of supported catalysts. To prepare uniform supported catalysts, the catalyst precursor should significantly dissolve in the chosen solvent. The term "uniform supported catalyst" means that the catalyst precursor or the activated catalyst approach uniform distribution upon the support's accessible surface area, including the interior pore surfaces of porous supports.

Invention supported catalyst systems may be prepared by any method effective to support other coordination catalyst systems, effective meaning that the catalyst so prepared can be used for oligomerizing olefin in a heterogeneous process. The catalyst precursor, activator, suitable solvent, and support may be added in any order or simultaneously. In one invention embodiment, the activator, dissolved in an appropriate solvent such as toluene is stirred with the support material for 1 minute to 10 hours. The total volume of the activation solution may be greater than the pore volume of the support, but some embodiments limit the total solution volume below that needed to form a gel or slurry (about 100–200% of the pore volume). The mixture is optionally heated from 30–200° C. during this time. The catalyst can be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution, and vacuum dried, or vacuum or evaporation alone removes the solvent.

In another invention embodiment, the catalyst precursor and activator are combined in solvent to form a solution. The support is then added to this solution and the mixture is stirred for 1 minute to 10 hours. The total volume of this solution may be greater than the pore volume of the support, but some embodiments limit the total solution volume below that needed to form a gel or slurry (about 100–200% pore volume). The residual solvent is then removed under vacuum, typically at ambient temperature and over 10–16 hours. But greater or lesser times are possible.

The catalyst precursor may also be supported in the absence of the activator, in which case the activator is added to the liquid phase of a slurry process. For example, a solution of catalyst precursor is mixed with a support material for a period of about 1 minute to 10 hours. The resulting pre-catalyst mixture is then filtered from the solution and dried under vacuum, or vacuum or evaporation alone removes the solvent. The total volume of the catalyst precursor solution may be greater than the pore volume of the support, but some embodiments limit the total solution volume below that needed to form a gel or slurry (about 100–200% of the pore volume).

Additionally, two or more different catalyst precursors may be place on the same support using any of the support methods disclosed above. Likewise, two or more activators may be placed on the same support.

Suitable solid particle supports typically comprise polymeric or refractory oxide materials. Some embodiments select porous supports (such as for example, talc, inorganic oxides, inorganic chlorides (magnesium chloride)) that have an average particle size greater than 10 □m. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

As is well know in the art, the support material may be pretreated by any number of methods. For example, inorganic oxides may be calcined, chemically treated with dehydroxylating agents such as aluminum alkyls and the like, or both.

Some embodiments select the carrier of invention catalysts to have a surface area of 10–700 m$^2$/g, or pore volume of 0.1–4.0 cc/g, and average particle size from 10–500 □m. But greater or lesser values may also be used.

Invention catalysts may generally be deposited on the support at a loading level of 10–100 micromoles of catalyst precursor per gram of solid support; alternately from 20–80 micromoles of catalyst precursor per gram of solid support; or from 40–60 micromoles of catalyst precursor per gram of support. But greater or lesser values may be used provided that the total amount of solid catalyst precursor does not exceed the support's pore volume.

Additionally, oxidizing agents may be added to the supported or unsupported catalyst as described in WO 01/68725.

Process

In the invention oligomerization processes, the process temperature may be −100° C. to 300° C., −20° C. to 200° C., or 0° C. to 150° C. Some embodiment select ethylene oligomerization pressures (gauge) from 0 kPa-35 MPa or 500 kPa–15 MPa. Some embodiments select conditions such that the oligomerization reaction is not significantly diffusion limited.

The preferred and primary feedstock for the oligomerization process is the α-olefin ethylene, however, other □-olefins including but not limited to propylene and 1-butene may also be used alone or in combination with ethylene.

Invention oligomerization processes may be run in the presence of various liquids, particularly aprotic organic liquids. The homogeneous catalyst system, ethylene, □-olefins, and product are soluble in these liquids. A supported (heterogeneous) catalyst system may also be used, but will form a slurry rather than a solution. Suitable liquids for both homo- and heterogeneous catalyst systems, include alkanes, alkenes, cycloalkanes, selected halogenated hydrocarbons, aromatic hydrocarbons, and in some cases, hydrofluorocarbons. Useful solvents specifically include hexane, toluene, cyclohexane, and benzene.

Also, under the correct conditions, mixtures of □-olefins containing desirable numbers of carbon atoms are obtained. Factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276) serves as a measure of these α-olefins' molecular weights. From this theory, $$K=n(C_{n+2} \text{ olefin})/n(C_n \text{ olefin})$$

where $n(C_n$ olefin) is the number of moles of olefin containing n carbon atoms, and $n(C_{n+2}$ olefin) is the number of moles of olefin containing n+2 carbon atoms, or in other words the next higher oligomer of $C_n$ olefin. From this can be determined the weight (mass) fractions of the various olefins in the resulting product. The ability to vary this factor provides the ability the then desired olefins.

Invention-made □-olefins may be further polymerized with other olefins to form polyolefins, especially linear low-density polyethylenes, which are copolymers containing ethylene. They may also be homopolymerized. These polymers may be made by a number of known methods, such as Ziegler-Natta-type polymerization, metallocene catalyzed polymerization, and other methods, see for instance WO 96/23010, see for instance *Angew. Chem., Int. Ed. Engl.*, vol. 34, p. 1143–1170 (1995); European Patent Application, 416,815; and U.S. Pat. No. 5,198,401 for information about metallocene-type catalysts, and J. Boor Jr., *Ziegler-Natta Catalysts and Polymerizations*, Academic Press, New York, 1979 and G. Allen, et al., Ed., *Compre* hensive Polymer Science, Vol. 4, Pergamon Press, Oxford, 1989, pp. 1–108, 409–412 and 533–584, for information about Ziegler-Natta-type catalysts, and H. Mark, et al., Ed., *Encyclopedia of Polymer Science and Engineering*, Vol. 6, John Wiley & Sons, New York, 1992, p. 383–522, for information about polyethylene.

Invention-made □-olefins may be converted to alcohols by known processes, these alcohols being useful for a variety of applications such as intermediates for detergents or plasticizers. The □-olefins may be converted to alcohols by a variety of processes, such as the oxo process followed by hydrogenation, or by a modified, single-step oxo process (the modified Shell process), see for instance B. Elvers, et al., Ed., *Ullmann's Encyclopedia of Chemical Technology*, 5th Ed., Vol. A18, VCH Verlagsgesellschaft mbH, Weinheim, 1991, p. 321–327.

A set of exemplary catalyst precursors is set out below. These are by way of example only and are not intended to list every catalyst precursor that is within the scope of the invention. Several structures are shown along with their corresponding name, as well.

[1-(3-butyl-4-methyl-phenyl)-2-(ethyl)-3-(methyl)-4-(3-ethyl-4-hexyl-5-butyl-phenyl)diazabuta-1,3-diene](hydrido)(dimethylamido)nickel

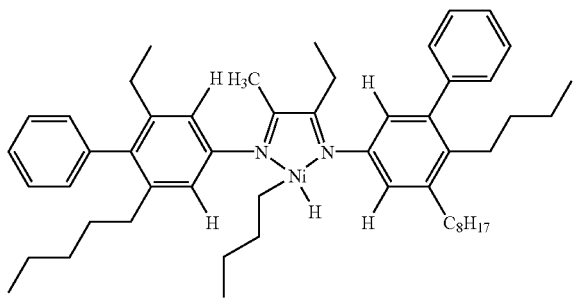

[1-(3-ethyl-4-phenyl-5-butyl-phenyl)-2-(methyl)-3-(ethyl)-4-(3-phenyl-4-butyl-5-octylphenyl)diazabuta-1,3-diene](hydrido)(n-butyl)nickel

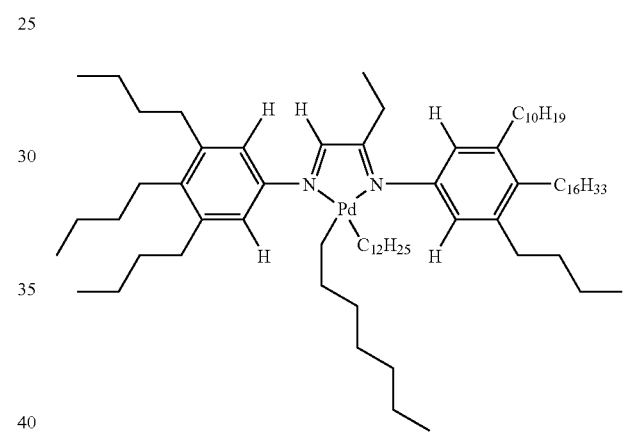

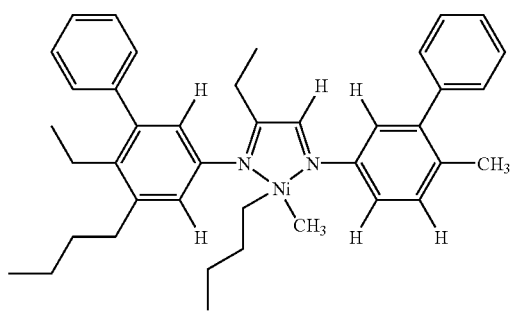

[1-(3-butyl-4-ethyl-5-phenylphenyl)-2-(ethyl)-3-(hydrido)-4-(3-phenyl-1-4-methylphenyl)diazabuta-1,3-diene](n-butyl)(methyl)nickel

[1-(3,4,5-tributylphenyl)-2-(hydrido)-3-(ethyl)-4-(3-decenyl-4-hexadecyl-5-butylphenyl) diazabuta-1,3-diene](heptyl)(dodecyl)palladium

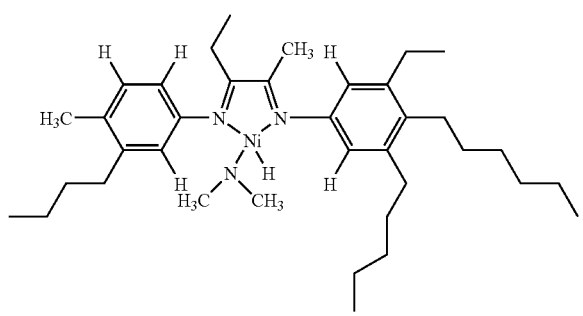

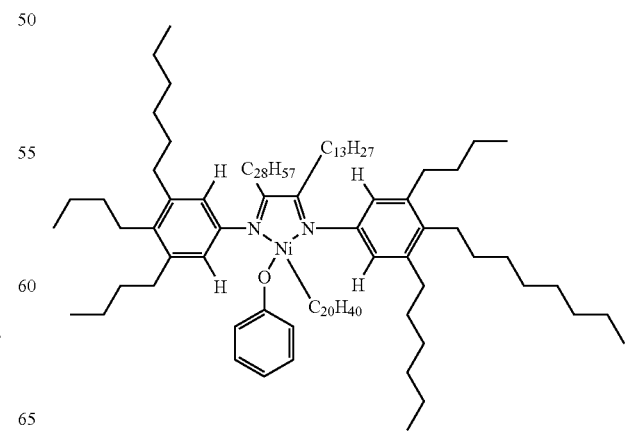

[1-(3,4-dibutyl-5-hexylphenyl)-2-(octacosyl)-3-(tridecyl)-4-(3-butyl-4-octyl-5-hexyl-phenyl) diazabuta-1,3-diene](phenoxy)(eicosenyl) nickel

[1-(3-phenyl-4-octyl-5-butylphenyl)-2-(ethyl)-3-(methyl)-4-(3-butyl-4-phenyl-5-hexylphenyl)diazabuta-1,3-diene](chloro)(dimethylamido)palladium; [1-(3,4-diethyl-5-hexylphenyl)-2-(methyl)-3-(hydrido)-4-(3-methyl-4-phenyl-5-butylphenyl)diazabuta-1,3-diene](diethylamido)(dimethylamido)nickel; [1-(3-methyl-5-phenylphenyl)-2-(hydrido)-3-(ethyl)-4-(3-methyl-5-hexylphenyl)diazabuta-1,3-diene](bromo)(chloro)palladium; [1-(3-phenyl-4-butyl-5-octylphenyl)-2-(methyl)-3-(ethyl)-4-(3-ethyl-4-phenyl-5-hexylphenyl)diazabuta-1,3-diene](chloro)(bromo)nickel; [1-(3-butyl-4-methyl-5-octylphenyl)-2,3-(diethyl)-4-(3,4-dibutyl-5-octylphenyl)diazabuta-1,3-diene](ethyl)(n-butyl) palladium; [1-(3-butyl-4-ethyl-5-phenylphenyl)-2-(ethyl)-3-(hydrido)-4-(3-phenyl-4-methylphenyl)diazabuta-1,3-diene](n-butyl)(methyl)nickel; [1-(3,4-diphenyl-5-butylphenyl)-2-(methyl)-3-(hydrido)-4-(3-ethyl-4-octyl-5-hexylphenyl)diazabuta-1,3-diene](chloro)(ethyl)nickel; [1-(3-hexyl-4-butylphenyl)-2,3-(dimethyl)-4-(3-methyl-4-octyl-5-phenylphenyl)diazabuta-1,3-diene](dimethylamido)(diethylamido)nickel; [1-(3,4-diphenyl-5-butylphenyl)-2,3-(diethyl)-4-(3,4-dimethyl-5-phenylphenyl)diazabuta-1,3-diene](diethylamido)(dimethylamido)nickel; [1-(3-butyl-4-methyl phenyl)-2-(methyl)-3-(ethyl)-4-(3-methyl-4,5-dibutylphenyl)diazabuta-1,3-diene]di(ethyl)nickel; [1-(3-phenyl-4-hexyl-5-octylphenyl)-2,3-(diethyl)-4-(3,5-diphenyl-4-butylphenyl)diazabuta-1,3-diene](bromo)(diethylamido)nickel; [1-(3-butyl-4-hexyl-5-octylphenyl)-2-(methyl)-3-(hydrido)-4-(3-methyl-5-octylphenyl)diazabuta-1,3-diene](n-butyl)(bromo)nickel; [1-(3,5-dibutyl-4-phenylphenyl)-2-(hydrido)-3-(methyl)-4-(3-hexyl-phenyl)diazabuta-1,3-diene](diethylamido)(hydrido) nickel; [1-(3-ethyl-4-butyl-5-phenylphenyl)-2-(methyl)-3-(ethyl)-4-(3,4-dimethyl-5-hexylphenyl)diazabuta-1,3-diene]di(chloro)nickel; [1-(3-butyl-4-phenylphenyl)-2,3-(dihydrido)-4-(3-hexyl-4-phenylphenyl)diazabuta-1,3-diene](bromo)(methyl)nickel; [1-(3-butyl-4-ethyl-5-octylphenyl)-2-(hydrido)-3-(methyl)-4-(3-methyl-5-phenylphenyl)diazabuta-1,3-diene](dimethylamido)(methyl)palladium; [1-(3-ethyl-4-butyl-5-hexylphenyl)-2-(hydrido)-3-(methyl)-4-(3-butyl-4-methyl phenyl)diazabuta-1,3-diene](diethylamido)(dimethylamido)nickel; [1-(3-ethyl-4-hexyl-5-octylphenyl)-2-(methyl)-3-(ethyl)-4-(3-hexyl-4-butylphenyl)diazabuta-1,3-diene](bromo)(methyl)nickel; [1-(3-phenyl-5-hexylphenyl)-2-(hydrido)-3-(methyl)-4-(3-methyl-5-phenylphenyl)diazabuta-1,3-diene](ethyl)(bromo)palladium; [1-(3-ethyl-4-octyl-5-phenylphenyl)-2-(hydrido)-3-(ethyl)-4-(3-ethyl-4-methyl-5-phenylphenyl)diazabuta-1,3-diene](dimethylamido)(ethyl)palladium; [1-(3-phenyl-5-butylphenyl)-2-(hydrido)-3-(methyl)-4-(3-methyl-4,5-dihexylphenyl)diazabuta-1,3-diene]di(bromo)nickel; [1-(3,5-dibutyl-4-methylphenyl)-2-(hydrido)-3-(ethyl)-4-(3-ethyl-4-hexyl-5-butylphenyl)diazabuta-1,3-diene](n-butyl)(dimethylamido)nickel; [1-(3,5-dibutyl-4-methyl phenyl)-2,3-(dimethyl)-4-(3-methyl-5-hexylphenyl)diazabuta-1,3-diene](bromo)(dimethylamido)nickel; [1-(3-methyl-4-hexyl-5-octylphenyl)-2,3-(diethyl)-4-(3-phenyl-phenyl)diazabuta-1,3-diene](methyl)(bromo)nickel; [1-(3-butyl-4-ethylphenyl)-2-(ethyl)-3-(methyl)-4-(3-phenyl-4-butylphenyl)diazabuta-1,3-diene](n-butyl)(methyl)nickel; [1-(3-butyl-5-octylphenyl)-2-(ethyl)-3-(methyl)-4-(3-phenyl-4-methyl-5-butylphenyl)diazabuta-1,3-diene](ethyl)(methyl)nickel; [1-(3-butyl-4-ethyl-5-hexylphenyl)-2,3-(dihydrido)-4-(3-methyl-4,5-dibutylphenyl)diazabuta-1,3-diene](diethylamido)(dimethylamido)nickel; [1-(3,5-diphenylphenyl)-2-(hydrido)-3-(methyl)-4-(3-methyl-5-octylphenyl)diazabuta-1,3-diene](ethyl)(chloro)nickel; [1-(3,4-dihexylphenyl)-2-(methyl)-3-(ethyl)-4-(3,4-dibutyl-5-phenylphenyl)diazabuta-1,3-diene](bromo)(dimethylamido)palladium; [1-(3-butyl-4-ethyl-5-octylphenyl)-2-(ethyl)-3-(hydrido)-4-(3-hexyl-4-ethylphenyl)diazabuta-1,3-diene](ethyl)(dimethylamido)palladium; [1-(3,5-dibutyl-4-ethylphenyl)-2,3-(dihydrido)-4-(3,5-diphenyl-4-methyl phenyl)diazabuta-1,3-diene](hydrido)(chloro)nickel; [1-(3-methyl-4-ethyl-5-butylphenyl)-2-(hydrido)-3-(methyl)-4-(3-hexyl-4-butylphenyl)diazabuta-1,3-diene](dimethylamido)(methyl)nickel; [1-(3-butyl-4-methyl phenyl)-2-(ethyl)-3-(methyl)-4-(3-ethyl-4-hexyl-5-butylphenyl)diazabuta-1,3-diene](hydrido)(dimethylamido)nickel; [1-(3-phenyl-4-octyl-5-hexylphenyl)-2-(methyl)-3-(ethyl)-4-(3-phenyl-4-butyl-5-octylphenyl)diazabuta-1,3-diene](methyl)(bromo)palladium; [1-(3-butyl-4-ethyl-5-octylphenyl)-2,3-(dimethyl)-4-(3-methyl-4-phenyl-5-octylphenyl)diazabuta-1,3-diene](ethyl)(dimethylamido)nickel; [1-(3-ethyl-4-phenyl-5-hexylphenyl)-2-(hydrido)-3-(ethyl)-4-(3-methyl-4,5-diphenylphenyl)diazabuta-1,3-diene](hydrido)(dimethylamido)nickel; [1-(3-ethyl-4-butyl-5-hexylphenyl)-2-(methyl)-3-(ethyl)-4-(3,4-diethyl-5-octylphenyl) diazabuta-1,3-diene](bromo)(chloro)nickel; [1-(3-phenyl-4-ethyl-5-butylphenyl)-2,3-(diethyl)-4-(3,4-dihexylphenyl) diazabuta-1,3-diene](hydrido)(ethyl)palladium; [1-(3-butyl-4,5-dihexylphenyl)-2-(hydrido)-3-(ethyl)-4-(3-phenyl-4-octyl-5-butylphenyl)diazabuta-1,3-diene](dimethylamido)(diethylamido)nickel; [1-(3,5-dibutyl-4-ethylphenyl)-2-(methyl)-3-(hydrido)-4-(3,5-dibutylphenyl)diazabuta-1,3-diene](methyl)(chloro)nickel; [1-(3-methyl-5-phenylphenyl)-2-(hydrido)-3-(ethyl)-4-(3-methyl-5-butylphenyl)diazabuta-1,3-diene](n-butyl)(methyl)nickel; [1-(3-methyl-5-butylphenyl)-2-(hydrido)-3-(ethyl)-4-(3,4-diphenyl-5-butylphenyl)diazabuta-1,3-diene](chloro)(ethyl)palladium; [1-(3-phenyl-4-butyl-5-octylphenyl)-2-(methyl)-3-(ethyl)-4-(3-butyl-4-methyl-5-hexylphenyl)diazabuta-1,3-diene](dimethylamido)(methyl)nickel; [1-(3-ethyl-4-hexyl-5-octylphenyl)-2,3-(dihydrido)-4-(3,4,5-tributylphenyl)diazabuta-1,3-diene](methyl)(n-butyl)palladium; [1-(3-methyl-4-hexyl-5-octylphenyl)-2-(methyl)-3-(hydrido)-4-(3-butyl-4-methyl-5-octylphenyl) diazabuta-1,3-diene](hydrido)(dimethylamido)palladium; [1-(3-phenyl-4,5-dihexylphenyl)-2-(hydrido)-3-(methyl)-4-(3-phenyl-4-methyl-5-butylphenyl)diazabuta-1,3-diene](diethylamido)(ethyl)nickel; [1-(3-methyl-4-hexyl-5-phenylphenyl)-2-(methyl)-3-(hydrido)-4-(3-ethyl-4,5-dioctylphenyl)diazabuta-1,3-diene](ethyl)(diethylamido)palladium; [1-(3-phenyl-4-octyl-5-hexylphenyl)-2,3-(diethyl)-4-(3-phenyl-4-butyl-5-hexylphenyl)diazabuta-1,3-diene](dimethylamido)(n-butyl)nickel; [1-(3,4-dimethyl-5-butylphenyl)-2-(ethyl)-3-(methyl)-4-(3,4-dimethyl-5-octylphenyl)diazabuta-1,3-diene](hydrido)(ethyl)nickel; [1-(3-butyl-4-methyl-5-phenylphenyl)-2-(ethyl)-3-(hydrido)-4-(3-ethyl-4-octyl-5-butylphenyl)diazabuta-1,3-diene](hydrido)(ethyl)nickel; [1-(3-butyl-phenyl)-2,3-(diethyl)-4-(3,4-dibutylphenyl)diazabuta-1,3-diene](hydrido)(bromo) nickel; [1-(3-ethyl-4,5-dioctylphenyl)-2-(hydrido)-3-(methyl)-4-(3-methyl-4,5-diphenylphenyl)diazabuta-1,3-diene](hydrido)(methyl)nickel; [1-(3-methyl-4-octyl-5-butylphenyl)-2,3-(dimethyl)-4-(3-phenyl-4-methyl-5-octylphenyl)diazabuta-1,3-diene](diethylamido)(ethyl) nickel; [1-(3,5-dibutyl-4-octylphenyl)-2-(methyl)-3-(hydrido)-4-(3-phenyl-4-butylphenyl)diazabuta-1,3-diene] di(dimethylamido)nickel; [1-(3-phenyl-4-methyl-5- butylphenyl)-2,3-(dimethyl)-4-(3-phenyl-4-butylphenyl) diazabuta-1,3-diene](diethylamido)(n-butyl)palladium; [1-(3-phenyl-phenyl)-2-(methyl)-3-(hydrido)-4-(3-ethyl-4-methyl-5-butylphenyl)diazabuta-1,3-diene]di(ethyl)nickel; [1-(3-methyl-4-octyl-5-phenylphenyl)-2,3(dimethyl)-4-(3-phenyl-4-ethylphenyl)diazabuta-1,3-diene](hydrido)(methyl)nickel; [1-(3,4-dimethyl-5-butylphenyl)-2-(hydrido)-3-(ethyl)-4-(3-butyl-4-methyl-5-octylphenyl)diazabuta-1,3-diene](hydrido)(diethylamido)nickel; [1-(3,4-diethyl-5-hexylphenyl)-2-(methyl)-3-(ethyl)-4-(3-ethyl-5-butylphenyl)diazabuta-1,3-diene](ethyl)(methyl)nickel; [1-(3-phenyl-5-octylphenyl)-2-(ethyl)-3-(hydrido)-4-(3-methyl-4-ethyl-5-octylphenyl)diazabuta-1,3-diene] (diethylamido)(ethyl)palladium; [1-(3-phenyl-5-octylphenyl)-2,3-(diethyl)-4-(3,4-diphenyl-5-hexylphenyl) diazabuta-1,3-diene](ethyl)(bromo)nickel; [1-(3-ethyl-4-octyl-5-hexylphenyl)-2-(hydrido)-3-(methyl)-4-(3-phenyl-4-ethylphenyl)diazabuta-1,3-diene](diethylamido) (dimethylamido)nickel; [1-(3-methyl-4-hexyl-5-butylphenyl)-2,3-(diethyl)-4-(3-methyl-5-hexylphenyl) diazabuta-1,3-diene](methyl)(diethylamido)nickel; [1-(3-methyl-5-octylphenyl)-2,3-(dimethyl)-4-(3-butyl-4-ethyl-5-hexylphenyl)diazabuta-1,3-diene](hydrido)(n-butyl)nickel; [1-(3,4,5-triphenylphenyl)-2-(methyl)-3-(ethyl)-4-(3,4-diphenyl-5-octylphenyl)diazabuta-1,3-diene](ethyl)(diethylamido)palladium; [1-(3-hexyl-4-methyl phenyl)-2,3-(dimethyl)-4-(3-phenyl-4-hexyl-5-butylphenyl)diazabuta-1,3-diene](bromo)(hydrido)nickel; [1-(3,4-dimethyl-5-butylphenyl)-2,3-(diethyl)-4-(3-butyl-4-methyl-5-phenylphenyl)diazabuta-1,3-diene](bromo)(chloro)nickel; [1-(3-ethyl-4,5-diphenylphenyl)-2,3-(diethyl)-4-(3-phenyl-4-hexyl-5-octylphenyl)diazabuta-1,3-diene](methyl)(hydrido)palladium; [1-(3,4-diphenyl-5-octylphenyl)-2-(ethyl)-3-(methyl)-4-(3-methyl-4,5-dioctylphenyl)diazabuta-1,3-diene](methyl)(hydrido)nickel; [1-(3-methyl-4-ethyl-5-octylphenyl)-2-(ethyl)-3-(methyl)-4-(3-phenyl-5-hexylphenyl)diazabuta-1,3-diene](ethyl)(chloro)nickel; [1-(3-phenyl-4-butyl-5-octylphenyl)-2,3-(dimethyl)-4-(3-phenyl-5-octylphenyl)diazabuta-1,3-diene](ethyl) (dimethylamido)nickel; [1-(3,4-diphenyl-5-butylphenyl)-2-(methyl)-3-(ethyl)-4-(3-methyl-4-phenyl-5-octylphenyl) diazabuta-1,3-diene](dimethylamido)(ethyl)nickel; [1-(3-methyl-4-hexyl-5-octylphenyl)-2-(ethyl)-3-(methyl)-4-(3-ethyl-4-octyl-5-phenylphenyl)diazabuta-1,3-diene] (hydrido)(chloro)nickel; [1-(3-butyl-4-methyl-5-octylphenyl)-2-(ethyl)-3-(methyl)-4-(3,5-diphenyl-4-octylphenyl)diazabuta-1,3-diene](dimethylamido)(hydrido) nickel; [1-(3-butyl-4-methyl-5-phenylphenyl)-2-(methyl)-3-(ethyl)-4-(3-butyl-5-phenylphenyl)diazabuta-1,3-diene] (hydrido)(n-butyl)nickel; [1-(3,4-dibutyl-5-hexylphenyl)-2-(ethyl)-3-(hydrido)-4-(3-phenyl-4-butylphenyl)diazabuta-1,3-diene](diethylamido)(methyl)nickel; [1-(3-ethyl-4-hexyl-5-phenylphenyl)-2,3-(diethyl)-4-(3-butyl-4-hexylphenyl) diazabuta-1,3-diene](chloro)(bromo)nickel; [1-(3-ethyl-4-hexyl-5-octylphenyl)-2,3-(dihydrido)-4-(3-butyl-4-hexyl-5-phenylphenyl)diazabuta-1,3-diene](ethyl)(hydrido)nickel; [1-(3-hexyl-4-phenylphenyl)-2,3-(dimethyl)-4-(3-ethyl-5-hexylphenyl)diazabuta-1,3-diene](ethyl)(dimethylamido) palladium; [1-(3-phenyl-4-methyl-5-octylphenyl)-2-(methyl)-3-(ethyl)-4-(3-hexyl-4-octylphenyl)diazabuta-1,3-diene](methyl)(hydrido)nickel; [1-(3-butyl-4,5-dioctylphenyl)-2,3-(dihydrido)-4-(3-ethyl-4-methyl-5-octylphenyl)diazabuta-1,3-diene]di(bromo)nickel; [1-(3,5-diphenyl-4-ethylphenyl)-2-(ethyl)-3-(hydrido)-4-(3-butyl-4-phenylphenyl)diazabuta-1,3-diene](methyl) (diethylamido)nickel; [1-(3-ethyl-4-butyl-5-hexylphenyl)-2-(ethyl)-3-(methyl)-4-(3-hexyl-4-phenylphenyl)diazabuta-1,3-diene](bromo)(methyl)nickel; [1-(3-methyl-4-octyl-5-phenylphenyl)-2-(hydrido)-3-(methyl)-4-(3-phenyl-4-hexylphenyl)diazabuta-1,3-diene](hydrido) (dimethylamido)nickel; [1-(3-methyl-4-ethyl-5-butylphenyl)-2,3-(diethyl)-4-(3-hexyl-4-phenyl)diazabuta-1, 3-diene]di(dimethylamido)nickel; [1-(3-methyl-5-butylphenyl)-2,3-(dimethyl)-4-(3-methyl-4-octyl-5-phenylphenyl)diazabuta-1,3-diene]di(dimethylamido) nickel; [1-(3-phenyl-4-octylphenyl)-2-(methyl)-3-(ethyl)-4-(3-butyl-4-octylphenyl)diazabuta-1,3-diene](chloro) (diethylamido)nickel; [1-(3-hexyl-4-phenylphenyl)-2,3-(dihydrido)-4-(3,4-dimethyl-5-phenylphenyl)diazabuta-1,3-diene](n-butyl)(bromo)nickel; [1-(3,5-diphenyl-4-octylphenyl)-2,3-(diethyl)-4-(3,5-dibutyl-4-octylphenyl) diazabuta-1,3-diene](diethylamido)(chloro)nickel; [1-(3,4-diethyl-5-phenylphenyl)-2-(hydrido)-3-(ethyl)-4-(3-octyl-4-methyl phenyl)diazabuta-1,3-diene](hydrido)(methyl) nickel; [1-(3-phenyl-5-butylphenyl)-2-(ethyl)-3-(hydrido)-4-(3-butyl-4-phenyl-5-hexylphenyl)diazabut-1,3-diene]di (chloro)nickel; [1-(3-hexyl-4-phenylphenyl)-2-(ethyl)-3-(methyl)-4-(3-phenyl-4-octyl-5-hexylphenyl)diazabuta-1,3-diene](hydrido)(bromo)palladium; [1-(3-ethyl-4-octyl-5-phenylphenyl)-2,3-(diethyl)-4-(3,5-dibutylphenyl) diazabuta-1,3-diene](n-butyl)(dimethylamido)nickel; [1-(3-methyl-4-butyl-5-octylphenyl)-2,3-(dimethyl)-4-(3-ethyl-4,5-dihexylphenyl)diazabuta-1,3-diene](methyl)(n-butyl) nickel; [1-(3-butyl-5-octylphenyl)-2,3-(dimethyl)-4-(3-ethyl-4-butyl-5-hexylphenyl)diazabuta-1,3-diene](ethyl) (hydrido)palladium; [1-(3,4-dihexylphenyl)-2-(methyl)-3-(ethyl)-4-(3-phenyl-4-octyl-5-hexylphenyl)diazabuta-1,3-diene](bromo)(ethyl)palladium; [1-(3-methyl-5-octylphenyl)-2,3-(dimethyl)-4-(3-hexyl-4-butylphenyl) diazabuta-1,3-diene](ethyl)(hydrido)nickel; [1-(3-phenyl-4-octyl-5-butylphenyl)-2,3-(dihydrido)-4-(3-methyl-4-ethyl-5-octylphenyl)diazabuta-1,3-diene](dimethylamido) (hydrido)nickel; [1-(3,5-diphenyl-4-methylphenyl)-2-(hydrido)-3-(ethyl)-4-(3,5-dibutyl-4-octylphenyl)diazabuta-1,3-diene](ethyl)(diethylamido)palladium; [1-(3-ethyl-4-phenyl-5-octylphenyl)-2-(ethyl)-3-(hydrido)-4-(3-butyl-4-phenyl-5-octylphenyl)diazabuta-1,3-diene](bromo)(n-butyl)palladium; [1-(3,5-diphenyl-4-octylphenyl)-2,3-(diethyl)-4-(3-ethyl-4-phenyl-5-butylphenyl)diazabuta-1,3-diene]di(diethylamido)nickel; [1-(3-ethyl-4-phenyl-5-butylphenyl)-2-(hydrido)-3-(ethyl)-4-(3-methyl-4-butyl-5-phenylphenyl)diazabuta-1,3-diene](bromo)(hydrido) palladium; [1-(3-butyl-4,5-diphenylphenyl)-2-(hydrido)-3-(ethyl)-4-(3-ethyl-4-butyl-5-hexylphenyl)-1,3-diene] (diethylamido)(n-butyl)nickel; [1-(3,4-diphenyl-5-octylphenyl)-2-(methyl)-3-(hydrido)-4-(3-butyl-4-methyl-5-hexylphenyl)diazabuta-1,3-diene](ethyl)(n-butyl) palladium; [1-(3,4-diethyl-5-butylphenyl)-2-(ethyl)-3-(hydrido)-4-(3-methyl-4-butyl-5-octylphenyl)diazabuta-1, 3-diene](ethyl)(methyl)nickel; [1-(3,4-diphenyl-5-butylphenyl)-2-(hydrido)-3-(methyl)-4-(3,4-dioctylphenyl) diazabuta-1,3-diene](chloro)(hydrido)nickel; [1-(3,4-dimethyl-5-phenylphenyl)-2,3-(diethyl)-4-(3-phenyl-4-ethyl-5-octylphenyl)diazabuta-1,3-diene](ethyl)(hydrido) nickel; [1-(3-butyl-4-methyl-5-octylphenyl)-2,3-(dimethyl)-4-(3-phenyl-4-methyl-5-butylphenyl)diazabuta-1,3-diene] (diethylamido)(chloro)palladium; [1-(3-ethyl-4,5-diphenylphenyl)-2-(hydrido)-3-(ethyl)-4-(3,5-dibutyl-4-methyl phenyl)diazabuta-1,3-diene](dimethylamido) (bromo)nickel; [1-(3-phenyl-4,5-dioctylphenyl)-2,3-(dimethyl)-4-(3-butyl-5-hexylphenyl)diazabuta-1,3-diene] (n-butyl)(methyl)palladium; [1-(3-methyl-4-phenyl-5-hexylphenyl)-2-(ethyl)-3-(hydrido)-4-(3-octyl-4-hexylphenyl)diazabuta-1,3-diene](hydrido)(n-butyl)nickel;

[1-(3,5-dibutyl-4-ethylphenyl)-2-(methyl)-3-(ethyl)-4-(3-methyl-4-butyl-5-phenylphenyl)-1,3-diene](dimethylamido)(ethyl)nickel; [1-(3-phenyl-4-butylphenyl)-2-(hydrido)-3-(ethyl)-4-(3-octyl-4-ethylphenyl)diazabuta-1,3-diene](hydrido)(chloro)palladium; [1-(3-ethyl-4-hexyl-5-phenylphenyl)-2,3-(diethyl)-4-(3-ethyl-4,5-dioctylphenyl)diazabuta-1,3-diene](hydrido)(dimethylamido)nickel; [1-(3-methyl-4,5-dioctylphenyl)-2,3-(dihydrido)-4-(3,4-dibutyl-5-octylphenyl)diazabuta-1,3-diene](ethyl)(hydrido)palladium; [1-(3-hexyl-4-octylphenyl)-2,3-(dihydrido)-4-(3,4-diethyl-5-butylphenyl)diazabuta-1,3-diene](methyl)(dimethylamido)nickel; [1-(3-butyl-5-hexylphenyl)-2,3-(dimethyl)-4-(3-butyl-4-octyl-5-hexylphenyl)diazabuta-1,3-diene](n-butyl)(methyl)nickel; [1-(3-octyl-4-ethylphenyl)-2,3-(diethyl)-4-(3,4-dioctylphenyl)diazabuta-1,3-diene](bromo)(ethyl)nickel; [1-(3,4-diethyl-5-hexylphenyl)-2,3-(dihydrido)-4-(3,5-diphenyl-4-octylphenyl)diazabuta-1,3-diene](n-butyl)(diethylamido)nickel; [1-(3-phenyl-4-ethyl-5-butylphenyl)-2,3-(dimethyl)-4-(3-octyl-phenyl)diazabuta-1,3-diene](diethylam ido)(dimethylamido)nickel; [1-(3,5-diphenyl-4-methyl phenyl)-2,3-(dimethyl)-4-(3,4-dibutyl-5-octylphenyl)diazabuta-1,3-diene](n-butyl)(chloro)nickel; [1-(3-ethyl-5-octylphenyl)-2,3-(dihydrido)-4-(3-phenyl-4-octyl-5-butylphenyl)diazabuta-1,3-diene](bromo)(chloro)nickel; [1-(3-butyl-4-phenyl-5-octylphenyl)-2,3-(dihydrido)-4-(3-phenyl-4-octyl-5-hexylphenyl)diazabuta-1,3-diene](n-butyl)(chloro)nickel; [1-(3-phenyl-4-hexyl-5-octylphenyl)-2-(hydrido)-3-(ethyl)-4-(3-methyl-4-hexyl-5-butylphenyl)diazabuta-1,3-diene](dimethylamido)(diethylamido)palladium; [1-(3-hexyl-4-methyl phenyl)-2,3-(dimethyl)-4-(3-phenyl-4-octyl-5-hexylphenyl)diazabuta-1,3-diene]di(bromo)nickel; [1-(3-methyl-5-phenylphenyl)-2-(methyl)-3-(ethyl)-4-(3-butyl-4-phenylphenyl)diazabuta-1,3-diene](bromo)(chloro)nickel; [1-(3-ethyl-4-methyl-5-butylphenyl)-2-(hydrido)-3-(ethyl)-4-(3,5-diphenyl-4-methyl phenyl)diazabuta-1,3-diene](bromo)(diethylamido)palladium; [1-(3-methyl-4-phenyl-5-butylphenyl)-2-(ethyl)-3-(methyl)-4-(3-phenyl-4-ethyl-5-hexylphenyl)diazabuta-1,3-diene](methyl)(bromo)nickel; [1-(3,4-diethyl-5-octylphenyl)-2-(hydrido)-3-(methyl)-4-(3-butyl-4-phenyl-5-hexylphenyl)diazabuta-1,3-diene]di(diethylamido)nickel; [1-(3-ethyl-4-phenyl-5-octylphenyl)-2-(hydrido)-3-(ethyl)-4-(3-phenyl-5-hexylphenyl)diazabuta-1,3-diene](hydrido)(bromo)palladium; [1-(3-hexyl-4-butylphenyl)-2-(hydrido)-3-(methyl)-4-(3-octyl-4-ethylphenyl)diazabuta-1,3-diene](n-butyl)(dimethylamido)nickel; [1-(3-butyl-5-hexylphenyl)-2-(ethyl)-3-(hydrido)-4-(3,4,5-tributylphenyl)diazabuta-1,3-diene](methyl)(dimethylamido)nickel; [1-(3-octyl-4-ethylphenyl)-2,3-(dimethyl)-4-(3-ethyl-4-butyl-5-octylphenyl)diazabuta-1,3-diene](ethyl)(diethylamido)palladium; [1-(3-butyl-4-ethyl-5-octylphenyl)-2-(methyl)-3-(hydrido)-4-(3-methyl-5-hexylphenyl)diazabuta-1,3-diene](chloro)(dimethylamido)palladium; [1-(3-phenyl-4-ethyl-5-hexylphenyl)-2,3-(dimethyl)-4-(3-phenyl-4,5-dioctylphenyl)diazabuta-1,3-diene](dimethylamido)(ethyl)nickel; [1-(3-methyl-4,5-dioctylphenyl)-2-(methyl)-3-(hydrido)-4-(3-phenyl-4-octyl-5-hexylphenyl)diazabuta-1,3-diene](hydrido)(ethyl)nickel; [1-(3-phenyl-4-ethyl-5-octylphenyl)-2-(hydrido)-3-(ethyl)-4-(3-methyl-4-ethyl-5-octylphenyl)diazabuta-1,3-diene]di(methyl)palladium; [1-(3-ethyl-4-butyl-5-octylphenyl)-2,3-(dihydrido)-4-(3,5-dibutyl-4-ethylphenyl)diazabuta-1,3-diene](diethylamido)(ethyl)nickel; [1-(3,4-dimethyl-5-butylphenyl)-2-(hydrido)-3-(ethyl)-4-(3-butyl-4-octyl-5-phenylphenyl)diazabuta-1,3-diene](methyl)(n-butyl)nickel; [1-(3-methyl-4-ethyl-5-butylphenyl)-2,3-(diethyl)-4-(3,4-diethyl-5-butylphenyl)diazabuta-1,3-diene](dimethylamido)(ethyl)nickel; [1-(3-hexyl-4-ethylphenyl)-2-(methyl)-3-(hydrido)-4-(3-ethyl-4-hexyl-5-phenylphenyl)diazabuta-1,3-diene](ethyl)(dimethylamido)nickel; [1-(3-methyl-5-octylphenyl)-2-(ethyl)-3-(methyl)-4-(3,5-dibutyl-4-ethylphenyl)diazabuta-1,3-diene](chloro)(methyl)palladium; [1-(3-butyl-5-phenylphenyl)-2-(hydrido)-3-(methyl)-4-(3-methyl-4-ethyl-5-hexylphenyl)diazabuta-1,3-diene](n-butyl)(diethylamido)nickel; [1-(3-ethyl-4-hexyl-5-phenylphenyl)-2-(ethyl)-3-(hydrido)-4-(3,5-dibutyl-4-ethylphenyl)diazabuta-1,3-diene] (methyl)(chloro)nickel; [1-(3-butyl-4-hexyl-5-octylphenyl)-2-(methyl)-3-(ethyl)-4-(3-butyl-4-phenyl-5-hexylphenyl)diazabuta-1,3-diene](n-butyl)(methyl)nickel; [1-(3-phenyl-4,5-dibutylphenyl)-2-(ethyl)-3-(hydrido)-4-(3,4-dibutylphenyl)diazabuta-1,3-diene](n-butyl)(bromo)nickel; [1-(3-octyl-4-ethylphenyl)-2-(hydrido)-3-(methyl)-4-(3-phenyl-4-methyl-5-hexylphenyl)diazabuta-1,3-diene](dimethylamido)(hydrido)nickel; [1-(3-methyl-4,5-diphenylphenyl)-2,3-(dimethyl)-4-(3-ethyl-4-hexyl-5-phenylphenyl)diazabuta-1,3-diene](n-butyl)(ethyl)nickel; [1-(3-butyl-4-ethyl-5-hexylphenyl)-2-(ethyl)-3-(hydrido)-4-(3,5-dibutyl-4-octylphenyl)diazabuta-1,3-diene](dimethylamido)(diethylamido)palladium; [1-(3-methyl-4-phenyl-5-octylphenyl)-2-(ethyl)-3-(hydrido)-4-(3-hexyl-phenyl)diazabuta-1,3-diene](dimethylamido)(methyl)nickel; [1-(3-methyl-4,5-dibutylphenyl)-2-(hydrido)-3-(methyl)-4-(3,4-dioctylphenyl)diazabuta-1,3-diene](methyl)(dimethylamido)palladium; [1-(3-butyl-4-octyl-5-phenylphenyl)-2-(ethyl)-3-(methyl)-4-(3-octyl-4-phenylphenyl)diazabuta-1,3-diene](bromo)(dimethylamido)nickel; [1-(3-phenyl-4,5-dioctylphenyl)-2-(ethyl)-3-(hydrido)-4-(3-phenyl-4-methyl-5-octylphenyl)diazabuta-1,3-diene](bromo)(n-butyl)nickel; [1-(3-butyl-4,5-dioctylphenyl)-2,3-(dihydrido)-4-(3,4-dibutyl-5-phenylphenyl)diazabuta-1,3-diene](methyl)(bromo)nickel; [1-(3,4-diethyl-5-phenylphenyl)-2,3-(dihydrido)-4-(3,4-di-hexylphenyl)diazabuta-1,3-diene](ethyl)(methyl)nickel; [1-(3-butyl-5-phenylphenyl)-2,3-(dimethyl)-4-(3,4-diphenyl-5-butylphenyl)diazabuta-1,3-diene]di(chloro)nickel; [1-(3-butyl-5-phenylphenyl)-2-(ethyl)-3-(methyl)-4-(3-butyl-4-phenyl-5-hexylphenyl)diazabuta-1,3-diene](bromo)(n-butyl)nickel; [1-(3-phenyl-4-ethyl-5-hexylphenyl)-2-(ethyl)-3-(hydrido)-4-(3-ethyl-4-methyl-5-butylphenyl)diazabuta-1,3-diene](n-butyl)(diethylamido)palladium; [1-(3-butyl-4-octylphenyl)-2-(hydrido)-3-(ethyl)-4-(3-ethyl-4,5-dibutylphenyl)diazabuta-1,3-diene](ethyl)(methyl)nickel; [1-(3-phenyl-4-octyl-5-hexylphenyl)-2,3-(dihydrido)-4-(3,4,5-triphenylphenyl)diazabuta-1,3-diene](methyl)(chloro)nickel; [1-(3-phenyl-4-ethylphenyl)-2-(hydrido)-3-(methyl)-4-(3-phenyl-4-butylphenyl)diazabuta-1,3-diene](n-butyl)(chloro)palladium; [1-(3-ethyl-4-hexyl-5-octylphenyl)-2-(ethyl)-3-(methyl)-4-(3-phenyl-4-hexyl-5-octylphenyl)diazabuta-1,3-diene](n-butyl)(ethyl)palladium; [1-(3,4-dioctylphenyl)-2-(methyl)-3-(hydrido)-4-(3-ethyl-4,5-dioctylphenyl)diazabuta-1,3-diene](bromo)(chloro)palladium; [1-(3-ethyl-4,5-dioctylphenyl)-2-(methyl)-3-(hydrido)-4-(3-ethyl-5-phenylphenyl)diazabuta-1,3-diene](methyl)(dimethylamido)nickel; [1-(3-phenyl-4-ethylphenyl)-2,3-(dihydrido)-4-(3-octyl-phenyl)diazabuta-1,3-diene](hydrido)(dimethylamido)nickel; [1-(3-methyl-4-phenyl-5-butylphenyl)-2-(ethyl)-3-(hydrido)-4-(3-methyl-4-phenyl-5-hexylphenyl)diazabuta-1,3-diene](ethyl)(diethylamido)nickel; [1-(3-phenyl-4-methyl-5-octylphenyl)-2-(hydrido)-3-(methyl)-4-(3-ethyl-4-phenyl-5-hexylphenyl)diazabuta-1,3-diene](dimethylamido)(chloro)nickel; [1-(3-methyl-4-ethyl-5-butylphenyl)-2-(methyl)-3-(ethyl)-4-(3-methyl-4-octyl-5-phenylphenyl)diazabuta-1,3-diene](ethyl)(n-butyl)nickel; [1-(3,5-diphenyl-4- octylphenyl)-2-(methyl)-3-(ethyl)-4-(3-phenyl-5-octylphenyl)diazabuta-1,3-diene](chloro)(hydrido)nickel; [1-(3-phenyl-4-methyl-5-butylphenyl)-2-(ethyl)-3-(methyl)-4-(3,4-dimethyl-5-hexylphenyl)diazabuta-1,3-diene]di(diethylamido)nickel; [1-(3-phenyl-5-hexylphenyl)-2,3-(diethyl)-4-(3-ethyl-4-phenyl-5-octylphenyl)diazabuta-1,3-diene](ethyl)(dimethylamido)nickel; [1-(3-methyl-4-phenyl-5-octylphenyl)-2,3-(diethyl)-4-(3-ethyl-4-methyl-5-butylphenyl)diazabuta-1,3-diene](bromo)(hydrido)nickel; [1-(3-methyl-4-phenyl-5-octylphenyl)-2-(ethyl)-3-(methyl)-4-(3-methyl-4-octyl-5-butylphenyl)diazabuta-1,3-diene]di(ethyl)nickel; [1-(3-hexyl-4-octylphenyl)-2-(ethyl)-3-(methyl)-4-(3-phenyl-4-hexyl-5-butylphenyl)diazabuta-1,3-diene](diethylamido)(hydrido)nickel; [1-(3-ethyl-4-octyl-5-phenylphenyl)-2,3-(dimethyl)-4-(3-ethyl-4-octyl-5-butylphenyl)diazabuta-1,3-diene](bromo)(chloro)nickel; [1-(3-phenyl-4,5-dihexylphenyl)-2-(hydrido)-3-(ethyl)-4-(3-butyl-4,5-dihexylphenyl)diazabuta-1,3-diene](ethyl)(dimethylamido)nickel; [1-(3-butyl-4-octyl-5-phenylphenyl)-2-(ethyl)-3-(hydrido)-4-(3,4-dioctylphenyl)diazabuta-1,3-diene](n-butyl)(dimethylamido)nickel; [1-(3-butyl-4,5-dihexylphenyl)-2-(ethyl)-3-(hydrido)-4-(3-methyl-4-phenyl-5-hexylphenyl)diazabuta-1,3-diene]di(diethylamido)nickel; [1-(3,4-dibutyl-5-octylphenyl)-2-(methyl)-3-(ethyl)-4-(3,4-dibutyl-5-octylphenyl)diazabuta-1,3-diene]di(ethyl)nickel; [1-(3-phenyl-4-methyl phenyl)-2,3-(dihydrido)-4-(3-hexyl-4-phenylphenyl)diazabuta-1,3-diene]di(n-butyl)nickel; [1-(3-phenyl-4-butyl-5-octylphenyl)-2-(hydrido)-3-(methyl)-4-(3-butyl-4-phenylphenyl)diazabuta-1,3-diene](diethylamido)(methyl)nickel; [1-(3,4-dibutyl-5-phenylphenyl)-2-(methyl)-3-(hydrido)-4-(3-ethyl-4-methyl-5-butylphenyl)diazabuta-1,3-diene]di(dimethylamido)nickel; [1-(3-methyl-4,5-dioctylphenyl)-2-(ethyl)-3-(hydrido)-4-(3-methyl-4-octyl-5-butylphenyl)diazabuta-1,3-diene] (bromo) (hydrido) nickel; [1-(3-butyl-4-ethyl-5-hexylphenyl)-2-(ethyl)-3-(methyl)-4-(3-ethyl-4-octyl-5-hexylphenyl)diazabuta-1,3-diene] (n-butyl) (diethylamido) nickel; [1-(3,4-diphenyl-5-octylphenyl)-2-(methyl)-3-(ethyl)-4-(3,4-diphenylphenyl)diazabuta-1,3-diene] (diethylamido) (bromo) nickel; [1-(3-methyl-4-hexyl-5-phenylphenyl)-2-(ethyl)-3-(hydrido)-4-(3-butyl-4-hexylphenyl)diazabuta-1,3-diene] (methyl) (n-butyl) nickel; [1-(3-ethyl-4,5-diphenylphenyl)-2-(ethyl)-3-(hydrido)-4-(3-methyl-4-ethyl-5-butylphenyl)diazabuta-1,3-diene] (hydrido) (dimethylamido) nickel; [1-(3-methyl-5-phenylphenyl)-2-(ethyl)-3-(methyl)-4-(3-ethyl-4-butyl-5-octylphenyl)diazabuta-1,3-diene] (ethyl) (bromo) palladium; [1-(3-butyl-4-methyl phenyl)-2-(ethyl)-3-(hydrido)-4-(3-phenyl-4-octyl-5-butylphenyl)diazabuta-1,3-diene] (methyl) (hydrido) palladium; [1-(3-phenyl-4-butyl-5-octylphenyl)-2-(hydrido)-3-(ethyl)-4-(3-ethyl-5-hexylphenyl)diazabuta-1,3-diene] (n-butyl) (hydrido) nickel; [1-(3-methyl-4,5-dioctylphenyl)-2,3-(dimethyl)-4-(3-phenyl-4-hexylphenyl)diazabuta-1,3-diene] (bromo) (chloro) nickel; [1-(3-butyl-5-phenylphenyl)-2-(hydrido)-3-(methyl)-4-(3-butyl-5-octylphenyl)diazabuta-1,3-diene] (bromo) (hydrido) palladium; [1-(3,4,5-tributylphenyl)-2-(ethyl)-3-(methyl)-4-(3,5-diphenyl-4-ethylphenyl)diazabuta-1,3-diene] (ethyl) (bromo) palladium; [1-(3-octyl-4-phenylphenyl)-2,3-(dihydrido)-4-(3-butyl-5-hexylphenyl)diazabuta-1,3-diene] (hydrido) (chloro) nickel; [1-(3-methyl-4-ethyl-5-phenylphenyl)-2,3-(dimethyl)-4-(3-butyl-4-methyl-5-phenylphenyl)diazabuta-1,3-diene] (diethylamido) (methyl) nickel; [1-(3-methyl-4-ethyl-5-butylphenyl)-2-(methyl)-3-(ethyl)-4-(3-butyl-5-hexylphenyl)diazabuta-1,3-diene] di(methyl) nickel; [1-(3-ethyl-4-methyl-5-hexylphenyl)-2-(methyl)-3-(hydrido)-4-(3,4-diphenyl-5-octylphenyl)diazabuta-1,3-diene] (n-butyl) (hydrido) palladium; [1-(3,5-diphenyl-4-hexylphenyl)-2-(hydrido)-3-(methyl)-4-(3-phenyl-4-butyl-5-octylphenyl)diazabuta-1,3-diene] (bromo) (n-butyl) nickel; [1-(3-octyl-4-hexylphenyl)-2-(hydrido)-3-(methyl)-4-(3-methyl-4-phenyl-5-octylphenyl)diazabuta-1,3-diene] (hydrido) (chloro) nickel; [1-(3-methyl-4-ethyl-5-butylphenyl)-2-(hydrido)-3-(ethyl)-4-(3-methyl-4-hexyl-5-butylphenyl)diazabuta-1,3-diene] (methyl) (diethylamido) nickel; [1-(3-methyl-4,5-dibutylphenyl)-2,3-(dimethyl)-4-(3-ethyl-4,5-dibutylphenyl)diazabuta-1,3-diene] (chloro) (diethylamido) nickel; [1-(3-ethyl-4-hexyl-5-octylphenyl)-2-(hydrido)-3-(ethyl)-4-(3-ethyl-5-octylphenyl)diazabuta-1,3-diene] di(ethyl) nickel; [1-(3-methyl-4-ethyl-5-hexylphenyl)-2-(ethyl)-3-(hydrido)-4-(3,4-dimethyl-5-octylphenyl)diazabuta-1,3-diene] (ethyl) (dimethylamido) nickel; [1-(3-butyl-4,5-diphenylphenyl)-2-(hydrido)-3-(ethyl)-4-(3-ethyl-4-butyl-5-hexylphenyl)diazabuta-1,3-diene] (n-butyl) (chloro) nickel; [1-(3-phenyl-5-octylphenyl)-2-(ethyl)-3-(hydrido)-4-(3-octyl-4-phenylphenyl)diazabuta-1,3-diene] (ethyl) (bromo) nickel; [1-(3-butyl-4,5-diphenylphenyl)-2-(hydrido)-3-(ethyl)-4-(3-ethyl-4-hexyl-5-butylphenyl)diazabuta-1,3-diene] (dimethylamido) (methyl) palladium; [1-(3-methyl-4-butyl-5-hexylphenyl)-2,3-(dimethyl)-4-(3-phenyl-5-hexylphenyl)diazabuta-1,3-diene] (chloro) (bromo) nickel; [1-(3-phenyl-5-octylphenyl)-2-(methyl)-3-(ethyl)-4-(3-methyl-4-phenyl-5-hexylphenyl)diazabuta-1,3-diene] (chloro) (dimethylamido) nickel; [1-(3-hexyl-4-phenylphenyl)-2,3-(diethyl)-4-(3-ethyl-4-methyl-5-hexylphenyl)diazabuta-1,3-diene] (diethylamido) (dimethylamido) nickel; [1-(3,5-diphenyl-4-octylphenyl)-2-(ethyl)-3-(methyl)-4-(3-ethyl-4,5-diphenylphenyl)diazabuta-1,3-diene] di(diethylamido) nickel; [1-(3,5-diphenyl-4-methyl phenyl)-2,3-(dimethyl)-4-(3,4-diphenyl-5-butylphenyl)diazabuta-1,3-diene] (chloro) (hydrido) nickel; [1-(3-ethyl-4-butyl-5-phenylphenyl)-2-(methyl)-3-(hydrido)-4-(3-methyl-4-butyl-5-hexylphenyl)diazabuta-1,3-diene] (dimethylamido) (n-butyl) nickel; [1-(3-methyl-4-octyl-5-hexylphenyl)-2-(ethyl)-3-(hydrido)-4-(3-ethyl-4-butyl-5-hexylphenyl)diazabuta-1,3-diene] di(dimethylamido) palladium; [1-(3-hexyl-4-octylphenyl)-2-(ethyl)-3-(methyl)-4-(3-methyl-4-octyl-5-butylphenyl)diazabuta-1,3-diene] di(hydrido) nickel; [1-(3-butyl-4-hexylphenyl)-2-(methyl)-3-(ethyl)-4-(3-phenyl-4,5-dibutylphenyl)diazabuta-1,3-diene] (ethyl) (diethylamido) nickel; [1-(3,5-dibutylphenyl)-2,3-(dihydrido)-4-(3,4,5-triphenylphenyl)diazabuta-1,3-diene] (dimethylamido) (methyl) palladium; [1-(3,5-diphenyl-4-hexylphenyl)-2-(ethyl)-3-(hydrido)-4-(3-phenyl-4,5-dibutylphenyl)diazabuta-1,3-diene] (methyl) (dimethylamido) nickel; [1-(3-phenyl-4-ethyl-5-octylphenyl)-2-(ethyl)-3-(methyl)-4-(3-methyl-4-ethyl-5-butylphenyl)diazabuta-1,3-diene] (chloro) (n-butyl) nickel; [1-(3-hexyl-4-ethylphenyl)-2-(hydrido)-3-(methyl)-4-(3-ethyl-4-octyl-5-hexylphenyl)diazabuta-1,3-diene] (bromo) (n-butyl) nickel; [1-(3-ethyl-4-methyl-5-octylphenyl)-2-(hydrido)-3-(methyl)-4-(3-phenyl-4-methyl-5-hexylphenyl)diazabuta-1,3-diene] (ethyl) (n-butyl) nickel; [1-(3-butyl-4-phenyl-5-octylphenyl)-2,3-(diethyl)-4-(3-phenyl-4-butyl-5-octylphenyl)diazabuta-1,3-diene] di(n-butyl) nickel; [1-(3-phenyl-4-ethyl-5-hexylphenyl)-2-(hydrido)-3-(methyl)-4-(3,4-dibutyl-5-hexylphenyl)diazabuta-1,3-diene] (diethylamido) (ethyl) nickel; [1-(3-methyl-4-phenyl-5-octylphenyl)-2,3-(dimethyl)-4-(3-ethyl-4-methyl-5-hexylphenyl)diazabuta-1,3-diene] (methyl) (hydrido) nickel; [1-(3-methyl-4-phenyl-5-hexylphenyl)-2-(hydrido)-3-(ethyl)-4-(3,4-dibutyl-5-phenylphenyl)diazabuta-1,3-diene] (dimethylamido) (diethylamido) nickel; [1-(3-ethyl-4-octyl- 5-phenylphenyl)-2-(hydrido)-3-(methyl)-4-(3-butyl-4-ethyl-5-phenylphenyl)diazabuta-1,3-diene] (chloro) (bromo) nickel; [1-(3,4-diethyl-5-octylphenyl)-2-(hydrido)-3-(methyl)-4-(3-ethyl-4-butyl-5-hexylphenyl)diazabuta-1,3-diene] (chloro) (bromo) nickel; [1-(3-butyl-4-ethyl-5-phenylphenyl)-2,3-(dimethyl)-4-(3-ethyl-4-methyl-5-hexylphenyl)diazabuta-1,3-diene] (ethyl) (hydrido) nickel; [1-(3-butyl-4-methyl-5-phenylphenyl)-2,3-(dihydrido)-4-(3-octyl-4-phenylphenyl)diazabuta-1,3-diene] di(hydrido) nickel; [1-(3-phenyl-4-ethyl-5-butylphenyl)-2-(ethyl)-3-(hydrido)-4-(3-ethyl-4-octyl-5-butylphenyl)diazabuta-1,3-diene] (chloro) (hydrido) nickel; [1-(3,4-diphenyl-5-hexylphenyl)-2,3-(dimethyl)-4-(3,5-diphenyl-4-methylphenyl)diazabuta-1,3-diene] (chloro) (hydrido) nickel; [1-(3-hexyl-4-octylphenyl)-2-(ethyl)-3-(methyl)-4-(3-methyl-4-ethyl-5-hexylphenyl)diazabuta-1,3-diene] (dimethylamido) (methyl) nickel; [1-(3-ethyl-4-phenyl-5-octylphenyl)-2,3-(dimethyl)-4-(3-methyl-4-phenyl-5-butylphenyl)diazabuta-1,3-diene] (chloro) (n-butyl) nickel; [1-(3,4,5-tributylphenyl)-2,3-(dimethyl)-4-(3-butyl-4-octyl-5-hexylphenyl)diazabuta-1,3-diene] (ethyl) (diethylamido) nickel; [1-(3-hexyl-4-butylphenyl)-2,3-(diethyl)-4-(3-octyl-4-butylphenyl)diazabuta-1,3-diene] (dimethylamido) (hydrido) palladium; [1-(3-phenyl-5-butylphenyl)-2-(ethyl)-3-(methyl)-4-(3-phenyl-4-methyl-5-butylphenyl)diazabuta-1,3-diene] (chloro) (diethylamido) nickel; [1-(3-phenyl-4-methyl-5-octylphenyl)-2-(methyl)-3-(hydrido)-4-(3-phenyl-4,5-dioctylphenyl)diazabuta-1,3-diene] (diethylamido) (chloro) palladium; [1-(3-ethyl-5-octylphenyl)-2,3-(diethyl)-4-(3-phenyl-4-ethylphenyl)diazabuta-1,3-diene] (dimethylamido) (chloro) palladium; [1-(3,4-dimethyl-5-butylphenyl)-2-(hydrido)-3-(methyl)-4-(3-ethyl-4-butyl-5-phenylphenyl)diazabuta-1,3-diene] (dimethylamido) (bromo) nickel; [1-(3-ethyl-4-butyl-5-hexylphenyl)-2-(methyl)-3-(ethyl)-4-(3-methyl-5-hexylphenyl)diazabuta-1,3-diene] (ethyl) (dimethylamido) nickel; [1-(3-ethyl-5-butylphenyl)-2-(ethyl)-3-(hydrido)-4-(3-hexyl-4-phenylphenyl)diazabuta-1,3-diene] (methyl) (n-butyl) nickel; [1-(3-ethyl-4-octyl-5-phenylphenyl)-2-(methyl)-3-(hydrido)-4-(3,4-dimethyl-5-phenylphenyl)diazabuta-1,3-diene] (bromo) (dimethylamido) nickel; [1-(3,4-dibutylphenyl)-2,3-(diethyl)-4-(3-ethyl-4-butyl-5-phenylphenyl) diazabuta-1,3-diene] (methyl) (n-butyl) palladium; [1-(3,4-dibutyl-5-octylphenyl)-2-(hydrido)-3-(ethyl)-4-(3,4-dibutyl-5-octylphenyl)diazabuta-1,3-diene] (bromo) (hydrido) nickel; [1-(3-phenyl-4-octyl-5-hexylphenyl)-2-(ethyl)-3-(hydrido)-4-(3-ethyl-4,5-diphenylphenyl)diazabuta-1,3-diene] (diethylamido) (n-butyl) nickel; [1-(3-phenyl-5-butylphenyl)-2-(methyl)-3-(hydrido)-4-(3,4-dimethyl-5-octylphenyl)diazabuta-1,3-diene] (diethylamido) (chloro) nickel; [1-(3-ethyl-5-octylphenyl)-2-(methyl)-3-(hydrido)-4-(3,4-diethyl-5-phenylphenyl)diazabuta-1,3-diene] (bromo) (dimethylamido) palladium; [1-(3-phenyl-4-methyl-5-butylphenyl)-2-(ethyl)-3-(methyl)-4-(3-ethyl-4,5-dioctylphenyl)diazabuta-1,3-diene] (bromo) (methyl) nickel; [1-(3,4-diethyl-5-hexylphenyl)-2-(ethyl)-3-(hydrido)-4-(3-methyl-4-ethyl-5-butylphenyl)diazabuta-1,3-diene] (ethyl) (diethylamido) palladium; [1-(3,5-diphenylphenyl)-2,3-(dimethyl)-4-(3,5-diphenylphenyl) diazabuta-1,3-diene] (bromo) (diethylamido) nickel; [1-(3,4-dibutyl-5-octylphenyl)-2,3-(dihydrido)-4-(3,4-dihexylphenyl)diazabuta-1,3-diene] (ethyl) (hydrido) nickel; [1-(3-ethyl-4,5-dioctylphenyl)-2-(methyl)-3-(hydrido)-4-(3-phenyl-4-ethylphenyl)diazabuta-1,3-diene] (bromo) (dimethylamido) nickel; [1-(3-ethyl-4-butyl-5-octylphenyl)-2-(methyl)-3-(ethyl)-4-(3,4-dibutyl-5-octylphenyl)diazabuta-1,3-diene] (bromo) (n-butyl) nickel; [1-(3,5-diphenyl-4-hexylphenyl)-2,3-(diethyl)-4-(3,4-diphenylphenyl)diazabuta-1,3-diene] (dimethylamido) (n-butyl) nickel; [1-(3-ethyl-4-octyl-5-phenylphenyl)-2,3-(dimethyl)-4-(3,5-diphenyl-4-methyl phenyl)diazabuta-1,3-diene] (diethylamido) (ethyl) nickel; [1-(3-butyl-4-hexylphenyl)-2,3-(dimethyl)-4-(3-phenyl-4-ethyl-5-butylphenyl)diazabuta-1,3-diene] (dimethylamido) (diethylamido) nickel; [1-(3-butyl-4-hexyl-5-octylphenyl)-2-(ethyl)-3-(methyl)-4-(3-butyl-4-octyl-5-hexylphenyl)diazabuta-1,3-diene] (n-butyl) (dimethylamido) nickel; [1-(3,5-diphenyl-4-ethylphenyl)-2-(hydrido)-3-(ethyl)-4-(3,4-diphenyl-5-butylphenyl)diazabuta-1,3-diene] (dimethylamido) (diethylamido) nickel; [1-(3-ethyl-4,5-dihexylphenyl)-2-(ethyl)-3-(hydrido)-4-(3-ethyl-5-hexylphenyl)diazabuta-1,3-diene] (methyl) (chloro) palladium; [1-(3-octyl-4-methyl phenyl)-2-(hydrido)-3(methyl)-4-(3-butyl-4,5-dihexylphenyl)diazabuta-1,3-diene] (chloro) (hydrido) nickel; [1-(3,5-dibutyl-4-phenylphenyl)-2-(hydrido)-3-(methyl)-4-(3-ethyl-4-hexyl-5-butylphenyl)diazabuta-1,3-diene] (methyl) (chloro) nickel; [1-(3-phenyl-4-butyl-5-hexylphenyl)-2-(hydrido)-3-(ethyl)-4-(3-butyl-5-hexylphenyl)diazabuta-1,3-diene] (diethylamido) (dimethylamido) nickel; [1-(3-ethyl-4,5-dioctylphenyl)-2-(ethyl)-3-(methyl)-4-(3-hexyl-phenyl)diazabuta-1,3-diene] (bromo) (diethylamido) nickel; [1-(3-ethyl-5-butylphenyl)-2-(hydrido)-3-(methyl)-4-(3,5-diphenyl-4-octylphenyl)diazabuta-1,3-diene] (diethylamido) (ethyl) nickel; [1-(3,4-dibutyl-5-phenylphenyl)-2,3-(dihydrido)-4-(3,5-dibutyl-4-ethylphenyl)diazabuta-1,3-diene] (ethyl) (hydrido) nickel; [1-(3-octyl-4-phenylphenyl)-2-(methyl)-3-(ethyl)-4-(3-butyl-5-octylphenyl) diazabuta-1,3-diene] (hydrido) (methyl) nickel; [1-(3-ethyl-4-hexyl-5-phenylphenyl)-2-(ethyl)-3-(hydrido)-4-(3-ethyl-4-octyl-5-butylphenyl)diazabuta-1,3-diene] (diethylamido) (chloro) palladium; [1-(3-methyl-5-hexylphenyl)-2-(hydrido)-3-(methyl)-4-(3-phenyl-5-hexylphenyl)diazabuta-1,3-diene] (ethyl) (methyl) nickel; [1-(3-methyl-4,5-diphenylphenyl)-2,3-(dihydrido)-4-(3-ethyl-4,5-dioctylphenyl) diazabuta-1,3-diene] (ethyl) (bromo) nickel; [1-(3-ethyl-4-methyl-5-octylphenyl)-2-(methyl)-3-(hydrido)-4-(3-methyl-5-phenylphenyl)diazabuta-1,3-diene] (bromo) (methyl) nickel; [1-(3-ethyl-4-hexyl-5-butylphenyl)-2-(methyl)-3-(ethyl)-4-(3,5-dibutyl-4-hexylphenyl)diazabuta-1,3-diene] (diethylamido) (n-butyl) palladium; [1-(3-methyl-5-phenylphenyl)-2,3-(dihydrido)-4-(3-butyl-4,5-diphenylphenyl) diazabuta-1,3-diene] (chloro) (diethylamido) nickel; [1-(3,5-dibutyl-4-ethylphenyl)-2,3-(dimethyl)-4-(3-methyl-4,5-dioctylphenyl)diazabuta-1,3-diene] (chloro) (diethylamido) nickel; [1-(3-methyl-5-octylphenyl)-2,3-(diethyl)-4-(3-ethyl-4-hexyl-5-octylphenyl)diazabuta-1,3-diene] di(chloro) palladium; [1-(3-methyl-4,5-dihexylphenyl)-2,3-(dimethyl)-4-(3-butyl-4-hexylphenyl)diazabuta-1,3-diene] (hydrido) (bromo) nickel; [1-(3,4-dimethyl-5-hexylphenyl)-2-(hydrido)-3-(methyl)-4-(3,4-dimethyl-5-phenylphenyl)diazabuta-1,3-diene] (n-butyl) (hydrido) nickel; [1-(3-butyl-4-phenylphenyl)-2,3-(dihydrido)-4-(3,4-dihexylphenyl) diazabuta-1,3-diene] (hydrido) (diethylamido) nickel; [1-(3-methyl-4-octyl-5-hexylphenyl)-2-(hydrido)-3-(ethyl)-4-(3-phenyl-4-hexyl-5-octylphenyl)diazabuta-1,3-diene] (methyl) (diethylamido) nickel; [1-(3-phenyl-4-ethyl-5-butylphenyl)-2-(methyl)-3-(ethyl)-4-(3-butyl-4-methyl-5-octylphenyl)diazabuta-1,3-diene] (bromo) (chloro) nickel; [1-(3-butyl-5-hexylphenyl)-2,3-(dimethyl)-4-(3,4,5-triphenylphenyl)diazabuta-1,3-diene] (hydrido) (dimethylamido) nickel; [1-(3-phenyl-4-octyl-5-butylphenyl)-2,3-(dimethyl)-4-(3,4-diethyl-5-phenylphenyl)diazabuta-1,3-diene] (hydrido) (chloro) palladium; [1-(3-butyl-4-octyl-5-hexylphenyl)-2-(ethyl)-3-(hydrido)-4-(3,5- diphenyl-4-hexylphenyl)diazabuta-1,3-diene] (diethylamido) (bromo) palladium; [1-(3-butyl-4,5-dioctylphenyl)-2,3-(dimethyl)-4-(3-ethyl-4-methyl-5-hexylphenyl)diazabuta-1,3-diene] (dimethylamido) (chloro) palladium; [1-(3-ethyl-4,5-diphenylphenyl)-2-(hydrido)-3-(methyl)-4-(3,4-dibutyl-5-hexylphenyl)diazabuta-1,3-diene] (chloro) (dimethylamido) nickel; [1-(3-ethyl-4,5-diphenylphenyl)-2-(methyl)-3-(hydrido)-4-(3-butyl-4-methyl-5-hexylphenyl)diazabuta-1,3-diene] (hydrido) (methyl) nickel; [1-(3,5-dibutyl-4-phenylphenyl)-2,3-(dimethyl)-4-(3-methyl-4-butyl-5-phenylphenyl)diazabuta-1,3-diene] (diethylamido) (ethyl) nickel; [1-(3-methyl-5-hexylphenyl)-2-(methyl)-3-(hydrido)-4-(3,4-dibutyl-5-hexylphenyl)diazabuta-1,3-diene] (diethylamido) (bromo) nickel; [1-(3-octyl-4-methyl phenyl)-2-(methyl)-3-(hydrido)-4-(3-phenyl-4-octyl-5-hexylphenyl)diazabuta-1,3-diene] (methyl) (chloro) nickel; [1-(3-phenyl-4-methyl-5-hexylphenyl)-2-(methyl)-3-(hydrido)-4-(3,4-diethyl-5-hexylphenyl)diazabuta-1,3-diene] (n-butyl) (dimethylamido) nickel; [1-(3-phenyl-4-octyl-5-hexylphenyl)-2-(hydrido)-3-(methyl)-4-(3-phenyl-4-hexyl-5-octylphenyl)diazabuta-1,3-diene] (hydrido) (n-butyl) nickel; [1-(3-methyl-4-phenyl-5-butylphenyl)-2-(hydrido)-3-(ethyl)-4-(3-methyl-4-butyl-5-hexylphenyl)diazabuta-1,3-diene] (ethyl) (chloro) nickel; [1-(3-butyl-4-octylphenyl)-2-(methyl)-3-(ethyl)-4-(3-phenyl-4,5-dihexylphenyl)diazabuta-1,3-diene] (hydrido) (bromo) nickel; [1-(3-phenyl-4-methylphenyl)-2-(ethyl)-3-(hydrido)-4-(3-phenyl-4-octylphenyl)diazabuta-1,3-diene] (n-butyl) (chloro) nickel; [1-(3-butyl-5-hexylphenyl)-2,3-(diethyl)-4-(3-methyl-4-ethyl-5-hexylphenyl)diazabuta-1,3-diene] (chloro) (bromo) nickel; [1-(3-ethyl-5-phenylphenyl)-2-(hydrido)-3-(ethyl)-4-(3-butyl-5-hexylphenyl)diazabuta-1,3-diene] (methyl) (n-butyl) nickel; [1-(3-ethyl-4-octyl-5-hexylphenyl)-2-(hydrido)-3-(ethyl)-4-(3-ethyl-4,5-dibutylphenyl)diazabuta-1,3-diene] (methyl) (n-butyl) palladium; [1-(3-phenyl-4-ethyl-5-hexylphenyl)-2,3-(diethyl)-4-(3-ethyl-4-octyl-5-hexylphenyl)diazabuta-1,3-diene] di(ethyl) nickel; [1-(3-ethyl-4-octyl-5-hexylphenyl)-2-(methyl)-3-(hydrido)-4-(3-hexyl-phenyl) diazabuta1,3-diene] (diethylamido) (methyl) nickel; [1-(3,5-diphenylphenyl)-2-(hydrido)-3-(methyl)-4-(3-phenyl-4-hexyl-5-octylphenyl)diazabuta-1,3-diene] (ethyl) (chloro) nickel; [1-(3-octyl-phenyl)-2-(methyl)-3-(hydrido)-4-(3-ethyl-5-hexylphenyl)diazabuta-1,3-diene] (diethylamido) (methyl) nickel; [1-(3,4-dimethyl-5-octylphenyl)-2-(methyl)-3-(ethyl)-4-(3-ethyl-4-methyl-5-phenylphenyl)diazabuta-1,3-diene] (n-butyl) (dimethylamido) nickel; [1-(3-methyl-4,5-dioctylphenyl)-2-(ethyl)-3-(methyl)-4-(3-methyl-4-phenyl-5-butylphenyl)diazabuta-1,3-diene] (chloro) (dimethylamido) nickel; [1-(3-butyl-4-ethyl-5-octylphenyl)-2-(hydrido)-3-(ethyl)-4-(3-ethyl-4-phenyl-5-hexylphenyl)diazabuta-1,3-diene] (n-butyl) (bromo) palladium; [1-(3-butyl-5-octylphenyl)-2,3-(dihydrido)-4-(3,5-diphenyl-4-methyl phenyl)diazabuta-1,3-diene] (ethyl) (hydrido) nickel; [1-(3-ethyl-4-butyl-5-hexylphenyl)-2,3-(dimethyl)-4-(3-ethyl-4-phenyl-5-octylphenyl)diazabuta-1,3-diene] (methyl) (bromo) palladium; [1-(3-butyl-phenyl)-2-(hydrido)-3-(ethyl)-4-(3,4-diphenyl-5-butylphenyl) diazabuta-1,3-diene] (chloro) (diethylamido) nickel; [1-(3-phenyl-4-octyl-5-butylphenyl)-2-(ethyl)-3-(hydrido)-4-(3,4-diphenyl-5-hexylphenyl)diazabuta-1,3-diene] (diethylamido) (dimethylamido) nickel; [1-(3,4-diethyl-5-phenylphenyl)-2-(hydrido)-3-(ethyl)-4-(3-methyl-4-hexyl-5-butylphenyl)diazabuta-1,3-diene] di(bromo) palladium; [1-(3,4-diphenylphenyl)-2-(ethyl)-3-(methyl)-4-(3-phenyl-4-octyl-5-hexylphenyl)diazabuta-1,3-diene] (diethylamido) (methyl) palladium; [1-(3-ethyl-4-butyl-5-hexylphenyl)-2-(methyl)-3-(ethyl)-4-(3,4-diethyl-5-octylphenyl)diazabuta-1,3-diene] (dimethylamido) (diethylamido) nickel; [1-(3-phenyl-4-butylphenyl)-2-(methyl)-3-(hydrido)-4-(3-butyl-4-ethyl-5-phenylphenyl)diazabuta-1,3-diene] (hydrido) (chloro) nickel; [1-(3,4,5-triphenylphenyl)-2,3-(diethyl)-4-(3,4-dihexylphenyl)diazabuta-1,3-diene] di(hydrido) nickel; [1-(3-methyl-4-ethyl-5-phenylphenyl)-2,3-(dihydrido)-4-(3-butyl-5-hexylphenyl)diazabuta-1,3-diene] (n-butyl) (ethyl) palladium; [1-(3-ethyl-4-hexyl-5-phenylphenyl)-2-(hydrido)-3-(methyl)-4-(3,4-diphenyl-5-butylphenyl)diazabuta-1,3-diene] (methyl) (hydrido) nickel; [1-(3-butyl-4-octylphenyl)-2-(methyl)-3-(hydrido)-4-(3-butyl-4-ethyl-5-phenylphenyl)diazabuta-1,3-diene] (dimethylamido) (diethylamido) nickel; [1-(3-ethyl-4-hexyl-5-butylphenyl)-2-(hydrido)-3-(methyl)-4-(3-phenyl-4-ethylphenyl)diazabuta-1,3-diene] (chloro) (diethylamido) palladium; [1-(3,4-diphenyl-5-butylphenyl)-2,3-(diethyl)-4-(3-ethyl-4,5-dioctylphenyl)diazabuta-1,3-diene] (methyl) (chloro) nickel; [1-(3-butyl-4-phenyl-5-octylphenyl)-2,3-(diethyl)-4-(3-butyl-5-hexylphenyl)diazabuta-1,3-diene] (ethyl) (chloro) nickel; [1-(3,4-diethyl-5-phenylphenyl)-2-(methyl)-3-(hydrido)-4-(3-butyl-4-hexylphenyl)diazabuta-1,3-diene] di(hydrido) palladium; [1-(3-phenyl-4-hexylphenyl)-2,3-(dimethyl)-4-(3-methyl-5-hexylphenyl)diazabuta-1,3-diene] (hydrido) (chloro) nickel; [1-(3-octyl-4-butylphenyl)-2-(hydrido)-3-(methyl)-4-(3-ethyl-4-butyl-5-octylphenyl) diazabuta-1,3-diene] (diethylamido) (methyl) nickel; [1-(3-octyl-4-butylphenyl)-2-(methyl)-3-(hydrido)-4-(3-butyl-4-methyl-5-hexylphenyl)diazabuta-1,3-diene] di(diethylamido) nickel; [1-(3-ethyl-5-phenylphenyl)-2,3-(dihydrido)-4-(3-octyl-4-hexylphenyl)diazabuta-1,3-diene] (hydrido) (chloro) palladium; [1-(3,5-diphenyl-4-methyl phenyl)-2-(hydrido)-3-(ethyl)-4-(3-ethyl-4,5-dihexylphenyl)diazabuta-1,3-diene] (dimethylamido) (methyl) nickel; [1-(3-phenyl-4-butyl-5-hexylphenyl)-2-(methyl)-3-(hydrido)-4-(3-methyl-4-phenyl-5-octylphenyl)diazabuta-1,3-diene] (diethylamido) (bromo) nickel; [1-(3-ethyl-4-methyl-5-hexylphenyl)-2,3-(dihydrido)-4-(3,4-dimethyl-5-octylphenyl)diazabuta-1,3-diene] (hydrido) (diethylamido) nickel; [1-(3,5-dibutyl-4-ethylphenyl)-2-(hydrido)-3-(ethyl)-4-(3-methyl-4-butyl-5-phenylphenyl)diazabuta-1,3-diene] (diethylamido) (dimethylamido) nickel; [1-(3-phenyl-4,5-dibutylphenyl)-2,3-(diethyl)-4-(3-ethyl-4-hexyl-5-phenylphenyl)diazabuta-1,3-diene] (ethyl) (diethylamido) nickel; [1-(3-octyl-4-ethylphenyl)-2-(methyl)-3-(ethyl)-4-(3-phenyl-4-methyl-5-hexylphenyl)diazabuta-1,3-diene] (hydrido) (diethylamido) nickel; [1-(3-methyl-5-octylphenyl)-2-(hydrido)-3-(methyl)-4-(3-butyl-4-ethyl-5-hexylphenyl)diazabuta-1,3-diene] (hydrido) (methyl) nickel; [1-(3,4-dimethyl-5-octylphenyl)-2,3-(diethyl)-4-(3-phenyl-4-ethylphenyl)diazabuta-1,3-diene] (hydrido) (methyl) nickel; [1-(3-phenyl-4-ethyl-5-hexylphenyl)-2-(methyl)-3-(hydrido)-4-(3-phenyl-4-ethyl-5-octylphenyl)diazabuta-1,3-diene] (ethyl) (bromo) nickel; [1-(3,4-dimethyl-5-phenylphenyl)-2,3-(dimethyl)-4-(3,4-dimethyl-5-butylphenyl) diazabuta-1,3-diene] (bromo) (dimethylamido) nickel; [1-(3-methyl-4-octyl-5-butylphenyl)-2-(hydrido)-3-(ethyl)-4-(3-methyl-4-butyl-5-phenylphenyl)diazabuta-1,3-diene] (dimethylamido) (methyl) palladium; [1-(3-hexyl-phenyl)-2-(methyl)-3-(hydrido)-4-(3-butyl-5-hexylphenyl)diazabuta-1,3-diene] (dimethylamido) (hydrido) nickel; [1-(3,4-diphenylphenyl)-2-(hydrido)-3-(methyl)-4-(3,5-diphenylphenyl)diazabuta-1,3-diene] (hydrido) (chloro) nickel; [1-(3,4-dibutyl-5-octylphenyl)-2,3-(dimethyl)-4-(3-butyl-4-phenylphenyl)diazabuta-1,3-diene] (diethylamido) (n-butyl) nickel; [1-(3-methyl-4-hexyl-5-octylphenyl)-2-(methyl)-3-(ethyl)-4-(3-methyl-4-butyl-5-hexylphenyl)diazabuta-1,3-diene] (chloro) (dimethylamido) nickel; [1-(3-ethyl-4-methyl-5-hexylphenyl)-2-(hydrido)-3-(methyl)-4-(3-phenyl-4-methyl-5-butylphenyl)diazabuta-1,3-diene] (methyl) (ethyl) palladium; [1-(3-ethyl-4-butyl-5-octylphenyl)-2-(hydrido)-3-(methyl)-4-(3-phenyl-4-octyl-5-hexylphenyl)diazabuta-1,3-diene] (chloro) (n-butyl) nickel; [1-(3-methyl-4-ethyl-5-butylphenyl)-2-(methyl)-3-(ethyl)-4-(3-butyl-4-ethylphenyl)diazabuta-1,3-diene] di(bromo) nickel; [1-(3-butyl-4-methyl-5-hexylphenyl)-2-(methyl)-3-(ethyl)-4-(3-octyl-4-ethylphenyl)diazabuta-1,3-diene] (bromo) (methyl) nickel; [1-(3,5-dibutyl-4-phenylphenyl)-2-(ethyl)-3-(hydrido)-4-(3-methyl-4-phenyl-5-octylphenyl)diazabuta-1,3-diene] (ethyl) (diethylamido) palladium; [1-(3,4-diphenyl-5-butylphenyl)-2-(hydrido)-3-(methyl)-4-(3-butyl-4-methyl-5-hexylphenyl)diazabuta-1,3-diene] (ethyl) (chloro) nickel; [1-(3-ethyl-4-octyl-5-phenylphenyl)-2,3-(diethyl)-4-(3-phenyl-4-methyl phenyl)diazabuta-1,3-diene] (ethyl) (bromo) palladium; [1-(3,5-dibutyl-4-hexylphenyl)-2-(methyl)-3-(hydrido)-4-(3-butyl-4-ethyl-5-octylphenyl)diazabuta-1,3-diene] (dimethylamido) (methyl) palladium; [1-(3-phenyl-4-butyl-5-octylphenyl)-2-(hydrido)-3-(methyl)-4-(3-butyl-5-octylphenyl)diazabuta-1,3-diene] (diethylamido) (bromo) nickel; [1-(3-hexyl-4-phenylphenyl)-2,3-(dihydrido)-4-(3-ethyl-4-butyl-5-hexylphenyl)diazabuta-1,3-diene] (n-butyl) (ethyl) nickel; [1-(3-methyl-5-octylphenyl)-2-(ethyl)-3-(hydrido)-4-(3,5-dibutyl-4-ethylphenyl)diazabuta-1,3-diene] di(hydrido) nickel; [1-(3-ethyl-4-butyl-5-octylphenyl)-2-(methyl)-3-(hydrido)-4-(3-butyl-4-phenyl-5-octylphenyl)diazabuta-1,3-diene] (bromo) (dimethylamido) nickel; [1-(3,4-dibutyl-5-phenylphenyl)-2-(methyl)-3-(ethyl)-4-(3-butyl-5-hexylphenyl)diazabuta-1,3-diene] di(ethyl) nickel; [1-(3-methyl-4-phenyl-5-octylphenyl)-2-(hydrido)-3-(methyl)-4-(3-methyl-4,5-diphenylphenyl)diazabuta-1,3-diene] (methyl) (diethylamido) nickel; [1-(3-ethyl-4-octyl-5-butylphenyl)-2,3-(dimethyl)-4-(3-methyl-5-hexylphenyl)diazabuta-1,3-diene] (dimethylamido) (hydrido) nickel; [1-(3-butyl-4-methyl phenyl)-2,3-(dihydrido)-4-(3-phenyl-4,5-dihexylphenyl)diazabuta-1,3-diene] di(diethylamido) nickel; [1-(3-phenyl-4-butylphenyl)-2-(ethyl)-3-(hydrido)-4-(3-butyl-4,5-dioctylphenyl)diazabuta-1,3-diene] (ethyl) (dimethylamido) nickel; [1-(3-methyl-4,5-dioctylphenyl)-2-(ethyl)-3-(hydrido)-4-(3,4-dibutyl-5-phenylphenyl)diazabuta-1,3-diene] (bromo) (hydrido) nickel; [1-(3-ethyl-4-phenyl-5-hexylphenyl)-2-(ethyl)-3-(methyl)-4-(3,4-diphenyl-5-hexylphenyl)diazabuta-1,3-diene] (ethyl) (methyl) nickel; [1-(3-phenyl-4-octylphenyl)-2,3-(diethyl)-4-(3-methyl-5-octylphenyl)diazabuta-1,3-diene] di(diethylamido) nickel; [1-(3-methyl-4-butyl-5-octylphenyl)-2-(ethyl)-3-(hydrido)-4-(3,4-dibutyl-5-phenylphenyl) diazobuta-1,3-diene] (diethylamido) (chloro) palladium; [1-(3-phenyl-4-methyl-5-hexylphenyl)-2-(ethyl)-3-(hydrido)-4-(3-methyl-4-butyl-5-octylphenyl)diazobuta-1,3-diene] (bromo) (methyl) nickel; [1-(3-butyl-4-ethyl-5-hexylphenyl)-2-(hydrido)-3-(methyl)-4-(3,4-dibutyl-5-octylphenyl)diazabuta-1,3-diene] di(diethylamido) nickel;

[1,4-bis(3,5-dibutylphenyl)-2-(octyl)-3-(butyl)diazobuta-1,3-diene] di(benzyl) nickel; [1,4-bis(3,5-dipentylphenyl)-2-(methyl)-3-(butyl)diazobuta-1,3-diene] di(allyl) palladium; [1,4-bis(3,5-dibutylphenyl)-2-(butyl)-3-(pentyl) diazobuta-1,3-diene] di(hydrido) nickel; [1,4-bis(3,5-diethylphenyl)-2-(octyl)-3-(butyl)diazobuta-1,3-diene] di(ethyl) nickel; [1,4-bis(3,5-dimethylphenyl)-2-(hexenyl)-3-(hydrido)diazobuta-1,3-diene] di(tetracosyl) nickel; [1,4-bis(3,5-diethylphenyl)-2-(butyl)-3-(methyl)diazobuta-1,3-diene] di(tetracosyl) nickel; [1,4-bis(3,5-dibutylphenyl)-2-(eicosyl)-3-(butenyl)diazobuta-1,3-diene] di(tridecyl) nickel; [1,4-bis(3,5-dihexylphenyl)-2-(hydrido)-3-(butyl) diazobuta-1,3-diene] di(tricosyl) nickel; [1,4-bis(3,5-dibutylphenyl)-2-(butyl)-3-(pentyl)diazobuta-1,3-diene] di(phenyl) nickel; [1,4-bis(3,5-dimethylphenyl)-2-(hydrido)-3-(tetradecenyl)diazobuta-1,3-diene] di(methyl) palladium; [1,4-bis(3,5-dibutylphenyl)-2-(tridecenyl)-3-(ethyl)diazobuta-1,3-diene] di(hydrido) nickel; [1,4-bis(3,5-dibutylphenyl)-2-(pentyl)-3-(butyl)diazobuta-1,3-diene] di(hydrido) nickel; [1,4-bis(3,5-dibutylphenyl)-2-(butyl)-3-(hydrido)diazobuta-1,3-diene] di(octadecyl) nickel; [1,4-bis(3,5-dioctylphenyl)-2-(pentyl)-3-(hydrido)diazobuta-1,3-diene] di(hydrido) palladium; [1,4-bis(3,5-dihexylphenyl)-2-(hexyl)-3-(hydrido)diazobuta-1,3-diene] di(dimethylamino) palladium; [1,4-bis(3,5-dibutylphenyl)-2-(octyl)-3-(butyl)diazobuta-1,3-diene] di(nonyl) palladium; [1,4-bis(3,5-dioctylphenyl)-2-(butyl)-3-(octyl)diazobuta-1,3-diene] di(butoxy) palladium; [1,4-bis(3,5-dihexylphenyl)-2-(tridecenyl)-3-(hydrido)diazobuta-1,3-diene] di(tetradecyl) nickel; [1,4-bis(3,5-dioctylphenyl)-2,3-(dibutyl)diazobuta-1,3-diene] di(butyl) palladium; [1,4-bis(3,5-dihexylphenyl)-2-(heptacosenyl)-3-(pentyl)diazobuta-1,3-diene] di(diethylamino) nickel; [1,4-bis(3,5-dioctadecenylphenyl)-2-(butyl)-3-(hydrido)diazobuta-1,3-diene] di(methyl) nickel; [1,4-bis(3,5-dioctylphenyl)-2-(docosenyl)-3-(butyl)diazobuta-1,3-diene] di(phenyl) nickel; [1,4-bis(3,5-dibutylphenyl)-2-(hexyl)-3-(pentadecenyl)diazobuta-1,3-diene] di(methyl) palladium; [1,4-bis(3,5-dioctylphenyl)-2-(butyl)-3-(octyl)diazobuta-1,3-diene] di(butyl) nickel; [1,4-bis(3,5-dioctylphenyl)-2-(butyl)-3-(hydrido)diazobuta-1,3-diene] di(ethyl) palladium; [1,4-bis(3,5-dibutylphenyl)-2-(methyl)-3-(octyl)diazobuta-1,3-diene] di(methyl) nickel; [1,4-bis(3,5-dibutylphenyl)-2-(hexyl)-3-(pentyl)diazobuta-1,3-diene] di(undecynyl) nickel; [1,4-bis(3,5-diethylphenyl)-2-(octyl)-3-(undecynyl) diazobuta-1,3-diene] di(butyl) palladium; [1,4-bis(3,5-dibutylphenyl)-2,3-(dihydrido)diazobuta-1,3-diene] di(octynyl) nickel; [1,4-bis(3,5-dibutylphenyl)-2-(hydrido)-3-(octyl)diazobuta-1,3-diene] di(methyl) nickel; [1,4-bis(3,5-didodecaphosphinophenyl)-2-(hexyl)-3-(butyl)diazobuta-1,3-diene] di(ethyl) nickel; [1,4-bis(3,5-dibutylphenyl)-2-(hexadecynyl)-3-(butyl)diazobuta-1,3-diene] di(benzoxy) palladium; [1,4-bis(3,5-dibutylphenyl)-2-(hydrido)-3-(octyl)diazobuta-1,3-diene] di(hydride) nickel; [1,4-bis(3,5-dibutylphenyl)-2-(pentyl)-3-(pentynyl)diazobuta-1,3-diene] di(phenoxy) palladium; [1,4-bis(3,5-di(triethylsilylmethyl) phenyl)-2-(pentyl)-3-(hydrido)diazobuta-1,3-diene] di(propyl) nickel; [1,4-bis(3,5-ditricosynylphenyl)-2-(butyl)-3-(ethyl)diazobuta-1,3-diene] di(octyl) palladium; [1,4-bis(3,5-dioctylphenyl)-2,3-(dibutyl)diazobuta-1,3-diene] di(phenoxy) nickel; [1,4-bis(3,5-dibutylphenyl)-2-(hydrido)-3-(butyl)diazobuta-1,3-diene] di(butyl) palladium; [1,4-bis(3,5-dibutylphenyl)-2-(hydrido)-3-(butyl)diazobuta-1,3-diene] di(tetradecyl) nickel; [1,4-bis(3,5-ditridecylphenyl)-2-(hexyl)-3-(hydrido)diazobuta-1,3-diene] di(hydrido) nickel; [1,4-bis(3,5-dihexylphenyl)-2,3-(dihydrido)diazobuta-1,3-diene] di(tridecyl) nickel; [1,4-bis(3,5-dibutylphenyl)-2-(tetradecenyl)-3-(methyl)diazobuta-1,3-diene] di(docosyl) palladium; [1,4-bis(3,5-dibutylphenyl)-2-(hexyl)-3-(hydrido)diazobuta-1,3-diene] di(nonadecyl) nickel; [1,4-bis(3,5-dimethylphenyl)-2-(butyl)-3-(octyl)diazobuta-1,3-diene] di(hydrido) nickel; [1,4-bis(3,5-dibutylphenyl)-2-(pentyl)-3-(hydrido)diazobuta-1,3-diene] di(hydrido) palladium; [1,4-bis(3,5-dibutylphenyl)-2-(butyl)-3-(octyl)diazobuta-1,3-diene] di(ethyl) nickel; [1,4-bis(3,5-dibutylphenyl)-2-(hydrido)-3-(pentadecenyl)diazobuta-1,3-diene] di(hydrido) nickel; [1,4-bis(3,5-dipentylphenyl)-2-(heptacosenyl)-3-(hexyl)diazobuta-1,3- diene] di(octadecyl) nickel; [1,4-bis(3,5-dibutylphenyl)-2-(octyl)-3-(nonacosynyl)diazobuta-1,3-diene] di(hydrido) nickel; [1,4-bis(3,5-dibutylphenyl)-2-(methyl)-3-(hydrido) diazobuta-1,3-diene] di(undecyl) nickel; [1,4-bis(3,5-dihexylphenyl)-2-(ethyl)-3-(hydrido)diazobuta-1,3-diene] di(hydrido) nickel; [1,4-bis(3,5-dibutylphenyl)-2,3-(dibutyl) diazobuta-1,3-diene] di(methylethylamino) palladium; [1,4-bis(3,5-dipentylphenyl)-2-(octyl)-3-(butyl)diazobuta-1,3-diene] di(propyl) nickel; [1,4-bis(3,5-dibutylphenyl)-2,3-(dibutyl)diazobuta-1,3-diene] di(ethyl) palladium; [1,4-bis(3,5-dioctadecylphenyl)-2-(hexyl)-3-(butyl)diazobuta-1,3-diene] di(hydrido) palladium; [1,4-bis(3,5-dimethylphenyl)-2,3-(dibutyl)diazobuta-1,3-diene] di(ethyl) nickel; [1,4-bis(3,5-dimethylphenyl)-2-(butyl)-3-(hydrido)diazobuta-1,3-diene] di(ethyl) nickel; [1,4-bis(3,5-dioctylphenyl)-2,3-(dibutyl)diazobuta-1,3-diene] di(bromo) nickel; [1,4-bis(3,5-dibutylphenyl)-2-(ethyl)-3-(butyl)diazobuta-1,3-diene] di(phenoxy) nickel; [1,4-bis(3,5-dinonenylphenyl)-2,3-(dibutyl)diazobuta-1,3-diene] di(hydrido) nickel; [1,4-bis(3,5-dibutylphenyl)-2,3-(dibutyl)diazobuta-1,3-diene] di(butyl) nickel; [1,4-bis(3,5-dibutylphenyl)-2,3-(dihexyl)diazobuta-1,3-diene] di(butyl) nickel; [1,4-bis(3,5-dimethylphenyl)-2-(butyl)-3-(hexyl)diazobuta-1,3-diene] di(ethyl) nickel; [1,4-bis(3,5-dibutylphenyl)-2-(butyl)-3-(hexyl)diazobuta-1,3-diene] di(tetradecyl) nickel; [1,4-bis(3,5-diheptadecenylphenyl)-2-(butyl)-3-(hydrido)diazobuta-1,3-diene] di(hydrido) nickel; [1,4-bis(3,5-didodecenylphenyl)-2-(pentyl)-3-(butyl)diazobuta-1,3-diene] di(hexacosyl) nickel; [1,4-bis(3,5-dibutylphenyl)-2-(nonyl)-3-(octyl)diazobuta-1,3-diene] di(nonadecyl) nickel; [1,4-bis(3,5-dibutylphenyl)-2-(heptacosyl)-3-(hydrido)diazobuta-1,3-diene] di(butoxy) palladium; [1,4-bis(3,5-diethylphenyl)-2-(hexyl)-3-(butyl)diazobuta-1,3-diene] di(bromo) nickel; [1,4-bis(3,5-dimethylphenyl)-2-(butyl)-3-(hydrido)diazobuta-1,3-diene] di(ethyl) palladium; [1,4-bis(3,5-dimethylphenyl)-2-(nonacosyl)-3-(butyl)diazobuta-1,3-diene] di(butyl) nickel; [1,4-bis(3,5-diheptynylphenyl)-2-(octyl)-3-(butyl)diazobuta-1,3-diene] di(eicosyl) nickel; [1,4-bis(3,5-dihexylphenyl)-2-(butyl)-3-(methyl)diazobuta-1,3-diene] di(heptadecyl) palladium; [1,4-bis(3,5-dipentylphenyl)-2-(butyl)-3-(hydrido)diazobuta-1,3-diene] di(hydrido) nickel; [1,4-bis(3,5-diethylphenyl)-2-(butyl)-3-(decenyl)diazobuta-1,3-diene] di(butyl) nickel; [1,4-bis(3,5-dimethylphenyl)-2-(hexyl)-3-(butyl)diazobuta-1,3-diene] di(hydrido) nickel; [1,4-bis(3,5-dipentylphenyl)-2-(butyl)-3-(pentadecynyl)diazobuta-1,3-diene] di(pentyl) nickel; [1,4-bis(3,5-dibutylphenyl)-2-(octyl)-3-(hydrido)diazobuta-1,3-diene] di(phenoxy) palladium; [1,4-bis(3,5-dibutylphenyl)-2,3-(dihexyl)diazobuta-1,3-diene] di(bromo) palladium; [1,4-bis(3,5-didecenylphenyl)-2-(hydrido)-3-(tetracosynyl)diazobuta-1,3-diene] di(hexadecyl) nickel; [1,4-bis(3,5-dihexylphenyl)-2-(butyl)-3-(pentyl)diazobuta-1,3-diene] di(tetracosyl) nickel; [1,4-bis(3,5-dibutylphenyl)-2-(ethyl)-3-(butyl)diazobuta-1,3-diene] di(dimethylamino) palladium; [1,4-bis(3,5-dibutylphenyl)-2-(butyl)-3-(pentyl)diazobuta-1,3-diene] di(nonyl) nickel; [1,4-bis(3,5-dimethylphenyl)-2-(butyl)-3-(butynyl)diazobuta-1,3-diene] di(docosyl) nickel; [1,4-bis(3,5-didocosylphenyl)-2-(butyl)-3-(hydrido)diazobuta-1,3-diene] di(octacosyl) nickel; [1,4-bis(3,5-dibutylphenyl)-2-(pentyl)-3-(hexyl)diazobuta-1,3-diene] di(nonacosyl) nickel; [1,4-bis(3,5-dihexylphenyl)-2-(hydrido)-3-(butyl)diazobuta-1,3-diene] di(octacosyl) nickel; [1,4-bis(3,5-dipentylphenyl)-2-(hydrido)-3-(butyl)diazobuta-1,3-diene] di(methyl) nickel; [1,4-bis(3,5-dibutylphenyl)-2-(butyl)-3-(pentyl)diazobuta-1,3-diene] di(hydrido) nickel; [1,4-bis(3,5-didecenylphenyl)-2-(octyl)-3-(pentyl)diazobuta-1,3-diene] di(methyl) nickel; [1,4-bis(3,5-dibutylphenyl)-2-(butyl)-3-(octyl)diazobuta-1,3-diene] di(ethyl) nickel; [1,4-bis(3,5-dibutylphenyl)-2-(butenyl)-3-(hexyl)diazobuta-1,3-diene] di(hexyl) nickel; [1,4-bis(3,5-didecenylphenyl)-2,3-(dibutyl)diazobuta-1,3-diene] di(ethoxy) nickel; [1,4-bis(3,5-dioctylphenyl)-2-(butyl)-3-(hexacosenyl)diazobuta-1,3-diene] di(hexyl) nickel; [1,4-bis(3,5-diethylphenyl)-2-(butyl)-3-(hexyl)diazobuta-1,3-diene] di(ethoxy) nickel; [1,4-bis(3,5-dioctylphenyl)-2-(butyl)-3-(octyl)diazobuta-1,3-diene] di(hydrido) palladium; [1,4-bis(3,5-dipentylphenyl)-2-(hydrido)-3-(octyl)diazobuta-1,3-diene] di(hydrido) palladium; [1,4-bis(3,5-dibutylphenyl)-2-(hydrido)-3-(tricosenyl)diazobuta-1,3-diene] di(nonadecyl) palladium; [1,4-bis(3,5-diethylphenyl)-2-(hexyl)-3-(pentyl)diazobuta-1,3-diene] di(triacontyl) nickel; [1,4-bis(3,5-dioctylphenyl)-2-(butyl)-3-(pentyl)diazobuta-1,3-diene] di(ethyl) nickel; [1,4-bis(3,5-dipentylphenyl)-2-(hydrido)-3-(butyl)diazobuta-1,3-diene] di(phenoxy) nickel; [1,4-bis(3,5-dihexylphenyl)-2-(butyl)-3-(ethyl)diazobuta-1,3-diene] di(heptacosyl) palladium; [1,4-bis(3,5-diundecenylphenyl)-2,3-(dibutyl)diazobuta-1,3-diene] di(iodo) nickel; [1,4-bis(3,5-dibutylphenyl)-2,3-(dibutyl)diazobuta-1,3-diene] di(ethyl) nickel; [1,4-bis(3,5-dipentylphenyl)-2,3-(dibutyl)diazobuta-1,3-diene] di(tolyl) nickel; [1,4-bis(3,5-diheptylphenyl)-2-(hydrido)-3-(octyl)diazobuta-1,3-diene] di(methylethylamino) nickel; [1,4-bis(3,5-dibutylphenyl)-2-(octyl)-3-(butyl)diazobuta-1,3-diene] di(hydrido) nickel; [1,4-bis(3,5-dibutylphenyl)-2-(hydrido)-3-(octyl)diazobuta-1,3-diene] di(butyl) nickel; [1,4-bis(3,5-dipentylphenyl)-2-(butyl)-3-(pentyl)diazobuta- ,3-diene] di(methoxy) nickel; [1,4-bis(3,5-dibutylphenyl)-2-(methyl)-3-(butyl)diazobuta-1,3-diene] di(ethyl) nickel; [1,4-bis(3,5-dibutylphenyl)-2-(pentyl)-3-(hexyl)diazobuta-1,3-diene] di(heneicosyl) nickel; [1,4-bis(3,5-dipentylphenyl)-2,3-(dipentyl)diazobuta-1,3-diene] di(propyl) nickel; [1,4-bis(3,5-dipentylphenyl)-2-(butyl)-3-(pentyl)diazobuta-1,3-diene] di(butoxy) nickel; [1,4-bis(3,5-dibutylphenyl)-2-(butyl)-3-(hydrido)diazobuta-1,3-diene] di(nonadecyl) nickel; [1,4-bis(3,5-dimethylphenyl)-2-(butyl)-3-(ethyl)diazobuta-1,3-diene] di(undecyl) palladium; [1,4-bis(3,5-diheptenylphenyl)-2-(butyl)-3-(pentyl)diazobuta-1,3-diene] di(hydrido) nickel; [1,4-bis(3,5-dibutylphenyl)-2-(tridecynyl)-3-(hydrido)diazobuta-1,3-diene] di(chloro) nickel; [1,4-bis(3,5-dibutylphenyl)-2-(hydrido)3-(butyl)diazobuta-1,3-diene] di(nonadecyl) nickel; [1,4-bis(3,5-dibutylphenyl)-2-(butyl)3-(hydrido)diazobuta-1,3-diene] di(tetradecyl) palladium; [1,4-bis(3,5-dibutylphenyl)-2(octyl)-3-(butyl)diazobuta-1,3-diene] di(butyl) nickel; [1,4-bis(3,5-dihexynylphenyl)-2(pentyl)-3-(butyl)diazobuta-1,3-diene] di(benzoxy) palladium; [1,4-bis(3,5-didecylphenyl)-2-(hydrido)-3-(octyl)diazobuta-1,3-diene] di(hydride) nickel; [1,4-bis(3,5-dimethylphenyl)-2-(hydrido)-3-(hexadecenyl)diazobuta-1,3-diene] di(diethylamino) nickel; [1,4-bis(3,5-dioctylphenyl)-2,3-(dihexyl)diazobuta-1,3-diene] di(methoxy) palladium; [1,4-bis(3,5-dibutylphenyl)-2-(octyl)-3-(butyl)diazobuta-1,3-diene] di(octacosyl) nickel; [1,4-bis(3,5-dibutylphenyl)-2-(hydrido)-3-(ethyl)diazobuta-1,3-diene] di(tetracosyl) palladium; [1,4-bis(3,5-dibutylphenyl)-2-(hydrido)-3-(hexyl)diazobuta-1,3-diene] di(ethoxy) nickel; [1,4-bis(3,5-dipentylphenyl)-2-(ethyl)-3-(butyl)diazobuta-1,3-diene] di(nonadecyl) nickel; [1,4-bis(3,5-dihexylphenyl)-2,3-(dibutyl)diazobuta-1,3-diene] di(phenethyl) nickel; [1,4-bis(3,5-dibutylphenyl)-2-(hydrido)-3-(hexyl)diazobuta-1,3-diene] di(methyl) nickel; [1,4-bis(3,5-dibutylphenyl)-2-(ethyl)-3-(pentyl)diazobuta-1,3-diene] di(tetracosyl) nickel; [1,4-bis(3,5-dibutylphenyl)-2-(octyl)-3-(hexyl)diazobuta-1,3-diene] di(butyl) nickel; [1,4-bis(3,5-dibutylphenyl)-2,3-(dibutyl)diazobuta-1,3-diene] di(iodo)

nickel; [1,4-bis(3,5-diundecylphenyl)-2,3-(dibutyl)diazobuta-1,3-diene] di(methylethylamino) nickel; [1,4-bis(3,5-diheptacosynylphenyl)-2-(octyl)-3-(butyl)diazobuta-1,3-diene] di(hydride) nickel; [1,4-bis(3,5-dimethylphenyl)-2,3-(dihexyl)diazobuta-1,3-diene] di(hydrido) nickel; [1,4-bis(3,5-dipentylphenyl)-2-(pentyl)-3-(hydrido)diazobuta-1,3-diene] di(nonyl) nickel; [1,4-bis(3,5-dibutylphenyl)-2-(butyl)-3-(heneicosyl)diazobuta-1,3-diene] di(methyl) nickel; [1,4-bis(3,5-dibutylphenyl)-2-(ethyl)-3-(butyl)diazobuta-1,3-diene] di(hexyl) nickel; [1,4-bis(3,5-dimethylphenyl)-2,3-(dibutyl)diazobuta-1,3-diene] di(bromo) nickel; [1,4-bis(3,5-dioctylphenyl)-2,3-(dibutyl)diazobuta-1,3-diene] di(methyl) palladium; [1,4-bis(3,5-dipentylphenyl)-2-(pentadecenyl)-3-(hexyl)diazobuta-1,3-diene] di(hydrido) nickel; [1,4-bis(3,5-dimethylphenyl)-2-(octyl)-3-(butyl)diazobuta-1,3-diene] di(nonyl) nickel; [1,4-bis(3,5-dihexylphenyl)-2-(butyl)-3-(hexyl)diazobuta-1,3-diene] di(dodecyl) nickel; [1,4-bis(3,5-dipentylphenyl)-2-(pentyl)-3-(butyl)diazobuta-1,3-diene] di(hydrido) nickel; [1,4-bis(3,5-dibutylphenyl)-2,3-(dibutyl)diazobuta-1,3-diene] di(methoxy) palladium; [1,4-bis(3,5-dipentylphenyl)-2-(hydrido)-3-(octyl)diazobuta-1,3-diene] di(docosyl) nickel; [1,4-bis(3,5-dihexadecynylphenyl)-2,3-(dibutyl)diazobuta-1,3-diene] di(phenethyl) nickel; [1,4-bis(3,5-dipentylphenyl)-2-(hexyl)-3-(octyl)diazobuta-1,3-diene] di(pentyl) nickel; [1,4-bis(3,5-dibutylphenyl)-2,3-(dibutyl)diazobuta-1,3-diene] di(dimethylamino) nickel; [1,4-bis(3,5-dibutylphenyl)-2-(butyl)-3-(ethyl)diazobuta-1,3-diene] di(methyl) palladium; [1,4-bis(3,5-dioctylphenyl)-2,3-(dibutyl)diazobuta-1,3-diene] di(butyl) nickel; [1,4-bis(3,5-diethylphenyl)-2,3-(dibutyl)diazobuta-1,3-diene] di(methyl) palladium; [1,4-bis(3,5-dibutylphenyl)-2-(hydrido)-3-(pentyl)diazobuta-1,3-diene] di(butyl) nickel; [1,4-bis(3,5-dioctylphenyl)-2-(pentyl)-3-(hydrido)diazobuta-1,3-diene] di(butyl) palladium; [1,4-bis(3,5-dioctylphenyl)-2-(methyl)-3-(butyl)diazobuta-1,3-diene] di(chloro) nickel; [1,4-bis(3,5-dibutylphenyl)-2,3-(dibutyl)diazobuta-1,3-diene] di(hydrido) nickel; [1,4-bis(3,5-dibutylphenyl)-2,3-(dibutyl)diazobuta-1,3-diene] di(heptadecyl) palladium; [1,4-bis(3,5-dimethylphenyl)-2-(ethyl)-3-(butyl)diazobuta-1,3-diene] di(hydrido) nickel; [1,4-bis(3,5-dibutylphenyl)-2-(methyl)-3-(butyl)diazobuta-1,3-diene] di(ethyl) nickel; [1,4-bis(3,5-dihexylphenyl)-2-(butyl)-3-(hexyl)diazobuta-1,3-diene] di(pentadecyl) nickel; [1,4-bis(3,5-dipentylphenyl)-2-(pentyl)-3-(butyl)diazobuta-1,3-diene] di(hydrido) nickel; [1,4-bis(3,5-dihexylphenyl)-2-(hydrido)-3-(butyl)diazobuta-1,3-diene] di(octacosyl) palladium; [1,4-bis(3,5-dibutylphenyl)-2-(methyl)-3-(pentyl)diazobuta-1,3-diene] di(heptacosyl) palladium; [1,4-bis(3,5-dioctylphenyl)-2,3-(dihydrido)diazobuta-1,3-diene] di(nonyl) nickel; [1,4-bis(3,5-dibutylphenyl)-2-(butyl)-3-(hydrido)diazobuta-1,3-diene] di(ethoxy) nickel; [1,4-bis(3,5-di(trimethylsilylmethyl)phenyl)-2,3-(dibutyl)diazobuta-1,3-diene] di(docosyl) palladium; [1,4-bis(3,5-diethylphenyl)-2-(pentyl)-3-(hydrido)diazobuta-1,3-diene] di(methyl) nickel; [1,4-bis(3,5-diethylphenyl)-2-(hydrido)-3-(methyl)diazobuta-1,3-diene] di(bromo) nickel; [1,4-bis(3,5-dibutylphenyl)-2-(hydrido)-3-(hexyl)diazobuta-1,3-diene] di(bromo) nickel; [1,4-bis(3,5-dioctacosylphenyl)-2-(pentyl)-3-(hydrido)diazobuta-1,3-diene] di(butyl) nickel; [1,4-bis(3,5-dinonylphenyl)-2-(butyl)-3-(hexadecynyl)diazobuta-1,3-diene] di(ethyl) nickel; [1,4-bis(3,5-dipentylphenyl)-2-(hydrido)-3-(ethyl)diazobuta-1,3-diene] di(octadecyl) nickel; [1,4-bis(3,5-didodecynylphenyl)-2,3-(dibutyl)diazobuta-1,3-diene] di(methyl) nickel; [1,4-bis(3,5-dihexadecylphenyl)-2-(pentyl)-3-(hydrido)diazobuta-1,3-diene] di(hydrido) nickel; [1,4-bis(3,5-diethylphenyl)-2-(hexyl)-3-(pentyl)diazobuta-1,3-diene] di(methyl) nickel; [1,4-bis(3,5-dihexynylphenyl)-2-(pentyl)-3-(methyl)diazobuta-1,3-diene] di(ethyl) nickel; [1,4-bis(3,5-dibutylphenyl)-2-(pentyl)-3-(butyl)diazobuta-1,3-diene] di(hydrido) palladium; [1,4-bis(3,5-dibutylphenyl)-2,3-(dihexyl)diazobuta-1,3-diene] di(hexyl) nickel; [1,4-bis(3,5-didecenylphenyl)-2-(hydrido)-3-(butyl)diazobuta-1,3-diene] di(tolyl) nickel; [1,4-bis(3,5-diheptacosynylphenyl)-2,3-(dibutyl)diazobuta-1,3-diene] di(butoxy) nickel; [1,4-bis(3,5-diethylphenyl)-2-(methyl)-3-(undecenyl)diazobuta-1,3-diene] di(diethylamino) nickel; [1,4-bis(3,5-dibutylphenyl)-2,3-(dibutyl)diazobuta-1,3-diene] di(docosynyl) nickel; [1,4-bis(3,5-dibutylphenyl)-2-(octyl)-3-(butyl)diazobuta-1,3-diene] di(hydrido) nickel; [1,4-bis(3,5-dibutylphenyl)-2-(pentyl)-3-(methyl)diazobuta-1,3-diene] di(nonadecyl) nickel; [1,4-bis(3,5-dibutylphenyl)-2-(hexyl)-3-(pentyl)diazobuta-1,3-diene] di(hydrido) palladium; [1,4-bis(3,5-dibutylphenyl)-2-(dodecyl)-3-(hydrido)diazobuta-1,3-diene] di(tetracosenyl) nickel; [1,4-bis(3,5-dibutylphenyl)-2-(butyl)-3-(hydrido)diazobuta-1,3-diene] di(nonadecyl) palladium; [1,4-bis(3,5-dibutylphenyl)-2-(ethyl)-3-(tetradecenyl)diazobuta-1,3-diene] di(butyl) nickel; [1,4-bis(3,5-dibutylphenyl)-2-(hydrido)-3-(dodecenyl)diazobuta-1,3-diene] di(pentadecyl) palladium; [1,4-bis(3,5-dibutylphenyl)-2-(octyl)-3-(methyl)diazobuta-1,3-diene] di(butoxy) nickel; [1,4-bis(3,5-dibutylphenyl)-2-(tetracosyl)-3-(butyl)diazobuta-1,3-diene] di(hexacosyl) palladium; [1,4-bis(3,5-dibutylphenyl)-2-(hexyl)-3-(pentyl)diazobuta-1,3-diene] di(octadecyl) nickel; [1,4-bis(3,5-didodecylphenyl)-2-(pentyl)-3-(butyl)diazobuta-1,3-diene] di(dimethylamino) palladium; [1,4-bis(3,5-diundecenylphenyl)-2-(octyl)-3-(pentyl)diazobuta-1,3-diene] di(hydrido) nickel; [1,4-bis(3,5-dibutylphenyl)-2-(hydrido)-3-(butyl)diazobuta-1,3-diene] di(diethylamino) palladium; [1,4-bis(3,5-dimethylphenyl)-2-(methyl)-3-(ethyl)diazobuta-1,3-diene] di(methyl) nickel; [1,4-bis(3,5-dibutylphenyl)-2-(hexyl)-3-(octyl)diazobuta-1,3-diene] di(hydrido) nickel; [1,4-bis(3,5-dibutylphenyl)-2-(hydrido)-3-(butyl)diazobuta-1,3-diene] di(tetracosyl) palladium; [1,4-bis(3,5-dibutylphenyl)-2,3-(dibutyl)diazobuta-1,3-diene] di(phenyl) palladium; [1,4-bis(3,5-dioctylphenyl)-2-(hexyl)-3-(butyl)diazobuta-1,3-diene] di(propoxy) palladium; [1,4-bis(3,5-dibutylphenyl)-2-(pentyl)-3-(butyl)diazobuta-1,3-diene] di(methoxy) palladium; [1,4-bis(3,5-dihexylphenyl)-2(hexyl)-3-(butyl)diazobuta-1,3-diene] di(hydride) palladium; [1,4-bis(3,5-dibutylphenyl)2-(pentacosyl)-3-(octyl)diazobuta-1,3-diene] di(hydrido) nickel; [1,4-bis(3,5-dibutylphenyl)-2-(methyl)-3-(hydrido)diazobuta-1,3-diene] di(hexacosyl) nickel; [1,4-bis(3,5-dibutylphenyl)-2-(octyl)-3-(heptacosynyl)diazobuta-1,3-diene] di(phenoxy) palladium; [1,4-bis(3,5-dipentylphenyl)-2-(octyl)-3-(hydrido)diazobuta-1,3-diene] di(methyl) palladium; [1,4-bis(3,5-dibutylphenyl)-2-(octyl)-3-(pentyl)diazobuta-1,3-diene] di(nonyl) nickel; [1,4-bis(3,5-dipentylphenyl)-2-(tricosenyl)-3-(butyl)diazobuta-1,3-diene] di(heptacosyl) nickel; [1,4-bis(3,5-dibutylphenyl)-2-(hydrido)-3-(butyl)diazobuta-1,3-diene] di(hexadecyl) nickel; [1,4-bis(3,5-diheneicosylphenyl)-2,3-(dibutyl)diazobuta-1,3-diene] di(undecyl) nickel; [1,4-bis(3,5-dihexylphenyl)-2-(hydrido)-3-(butyl)diazobuta-1,3-diene] di(ethyl) palladium; [1,4-bis(3,5-dibutylphenyl)-2-(butyl)-3-(hexyl)diazobuta-1,3-diene] di(methyl) nickel; [1,4-bis(3,5-dipentylphenyl)-2-(ethyl)-3-(butyl)diazobuta-1,3-diene] di(hydrido) palladium; [1,4-bis(3,5-dioctylphenyl)-2-(octyl)-3-(docosenyl)diazobuta-1,3-diene] di(methoxy) nickel; [1,4-bis(3,5-dibutylphenyl)-2-(hydrido)-3-(pentyl)diazobuta-1,3-diene] di(methoxy) palladium; [1,4-bis(3,5-di(trimethylsilylethyl)phenyl)-2,3-(dibutyl)diazobuta-1,3-diene] di(tolyl) palladium; [1,4-bis (3,5-dibutylphenyl)-2-(hydrido)-3-(butenyl)diazobuta-1,3-diene] di(hydrido) nickel; [1,4-bis(3,5-dihexylphenyl)-2,3-(dibutyl)diazobuta-1,3-diene] di(heptyl) nickel; [1,4-bis(3,5-dibutylphenyl)-2-(hexyl)-3-(butyl)diazobuta-1,3-diene] di(methyl) nickel; [1,4-bis(3,5-dimethylphenyl)-2-(pentyl)-3-(hydrido)diazobuta-1,3-diene] di(butyl) palladium; [1,4-bis(3,5-dipentylphenyl)-2-(pentyl)-3-(hydrido)diazobuta-1,3-diene] di(ethyl) palladium; [1,4-bis(3,5-diethylphenyl)-2-(hydrido)-3-(butyl)diazobuta-1,3-diene] di(hydrido) palladium; [1,4-bis(3,5-dibutylphenyl)-2-(butyl)-3-(hydrido)diazobuta-1,3-diene] di(methylethylamino) nickel; [1,4-bis(3,5-dioctylphenyl)-2-(hydrido)-3-(butyl)diazobuta-1,3-diene] di(hydrido) nickel; [1,4-bis(3,5-dibutylphenyl)-2-(octyl)-3-(butyl)diazobuta-1,3-diene] di(hydrido) nickel; [1,4-bis(4-pentylphenyl)-2-(octyl)-3-(butyl)diazobuta-1,3-diene] di(methyl) nickel; [1,4-bis(4-pentylphenyl)-2-(octyl)-3-(pentyl)diazobuta-1,3-diene] di(tetracosyl) palladium; [1,4-bis(4-pentylphenyl)-2-(nonadecyl)-3-(hexyl)diazobuta-1,3-diene] di(triacontyl) palladium; [1,4-bis(4-dodecynylphenyl)-2-(ethyl)-3-(hydrido)diazobuta-1,3-diene] di(methyl) palladium; [1,4-bis(4-decynylphenyl)-2-(hexyl)-3-(pentyl)diazobuta-1,3-diene] di(hydrido) nickel; [1,4-bis(4-proponylphenyl)-2,3-(dipentyl)diazobuta-1,3-diene] di(dimethylamino) palladium; [1,4-bis(4-butylphenyl)-2-(butyl)-3-(hydrido)diazobuta-1,3-diene] di(propyl) nickel; [1,4-bis(4-tetracosenylphenyl)-2-(butyl)-3-(methyl)diazobuta-1,3-diene] di(octyl) nickel; [1,4-bis(4-butylphenyl)-2-(pentyl)-3-(methyl)diazobuta-1,3-diene] di(undecyl) nickel; [1,4-bis(4-hexylphenyl)-2,3-(dibutyl)diazobuta-1,3-diene] di(butyl) nickel; [1,4-bis(4-butylphenyl)-2-(hexyl)-3-(octyl)diazobuta-1,3-diene] di(tricosynyl) nickel; [1,4-bis(4-heptacosenylphenyl)-2-(hydrido)-3-(butyl)diazobuta-1,3-diene] di(ethyl) nickel; [1,4-bis(4-butylphenyl)-2,3-(dibutyl)diazobuta-1,3-diene] di(hexacosyl) nickel; [1,4-bis(4-butylphenyl)-2-(butyl)-3-(hydrido)diazobuta-1,3-diene] di(hexadecyl) nickel; [1,4-bis(4-octylphenyl)-2-(hexynyl)-3-(methyl)diazobuta-1,3-diene] di(nonacosyl) nickel; [1,4-bis(4-methylphenyl)-2-(butyl)-3-(pentyl)diazobuta-1,3-diene] di(allyl) palladium; [1,4-bis(4-butylphenyl)-2,3-(dibutyl)diazobuta-1,3-diene] di(tridecyl) nickel; [1,4-bis(4-butylphenyl)-2-(methyl)-3-(hydrido)diazobuta-1,3-diene] di(hydride) nickel; [1,4-bis(4-pentylphenyl)-2,3-(dibutyl)diazobuta-1,3-diene] di(octyl) nickel; [1,4-bis(4-butylphenyl)-2,3-(dihydrido)diazobuta-1,3-diene] di(pentacosyl) nickel; [1,4-bis(4-hexylphenyl)-2-(octyl)-3-(hydrido)diazobuta-1,3-diene] di(butoxy) palladium; [1,4-bis(4-octacosylphenyl)-2-(pentyl)-3-(hexyl)diazobuta-1,3-diene] di(hexyl) nickel; [1,4-bis(4-octadecenylphenyl)-2-(butyl)-3-(triacontenyl)diazobuta-1,3-diene] di(allyl) palladium; [1,4-bis(4-octylphenyl)-2,3-(dibutyl)diazobuta-1,3-diene] di(ethyl) nickel; [1,4-bis(4-butylphenyl)-2-(hydrido)-3-(butyl)diazobuta-1,3-diene] di(hydrido) palladium; [1,4-bis(4-butylphenyl)-2-(butyl)-3-(pentyl)diazobuta-1,3-diene] di(methyl) palladium; [1,4-bis(4-methylphenyl)-2-(hexacosenyl)-3-(hexyl)diazobuta-1,3-diene] di(ethyl) palladium; [1,4-bis(4-octylphenyl)-2-(methyl)-3-(hexyl)diazobuta-1,3-diene] di(hydrido) nickel; [1,4-bis(4-pentylphenyl)-2-(butyl)-3-(hexacosyl)diazobuta-1,3-diene] di(tetradecyl) nickel; [1,4-bis(4-pentylphenyl)-2-(hydrido)-3-(butyl)diazobuta-1,3-diene] di(methylethylamino) nickel; [1,4-bis(4-butylphenyl)-2-(hydrido)-3-(butyl)diazobuta-1,3-diene] di(pentacosyl) nickel; [1,4-bis(4-butylphenyl)-2-(hexyl)-3-(pentyl)diazobuta-1,3-diene] di(undecyl) nickel; [1,4-bis(4-methylphenyl)-2-(pentyl)-3-(butyl)diazobuta-1,3-diene] di(dodecyl) nickel; [1,4-bis(4-butylphenyl)-2-(methyl)-3-(pentyl)diazobuta-1,3-diene] di(ethyl) nickel; [1,4-bis(4-pentacosylphenyl)-2,3-(dibutyl)diazobuta-1,3-diene] di(nonyl) nickel; [1,4-bis(4-octylphenyl)-2-(tetradecynyl)-3-(octyl)diazobuta-1,3-diene] di(methyl) nickel; [1,4-bis(4-hexylphenyl)-2-(nonyl)-3-(butyl)diazobuta-1,3-diene] di(heneicosyl) palladium; [1,4-bis(4-pentacosylphenyl)-2-(pentyl)-3-(butyl)diazobuta-1,3-diene] di(hydrido) nickel; [1,4-bis(4-butylphenyl)-2-(butyl)-3-(hydrido)diazobuta-1,3-diene] di(methyl) nickel; [1,4-bis(4-octylphenyl)-2-(hexyl)-3-(docosenyl)diazobuta-1,3-diene] di(tetradecyl) nickel; [1,4-bis(4-butylphenyl)-2-(hydrido)-3-(butyl)diazobuta-1,3-diene] di(methyl) nickel; [1,4-bis(4-butylphenyl)-2-(hydrido)-3-(pentyl)diazobuta-1,3-diene] di(hydrido) nickel; [1,4-bis(4-butylphenyl)-2-(eicosenyl)-3-(butyl)diazobuta-1,3-diene] di(methyl) nickel; [1,4-bis(4-pentylphenyl)-2-(hexyl)-3-(heneicosynyl)diazobuta-1,3-diene] di(methyl) nickel; [1,4-bis(4-butylphenyl)-2-(hydrido)-3-(pentadecyl)diazobuta-1,3-diene] di(butoxy) nickel; [1,4-bis(4-hexadecenylphenyl)-2-(methyl)-3-(butyl)diazobuta-1,3-diene] di(pentyl) nickel; [1,4-bis(4-tetracosynylphenyl)-2-(heneicosyl)-3-(hydrido)diazobuta-1,3-diene] di(ethyl) nickel; [1,4-bis(4-heptadecenylphenyl)-2-(butyl)-3-(pentyl)diazobuta-1,3-diene] di(hydrido) nickel; [1,4-bis(4-ethylphenyl)-2-(propyl)-3-(hydrido)diazobuta-1,3-diene] di(hydrido) nickel; [1,4-bis(4-pentynylphenyl)-2,3-(dibutyl)diazobuta-1,3-diene] di(tolyl) palladium; [1,4-bis(4-butylphenyl)-2,3-(dibutyl)diazobuta-1,3-diene] di(ethyl) palladium; [1,4-bis(4-ethylphenyl)-2-(hexadecyl)-3-(butyl)diazobuta-1,3-diene] di(tetracosyl) nickel; [1,4-bis(4-butylphenyl)-2-(hydrido)-3-(triacontyl)diazobuta-1,3-diene] di(methyl) nickel; [1,4-bis(4-hexylphenyl)-2-(hydrido)-3-(dodecenyl)diazobuta-1,3-diene] di(pentyl) nickel; [1,4-bis(4-butylphenyl)-2-(pentyl)-3-(butyl)diazobuta-1,3-diene] di(butyl) nickel; [1,4-bis(4-hexylphenyl)-2-(hexyl)-3-(methyl)diazobuta-1,3-diene] di(hexadecyl) nickel; [1,4-bis(4-butylphenyl)-2-(octyl)-3-(undecynyl)diazobuta-1,3-diene] di(ethyl) palladium; [1,4-bis(4-heneicosenylphenyl)-2-(butyl)-3-(octyl)diazobuta-1,3-diene] di(heptyl) nickel; [1,4-bis(4-butylphenyl)-2-(butyl)-3-(octyl)diazobuta-1,3-diene] di(butyl) nickel; [1,4-bis(4-butylphenyl)-2-(octyl)-3-(propynyl)diazobuta-1,3-diene] di(phenoxy) nickel; [1,4-bis(4-butylphenyl)-2-(hexyl)-3-(butyl)diazobuta-1,3-diene] di(undecyl) nickel; [1,4-bis(4-pentacosylphenyl)-2-(octyl)-3-(heptadecenyl)diazobuta-1,3-diene] di(hydrido) nickel; [1,4-bis(4-butylphenyl)-2-(butyl)-3-(octyl)diazobuta-1,3-diene] di(hydrido) nickel; [1,4-bis(4-tetracosylphenyl)-2-(hydrido)-3-(octyl)diazobuta-1,3-diene] di(methyl) nickel; [1,4-bis(4-pentylphenyl)-2-(pentyl)-3-(ethyl)diazobuta-1,3-diene] di(methyl) palladium; [1,4-bis(4-hexylphenyl)-2-(ethyl)-3-(pentadecynyl)diazobuta-1,3-diene] di(chloro) nickel; [1,4-bis(4-octylphenyl)-2-(butyl)-3-(tridecenyl)diazobuta-1,3-diene] di(heptacosyl) palladium; [1,4-bis(4-methylphenyl)-2-(hexyl)-3-(butyl)diazobuta-1,3-diene] di(docosyl) nickel; [1,4-bis(4-butylphenyl)-2-(butyl)-3-(hydrido)diazobuta-1,3-diene] di(butyl) nickel; [1,4-bis(4-butylphenyl)-2-(butyl)-3-(octyl)diazobuta-1,3-diene] di(hydrido) nickel; [1,4-bis(4-butylphenyl)-2-(hexyl)-3-(butyl)diazobuta-1,3-diene] di(ethyl) nickel; [1,4-bis(4-octylphenyl)-2-(pentyl)-3-(butyl)diazobuta-1,3-diene] di(diethylamino) palladium; [1,4-bis(4-butylphenyl)-2-(butyl)-3-(ethyl)diazobuta-1,3-diene] di(hydrido) palladium; [1,4-bis(4-butylphenyl)-2,3-(dioctyl)diazobuta-1,3-diene] di(butyl) nickel; [1,4-bis(4-pentylphenyl)-2-(butyl)-3-(ethyl)diazobuta-1,3-diene] di(tricosyl) nickel; [1,4-bis(4-pentylphenyl)-2-(ethyl)-3-(butyl)diazobuta-1,3-diene] di(pentacosyl) nickel; [1,4-bis(4-butylphenyl)-2-(undecynyl)-3-(tetradecynyl)diazobuta-1,3-diene] di(hydrido) nickel; [1,4-bis(4-octylphenyl)-2,3-(dibutyl)diazobuta-1,3-diene] di(tolyl) nickel; [1,4-bis(4-hexylphenyl)-2-(butyl)-3-(hydrido)diazobuta-1,3-diene] di(hydrido) nickel; [1,4-bis(4-butylphenyl)-2-(octyl)-3-(methyl)diazobuta-1,3-diene] di(hexadecyl) palladium; [1,4-bis(4-pentylphenyl)-2,3-(diheptadecynyl)diazobuta-1,3-diene] di(methyl) nickel; [1,4-bis(4-heneicosylphenyl)-2-(tricosyl)-3-(octacosenyl) diazobuta-1,3-diene] di(hydrido) nickel; [1,4-bis(4-hexylphenyl)-2-(butyl)-3-(ethyl)diazobuta-1,3-diene] di(hydrido) nickel; [1,4-bis(4-dodecanonylphenyl)-2-(hexyl)-3-(hydrido)diazobuta-1,3-diene] di(propyl) nickel; [1,4-bis(4-hexacosylphenyl)-2-(hexyl)-3-(hydrido)diazobuta-1,3-diene] di(methyl) palladium; [1,4-bis(4-butylphenyl)-2-(hexyl)-3-(butyl)diazobuta-1,3-diene] di(chloro) nickel; [1,4-bis(4-butylphenyl)-2-(octacosyl)-3-(hydrido)diazobuta-1,3-diene] di(phenyl) nickel; [1,4-bis(4-butylphenyl)-2-(butyl)-3-(nonadecyl)diazobuta-1,3-diene] di(tolyl) nickel; [1,4-bis(4-hexylphenyl)-2-(butyl)-3-(octyl)diazobuta-1,3-diene] di(hexyl) nickel; [1,4-bis(4-octylphenyl)-2-(methyl)-3-(heptynyl)diazobuta-1,3-diene] di(methyl) nickel; [1,4-bis(4-methylphenyl)-2-(hydrido)-3-(decenyl) diazobuta-1,3-diene] di(heptyl) nickel; [1,4-bis(4-butylphenyl)-2,3-(dihexyl)diazobuta-1,3-diene] di(bromo) nickel; [1,4-bis(4-butylphenyl)-2-(octyl)-3-(butyl)diazobuta-1,3-diene] di(bromo) nickel; [1,4-bis(4-butylphenyl)-2,3-(dibutyl) diazobuta-1,3-diene] di(methyl) palladium; [1,4-bis(4-ethylphenyl)-2-(methyl)-3-(hydrido)diazobuta-1,3-diene] di(hydrido) nickel; [1,4-bis(4-pentylphenyl)-2-(butyl)-3-(ethyl)diazobuta-1,3-diene] di(hydride) nickel; [1,4-bis(4-butylphenyl)-2-(hexyl)-3-(hydrido)diazobuta-1,3-diene] di(triacontyl) nickel; [1,4-bis(4-pentylphenyl)-2-(hydrido)-3-(octyl)diazobuta-1,3-diene] di(heptadecyl) palladium; [1,4-bis(4-octylphenyl)-2-(heptenyl)-3-(hexyl)diazobuta-1,3-diene] di(octacosyl) nickel; [1,4-bis(4-butenylphenyl)-2-(ethyl)-3-(butyl)diazobuta-1,3-diene] di(methyl) nickel; [1,4-bis(4-octylphenyl)-2-(octyl)-3-(pentyl)diazobuta-1,3-diene] di(heptacosyl) nickel; [1,4-bis(4-butylphenyl)-2-(methyl)-3-(pentyl)diazobuta-1,3-diene] di(octyl) nickel; [1,4-bis(4-butylphenyl)-2-(hydrido)-3-(pentyl)diazobuta-1,3-diene] di(nonynyl) nickel; [1,4-bis(4-pentylphenyl)-2-(hexyl)-3-(hydrido)diazobuta-1,3-diene] di(hexacosynyl) nickel; [1,4-bis(4-butylphenyl)-2-(nonacosynyl)-3-(butyl) diazobuta-1,3-diene] di(hydrido) palladium; [1,4-bis(4-butylphenyl)-2-(hydrido)-3-(hexyl)diazobuta-1,3-diene] di(methyl) nickel; [1,4-bis(4-butylphenyl)-2-(butyl)-3-(hydrido) diazobuta-1,3-diene] di(pentacosyl) nickel; [1,4-bis(4-hexylphenyl)-2-(pentyl)-3-(ethyl)diazobuta-1,3-diene] di(methoxy) nickel; [1,4-bis(4-butylphenyl)-2-(octacosynyl)-3-(heptyl)diazobuta-1,3-diene] di(butyl) nickel; [1,4-bis(4-octylphenyl)-2-(hydrido)-3-(pentyl)diazobuta-1,3-diene] di(hydride) nickel; [1,4-bis(4-methylphenyl)-2-(octyl)-3-(pentadecyl)diazobuta-1,3-diene] di(octyl) nickel; [1,4-bis(4-butylphenyl)-2-(hydrido)-3-(butyl)diazobuta-1,3-diene] di(butyl) nickel; [1,4-bis(4-ethylphenyl)-2-(hydrido)-3-(hexyl)diazobuta-1,3-diene] di(diethylamino) nickel; [1,4-bis(4-ethylphenyl)-2-(butyl)-3-(hexyl)diazobuta-1,3-diene] di(heneicosenyl) nickel; [1,4-bis(4-methylphenyl)-2,3-(dipentyl)diazobuta-1,3-diene] di(ethyl) palladium; [1,4-bis(4-butylphenyl)-2-(hydrido)-3-(methyl)diazobuta-1,3-diene] di(methyl) palladium; [1,4-bis(4-heptacosylphenyl)-2-(butyl)-3-(hydrido)diazobuta-1,3-diene] di(diethylamino) nickel; [1,4-bis(4-diethylaminophenyl)-2-(butyl)-3-(nonenyl)diazobuta-1,3-diene] di(hydrido) nickel; [1,4-bis(4-butylphenyl)-2-(hexyl)-3-(octacosyl)diazobuta-1,3-diene] di(hydrido) palladium; [1,4-bis(4-butylphenyl)-2-(octyl)-3-(hexyl)diazobuta-1,3-diene] di(methyl) nickel; [1,4-bis(4-octylphenyl)-2-(hydrido)diazobuta-1,3-diene] di(methyl) nickel; [1,4-bis(4-butylphenyl)-2-(hydrido)-3-(dodecenyl)diazobuta-1,3-diene] di(butyl) palladium; [1,4-bis(4-octylphenyl)-2-(hydrido)-3-(hexyl)diazobuta-1,3-diene] di(heptadecyl) nickel; [1,4-bis(4-butylphenyl)-2-(heptenyl)-3-(butyl)diazobuta-1,3-diene] di(hydrido) nickel; [1,4-bis(4-hexylphenyl)-2-(tridecyl)-3-(butyl)diazobuta-1,3-diene] di(benzyl) nickel; [1,4-bis(4-tetracosynylphenyl)-2-(hydrido)-3-(heptacosynyl)diazobuta-1,3-diene] di(butoxy) palladium; [1,4-bis(4-butylphenyl)-2-(hydrido)-3-(butyl)diazobuta-1,3-diene] di(pentadecyl) palladium; [1,4-bis(4-pentylphenyl)-2-(ethyl)-3-(eicosyl)diazobuta-1,3-diene] di(hydrido) palladium; [1,4-bis(4-butylphenyl)-2-(butyl)-3-(hydrido)diazobuta-1,3-diene] di(tetradecyl) nickel; [1,4-bis(4-pentylphenyl)-2-(undecynyl)-3-(hexynyl) diazobuta-1,3-diene] di(hydrido) nickel; [1,4-bis(4-methylphenyl)-2-(hydrido)-3-(hexyl)diazobuta-1,3-diene] di(methyl) nickel; [1,4-bis(4-hexylphenyl)-2-(hexyl)-3-(pentyl) diazobuta-1,3-diene] di(methyl) nickel; [1,4-bis(4-butylphenyl)-2,3-(dipentyl)diazobuta-1,3-diene] di(ethyl) palladium; [1,4-bis(4-octylphenyl)-2-(hydrido)-3-(nonacosenyl)diazobuta-1,3-diene] di(butyl) palladium; [1,4-bis(4-pentylphenyl)-2-(hydrido)-3-(butyl)diazobuta-1,3-diene] di(methyl) nickel; [1,4-bis(4-butylphenyl)-2-(hydrido)-3-(ethyl)diazobuta-1,3-diene] di(dodecyl) nickel; [1,4-bis(4-butylphenyl)-2,3-(dibutyl)diazobuta-1,3-diene] di(docosyl) nickel; [1,4-bis(4-pentadecylphenyl)-2-(butyl)-3-(ethyl)diazobuta-1,3-diene] di(methyl) nickel; [1,4-bis(4-butylphenyl)-2-(pentyl)-3-(tricosyl)diazobuta-1,3-diene] di(triacontyl) nickel; [1,4-bis(4-butylphenyl)-2-(hexyl)-3-(butyl) diazobuta-1,3-diene] di(hydrido) nickel; [1,4-bis(4-butylphenyl)-2-(hydrido)-3-(methyl)diazobuta-1,3-diene] di(methyl) nickel; [1,4-bis(4-pentylphenyl)-2-(hexyl)-3-(hydrido)diazobuta-1,3-diene] di(hydrido) palladium; [1,4-bis(4-octylphenyl)-2,3-(dihexyl)diazobuta-1,3-diene] di(nonadecyl) nickel; [1,4-bis(4-ethylphenyl)-2-(ethyl)-3-(butyl)diazobuta-1,3-diene] di(methyl) nickel; [1,4-bis(4-octylphenyl)-2-(ethyl)-3-(hydrido)diazobuta-1,3-diene] di(hydrido) nickel; [1,4-bis(4-methylphenyl)-2-(pentyl)-3-(hydrido)diazobuta-1,3-diene] di(methyl) nickel; [1,4-bis(4-butylphenyl)-2,3-(dibutyl)diazobuta-1,3-diene] di(phenoxy) palladium; [1,4-bis(4-butylphenyl)-2-(octyl)-3-(tridecyl) diazobuta-1,3-diene] di(nonadecyl) nickel; [1,4-bis(4-butylphenyl)-2-(hydrido)-3-(butyl)diazobuta-1,3-diene] di(octyl) nickel; [1,4-bis(4-methylphenyl)-2-(hydrido)-3-(octacosynyl)diazobuta-1,3-diene] di(hydrido) nickel; [1,4-bis(4-hexylphenyl)-2-(methyl)-3-(octyl)diazobuta-1,3-diene] di(iodo) nickel; [1,4-bis(4-octylphenyl)-2,3-(dihydrido)diazobuta-1,3-diene] di(propyl) nickel; [1,4-bis(4-butylphenyl)-2-(hydrido)-3-(triacontynyl)diazobuta-1,3-diene] di(hydrido) nickel; [1,4-bis(4-butylphenyl)-2-(butyl)-3-(hydrido)diazobuta-1,3-diene] di(benzyl) palladium; [1,4-bis(4-octylphenyl)-2-(pentyl)-3-(butyl)diazobuta-1,3-diene] di(benzoxy) nickel; [1,4-bis(4-octylphenyl)-2-(butyl)-3-(hydrido)diazobuta-1,3-diene] di(hydrido) palladium; [1,4-bis(4-octylphenyl)-2-(butyl)-3-(hydrido)diazobuta-1,3-diene] di(benzoxy) nickel; [1,4-bis(4-butylphenyl)-2-(octyl)-3-(butyl)diazobuta-1,3-diene] di(tridecyl) nickel; [1,4-bis(4-octylaminophenyl)-2-(tricosyl)-3-(octyl)diazobuta-1,3-diene] di(hydrido) nickel; [1,4-bis(4-butylphenyl)-2-(hydrido)-3-(nonadecyl)diazobuta-1,3-diene] di(heptyl) nickel; [1,4-bis(4-butylphenyl)-2-(butyl)-3-(eicosyl)diazobuta-1,3-diene] di(ethyl) nickel; [1,4-bis(4-pentylphenyl)-2-(hydrido)-3-(methyl)diazobuta-1,3-diene] di(hydrido) nickel; [1,4-bis(4-butylphenyl)-2-(dodecynyl)-3-(hydrido)diazobuta-1,3-diene] di(heptyl) palladium; [1,4-bis(4-heptacosynylphenyl)-2-(pentyl)-3-(decynyl)diazobuta-1,3-diene] di(pentacosyl) nickel; [1,4-bis(4-heneicosenylphenyl)-2-(pentyl)-3-(butyl) diazobuta-1,3-diene] di(chloro) nickel; [1,4-bis(4-butylphenyl)-2-(butyl)-3-(hydrido)diazobuta-1,3-diene] di(ethyl)

nickel; [1,4-bis(4-butylphenyl)-2-(butyl)-3-(hydrido)diazobuta-1,3-diene] di(nonadecyl) nickel; [1,4-bis(4-octadecynylphenyl)-2-(octenyl)-3-(hydrido)diazobuta-1,3-diene] di(heptyl); [1,4-bis(4-proponylphenyl)-2,3-(dibutyl) diazobuta-1,3-diene] di(hexyl) nickel; [1,4-bis(4-butylphenyl)-2-(hydrido)-3-(butyl)diazobuta-1,3-diene] di(butyl) palladium; [1,4-bis(4-butylphenyl)-2-(hydrido)-3-(methyl) diazobuta-1,3-diene] di(diethylamino) nickel; [1,4-bis(4-butylphenyl)-2-(hydrido)-3-(octyl)diazobuta-1,3-diene] di(eicosyl) palladium; [1,4-bis(4-octylphenyl)-2-(hexyl)-3-(hydrido)diazobuta-1,3-diene] di(hydrido) nickel; [1,4-bis(4-hexylphenyl)-2,3-(dihexyl)diazobuta-1,3-diene] di(hydrido) palladium; [1,4-bis(4-(trimethylsilylethyl)phenyl)-2-(hexyl)-3-(hydrido)diazobuta-1,3-diene] di(hexadecenyl) nickel; [1,4-bis(4-butylphenyl)-2-(octacosynyl)-3-(tridecyl) diazobuta-1,3-diene] di(butyl) nickel; [1,4-bis(4-hexylphenyl)-2-(butyl)-3-(ethyl)diazobuta-1,3-diene] di(phenoxy) palladium; [1,4-bis(4-butylphenyl)-2,3-(dibutyl)diazobuta-1,3-diene] di(methyl) nickel; [1,4-bis(4-butylphenyl)-2-(pentyl)-3-(butyl)diazobuta-1,3-diene] di(tolyl) nickel; [1,4-bis(4-pentylphenyl)-2-(hexyl)-3-(hydrido)diazobuta-1,3-diene] di(methyl) palladium; [1,4-bis(4-ethylphenyl)-2-(butyl)-3-(decyl)diazobuta-1,3-diene] di(phenyl) nickel; [1,4-bis(4-pentylphenyl)-2-(butyl)-3-(pentyl)diazobuta-1,3-diene] di(docosyl) palladium; [1,4-bis(4-butylphenyl)-2-(hydrido)-3-(tridecyl)diazobuta-1,3-diene] di(heptyl) palladium; [1,4-bis(3-octylphenyl)-2-(pentyl)-3-(butyl) diazobuta-1,3-diene] di(ethyl) nickel; [1,4-bis(3-octylphenyl)-2,3-(diethyl)diazobuta-1,3-diene] di(octyl) nickel; [1,4-bis(3-octacosenylphenyl)-2-(butyl)-3-(octyl) diazobuta-1,3-diene] di(chloro) nickel; [1,4-bis(3-butylphenyl)-2-(butyl)-3-(hexyl) -diazobuta-1,3-diene]di(hydrido) nickel; [1,4-bis(3-ethylphenyl)-2-(butyl)-3-(octyl) diazobuta-1,3-diene]di(decyl)palladium; [1,4-bis(3-hexylphenyl)-2-(butyl)-3-(nonacosynyl)diazobuta-1,3-diene]di(hydride)nickel; [1,4-bis(3-butylphenyl)-2-(butyl)-3-(octyl)diazobuta-1,3-diene]di(heptacosyl)nickel; [1,4-bis(3-docosynylphenyl)-2-(hydrido)-3-(methyl)diazobuta-1,3-diene]di(heptacosyl)palladium; [1,4-bis(3-heneicosynylphenyl)-2-(ethyl)-3-(pentyl)diazobuta-1,3-diene]di(heptadecyl)nickel; [1,4-bis(3-butylphenyl)-2,3-(dibutyl)diazobuta-1,3-diene]di(tridecyl)nickel; [1,4-bis(3-butylphenyl)-2-(hexyl)-3-(hydrido)diazobuta-1,3-diene]di(allyl)nickel; [1,4-bis(3-octylphenyl)-2-(hydrido)-3-(pentyl) diazobuta-1,3-diene]di(butyl)nickel; [1,4-bis(3-dodecenylphenyl)-2-(pentyl)-3-(butyl)diazobuta-1,3-diene] di(methyl)nickel; [1,4-bis(3-butylphenyl)-2-(hexyl)-3-(heneicosynyl)diazobuta-1,3-diene]di(methyl)nickel; [1,4-bis(3-pentylphenyl)-2-(hexyl)-3-(octyl)diazobuta-1,3-diene]di(methyl)nickel; [1,4-bis(3-tetradecylphenyl)-2-(hexyl)-3-(nonadecenyl)diazobuta-1,3-diene]di(methyl) palladium; [1,4-bis(3-methylphenyl)-2-(dodecyl)-3-(butyl) diazobuta-1,3-diene]di(iodo)palladium; [1,4-bis(3-butylphenyl)-2-(butyl)-3-(hydrido)diazobuta-1,3-diene]di (methoxy)nickel; [1,4-bis(3-butylphenyl)-2-(pentyl)-3-(hydrido)diazobuta-1,3-diene]di(tetracosyl)nickel; [1,4-bis(3-octylphenyl)-2-(butyl)-3-(ethyl)diazobuta-1,3-diene]di (phenethyl)nickel; [1,4-bis(3-heptacosenylphenyl)-2-(octyl)-3-(ethyl)diazobuta-1,3-diene]di(phenoxy)palladium; [1,4-bis(3-dodecylphenyl)-2,3-(dihydrido)diazobuta-1,3-diene]di(dodecyl)nickel; [1,4-bis(3-methylphenyl)-2-(butyl)-3-(pentyl)diazobuta-1,3-diene]di(diethylamino)nickel; [1,4-bis(3-octylphenyl)-2,3-(dibutyl)diazobuta-1,3-diene]di (tolyl)nickel; [1,4-bis(3-hexylphenyl)-2-(hydrido)-3-(pentyl)diazobuta-1,3-diene]di(pentyl)nickel; [1,4-bis(3-pentylphenyl)-2-(butyl)-3-(pentyl)diazobuta-1,3-diene]di (ethyl)palladium; [1,4-bis(3-butylphenyl)-2-(butyl)-3-(pentyl)diazobuta-1,3-diene]di(benzyl)nickel; [1,4-bis(3-hexylphenyl)-2-(hydrido)-3-(tetradecynyl)diazobuta-1,3-diene]di(tetradecyl)nickel; [1,4-bis(3-pentylphenyl)-2-(pentyl)-3-(decyl)diazobuta-1,3-diene]di(octyl)nickel; [1,4-bis (3-butylphenyl)-2-(pentyl)-3-(heneicosynyl)diazobuta-1,3-diene]di(ethyl)nickel; [1,4-bis(3-dodecaminophenyl)-2-(ethyl)-3-(hydrido)diazobuta-1,3-diene]di(pentacosyl) palladium; [1,4-bis(3-hexylphenyl)-2-(butyl)-3-(octyl) diazobuta-1,3-diene]di(butyl)palladium; [1,4-bis(3-butylphenyl)-2-(butyl)-3-(octyl)diazobuta-1,3-diene]di (ethoxy)nickel; [1,4-bis(3-hexylphenyl)-2-(heptacosynyl)-3-(pentyl)diazobuta-1,3-diene]di(methyl)nickel; [1,4-bis(3-heptacosylphenyl)-2,3-(dibutyl)diazobuta-1,3-diene]di (benzyl)palladium; [1,4-bis(3-pentylphenyl)-2-(ethyl)-3-(tetracosynyl)diazobuta-1,3-diene]di(hydrido)nickel; [1,4-bis(3-butylphenyl)-2-(octyl)-3-(octadecyl)diazobuta-1,3-diene]di(methyl)nickel; [1,4-bis(3-butylphenyl)-2-(hydrido)-3-(nonenyl)diazobuta-1,3-diene]di(benzyl)nickel; [1,4-bis(3-pentylphenyl)-2-(hydrido)-3-(butyl)diazobuta-1, 3-diene]di(eicosyl)palladium; [1,4-bis(3-butylphenyl)-2-(methyl)-3-(hexyl)diazobuta-1,3-diene]di(nonacosyl) nickel; [1,4-bis(3-butylphenyl)-2-(butyl)-3-(octyl) diazobuta-1,3-diene]di(butyl)nickel; [1,4-bis(3-butylphenyl)-2-(butyl)-3-(hexyl)diazobuta-1,3-diene]di (hydrido)nickel; [1,4-bis(3-butylphenyl)-2-(hexyl)-3-(butyl) diazobuta-1,3-diene]di(nonadecyl)nickel; [1,4-bis(3-octylphenyl)-2-(hydrido)-3-(hexyl)diazobuta-1,3-diene]di (methylethylamino)palladium; [1,4-bis(3-dodecenylphenyl)-2,3-(dihydrido)diazobuta-1,3-diene]di (tetradecyl)nickel; [1,4-bis(3-butylphenyl)-2,3-(dihydrido) diazobuta-1,3-diene]di(hydrido)nickel; [1,4-bis(3-pentylphenyl)-2-(ethyl)-3-(hydrido)diazobuta-1,3-diene]di (octyl)palladium; [1,4-bis(3-octylphenyl)-2-(butyl)-3-(methyl)diazobuta-1,3-diene]di(hexacosyl)palladium; [1,4-bis(3-butylphenyl)-2-(hydrido)-3-(butyl)diazobuta-1,3-diene]di(propyl)palladium; [1,4-bis(3-ethylphenyl)-2-(butyl)-3-(pentyl)diazobuta-1,3-diene]di(hydrido)nickel; [1,4-bis(3-hexylphenyl)-2-(octyl)-3-(butyl)diazobuta-1,3-diene]di(methyl)nickel; [1,4-bis(3-nonacosenylphenyl)-2,3-(dipentyl)diazobuta-1,3-diene]di(methyl)nickel; [1,4-bis(3-butylphenyl)-2-(hexyl)-3-(octyl)diazobuta-1,3-diene]di (butyl)nickel; [1,4-bis(3-butylphenyl)-2-(hydrido)-3-(methyl)diazobuta-1,3-diene]di(octyl)nickel; [1,4-bis(3-butylphenyl)-2-(octyl)-3-(hexyl)diazobuta-1,3-diene]di (propyl)nickel; [1,4-bis(3-hexylphenyl)-2,3-(dihydrido) diazobuta-1,3-diene]di(nonadecyl)nickel; [1,4-bis(3-butylphenyl)-2-(pentyl)-3-(butyl)diazobuta-1,3-diene]di (hexacosyl)palladium; [1,4-bis(3-pentylphenyl)-2,3-(dibutyl)diazobuta-1,3-diene]di(hydrido)nickel; [1,4-bis(3-hexylphenyl)-2,3-(dibutyl)diazobuta-1,3-diene]di(hydrido) palladium; [1,4-bis(3-butylphenyl)-2,3-(dihydrido) diazobuta-1,3-diene]di(phenyl)nickel; [1,4-bis(3-octylphenyl)-2-(tridecynyl)-3-(pentyl)diazobuta-1,3-diene] di(methyl)nickel; [1,4-bis(3-butylphenyl)-2-(butyl)-3-(hexyl)diazobuta-1,3-diene]di(pentacosyl)nickel; [1,4-bis (3-butylphenyl)-2,3-(dihydrido)diazobuta-1,3-diene]di (hydride)palladium; [1,4-bis(3-butylphenyl)-2-(butyl)-3-(pentyl)diazobuta-1,3-diene]di(hexadecyl)palladium; [1,4-bis(3-octylphenyl)-2-(octyl)-3-(hydrido)diazobuta-1,3-diene]di(hydrido)nickel; [1,4-bis(3-undecynylphenyl)-2-(butyl)-3-(ethyl)diazobuta-1,3-diene]di(pentynyl)nickel; [1,4-bis(3-methylphenyl)-2-(ethyl)-3-(hydrido)diazobuta-1, 3-diene]di(hexacosyl)nickel; [1,4-bis(3-butylphenyl)-2-(methyl)-3-(hydrido)diazobuta-1,3-diene]di(hydrido)nickel; [1,4-bis(3-pentadecenylphenyl)-2-(hydrido)-3-(butyl)diazobuta-1,3-diene]di(methyl)nickel; [1,4-bis(3-ethylphenyl)-2-(butyl)-3-(methyl)diazobuta-1,3-diene]di(hexadecyl)palladium; [1,4-bis(3-butylphenyl)-2-(hexyl)-3-(hydrido) diazobuta-1,3-diene]di(nonacosyl)nickel; [1,4-bis(3-nonadecylphenyl)-2-(butyl)-3-(hydrido)diazobuta-1,3-diene]di(ethyl)nickel; [1,4-bis(3-pentylphenyl)-2-(butyl)-3-(hexyl)diazobuta-1,3-diene]di(hydrido)palladium; [1,4-bis(3-butylphenyl)-2-(hydrido)-3-(butyl)diazobuta-1,3-diene]di(phenyl)palladium; [1,4-bis(3-butylphenyl)-2-(butyl)-3-(hydrido)diazobuta-1,3-diene]di(dodecyl)nickel; [1,4-bis(3-butylphenyl)-2-(butyl)-3-(octyl)diazobuta-1,3-diene]di(butyl)palladium; [1,4-bis(3-butylphenyl)-2-(butyl)-3-(hydrido)diazobuta-1,3-diene]di(diethylamino)nickel; [1,4-bis(3-heptacosylphenyl)-2-(pentyl)-3-(hydrido)diazobuta-1,3-diene]di(pentacosyl)palladium; [1,4-bis(3-butonylphenyl)-2-(butyl)-3-(hydrido)diazobuta-1,3-diene]di(hydrido)nickel; [1,4-bis(3-nonadecynylphenyl)-2,3-(dihydrido)diazobuta-1,3-diene]di(pentacosyl)nickel; [1,4-bis(3-butylphenyl)-2-(methyl)-3-(hexyl)diazobuta-1,3-diene]di(methylethylamino)nickel; [1,4-bis(3-butylphenyl)-2,3-(dibutyl)diazobuta-1,3-diene]di(heptadecyl)nickel; [1,4-bis(3-octylphenyl)-2,3-(dibutyl)diazobuta-1,3-diene]di(nonadecyl)palladium; [1,4-bis(3-butylphenyl)-2-(butyl)-3-(propyl)diazobuta-1,3-diene]di(tetradecyl)nickel; [1,4-bis(3-butenylphenyl)-2-(hydrido)-3-(butyl)diazobuta-1,3-diene]di(octacosyl)nickel; [1,4-bis(3-tetracosylphenyl)-2-(butyl)-3-(methyl)diazobuta-1,3-diene]di(octyl)palladium; [1,4-bis(3-butylphenyl)-2,3-(dibutyl)diazobuta-1,3-diene]di(pentacosyl)nickel; [1,4-bis(3-butylphenyl)-2-(pentyl)-3-(butyl)diazobuta-1,3-diene]di(methyl)nickel; [1,4-bis(3-octylphenyl)-2-(pentyl)-3-(hexyl)diazobuta-1,3-diene]di(octyl)palladium; [1,4-bis(3-heptacosylphenyl)-2-(hydrido)-3-(nonacosyl)diazobuta-1,3-diene]di(hexyl)nickel; [1,4-bis(3-butylphenyl)-2-(butyl)-3-(octyl)diazobuta-1,3-diene]di(propoxy)nickel; [1,4-bis(3-hexylphenyl)-2-(ethyl)-3-(butyl)diazobuta-1,3-diene]di(ethyl)palladium; [1,4-bis(3-butylphenyl)-2-(hydrido)-3-(methyl)diazobuta-1,3-diene]di(hexadecyl)nickel; [1,4-bis(3-octylphenyl)-2-(octyl)-3-(butyl)diazobuta-1,3-diene]di(phenethyl)palladium; [1,4-bis(3-pentylphenyl)-2-(triacontynyl)3-(butyl)diazobuta-1,3-diene]di(tricosyl)nickel; [1,4-bis(3-butylphenyl)-2-(pentyl)-3(hexyl)diazobuta-1,3-diene]di(heptyl)nickel; [1,4-bis(3-butylphenyl)-2,3-(dibutyl)diazobuta-1,3-diene]di(butyl)palladium; [1,4-bis(3-butylphenyl)-2-(butyl)-3-(hydrido)diazobuta-1,3-diene]di(hexacosyl)nickel; [1,4-bis(3-pentylphenyl)-2-(butyl)-3-(hydrido)diazobuta-1,3-diene]di(tridecyl)nickel; [1,4-bis(3-butylphenyl)-2-(butyl)-3-(hydrido)diazobuta-1,3-diene]di(ethyl)nickel; [1,4-bis(3-eicosylphenyl)-2,3-(dihydrido)diazobuta-1,3-diene]di(tetradecyl)nickel; [1,4-bis(3-ethylphenyl)-2-(hexyl)-3-(butyl)diazobuta-1,3-diene]di(butoxy)nickel; [1,4-bis(3-butylphenyl)-2-(hydrido)-3-(pentyl)diazobuta-1,3-diene]di(tricosyl)nickel; [1,4-bis(3-octylphenyl)-2-(butyl)-3-(pentyl)diazobuta-1,3-diene]di(dimethylamino)nickel; [1,4-bis(3-ethylphenyl)-2-(eicosynyl)-3-(butyl)diazobuta-1,3-diene]di(butyl)nickel; [1,4-bis(3-(trimethylsilylethyl) phenyl)-2-(hexyl)-3-(butyl)diazobuta-1,3-diene]di(phenethyl)nickel; [1,4-bis(3-butylphenyl)-2-(butyl)-3-(methyl)diazobuta-1,3-diene]di(undecyl)nickel; [1,4-bis(3-butylphenyl)-2-(octyl)-3-(hydrido)diazobuta-1,3-diene]di(hexacosyl)nickel; [1,4-bis(3-methyldiethylsilylmethyl)phenyl)-2-(butyl)-3-(heptynyl)diazobuta-1,3-diene]di(diethylamino)nickel; [1,4-bis(3-butylphenyl)-2-(octyl)-3-(hydrido)diazobuta-1,3-diene]di(methylethylamino)nickel; [1,4-bis(3-eicosynylphenyl)-2-(butyl)-3-(hexyl)diazobuta-1,3-diene]di(nonyl)palladium; [1,4-bis(3-butylphenyl)-2,3-(dibutyl)diazobuta-1,3-diene]di(methyl)nickel; [1,4-bis(3-butylphenyl)-2-(butyl)-3-(pentyl)diazobuta-1,3-diene]di(benzyl)nickel; [1,4-bis(3-pentylphenyl)-2-(butyl)-3-(pentyl)diazobuta-1,3-diene]di(hydrido)nickel; [1,4-bis(3-butylphenyl)-2-(butyl)-3-(tridecyl)diazobuta-1,3-diene]di(methylethylamino)nickel; [1,4-bis(3-pentylphenyl)-2-(pentadecenyl)-3-(hydrido)diazobuta-1,3-diene]di(ethyl)nickel; [1,4-bis(3-butylphenyl)-2,3-(dihydrido)diazobuta-1,3-diene]di(methyl)nickel; [1,4-bis(3-pentylphenyl)-2-(hydrido)-3-(butyl)diazobuta-1,3-diene]di(methyl)nickel; [1,4-bis(3-methylphenyl)-2-(butyl)-3-(hydrido)diazobuta-1,3-diene]di(nonacosenyl)palladium; [1,4-bis(3-butanalylphenyl)-2-(hexyl)-3-(butyl)diazobuta-1,3-diene]di(hexacosyl)nickel; [1,4-bis(3-methylphenyl)-2-(octyl)-3-(hydrido)diazobuta-1,3-diene]di(ethyl)nickel; [1,4-bis(3-octylphenyl)-2-(butyl)-3-(hydrido)diazobuta-1,3-diene]di(heptacosenyl)palladium; [1,4-bis(3-hexylphenyl)-2-(methyl)-3-(butyl)diazobuta-1,3-diene]di(heneicosyl)nickel; [1,4-bis(3-butylphenyl)-2-(butyl)-3-(methyl)diazobuta-1,3-diene]di(decyl)nickel; [1,4-bis(3-hexylphenyl)-2-(butyl)-3-(ethyl)diazobuta-1,3-diene]di(decyl)palladium; [1,4-bis(3-hexacosylphenyl)-2-(butyl)-3-(hydrido)diazobuta-1,3-diene]di(methyl)nickel; [1,4-bis(3-butylphenyl)-2-(octyl)-3-(butyl)diazobuta-1,3-diene]di(tetradecyl)nickel; [1,4-bis(3-octylphenyl)-2-(pentyl)-3-(butyl)diazobuta-1,3-diene]di(butyl)palladium; [1,4-bis(3-hexylphenyl)-2-(triacontynyl)-3-(undecynyl)diazobuta-1,3-diene]di(methyl)palladium; [1,4-bis(3-butylphenyl)-2-(ethyl)-3-(hydrido)diazobuta-1,3-diene]di(ethyl)nickel; [1,4-bis(3-ethylphenyl)-2-(methyl)-3-(pentyl)diazobuta-1,3-diene]di(ethyl)nickel; [1,4-bis(3-octylphenyl)-2-(undecyl)-3-(butyl)diazobuta-1,3-diene]di(ethyl)palladium; [1,4-bis(3-octylphenyl)-2-(undecyl)-3-(methyl)diazobuta-1,3-diene]di(methyl)nickel; [1,4-bis(3-butylphenyl)-2-(butyl)-3-(octyl)diazobuta-1,3-diene]di(ethyl)palladium; [1,4-bis(3-ethylphenyl)-2-(butyl)-3-(ethyl)diazobuta-1,3-diene]di(dodecyl)nickel; [1,4-bis(3-butylphenyl)-2-(methyl)-3-(butyl)diazobuta-1,3-diene]di(eicosyl)palladium; [1,4-bis(3-butylphenyl)-2-(pentyl)-3-(hexyl)diazobuta-1,3-diene]di(heneicosyl)nickel; [1,4-bis(3-pentylphenyl)-2-(decynyl)-3-(methyl)diazobuta-1,3-diene]di(chloro)nickel; [1,4-bis(3-hexylphenyl)-2-(hexyl)-3-(pentyl)diazobuta-1,3-diene]di(hydrido)nickel; [1,4-bis(3-octylphenyl)-2-(nonadecyl)-3-(hexyl)diazobuta-1,3-diene]di(decyl)nickel; [1,4-bis(3-pentylphenyl)-2,3-(dibutyl)diazobuta-1,3-diene]di(ethyl)nickel; [1,4-bis(3-butylphenyl)-2-(butyl)-3-(pentyl)diazobuta-1,3-diene]di(hexacosyl)nickel; [1,4-bis(3-butylphenyl)-2-(pentyl)-3-(hydrido)diazobuta-1,3-diene]di(ethyl)nickel; [1,4-bis(3-ethylphenyl)-2-(octyl)-3-(butyl)diazobuta-1,3-diene]di(phenethyl)nickel; [1,4-bis(3-methylphenyl)-2-(butyl)-3-(octyl)diazobuta-1,3-diene]di(propyl)palladium; [1,4-bis(3-butylphenyl)-2-(heptyl)-3-(hexyl)diazobuta-1,3-diene]di(butyl)nickel; [1,4-bis(3-butylphenyl)-2-(hydrido)-3-(butyl)diazobuta-1,3-diene]di(propoxy)nickel; [1,4-bis(3-hexylphenyl)-2-(octyl)-3-(hexenyl)diazobuta-1,3-diene]di(tridecyl)nickel; [1,4-bis(3-hexylphenyl)-2-(hydrido)-3-(butyl)diazobuta-1,3-diene]di(ethyl)nickel; [1,4-bis(3-butylphenyl)-2-(butyl)-3-(docosenyl)diazobuta-1,3-diene]di(docosyl)nickel; [1,4-bis(3-pentylphenyl)-2-(hydrido)-3-(pentadecyl)diazobuta-1,3-diene]di(allyl)palladium; [1,4-bis(3-butylphenyl)-2-(hexyl)-3-(pentyl)diazobuta-1,3-diene]di(hexadecyl)nickel; [1,4-bis(3-butylphenyl)-2,3-(dibutyl)diazobuta-1,3-diene]di(phenoxy)nickel; [1,4-bis(3-butylphenyl)-2-(butyl)-3-(hexyl)diazobuta-1,3-diene]di(ethyl)nickel; [1,4-bis(3-pentylphenyl)-2-(hexyl)-3-(pentacosenyl)diazobuta-1,3-diene]di(hexadecyl)nickel; [1,4-bis(3-butylphenyl)-2-(octadecyl)-3-(pentyl)diazobuta-1,3-diene]di(butyl)palladium; [1,4-bis(3-butylphenyl)-2,3-(dipentyl)diazobuta-1,3-diene]di(pentacosyl)nickel; [1,4-bis(3-methylphenyl)-2-

(hydrido)-3-(pentyl)diazobuta-1,3-diene]di(butyl)nickel; [1,4-bis(3-tetracosenylphenyl)-2-(heptacosynyl)-3-(butyl)diazobuta-1,3-diene]di(allyl)nickel; [1,4-bis(3-octylphenyl)-2,3-(dimethyl)diazobuta-1,3-diene]di(tolyl)nickel; [1,4-bis(3-octylphenyl)-2,3-(dibutyl)diazobuta-1,3-diene]di(docosyl)nickel; [1,4-bis(3-butylphenyl)-2-(hexyl)-3-(hydrido)diazobuta-1,3-diene]di(phenoxy)palladium; [1,4-bis(3-butylphenyl)-2-(ethyl)-3-(octyl)diazobuta-1,3-diene]di(methyl)nickel; [1,4-bis(3-butylphenyl)-2-(octyl)-3-(butyl)diazobuta-1,3-diene]di(butyl)nickel; [1,4-bis(3-octylphenyl)-2-(hydrido)-3-(octyl)diazobuta-1,3-diene]di(methylethylamino)nickel; [1,4-bis(3-pentylphenyl)-2-(octyl)-3-(butyl)diazobuta-1,3-diene]di(ethyl)nickel; [1,4-bis(3-ethylphenyl)-2-(butyl)-3-(octyl)diazobuta-1,3-diene]di(hydrido)nickel; [1,4-bis(3-butylphenyl)-2-(ethyl)-3-(butyl)diazobuta-1,3-diene]di(iodo)nickel; [1,4-bis(3-ethylphenyl)-2-(butyl)-3-(tetracosenyl)diazobuta-1,3-diene]di(butyl)palladium; [1,4-bis(3-pentylphenyl)-2,3-(dibutyl)diazobuta-1,3-diene]di(hydrido)palladium; [1,4-bis(3-butynylphenyl)-2-(pentyl)-3-(hydrido)diazobuta-1,3-diene]di(hydrido)nickel; [1,4-bis(3-ethylphenyl)-2-(butyl)-3-(eicosyl)diazobuta-1,3-diene]di(dimethylamino)nickel; [1,4-bis(3-butylphenyl)-2-(nonenyl)-3-(pentyl)diazobuta-1,3-diene]di(butyl)nickel; [1,4-bis(3-hexacosenylphenyl)-2,3-(dihydrido)diazobuta-1,3-diene]di(bromo)nickel; [1,4-bis(3-methylphenyl)-2-(hexyl)-3-(hydrido)diazobuta-1,3-diene]di(heptadecyl)nickel; [1,4-bis(3-hexylphenyl)-2-(octyl)-3-(butyl)diazobuta-1,3-diene]di(ethyl)palladium; [1,4-bis(3-butylphenyl)-2-(butyl)-3-(pentyl)diazobuta-1,3-diene]di(eicosyl)nickel; [1,4-bis(3-hexylphenyl)-2-(hexyl)-3-(methyl)diazobuta-1,3-diene]di(butyl)nickel; [1,4-bis(3-butylphenyl)-2,3-(dihydrido)diazobuta-1,3-diene]di(heptadecyl)palladium; [1,4-bis(3-hexylphenyl)-2-(hydrido)-3-(methyl)diazobuta-1,3-diene]di(butyl)nickel; [1,4-bis(3-butylphenyl)-2-(butyl)-3-(nonacosyl)diazobuta-1,3-diene]di(decenyl)nickel; [1,4-bis(3-tetracosylphenyl)-2-(hydrido)-3-(dodecyl)diazobuta-1,3-diene]di(tetradecyl)nickel; [1,4-bis(3-butylphenyl)-2-(hexyl)-3-(hydrido)diazobuta-1,3-diene]di(ethyl)nickel; [1,4-bis(3-octylphenyl)-2-(octyl)-3-(butyl)diazobuta-1,3-diene]di(butyl)nickel; [1,4-bis(3-pentylphenyl)-2-(pentacosyl)-3-(pentyl)diazobuta-1,3-diene]di(hydrido)nickel; [1,4-bis(3-triacontenylphenyl)-2-(hydrido)-3-(pentyl)diazobuta-1,3-diene]di(heptacosyl)nickel; [1,4-bis(3-butylphenyl)-2-(eicosynyl)-3-(butyl)diazobuta-1,3-diene]di(ethyl)nickel; [1,4-bis(3-butylphenyl)-2-(octyl)-3-(butyl)diazobuta-1,3-diene]di(methyl)nickel; [1,4-bis(3-butylphenyl)-2-(hydrido)-3-(butyl)diazobuta-1,3-diene]di(methylethylamino)nickel; [1,4-bis(3-hexylphenyl)-2,3-(dibutyl)diazobuta-1,3-diene]di(eicosynyl)nickel; [1,4-bis(3-butylphenyl)-2,3-(dibutyl)diazobuta-1,3-diene]di(diethylamino)nickel; [1,4-bis(3-butylphenyl)-2-(methyl)-3-(butyl)diazobuta-1,3-diene]di(benzyl)palladium; [1,4-bis(3-dodecylphenyl)-2-(butyl)-3-(hydrido)diazobuta-1,3-diene]di(pentadecyl)nickel; [1,4-bis(3-heneicosenylphenyl)-2-(pentyl)-3-(hydrido)diazobuta-1,3-diene]di(heptacosyl)nickel; [1,4-bis(3-butylphenyl)-2-(butyl)-3-(hexyl)diazobuta-1,3-diene]di(propoxy)nickel; [1,4-bis(3-octacosenylphenyl)-2-(hydrido)-3-(butyl)diazobuta-1,3-diene]di(butyl)nickel; [1,4-bis(3-methylphenyl)-2-(hydrido)-3-(octyl)diazobuta-1,3-diene]di(ethyl)nickel; [1,4-bis(3-pentylphenyl)-2,3-(dioctyl)diazobuta-1,3-diene]di(hydrido)palladium; [1,4-bis(3-butylphenyl)-2-(undecyl)-3-(triacontynyl)diazobuta-1,3-diene]di(phenyl)palladium; [1,4-bis(3-ethylphenyl)-2-(butyl)-3-(tetracosynyl)diazobuta-1,3-diene]di(propoxy)nickel; [1,4-bis(3-octylphenyl)-2-(hydrido)-3-(butyl)diazobuta-1,3-diene]di(hydride)palladium; [1,4-bis(3-pentylphenyl)-2-(hexyl)-3-(butyl)diazobuta-1,3-diene]di(methyl)nickel; [1,4-bis(3-octylphenyl)-2-(octyl)-3-(hydrido)diazobuta-1,3-diene]di(tricosyl)nickel; [1,4-bis(3-butylphenyl)-2-(docosenyl)-3-(butyl)diazobuta-1,3-diene]di(pentadecyl)palladium; [1,4-bis(3-hexylphenyl)-2,3-(dihydrido)diazobuta-1,3-diene]di(tolyl)nickel; [1,4-bis(3-butylphenyl)-2-(hexyl)-3-(hydrido)diazobuta-1,3-diene]di(nonadecyl)nickel; [1,4-bis(3-butylphenyl)-2-(pentacosynyl)-3-(hydrido)diazobuta-1,3-diene]di(undecyl)nickel; [1,4-bis(3-butylphenyl)-2-(hydrido)-3-(hexyl)diazobuta-1,3-diene]di(hydrido)nickel; [1,4-bis(3-butylphenyl)-2,3-(diethyl)diazobuta-1,3-diene]di(undecyl)palladium; [1,4-bis(3-butylphenyl)-2-(hexyl)-3-(ethyl)diazobuta-1,3-diene]di(tetradecyl)nickel; [1,4-bis(3-butylphenyl)-2,3-(dibutyl)diazobuta-1,3-diene]di(hydrido)nickel; [1,4-bis(3-octylphenyl)-2-(methyl)-3-(hexyl)diazobuta-1,3-diene]di(nonyl)nickel; [1,4-bis(3-pentylphenyl)-2-(octyl)-3-(butyl)diazobuta-1,3-diene]di(ethyl)palladium; [1,4-bis(3-ethylphenyl)-2-(butyl)-3-(hexyl)diazobuta-1,3-diene]di(dodecyl)nickel; [1,4-bis(3-ethylphenyl)-2-(ethyl)-3-(butyl)diazobuta-1,3-diene]di(octadecyl)nickel; [1,4-bis(3-nonynylphenyl)-2-(pentyl)-3-(hydrido)diazobuta-1,3-diene]di(hydrido)nickel; [1,4-bis(3-hexylphenyl)-2-(ethyl)-3-(methyl)diazobuta-1,3-diene]di(decyl)nickel; [1,4-bis(3-butylphenyl)-2-(butyl)-3-(octyl)diazobuta-1,3-diene]di(hydrido)nickel; [1,4-bis(3-butylphenyl)-2-(octadecenyl)-3-(hydrido)diazobuta-1,3-diene]di(dimethylamino)nickel; [1,4-bis(3-hexylphenyl)-2,3-(dibutyl)diazobuta-1,3-diene]di(hydrido)nickel; [1,4-bis(3-tridecynylphenyl)-2,3-(dihexyl)diazobuta-1,3-diene]di(hexacosyl)nickel; [1,4-bis(3-hexylphenyl)-2,3-(dibutyl)diazobuta-1,3-diene]di(hydrido)palladium; [1,4-bis(3-pentylphenyl)-2-(hydrido)-3-(butyl)diazobuta-1,3-diene]di(hexyl)nickel; [1,4-bis(3-methyldiethylsilylmethyl)phenyl)-2,3-(dibutyl)diazobuta-1,3-diene]di(tricosyl)nickel; [1,4-bis(3-butenylphenyl)-2-(tricosyl)-3-(hydrido)diazobuta-1,3-diene]di(iodo)palladium; [1,4-bis(3-octylphenyl)-2-(octacosyl)-3-(hydrido)diazobuta-1,3-diene]di(ethyl)nickel; [1,4-bis(3-hexylphenyl)-2,3-(dibutyl)diazobuta-1,3-diene]di(tolyl)palladium; [1,4-bis(3-hexylphenyl)-2-(octyl)-3-(butyl)diazobuta-1,3-diene]di(hexadecyl)nickel; [1,4-bis(3-butylphenyl)-2-(tetracosynyl)-3-(hydrido)diazobuta-1,3-diene]di(hydrido)nickel; [1,4-bis(3-pentylphenyl)-2-(butyl)-3-(methyl)diazobuta-1,3-diene]di(ethyl)nickel; [1,4-bis(3-butylphenyl)-2,3-(dibutyl)diazobuta-1,3-diene]di(iodo)palladium; [1,4-bis(3-butylphenyl)-2-(triacontyl)-3-(butyl)diazobuta-1,3-diene]di(hydrido)nickel; [1,4-bis(3-pentylphenyl)-2-(pentyl)-3-(hexyl)diazobuta-1,3-diene]di(methyl)nickel; [1,4-bis(3-butylphenyl)-2-(propynyl)-3-(hydrido)diazobuta-1,3-diene]di(bromo)nickel; [1,4-bis(3-butylphenyl)-2-(hydrido)-3-(methyl)diazobuta-1,3-diene]di(tridecyl)nickel; [1,4-bis(3-pentylphenyl)-2-(butynyl)-3-(pentyl)diazobuta-1,3-diene]di(tricosyl)nickel; [1,4-bis(3-butylphenyl)-2-(butyl)-3-(tricosyl)diazobuta-1,3-diene]di(propyl)nickel; [1,4-bis(3-hexylphenyl)-2-(butyl)-3-(octyl)diazobuta-1,3-diene]di(methylethylamino)nickel; [1,4-bis(3-pentynylphenyl)-2,3-(dibutyl)diazobuta-1,3-diene]di(nonacosyl)palladium; [1,4-bis(3-pentylphenyl)-2-(heptadecynyl)-3-(butyl)diazobuta-1,3-diene]di(heptacosyl)nickel; [1,4-bis(3-octylphenyl)-2-(hydrido)-3-(butyl)diazobuta-1,3-diene]di(hydrido)nickel; [1,4-bis(3-pentylphenyl)-2-(hexyl)-3-(octyl)diazobuta-1,3-diene]di(hydrido)palladium; [1,4-bis(3-hexylphenyl)-2-(heneicosenyl)-3-(hydrido)diazobuta-1,3-diene]di(hydrido)nickel; [1,4-bis(3-pentylphenyl)-2-(octyl)-3-(pentyl)diazobuta-1,3-diene]di(methyl)nickel; [1,4-bis(3-pentylphenyl)-2-(octyl)-3-(hexacosynyl)diazobuta-1,3-diene]di(ethyl)palladium; [1,4-bis(3-ethylphenyl)-2-

(hydrido)-3-(pentyl)diazobuta-1,3-diene]di(pentadecyl) nickel; [1,4-bis(3-butylphenyl)-2-(hexyl)-3-(hydrido) diazobuta-1,3-diene]di(phenyl)nickel; [1,4-bis(3-hexylphenyl)-2-(octyl)-3-(butyl)diazobuta-1,3-diene]di (butyl)nickel; [1,4-bis(3-butylphenyl)-2-(butyl)-3-(ethyl) diazobuta-1,3-diene]di(allyl)nickel; [1,4-bis(3-butylphenyl)-2-(octyl)-3-(heneicosenyl)diazobuta-1,3-diene]di(ethyl)nickel; [1,4-bis(3-butylphenyl)-2-(hexyl)-3-(octyl)diazobuta-1,3-diene]di(heptacosyl)nickel; [1,4-bis(3-butylphenyl)-2,3-(dihydrido)diazobuta-1,3-diene]di (nonacosyl)nickel; [1,4-bis(3-pentylphenyl)-2-(hydrido)-3-(butyl)diazobuta-1,3-diene]di(propoxy)nickel; [1,4-bis(3-butylphenyl)-2-(butyl)-3-(pentyl)diazobuta-1,3-diene]di (methoxy)nickel; [1,4-bis(3-ethylphenyl)-2,3-(dipentyl) diazobuta-1,3-diene]di(tolyl)palladium; [1,4-bis(3-butylphenyl)-2-(octyl)-3-(butyl)diazobuta-1,3-diene]di (methylethylamino)palladium; [1,4-bis(3-pentacosenylphenyl)-2,3-(dibutyl)diazobuta-1,3-diene]di (pentacosyl)nickel; [1,4-bis(3-hexylphenyl)-2-(pentyl)-3-(butyl)diazobuta-1,3-diene]di(methyl)nickel; [1,4-bis(3-butylphenyl)-2,3-(dipentyl)diazobuta-1,3-diene]di(methyl) palladium; [1,4-bis(3-butylphenyl)-2-(pentyl)-3-(butyl) diazobuta-1,3-diene]di(hexacosyl)palladium; [1,4-bis(3-butylphenyl)-2-(butyl)-3-(pentyl)diazobuta-1,3-diene]di (butyl)nickel; [1,4-bis(3-butylphenyl)-2-(butyl)3-(nonacosyl)diazobuta-1,3-diene]di(ethyl)nickel; [1,4-bis(3-heptadecylphenyl)2-(hydrido)-3-(butyl)diazobuta-1,3-diene]di(methyl)nickel; [1,4-bis(3-methylphenyl)-2-(decyl)-3-(butyl)diazobuta-1,3-diene]di(ethyl)palladium; [1,4-bis(3-butylphenyl)-2-(octyl)-3-(butyl)diazobuta-1,3-diene]di(hydrido)nickel; [1,4-bis(3-butylphenyl)-2-(pentyl)3-(hydrido)diazobuta-1,3-diene]di(hexyl)nickel; [1,4-bis(3-ethylphenyl)-2,3-(dioctyl)diazobuta-1,3-diene]di(heptyl) nickel; [1,4-bis(3-octylphenyl)-2-(hexyl)-3-(butyl) diazobuta-1,3-diene]di(hydrido)nickel; [1,4-bis(3-butylphenyl)-2,3-(dihydrido)diazobuta-1,3-diene]di (diethylamino)palladium; [1,4-bis(3-butylphenyl)-2-(hydrido)-3-(butyl)diazobuta-1,3-diene]di(undecenyl) palladium; [1,4-bis(3-butylphenyl)-2-(octenyl)-3-(hydrido) diazobuta-1,3-diene]di(methyl)nickel; [1,4-bis(3-triacontynylphenyl)-2-(pentyl)-3-(hydrido)diazobuta-1,3-diene]di(phenyl)palladium; [1,4-bis(3-hexylphenyl)-2-(pentyl)-3-(hydrido)diazobuta-1,3-diene]di(methoxy) nickel; [1,4-bis(3-ethylphenyl)-2-(methyl)-3-(octyl) diazobuta-1,3-diene]di(butyl)nickel; [1,4-bis(3-ethylphenyl)-2,3-(dihydrido)diazobuta-1,3-diene]di (benzoxy)nickel; [1,4-bis(3-butylphenyl)-2,3-(dibutyl) diazobuta-1,3-diene]di(heptadecenyl)nickel; [1,4-bis(3-butylphenyl)-2-(butyl)-3-(hydrido)diazobuta-1,3-diene]di (ethyl)nickel; [1,4-bis(3-butylphenyl)-2-(butyl)-3-(hydrido) diazobuta-1,3-diene]di(chloro)nickel; [1,4-bis(3-pentylphenyl)-2-(butyl)-3-(hexyl)diazobuta-1,3-diene]di (butyl)nickel; [1,4-bis(3-methylphenyl)-2-(methyl)-3-(hydrido)diazobuta-1,3-diene]di(diethylamino)nickel; [1,4-bis(3-butylphenyl)-2-(hydrido)-3-(butyl)diazobuta-1,3-diene]di(hydrido)nickel; [1,4-bis(3-dodecanonylphenyl)-2-(butyl)-3-(dodecyl)diazobuta-1,3-diene]di(hexyl)palladium; [1,4-bis(3-ethylphenyl)-2-(butyl)-3-(pentadecyl)diazobuta-1,3-diene]di(heptacosenyl)nickel; [1,4-bis(3-butylphenyl)-2-(octyl)-3-(butyl)diazobuta-1,3-diene]di(hexacosyl)nickel; [1,4-bis(3-butylphenyl)-2-(hexadecynyl)-3-(butyl)diazobuta-1,3-diene]di(nonadecyl)nickel; [1,4-bis(3-octylphenyl)-2-(hexyl)-3-(hydrido)diazobuta-1,3-diene]di(nonyl) nickel; [1,4-bis(3-butylphenyl)-2-(butyl)-3-(hydrido) diazobuta-1,3-diene]di(hydrido)nickel; [1,4-bis(3-butylphenyl)-2-(ethyl)-3-(hydrido)diazobuta-1,3-diene]di (hydrido)nickel; [1,4-bis(3-butylphenyl)-2-(hydrido)-3-(butyl)diazobuta-1,3-diene]di(hydrido)palladium; [1,4-bis (3-octylphenyl)-2,3-(dibutyl)diazobuta-1,3-diene]di (hexadecyl)nickel; [1,4-bis(3-butylphenyl)-2-(ethyl)-3-(butyl)diazobuta-1,3-diene]di(pentyl)nickel; [1,4-bis(3-pentylphenyl)-2-(octyl)-3-(hydrido)diazobuta-1,3-diene]di (ethyl)nickel; [1,4-bis(3-butylphenyl)-2,3-(dihydrido) diazobuta-1,3-diene]di(propyl)nickel; [1,4-bis(3-butylphenyl)-2-(ethyl)-3-(tetradecenyl)diazobuta-1,3-diene] di(butyl)nickel; [1,4-bis(3-butylphenyl)-2-(pentyl)-3-(hydrido)diazobuta-1,3-diene]di(propoxy)nickel; [1,4-bis (3-butylphenyl)-2-(tridecenyl)-3-(methyl)diazobuta-1,3-diene]di(eicosyl)nickel; [1,4-bis(3-butylphenyl)-2-(butyl)-3-(octyl)diazobuta-1,3-diene]di(phenoxy)nickel; [1,4-bis(3-nonylphenyl)-2-(butyl)-3-(octyl)diazobuta-1,3-diene]di (dodecyl)nickel; [1,4-bis(3-butylphenyl)-2-(hexyl)-3-(butyl)diazobuta-1,3-diene]di(butoxy)nickel; [1,4-bis(3,4,5-triethylphenyl)-2-(hydrido)-3-(butyl)diazobuta-1,3-diene]di (methyl)nickel; [1,4-bis(3,4,5-trihexylphenyl)-2,3-(dibutyl) diazobuta-1,3-diene]di(hydrido)nickel; [1,4-bis(3,4,5-triethylphenyl)-2-(pentyl)-3-(octyl)diazobuta-1,3-diene]di (benzyl)nickel; [1,4-bis(3,4,5-tributylphenyl)-2-(hexyl)-3-(pentyl)diazobuta-1,3-diene]di(benzoxy)nickel; [1,4-bis(3, 4,5-trihexylphenyl)-2-(ethyl)-3-(eicosyl)diazobuta-1,3-diene]di(tetracosyl)nickel; [1,4-bis(3,4,5-tributylphenyl)-2, 3-(dibutyl)diazobuta-1,3-diene]di(pentyl)palladium; [1,4-bis(3,4,5-trihexylphenyl)-2-(butyl)-3-(octacosenyl) diazobuta-1,3-diene]di(tridecynyl)palladium; [1,4-bis(3,4, 5-tributylphenyl)-2-(hydrido)-3-(butyl)diazobuta-1,3-diene] di(tetracosyl)nickel; [1,4-bis(3,4,5-triethanalylphenyl)-2-(pentyl)-3-(butyl)diazobuta-1,3-diene]di(hydrido)nickel; [1,4-bis(3,4,5-trihexylphenyl)-2-(butyl)-3-(hydrido)diazobuta-1,3-diene]di(methyl)nickel; [1,4-bis(3,4,5-trihexylphenyl)-2-(hydrido)-3-(hexyl)diazobuta-1,3-diene]di(diethylamino)nickel; [1,4-bis(3,4,5-tripropylphenyl)-2-(hydrido)-3-(butyl)diazobuta-1,3-diene]di(hydrido) palladium; [1,4-bis(3,4,5-triethylphenyl)-2,3-(dihydrido) diazobuta-1,3-diene]di(hexadecyl)palladium; [1,4-bis(3,4, 5-tributylphenyl)-2-(undecenyl)-3-(hydrido)diazobuta-1,3-diene]di(nonacosyl)nickel; [1,4-bis(3,4,5-tributylphenyl)-2, 3-(dihydrido)diazobuta-1,3-diene]di(ethyl)nickel; [1,4-bis (3,4,5-trimethylphenyl)-2-(butyl)-3-(pentyl)diazobuta-1,3-diene]di(eicosyl)nickel; [1,4-bis(3,4,5-trihexylphenyl)-2-(butyl)-3-(hydrido)diazobuta-1,3-diene]di(hexadecyl) nickel; [1,4-bis(3,4,5-tripropylphenyl)-2-(pentyl)-3-(butyl) diazobuta-1,3-diene]di(butyl)nickel; [1,4-bis(3,4,5-trihexylphenyl)-2-(pentyl)-3-(hydrido)diazobuta-1,3-diene] di(heneicosyl)nickel; [1,4-bis(3,4,5-trimethylphenyl)-2-(octadecynyl)-3-(metbyl)diazobuta-1,3-diene]di(ethoxy) nickel; [1,4-bis(3,4,5-tripropylphenyl)-2-(heptynyl)-3-(butyl)diazobuta-1,3-diene]di(pentacosyl)nickel; [1,4-bis(3, 4,5-tripentylphenyl)-2-(hydrido)-3-(hexyl)diazobuta-1,3-diene]di(butyl)nickel; [1,4-bis(3,4,5-tripropylphenyl)-2-(hexyl)-3-(hydrido)diazobuta-1,3-diene]di(undecyl)nickel; [1,4-bis(3,4,5-tripentylphenyl)-2-(pentyl)-3-(hydrido)diazobuta-1,3-diene]di(ethyl)nickel; [1,4-bis(3,4,5-trihexylphenyl)-2,3-(dihexyl)diazobuta-1,3-diene]di(propyl)nickel; [1,4-bis(3,4,5-tripentylphenyt)-2-(hydrido)-3-(pentyl)diazobuta-1,3-diene]di(allyl)palladium; [1,4-bis(3,4,5-triethylphenyl)-2-(hydrido)-3-(butyl)diazobuta-1,3-diene]di(undecyl)nickel; [1,4-bis(3,4,5-tripentylphenyl)-2,3-(dibutyl) diazobuta-1,3-diene]di(methyl)nickel; [1,4-bis(3,4,5-tripentylphenyl)-2-(butyl)-3-(heptacosenyl)diazobuta-1,3-diene]di(ethyl)nickel; [1,4-bis(3,4,5-triethylphenyl)-2-(butyl)-3-(hexyl)diazobuta-1,3-diene]di(hexadecyl) palladium; [1,4-bis(3,4,5-tributylphenyl)-2,3-(dibutyl) diazobuta-1,3-diene]di(hydrido)nickel; [1,4-bis(3,4,5-tripentylphenyl)-2,3(dihydrido)diazobuta-1,3-diene]di (butyl)nickel; [1,4-bis(3,4,5-tributylphenyl)-2,3-(dibutyl) diazobuta-1,3-diene]di(triacontyl)nickel; [1,4-bis(3,4,5-tripentylphenyl)-2-(methyl)-3-(pentyl)diazobuta-1,3-diene] di(butoxy)nickel; [1,4-bis(3,4,5-trihexylphenyl)-2-(butyl)-3-(octyl)diazobuta-1,3-diene]di(methyl)nickel; [1,4-bis(3,4,5-tributylphenyl)-2-(butyl)-3-(pentyl)diazobuta-1,3-diene] di(methylethylamino)nickel; [1,4-bis(3,4,5-tripentylphenyl)-2-(hydrido)-3-(octyl)diazobuta-1,3-diene] di(ethoxy)nickel; [1,4-bis(3,4,5-trimethylphenyl)-2-(dodecenyl)-3-(butyl)diazobuta-1,3-diene]di(hydrido) nickel; [1,4-bis(3,4,5-tributylphenyl)-2-(butyl)-3-(pentyl) diazobuta-1,3-diene]di(ethyl)palladium; [1,4-bis(3,4,5-tripropylphenyl)-2-(pentyl)-3-(butyl)diazobuta-1,3-diene]di (docosyl)palladium; [1,4-bis(3,4,5-tributylphenyl)-2,3-(dibutyl)diazobuta-1,3-diene]di(tetradecyl)nickel; [1,4-bis(3,4,5-triethylphenyl)-2-(methyl)-3-(butyl)diazobuta-1,3-diene]di(ethyl)nickel; [1,4-bis(3,4,5-tributylphenyl)-2-(butyl)-3-(hydrido)diazobuta-1,3-diene]di(benzyl)nickel; [1,4-bis(3,4,5-trihexylphenyl)-2-(butyl)-3-(hexyl)diazobuta-1,3-diene]di(hexacosyl)nickel; [1,4-bis(3,4,5-trihexylphenyl)-2-(butyl)-3-(hexyl)diazobuta-1,3-diene]di(methyl) nickel; [1,4-bis(3,4,5-tripentylphenyl)-2-(butyl)-3-(hydrido) diazobuta-1,3-diene]di(propoxy)nickel; [1,4-bis(3,4,5-trimethylphenyl)-2-(pentacosyl)-3-(heptadecenyl) diazobuta-1,3-diene]di(ethyl)nickel; [1,4-bis(3,4,5-triethylphenyl)-2-(octyl)-3-(butyl)diazobuta-1,3-diene]di (hydrido)nickel; [1,4-bis(3,4,5-trimethylphenyl)-2-(hydrido)-3-(butyl)diazobuta-1,3-diene]di(butyl)nickel; [1,4-bis(3,4,5-trihexylphenyl)-2-(hexyl)-3-(butyl)diazobuta-1,3-diene]di(methyl)nickel; [1,4-bis(3,4,5-triethylphenyl)-2-(hexyl)-3-(octyl)diazobuta-1,3-diene]di(methyl)nickel; [1,4-bis(3,4,5-tributylphenyl)-2-(pentyl)-3-(ethyl)diazobuta-1,3-diene]di(benzoxy)nickel; [1,4-bis(3,4,5-tributylphenyl)-2-(butyl)-3-(octyl)diazobuta-1,3-diene]di (ethyl)nickel; [1,4-bis(3,4,5-tributylphenyl)-2-(hydrido)-3-(butyl)diazobuta-1,3-diene]di(dodecyl)nickel; [1,4-bis(3,4,5-trihexylphenyl)-2,3-(dibutyl)diazobuta-1,3-diene]di (octadecyl)nickel; [1,4-bis(3,4,5-tripropylphenyl)-2-(hexyl)-3-(methyl)diazobuta-1,3-diene]di(pentynyl) palladium; [1,4-bis(3,4,5-trihexylphenyl)-2-(hexyl)-3-(hydrido)diazobuta-1,3-diene]di(bromo)palladium; [1,4-bis(3,4,5-tripentylphenyl)-2-(butyl)-3-(hydrido)diazobuta-1,3-diene]di(nonadecyl)nickel; [1,4-bis(3,4,5-tributylphenyl)-2,3-(dibutyl)diazobuta-1,3-diene]di(butyl)nickel; [1,4-bis(3,4,5-tributylphenyl)-2-(butyl)-3-(hydrido)diazobuta-1,3-diene] di(dimethylamino)palladium; [1,4-bis(3,4,5-tripropylphenyl)-2,3-(dibutyl)diazobuta-1,3-diene]di (hydrido)nickel; [1,4-bis(3,4,5-tributylphenyl)-2-(octenyl)-3-(hexyl)diazobuta-1,3-diene]di(benzyl)nickel; [1,4-bis(3,4,5-trihexylphenyl)-2-(heptynyl)-3-(hydrido)diazobuta-1,3-diene]di(ethyl)nickel; [1,4-bis(3,4,5-tributylphenyl)-2-(butyl)-3-(octyl)diazobuta-1,3-diene]di(ethyl)nickel; [1,4-bis(3,4,5-tributylphenyl)-2,3-(dibutyl)diazobuta-1,3-diene] di(hydrido)palladium; [1,4-bis(3,4,5-triethylphenyl)-2-(butyl)-3-(pentyl)diazobuta-1,3-diene]di(ethyl)palladium; [1,4-bis(3,4,5-tributylphenyl)-2,3-(dihexyl)diazobuta-1,3-diene]di(nonadecyl)palladium; [1,4-bis(3,4,5-triethylphenyl)-2-(butyl)-3-(octyl)diazobuta-1,3-diene]di(benzoxy) nickel; [1,4-bis(3,4,5-tripentylphenyl)2-(hexyl)-3-(undecynyl)diazobuta-1,3-diene]di(iodo)nickel; [1,4-bis(3,4,5-tripropylphenyl)-2-(butyl)-3-(tetracosenyl)diazobuta-1,3-diene]di(dimethylamino)palladium; [1,4-bis(3,4,5-tripentylphenyl)-2-(hydrido)-3-(pentacosenyl)diazobuta-1,3-diene]di(pentadecyl)nickel; [1,4-bis(3,4,5-triethylphenyl)-2-(hexyl)-3-(butyl)diazobuta-1,3-diene]di (butoxy)palladium; [1,4-bis(3,4,5-trihexylphenyl)-2-(octyl)-3-(hexyl)diazobuta-1,3-diene]di(methyl)palladium; [1,4-bis(3,4,5-tributylphenyl)-2-(butyl)-3-(octyl)diazobuta-1,3-diene]di(hydrido)nickel; [1,4-bis(3,4,5-tributylphenyl)-2-(octyl)-3-(hexyl)diazobuta-1,3-diene]di(nonadecyl)nickel; [1,4-bis(3,4,5-tributylphenyl)-2-(dodecenyl)-3-(butyl)diazobuta-1,3-diene]di(undecyl)nickel; [1,4-bis(3,4,5-tributylphenyl)-2-(butyl)-3-(hydrido)diazobuta-1,3-diene]di (iodo)nickel; [1,4-bis(3,4,5-triethylphenyl)-2-(hydrido)-3-(butyl)diazobuta-1,3-diene]di(butoxy)nickel; [1,4-bis(3,4,5-tributylphenyl)-2-(butyl)-3-(octyl)diazobuta-1,3-diene]di (nonyl)nickel; [1,4-bis(3,4,5-tripentylphenyl)-2-(tricosynyl)-3-(butyl)diazobuta-1,3-diene]di(benzyl)nickel; [1,4-bis(3,4,5-triethylphenyl)-2-(hydrido)-3-(butyl)diazobuta-1,3-diene]di(propoxy)palladium; [1,4-bis(3,4,5-tripropylphenyl)-2-(hexadecenyl)-3-(hydrido)diazobuta-1,3-diene]di(ethyl)nickel; [1,4-bis(3,4,5-tripropylphenyl)-2-(hexyl)-3-(nonenyl)diazobuta-1,3-diene]di(undecyl)nickel; [1,4-bis(3,4,5-tributylphenyl)-2-(tricosyl)-3-(butyl)diazobuta-1,3-diene]di(benzyl)palladium; [1,4-bis(3,4,5-tripropylphenyl)-2-(pentyl)-3-(hydrido)diazobuta-1,3-diene]di (tridecyl)nickel; [1,4-bis(3,4,5-trimethylphenyl)-2-(butyl)-3-(hydrido)diazobuta-1,3-diene]di(methoxy)nickel; [1,4-bis(3,4,5-trihexylphenyl)-2-(butyl)-3-(pentynyl)diazobuta-1,3-diene]di(tetracosyl)palladium; [1,4-bis(3,4,5-triethylphenyl)-2-(hexyl)-3-(butyl)diazobuta-1,3-diene]di (hydrido)nickel; [1,4-bis(3,4,5-triethylphenyl)-2-(octadecyl)-3-(butyl)diazobuta-1,3-diene]di(decyl)nickel; [1,4-bis(3,4,5-triethylphenyl)-2,3-(dibutyl)diazobuta-1,3-diene]di(heptadecyl)palladium; [1,4-bis(3,4,5-tripentylphenyl)-2-(butyl)-3-(hexadecynyl)diazobuta-1,3-diene]di(butyl)palladium; [1,4-bis(3,4,5-triethylphenyl)-2-(hydrido)-3-(butyl)diazobuta-1,3-diene]di(methyl)nickel; [1,4-bis(3,4,5-tripropylphenyl)-2,3-(dihexyl)diazobuta-1,3-diene]di (hydrido)nickel; [1,4-bis(3,4,5-triethylphenyl)-2-(hexyl)-3-(butyl)diazobuta-1,3-diene]di(phenoxy)nickel; [1,4-bis(3,4,5-trimethylphenyl)-2-(octyl)-3-(butyl)diazobuta-1,3-diene] di(ethyl)nickel; [1,4-bis(3,4,5-trihexylphenyl)-2-(hexyl)-3-(butyl)diazobuta-1,3-diene]di(heneicosyl)nickel; [1,4-bis(3,4,5-tributylphenyl)-2-(hydrido)-3-(butyl)diazobuta-1,3-diene]di(methyl)nickel; [1,4-bis(3,4,5-tributylphenyl)-2-(heneicosyl)-3-(octyl)diazobuta-1,3-diene]di(allyl)nickel; [1,4-bis(3,4,5-tripropylphenyl)-2-(butyl)-3-(hexyl)diazobuta-1,3-diene]di(hexacosyl)nickel; [1,4-bis(3,4,5-tripentylphenyl)-2-(hydrido)-3-(pentyl)diazobuta-1,3-diene]di (tetradecyl)nickel; [1,4-bis(3,4,5-tributylphenyl)-2-(hexyl)-3-(butyl)diazobuta-1,3-diene]di(tridecyl)nickel; [1,4-bis(3,4,5-triethylphenyl)-2-(butyl)-3-(octyl)diazobuta-1,3-diene] di(tetradecyl)nickel; [1,4-bis(3,4,5-tributylphenyl)-2-(octyl)-3-(decynyl)diazobuta-1,3-diene]di(tolyl)nickel; [1,4-bis(3,4,5-trimethylphenyl)-2,3-(dihydrido)diazobuta-1,3-diene]di(tolyl)nickel; [1,4-bis(3,4,5-tripentylphenyl)-2-(hydrido)-3-(octadecyl)diazobuta-1,3-diene]di(butoxy) nickel; [1,4-bis(3,4,5-tripentylphenyl)-2-(heptacosynyl)-3-(hydrido)diazobuta-1,3-diene]di(hydrido)palladium; [1,4-bis(3,4,5-trihexylphenyl)-2-(butyl)-3-(ethyl)diazobuta-1,3-diene]di(heptadecyl)nickel; [1,4-bis(3,4,5-trimethylphenyl)-2-(hexyl)-3-(butyl)diazobuta-1,3-diene]di(ethyl)nickel; [1,4-bis(3,4,5-tributylphenyl)-2,3-(dihexyl)diazobuta-1,3-diene]di(butyl)nickel; [1,4-bis(3,4,5-trimethylphenyl)-2-(hydrido)-3-(hexyl)diazobuta-1,3-diene]di(hydrido)nickel; [1,4-bis(3,4,5-trimethylphenyl)-2,3-(dibutyl)diazobuta-1,3-diene]di(hexacosyl)nickel; [1,4-bis(3,4,5-tripentylphenyl)-2-(hydrido)-3-(propyl)diazobuta-1,3-diene]di(butyl)nickel; [1,4-bis(3,4,5-trimethylphenyl)-2-(ethyl)-3-(butyl)diazobuta-1,3-diene]di(hydrido)nickel; [1,4-bis(3,4,5-tripropylphenyl)-2-(butyl)-3-(ethyl)diazobuta-1,3-diene]di(methyl) nickel; [1,4-bis(3,4,5-tripropylphenyl)-2-(hydrido)-3-(butyl)diazobuta-1,3-diene]di(ethyl)palladium; [1,4-bis(3,4, 5-tripentylphenyl)-2-(butyl)-3-(hydrido)diazobuta-1,3-diene]di(ethyl)nickel; [1,4-bis(3,4,5-tributylphenyl)-2,3-(dibutyl)diazobuta-1,3-diene]di(dodecyl)nickel; [1,4-bis(3,4,5-trihexylphenyl)-2-(butyl)-3-(hydrido)diazobuta-1,3-diene]di(methyl)palladium; [1,4-bis(3,4,5-trimethylphenyl)-2-(hydrido)-3-(pentyl)diazobuta-1,3-diene]di(hydrido)nickel; [1,4-bis(3,4,5-triethylphenyl)-2-(hydrido)-3-(pentyl)diazobuta-1,3-diene]di(hydrido)nickel; [1,4-bis(3,4,5-tripentylphenyl)-2-(butyl)-3-(methyl)diazobuta-1,3-diene]di(butoxy)palladium; [1,4-bis(3,4,5-trihexylphenyl)-2,3-(dibutyl)diazobuta-1,3-diene]di(eicosyl)nickel; [1,4-bis(3,4,5-tripropylphenyl)-2,3-(dibutyl)diazobuta-1,3-diene]di(chloro)nickel; [1,4-bis(3,4,5-tributylphenyl)-2-(butyl)-3-(octyl)diazobuta-1,3-diene]di(octyl)nickel; [1,4-bis(3,4,5-tripropylphenyl)-2-(pentyl)-3-(hydrido)diazobuta-1,3-diene]di(dodecyl)nickel; [1,4-bis(3,4,5-tributylphenyl)-2-(heptadecenyl)-3-(butynyl)diazobuta-1,3-diene]di(tetracosenyl)palladium; [1,4-bis(3,4,5-triethylphenyl)-2-(hydrido)-3-(butyl)diazobuta-1,3-diene]di(butyl)nickel; [1,4-bis(3,4,5-tributylphenyl)-2-(pentyl)-3-(methyl)diazobuta-1,3-diene]di(methyl)nickel; [1,4-bis(3,4,5-tributylphenyl)-2-(hydrido)-3-(pentadecyl)diazobuta-1,3-diene]di(nonadecyl)palladium; [1,4-bis(3,4,5-tripropylphenyl)-2-(hexyl)-3-(butyl)diazobuta-1,3-diene]di(hexadecyl)nickel; [1,4-bis(3,4,5-triethylphenyl)-2,3-(dioctyl)diazobuta-1,3-diene]di(benzoxy)nickel; [1,4-bis(3,4,5-tributylphenyl)-2-(hydrido)-3-(hexyl)diazobuta-1,3-diene]di(propoxy)nickel; [1,4-bis(3,4,5-tributylphenyl)-2-(hexyl)-3-(ethyl)diazobuta-1,3-diene]di(octacosyl)palladium; [1,4-bis(3,4,5-tributylphenyl)-2-(hydrido)-3-(octyl)diazobuta-1,3-diene]di(eicosyl)nickel; [1,4-bis(3,4,5-tripropylphenyl)-2,3-(dihexyl)diazobuta-1,3-diene]di(benzoxy)palladium; [1,4-bis(3,4,5-tripropanalylphenyl)-2-(hexyl)-3-(butyl)diazobuta-1,3-diene]di(pentadecynyl)palladium; [1,4-bis(3,4,5-trihexylphenyl)-2-(methyl)-3-(butyl)diazobuta-1,3-diene]di(hydrido)nickel; [1,4-bis(3,4,5-tripropylphenyl)-2,3-(dibutyl)diazobuta-1,3-diene]di(decyl)nickel; [1,4-bis(3,4,5-tripentylphenyl)-2-(butyl)-3-(pentyl)diazobuta-1,3-diene]di(iodo)palladium; [1,4-bis(3,4,5-trimethylphenyl)-2-(hydrido)-3-(butyl)diazobuta-1,3-diene]di(hydrido)palladium; [1,4-bis(3,4,5-tributylphenyl)-2,3-(dibutyl)diazobuta-1,3-diene]di(methyl)palladium; [1,4-bis(3,4,5-tripropylphenyl)-2-(butyl)-3-(pentyl)diazobuta-1,3-diene]di(ethyl)palladium; [1,4-bis(3,4,5-triethylphenyl)-2,3-(dihydrido)diazobuta-1,3-diene]di(decyl)palladium; [1,4-bis(3,4,5-tributylphenyl)-2-(hexyl)-3-(butyl)diazobuta-1,3-diene]di(docosyl)palladium; [1,4-bis(3,4,5-trihexylphenyl)-2-(hexyl)-3-(ethyl)diazobuta-1,3-diene]di(hydrido)nickel; [1,4-bis(3,4,5-tripropylphenyl)-2-(butyl)-3-(hexyl)diazobuta-1,3-diene]di(pentadecyl)nickel; [1,4-bis(3,4,5-trihexylphenyl)-2-(heneicosyl)-3-(hydrido)diazobuta-1,3-diene]di(dimethylamino)palladium; [1,4-bis(3,4,5-tributylphenyl)-2-(butyl)-3-(hydrido)diazobuta-1,3-diene]di(diethylamino)palladium; [1,4-bis(3,4,5-trihexylphenyl)-2-(pentyl)-3-(hydrido)diazobuta-1,3-diene]di(hydrido)nickel; [1,4-bis(3,4,5-tributylphenyl)-2-(butyl)-3-(methyl)diazobuta-1,3-diene]di(butyl)palladium; [1,4-bis(3,4,5-tributylphenyl)-2-(heptyl)-3-(hexyl)diazobuta-1,3-diene]di(undecyl)nickel; [1,4-bis(3,4,5-trimethylphenyl)-2-(hexyl)-3-(hydrido)diazobuta-1,3-diene]di(octadecyl)nickel; [1,4-bis(3,4,5-tributylphenyl)-2-(pentyl)-3-(hexyl)diazobuta-1,3-diene]di(octyl)palladium; [1,4-bis(3,4,5-tripentylphenyl)-2,3-(dibutyl)diazobuta-1,3-diene]di(phenethyl)palladium; [1,4-bis(3,4,5-triethylphenyl)-2,3-(dibutyl)-3-(butyl)diazobuta-1,3-diene]di(hydrido)nickel; [1,4-bis(3,4,5-tripentylphenyl)-2-(methyl)-3-(hexyl)diazobuta-1,3-diene]di(pentacosyl)nickel; [1,4-bis(3,4,5-tributylphenyl)-2-(hydrido)-3-(butyl)diazobuta-1,3-diene]di(nonadecyl)palladium; [1,4-bis(3,4,5-tributylphenyl)-2-(pentyl)-3-(decenyl)diazobuta-1,3-diene]di(methyl)nickel; [1,4-bis(3,4,5-tributylphenyl)-2,3-(dibutyl)diazobuta-1,3-diene]di(heptyl)nickel; [1,4-bis(3,4,5-tributylphenyl)-2,3-(dihydrido)diazobuta-1,3-diene]di(methyl)palladium; [1,4-bis(3,4,5-tributylphenyl)-2-(pentyl)-3-(butyl)diazobuta-1,3-diene]di(diethylamino)nickel; [1,4-bis(3,4,5-tributylphenyl)-2-(hydrido)-3-(butyl)diazobuta-1,3-diene]di(heptacosyl)nickel; [1,4-bis(3,4,5-tripentylphenyl)-2-(butyl)-3-(octyl)diazobuta-1,3-diene]di(ethyl)palladium; [1,4-bis(3,4,5-tripropylphenyl)-2-(butyl)-3-(octyl)diazobuta-1,3-diene]di(tricosyl)palladium; [1,4-bis(3,4,5-tributylphenyl)-2-(ethyl)-3-(hydrido)diazobuta-1,3-diene]di(hydride)nickel; [1,4-bis(3,4,5-trimethylphenyl)-2-(hexyl)-3-(pentyl)diazobuta-1,3-diene]di(phenethyl)nickel; [1,4-bis(3,4,5-tributylphenyl)-2-(octyl)-3-(pentyl)diazobuta-1,3-diene]di(hydrido)palladium; [1,4-bis(3,4,5-triethylphenyl)-2-(butyl)-3-(hexadecyl)diazobuta-1,3-diene]di(methoxy)nickel; [1,4-bis(3,4,5-tributylphenyl)-2,3-(dibutyl)diazobuta-1,3-diene]di(octyl)palladium; [1,4-bis(3,4,5-trihexylphenyl)-2-(hydrido)-3-(pentyl)diazobuta-1,3-diene]di(nonadecyl)palladium; [1,4-bis(3,4,5-tributylphenyl)-2,3-(dibutyl)diazobuta-1,3-diene]di(ethyl)nickel; [1,4-bis(3,4,5-tributylphenyl)-2,3-(dibutyl)diazobuta-1,3-diene]di(benzoxy)nickel; [1,4-bis(3,4,5-triethylphenyl)-2-(hydrido)-3-(butyl)diazobuta-1,3-diene]di(ethyl)palladium; [1,4-bis(3,4,5-tributylphenyl)-2-(methyl)-3-(butyl)diazobuta-1,3-diene]di(dodecyl)nickel; [1,4-bis(3,4,5-tripropylphenyl)-2-(tetradecyl)-3-(pentyl)diazobuta-1,3-diene]di(methyl)nickel; [1,4-bis(3,4,5-tripropylphenyl)-2,3-(dihexyl)diazobuta-1,3-diene]di(hydrido)palladium; [1,4-bis(3,4,5-tributylphenyl)-2,3-(dibutyl)diazobuta-1,3-diene]di(heptyl)palladium; [1,4-bis(3,4,5-tripentylphenyl)-2-(tridecynyl)-3-(pentyl)diazobuta-1,3-diene]di(pentadecynyl)nickel; [1,4-bis(3,4,5-trimethylphenyl)-2-(hexyl)-3-(butyl)diazobuta-1,3-diene]di(nonadecyl)nickel; [1,4-bis(3,4,5-trihexylphenyl)-2-(octynyl)-3-(nonacosenyl)diazobuta-1,3-diene]di(decyl)palladium; [1,4-bis(3,4,5-triethylphenyl)-2-(methyl)-3-(hydrido)diazobuta-1,3-diene]di(hexyl)nickel; [1,4-bis(3,4,5-triethylphenyl)-2-(butyl)-3-(decynyl)diazobuta-1,3-diene]di(hexadecyl)nickel; [1,4-bis(3,4,5-trihexylphenyl)-2-(butyl)-3-(hydrido)diazobuta-1,3-diene]di(ethyl)nickel; [1,4-bis(3,4,5-tributylphenyl)-2,3-(dibutyl)diazobuta-1,3-diene]di(hydrido)palladium; [1,4-bis(3,4,5-tripentylphenyl)-2-(octyl)-3-(butyl)diazobuta-1,3-diene]di(phenyl)palladium; [1,4-bis(3,4,5-trimethylphenyl)-2,3-(dibutyl)diazobuta-1,3-diene]di(pentadecyl)nickel; [1,4-bis(3,4,5-tripentylphenyl)-2-(hydrido)-3-(hexyl)diazobuta-1,3-diene]di(methyl)palladium; [1,4-bis(3,4,5-trimethylphenyl)-2-(butyl)-3-(octyl)diazobuta-1,3-diene]di(ethoxy)nickel; [1,4-bis(3,4,5-trimethylphenyl)-2-(pentyl)-3-(dodecenyl)diazobuta-1,3-diene]di(ethyl)nickel; [1,4-bis(3,4,5-trihexylphenyl)-2-(pentynyl)-3-(hydrido)diazobuta-1,3-diene]di(butyl)nickel; [1,4-bis(3,4,5-tripropylphenyl)-2-(tridecyl)-3-(octyl)diazobuta-1,3-diene]di(tetracosyl)nickel; [1,4-bis(3,4,5-triethylphenyl)-2,3-(dihydrido)diazobuta-1,3-diene]di(ethoxy)nickel; [1,4-bis(3,4,5-triethylphenyl)-2,3-(dibutyl)diazobuta-1,3-diene]di(methyl)palladium; [1,4-bis(3,4,5-tributylphenyl)-2-(hexyl)-3-(octyl)diazobuta-1,3-diene]di(ethyl)palladium; [1,4-bis(3,4,5-tributylphenyl)-2,3-(dihydrido)diazobuta-1,3-diene]di(phenyl)nickel; [1,4-bis(3,4,5-tributylphenyl)-2-(tridecyl)-3-(octyl)diazobuta-1,3-diene]di(octyl)nickel; [1,4-bis(3,4,5-trihexylphenyl)-2-(pentenyl)-3-(butyl)diazobuta-1,3-diene]di(heptadecyl)nickel; [1,4-bis(3,4,5-trimethylphenyl)-2-(octyl)-3-(methyl)diazobuta-1,3-diene]di(nonacosyl)nickel; [1,4-bis(3,4,5-tripropylphenyl)-2,3-(dibutyl)diazobuta-1,3-diene]di (benzyl)palladium; [1,4-bis(3,4,5-tripentylphenyl)-2-(octyl)-3-(heptynyl)diazobuta-1,3-diene]di(hydrido)nickel; [1,4-bis(3,4,5-tripentylphenyl)-2,3-(dibutyl)diazobuta-1,3-diene]di(ethyl)nickel; [1,4-bis(3,4,5-tripentylphenyl)-2-(butyl)-3-(ethyl)diazobuta-1,3-diene]di(hexacosyl)nickel; [1,4-bis(3,4,5-tripropylphenyl)-2-(butyl)-3-(hydrido)diazobuta-1,3-diene]di(tetracosyl)nickel; [1,4-bis(3,4,5-trimethylphenyl)-2-(hexyl)-3-(hydrido)diazobuta-1,3-diene]di(diethylamino)nickel; [1,4-bis(3,4,5-tributylphenyl)-2-(butyl)-3-(octyl)diazobuta-1,3-diene]di(hydrido)palladium; [1,4-bis(3,4,5-trimethylphenyl)-2,3-(dihydrido)diazobuta-1,3-diene]di(hexadecyl)palladium; [1,4-bis(3,4,5-tributylphenyl)-2-(octyl)-3-(butyl)diazobuta-1,3-diene]di(methyl)nickel; [1,4-bis(3,4,5-trimethylphenyl)-2-(octyl)-3-(pentyl)diazobuta-1,3-diene]di(undecyl)nickel; [1,4-bis(3,4,5-trimethylphenyl)-2-(hydrido)-3-(hexacosynyl)diazobuta-1,3-diene]di(tricosyl)nickel; [1,4-bis(3,4,5-trimethylphenyl)-2-(octyl)-3-(pentyl)diazobuta-1,3-diene]di(pentacosyl)nickel; [1,4-bis(3,4,5-tripentylphenyl)-2-(butyl)-3-(octyl)diazobuta-1,3-diene]di(hydrido)nickel; [1,4-bis(3,4,5-tributylphenyl)-2,3-(dibutyl)diazobuta-1,3-diene]di(octadecyl)nickel; [1,4-bis(3,4,5-trimethylphenyl)-2-(butyl)-3-(hydrido)diazobuta-1,3-diene]di(phenethyl)nickel; [1,4-bis(3,4,5-trimethylphenyl)-2-(hexyl)-3-(butyl)diazobuta-1,3-diene]di(hydrido)nickel; [1,4-bis(3,4,5-trimethylphenyl)-2-(octyl)-3-(hydrido)diazobuta-1,3-diene]di(iodo)nickel; [1,4-bis(3,4,5-tributylphenyl)-2-(octyl)-3-(pentadecyl)diazobuta-1,3-diene]di(hydrido)nickel; [1,4-bis(3,4,5-trimethylphenyl)-2-(methyl)-3-(nonacosyl)diazobuta-1,3-diene]di(hydrido)nickel; [1,4-bis(3,4,5-triethylphenyl)-2-(pentyl)-3-(butyl)diazobuta-1,3-diene]di(methyl)nickel; [1,4-bis(3,4,5-triethylphenyl)-2-(hydrido)-3-(hexyl)diazobuta-1,3-diene]di(heptadecyl)nickel; [1,4-bis(3,4,5-tripropylphenyl)-2-(pentyl)-3-(butyl)diazobuta-1,3-diene]di(phenyl)nickel; [1,4-bis(3,4,5-trimethylphenyl)-2-(ethyl)-3-(octyl)diazobuta-1,3-diene]di(butyl)nickel; [1,4-bis(3,4,5-trihexylphenyl)-2-(hydrido)-3-(butyl)diazobuta-1,3-diene]di(benzyl)palladium; [1,4-bis(3,4,5-triethylphenyl)-2-(nonadecynyl)-3-(hexyl)diazobuta-1,3-diene]di(phenoxy)nickel; [1,4-bis(3,4,5-tributylphenyl)-2-(butyl)-3-(hydrido)diazobuta-1,3-diene]di(eicosynyl)nickel; [1,4-bis(3,4,5-trihexylphenyl)-2-(methyl)-3-(butyl)diazobuta-1,3-diene]di(octacosyl)palladium; [1,4-bis(3,4,5-trihexylphenyl)-2-(butyl)-3-(hydrido)diazobuta-1,3-diene]di(decyl)nickel; [1,4-bis(3,4,5-tributylphenyl)-2-(hexyl)-3-(butyl)diazobuta-1,3-diene]di(docosenyl)nickel; [1,4-bis(3,4,5-tripentylphenyl)-2-(methyl)-3-(butyl)diazobuta-1,3-diene]di(pentyl)nickel; [1,4-bis(3,4,5-tributylphenyl)-2-(octyl)-3-(hydrido)diazobuta-1,3-diene]di(benzoxy)nickel; [1,4-bis(3,4,5-tripentylphenyl)-2-(butyl)-3-(heptacosynyl)diazobuta-1,3-diene]di(heptyl)nickel; [1,4-bis(3,4,5-tributylphenyl)-2-(octyl)-3-(pentyl)diazobuta-1,3-diene]di(methyl)nickel; [1,4-bis(3,4,5-tributylphenyl)-2,3-(dibutyl)diazobuta-1,3-diene]di(tridecyl)palladium; [1,4-bis(3,4,5-tributylphenyl)-2-(butyl)-3-(pentyl)diazobuta-1,3-diene]di(butoxy)nickel; [1,4-bis(3,4,5-triethylphenyl)-2,3-(dihydrido)diazobuta-1,3-diene]di(tetracosyl)palladium; [1,4-bis(3,4,5-tributylphenyl)-2-(butyl)-3-(nonadecyl)diazobuta-1,3-diene]di(iodo)nickel; [1,4-bis(3,4,5-tripentylphenyl)-2-(pentyl)-3-(butyl)diazobuta-1,3-diene]di(octadecyl)nickel; [1,4-bis(3,4,5-tripentylphenyl)-2-(ethyl)-3-(tetradecyl)diazobuta-1,3-diene]di(tetracosyl)nickel; [1,4-bis(3,4,5-tripentylphenyl)-2-(hexyl)-3-(butyl)diazobuta-1,3-diene]di(hydrido)nickel; [1,4-bis(3,4,5-triethylphenyl)-2-(hydrido)-3-(pentacosyl)diazobuta-1,3-diene]di(methyl)nickel; [1,4-bis(3,4,5-trihexylphenyl)-2-(hydrido)-3-(pentacosynyl)diazobuta-1,3-diene]di(butoxy)nickel; [1,4-bis(3,4,5-triethylphenyl)-2,3-(dibutyl)diazobuta-1,3-diene]di(butyl)palladium; [1,4-bis(3,4,5-tributylphenyl)-2-(hexyl)-3-(butyl)diazobuta-1,3-diene]di(butoxy)nickel; [1,4-bis(3,4,5-triethylphenyl)-2,3-(dibutyl)diazobuta-1,3-diene]di(hydrido)nickel; [1,4-bis(3,4,5-trihexylphenyl)-2-(ethyl)-3-(butyl)diazobuta-1,3-diene]di(hydrido)nickel; [1,4-bis(3,4,5-tributylphenyl)-2-(ethyl)-3-(butyl)diazobuta-1,3-diene]di(hexadecyl)nickel; [1,4-bis(3,4,5-tripentylphenyl)-2,3-(dimethyl)diazobuta-1,3-diene]di(ethyl)nickel; [1,4-bis(3,4,5-tripentylphenyl)-2,3-(dibutyl)diazobuta-1,3-diene]di(pentadecynyl)palladium; [1,4-bis(3,4,5-tributylphenyl)-2-(hexyl)-3-(hydrido)diazobuta-1,3-diene]di(butoxy)nickel; [1,4-bis(3,4,5-triethylphenyl)-2-(butyl)-3-(propynyl)diazobuta-1,3-diene]di(benzyl)nickel; [1,4-bis(3,4,5-tripropylphenyl)-2-(hydrido)-3-(octyl)diazobuta-1,3-diene]di(ethyl)nickel; [1,4-bis(3,4,5-trimethylphenyl)-2,3-(dibutyl)diazobuta-1,3-diene]di(methyl)nickel; [1,4-bis(3,4,5-trihexylphenyl)-2-(octyl)-3-(hydrido)diazobuta-1,3-diene]di(nonadecyl)nickel; [1,4-bis(3,4,5-trimethylphenyl)-2-(butyl)-3-(pentyl)diazobuta-1,3-diene]di(allyl)palladium; [1,4-bis(3,4,5-triethylphenyl)-2-(pentyl)-3-(butyl)diazobuta-1,3-diene]di(ethyl)palladium; [1,4-bis(3,4,5-tributylphenyl)-2-(hydrido)-3-(hexyl)diazobuta-1,3-diene]di(ethoxy)nickel; [1,4-bis(3,4,5-tripropylphenyl)-2-(heptenyl)-3-(butyl)diazobuta-1,3-diene]di(undecyl)nickel; [1,4-bis(3,4,5-trimethylphenyl)-2-(hydrido)-3-(octyl)diazobuta-1,3-diene]di(nonacosyl)nickel; [1,4-bis(3,4,5-tributylphenyl)-2-(heptacosyl)-3-(hydrido)diazobuta-1,3-diene]di(ethyl)nickel; [1,4-bis(3,4,5-tripentylphenyl)-2-(octenyl)-3-(octyl)diazobuta-1,3-diene]di(methyl)palladium; [1,4-bis(3,4,5-triethylphenyl)-2-(hydrido)-3-(butyl)diazobuta-1,3-diene]di(hexacosyl)nickel; [1,4-bis(3,4,5-tripentylphenyl)-2-(butyl)-3-(pentyl)diazobuta-1,3-diene]di(docosyl)nickel; [1,4-bis(3,4,5-triethylphenyl)-2-(hydrido)-3-(octyl)diazobuta-1,3-diene]di(hydrido)nickel; [1,4-bis(3,4,5-tributylphenyl)-2,3-(dibutyl)diazobuta-1,3-diene]di(butyl)nickel; [1,4-bis(3,4,5-tripentylphenyl)-2,3-(dibutyl)diazobuta-1,3-diene]di(tolyl)nickel; [1,4-bis(3,4,5-tributylphenyl)-2-(hexyl)-3-(hydrido)diazobuta-1,3-diene]di(tetradecyl)nickel; [1,4-bis(3,5-diethyl-4-octadecenylphenyl)-2-(heptynyl)-3-(hexyl)diazobuta-1,3-diene]di(methyl)nickel; [1,4-bis(3,5-dipentyl-4-octylphenyl)-2-(octadecyl)-3-(hydrido)diazobuta-1,3-diene]di(ethyl)nickel; [1,4-bis(3,5-dipentyl-4-methylphenyl)-2-(hydrido)-3-(pentyl)diazobuta-1,3-diene]di(hydrido)nickel; [1,4-bis(3,5-dihexyl-4-butylphenyl)-2,3-(dihexyl)diazobuta-1,3-diene]di(dodecyl)nickel; [1,4-bis(3,5-dibutonyl-4-butylphenyl)-2-(hexadecynyl)-3-(hydrido)diazobuta-1,3-diene]di(phenoxy)nickel; [1,4-bis(3,5-dipentyl-4-octylphenyl)-2,3-(dibutyl)diazobuta-1,3-diene]di(dimethylamino)nickel; [1,4-bis(3,5-dihexyl-4-methylethylaminophenyl)-2,3-(dibutyl)diazobuta-1,3-diene]di(pentyl)nickel; [1,4-bis(3,5-dipropyl-4-butylphenyl)-2-(pentyl)-3-(butyl)diazobuta-1,3-diene]di(methyl)nickel; [1,4-bis(3,5-dihexonyl-4-methylphenyl)-2-(ethyl)-3-(butyl)diazobuta-1,3-diene]di(ethyl)nickel; [1,4-bis(3,5-diethyl-4-octacosylphenyl)-2-(butyl)-3-(octyl)diazobuta-1,3-diene]di(nonadecyl)nickel; [1,4-bis(3,5-dipropyl-4-butanalylphenyl)-2-(butyl)-3-(octyl)diazobuta-1,3-diene]di(ethoxy)nickel; [1,4-bis(3,5-dihexyl-4-butylphenyl)-2-(methyl)-3-(hydrido)diazobuta-1,3-diene]di(hexadecyl)palladium; [1,4-bis(3,5-dipropyl-4-pentacosynylphenyl)-2-(butyl)-3-(hydrido)diazobuta-1,3-diene]di(ethyl)palladium; [1,4-bis(3,5-dimethyl-4-butylphenyl)-2-(hydrido)-3-(butyl)diazobuta-1,3-diene]di(phenyl)nickel; [1,4-bis(3,5-d ibutyl-4-methylphenyl)-2-(butyl)-3-(hydrido)diazobuta-1,3-diene]di(butoxy)nickel;

[1,4-bis(3,5-dipropyl-4-pentylphenyl)-2-(pentacosyl)-3-(pentyl)diazobuta-1,3-diene]di(methyl)palladium; [1,4-bis(3,5-diethyl-4-pentacosenylphenyl)-2-(butyl)-3-(tridecyl)diazobuta-1,3-diene]di(butoxy)palladium; [1,4-bis(3,5-dihexyl-4-butylphenyl)-2-(octyl)-3-(hydrido)diazobuta-1,3-diene]di(benzyl)nickel; [1,4-bis(3,5-dipropyl-4-butylphenyl)-2-(hydrido)-3-(pentyl)diazobuta-1,3-diene]di(methyl)nickel; [1,4-bis(3,5-dimethyl-4-butylphenyl)-2-(hydrido)-3-(butyl)diazobuta-1,3-diene]di(hydrido)palladium; [1,4-bis(3,5-dibutyl-4-tridecynylphenyl)-2-(hydrido)-3-(octyl)diazobuta-1,3-diene]di(butyl)nickel; [1,4-bis(3,5-dimethyl-4-butylphenyl)-2-(pentyl)-3-(octynyl)diazobuta-1,3-diene]di(docosyl)nickel; [1,4-bis(3,5-dibutyl-4-hexylphenyl)-2-(pentyl)-3-(tricosenyl)diazobuta-1,3-diene]di(docosyl)palladium; [1,4-bis(3,5-dimethyl-4-octylphenyl)-2-(butyl)-3-(octyl)diazobuta-1,3-diene]di(tetracosyl)nickel; [1,4-bis(3,5-dipentyl-4-butylphenyl)-2-(ethyl)-3-(hexyl)diazobuta-1,3-diene]di(hydrido)palladium; [1,4-bis(3,5-dipentyl-4-butylphenyl)-2-(triacontyl)-3-(pentyl)diazobuta-1,3-diene]di(iodo)nickel; [1,4-bis(3,5-dihexyl-4-butylphenyl)-2-(octyl)-3-(hydrido)diazobuta-1,3-diene]di(benzoxy)nickel; [1,4-bis(3,5-dihexyl-4-ethylphenyl)-2,3-(dibutyl)diazobuta-1,3-diene]di(methyl)nickel; [1,4-bis(3,5-dimethyl-4-pentylphenyl)-2-(hydrido)-3-(henecosenyl)diazobuta-1,3-diene]di(tolyl)nickel; [1,4-bis(3,5-dihexyl-4-methylphenyl)-2-(ethyl)-3-(pentynyl)diazobuta-1,3-diene]di(butyl)nickel; [1,4-bis(3,5-diethyl-4-octylphenyl)-2-(octyl)-3-(butyl)diazobuta-1,3-diene]di(phenoxy)nickel; [1,4-bis(3,5-dipropyl-4-ethylphenyl)-2-undecynyl)-3-(heneicosyl)diazobuta-1,3-diene]di(ethyl)nickel; [1,4-bis(3,5-diethyl-4-butylphenyl)-2-(hydrido)-3-(pentyl)diazobuta-1,3-diene]di(methylethylamino)nickel; [1,4-bis(3,5-dimethyl-4-butylphenyl)-2-(butyl)-3-(hydrido)diazobuta-1,3-diene]di(ethyl)palladium; [1,4-bis(3,5-dimethyl-4-ethylphenyl)-2-(butyl)-3-(hydrido)diazobuta-1,3-diene]di(ethyl)nickel; [1,4-bis(3,5-diethyl-4-hexylphenyl)-2-(triacontenyl)-3-(ethyl)diazobuta-1,3-diene]di(tetracosyl)nickel; [1,4-bis(3,5-dipentyl-4-butylphenyl)-2-(propynyl)-3-(hydrido)diazobuta-1,3-diene]di(methyl)nickel; [1,4-bis(3,5-dipentyl-4-butylphenyl)-2-(butyl)-3-(hydrido)diazobuta-1,3-diene]di(hexacosyl)palladium; [1,4-bis(3,5-dipentyl-4-heptynylphenyl)-2-(octyl)-3-(pentyl)diazobuta-1,3-diene]di(docosyl)nickel; [1,4-bis(3,5-dipentyl-4-butylphenyl)-2-(butyl)-3-(hydrido)diazobuta-1,3-diene]di(butyl)nickel; [1,4-bis(3,5-dihexyl-4-decenylphenyl)-2-(butyl)-3-(hydrido)diazobuta-1,3-diene]di(heptacosyl)nickel; [1,4-bis(3,5-dibutyl-4-pentylphenyl)-2-(methyl)-3-(butyl)diazobuta-1,3-diene]di(hydrido)nickel; [1,4-bis(3,5-dihexyl-4-dodecenylphenyl)-2-(butyl)-3-(pentyl)diazobuta-1,3-diene]di(ethyl)nickel; [1,4-bis(3,5-dihexyl-4-ethylphenyl)-2-(butyl)-3-(pentyl)diazobuta-1,3-diene]di(undecyl)nickel; [1,4-bis(3,5-dihexyl-4-butylphenyl)-2-(hexyl)-3-(butyl)diazobuta-1,3-diene]di(ethyl)palladium; [1,4-bis(3,5-dipropyl-4-triacontynylphenyl)-2,3-(dibutyl)diazobuta-1,3-diene]di(ethyl)nickel; [1,4-bis(3,5-dibutyl-4-hexylphenyl)-2-(pentyl)-3-(hydrido)diazobuta-1,3-diene]di(hydrido)nickel; [1,4-bis(3,5-dimethyl-4-pentylphenyl)-2-(hexyl)-3-(butyl)diazobuta-1,3-diene]di(butyl)nickel; [1,4-bis(3,5-dihexyl-4-butylphenyl)-2-(butyl)-3-(octyl)diazobuta-1,3-diene]di(hydrido)palladium; [1,4-bis(3,5-dimethyl-4-pentylphenyl)-2-(butyl)-3-(hydrido)diazobuta-1,3-diene]di(hexadecyl)nickel; [1,4-bis(3,5-dipentyl-4-diethylaminophenyl)-2-(pentynyl)-3-(hydrido)diazobuta-1,3-diene]di(hydrido)palladium; [1,4-bis(3,5-dibutyl-4-tetracosynylphenyl)-2,3-(dibutyl)diazobuta-1,3-diene]di(nonacosenyl)nickel; [1,4-bis(3,5-diethyl-4-octylphenyl)-2-(butyl)-3-(methyl)diazobuta-1,3-diene]di(methyl)nickel; [1,4-bis(3,5-dimethyl-4-butylphenyl)-2-(methyl)-3-(butyl)diazobuta-1,3-diene]di(decyl)palladium; [1,4-bis(3,5-diethyl-4-hexylphenyl)-2-(hydrido)-3-(butyl)diazobuta-1,3-diene]di(ethyl)palladium; [1,4-bis(3,5-dibutyl-4-ethylphenyl)-2,3-(dihexyl)diazobuta-1,3-diene]di(hexacosyl)palladium; [1,4-bis(3,5-dimethyl-4-butylphenyl)-2-(octyl)-3-(butyl)diazobuta-1,3-diene]di(tridecenyl)nickel; [1,4-bis(3,5-dipropyl-4-heneicosylphenyl)-2,3-(dihexyl)diazobuta-1,3-diene]di(octyl)palladium; [1,4-bis(3,5-dibutyl-4-octylphenyl)-2-(hexyl)-3-(hydrido)diazobuta-1,3-diene]di(ethoxy)palladium; [1,4-bis(3,5-dibutyl-4-nonadecylphenyl)-2-(butyl)-3-(hydrido)diazobuta-1,3-diene]di(benzoxy)nickel; [1,4-bis(3,5-dimethyl-4-hexylphenyl)-2-(pentyl)-3-(methyl)diazobuta-1,3-diene]di(butoxy)palladium; [1,4-bis(3,5-diethyl-4-undecynylphenyl)-2-(butyl)-3-(pentyl)diazobuta-1,3-diene]di(propyl)palladium; [1,4-bis(3,5-dibutyl-4-hexylphenyl)-2-(butyl)-3-(octacosenyl)diazobuta-1,3-diene]di(methylethylamino)palladium; [1,4-bis(3,5-dibutyl-4-eicosynylphenyl)-2-(butyl)-3-(pentyl)diazobuta-1,3-diene]di(hydrido)nickel; [1,4-bis(3,5-dimethyl-4-pentylphenyl)-2-(octyl)-3-(butyl)diazobuta-1,3-diene]di(hydride)palladium; [1,4-bis(3,5-dibutyl-4-octylphenyl)-2-(tetradecenyl)-3-(hydrido)diazobuta-1,3-diene]di(diethylamino)nickel; [1,4-bis(3,5-dipropyl-4-eicosynylphenyl)-2-(heneicosanyl)-3-(pentynyl)diazobuta-1,3-diene]di(hydrido)palladium; [1,4-bis(3,5-dipropyl-4-propynylphenyl)-2-(butyl)-3-(triacontenyl)diazobuta-1,3-diene]di(hexadecyl)nickel; [1,4-bis(3,5-dipentyl-4-octylphenyl)-2-(pentyl)-3-(hydrido)diazobuta-1,3-diene]di(octacosyl)palladium; [1,4-bis(3,5-dihexyl-4-docosynylphenyl)-2-(hydrido)-3-(pentyl)diazobuta-1,3-diene]di(hexadecyl)nickel; [1,4-bis(3,5-dipentyl-4-octylphenyl)-2-(hexyl)-3-(hydrido)diazobuta-1,3-diene]di(methyl)nickel; [1,4-bis(3,5-dimethyl-4-octylphenyl)-2-(hydrido)-3-(butyl)diazobuta-1,3-diene]di(allyl)palladium; [1,4-bis(3,5-dibutyl-4-octylphenyl)-2-(hexyl)-3-(butyl)diazobuta-1,3-diene]di(pentadecyl)nickel; [1,4-bis(3,5-dibutyl-4-(triethylsilylmethyl)phenyl)-2-(butyl)-3-(methyl)diazobuta-1,3-diene]di(undecyl)nickel; [1,4-bis(3,5-dibutyl-4-hexylphenyl)-2,3-(dibutyl)diazobuta-1,3-diene]di(dodecyl)nickel; [1,4-bis(3,5-dipropyl-4-pentylphenyl)-2-(butyl)-3-(octyl)diazobuta-1,3-diene]di(pentacosyl)palladium; [1,4-bis(3,5-dipropyl-4-butanalylphenyl)-2-(butyl)-3-(hydrido)diazobuta-1,3-diene]di(hydrido)nickel; [1,4-bis(3,5-diethyl-4-methyldiethylsilylmethyl)phenyl)-2-(hexyl)-3-(pentyl)diazobuta-1,3-diene]di(nonadecyl)palladium; [1,4-bis(3,5-diethyl-4-octylphenyl)-2-(hydrido)-3-(butyl)diazobuta-1,3-diene]di(propoxy)nickel; [1,4-bis(3,5-diethyl-4-diethylaminophenyl)-2-(butyl)-3-(heptacosenyl)diazobuta-1,3-diene]di(butyl)nickel; [1,4-bis(3,5-dimethyl-4-hexylphenyl)-2-(pentyl)-3-(hexadecynyl)diazobuta-1,3-diene]di(hydride)nickel; [1,4-bis(3,5-dimethyl-4-octylphenyl)-2-(butyl)-3-(hexacosenyl)diazobuta-1,3-diene]di(nonadecyl)palladium; [1,4-bis(3,5-dihexyl-4-pentylphenyl)-2,3-(dibutyl)diazobuta-1,3-diene]di(nonadecenyl)nickel; [1,4-bis(3,5-diethyl-4-octadecenylphenyl)-2-(octyl)-3-(heneicosyl)diazobuta-1,3-diene]di(benzyl)palladium; [1,4-bis(3,5-dipentyl-4-butylphenyl)-2,3-(dihydrido)diazobuta-1,3-diene]di(eicosyl)palladium; [1,4-bis(3,5-dihexyl-4-pentylphenyl)-2-(pentyl)-3-(hydrido)diazobuta-1,3-diene]di(heneicosyl)nickel; [1,4-bis(3,5-dihexyl-4-butylphenyl)-2,3-(dihydrido)diazobuta-1,3-diene]di(nonadecyl)palladium; [1,4-bis(3,5-dibutyl-4-octylphenyl)-2-(triacontenyl)-3-(butyl)diazobuta-1,3-diene]di(hydrido)nickel; [1,4-bis(3,5-dimethyl-4-octylphenyl)-2-(undecyl)-3-(methyl)diazobuta-1,3-diene]di (methyl)palladium; [1,4-bis(3,5-dipentyl-4-butylphenyl)-2,3-(dibutyl)diazobuta-1,3-diene]di(phenyl)nickel; [1,4-bis(3,5-dipropyl-4-pentylphenyl)-2,3-(dibutyl)diazobuta-1,3-diene]di(bromo)palladium; [1,4-bis(3,5-dibutyl-4-hexylphenyl)-2,3-(dihydrido)diazobuta-1,3-diene]di(hydride)palladium; [1,4-bis(3,5-dihexyl-4-butylphenyl)-2-(tetracosenyl)-3-(undecyl)diazobuta-1,3-diene]di(methylethylamino)nickel; [1,4-bis(3,5-dimethyl-4-octylphenyl)-2-(hexyl)-3-(pentyl)diazobuta-1,3-diene]di(heneicosynyl)nickel; [1,4-bis(3,5-dihexyl-4-methylphenyl)-2-(butyl)-3-(docosynyl)diazobuta-1,3-diene]di(hydrido)nickel; [1,4-bis(3,5-diethyl-4-butylphenyl)-2-(pentyl)-3-(octyl)diazobuta-1,3-diene]di(phenethyl)palladium; [1,4-bis(3,5-dibutanalyl-4-octylphenyl)-2-(butyl)-3-(tetradecynyl)diazobuta-1,3-diene]di(octadecyl)palladium; [1,4-bis(3,5-diethyl-4-butylphenyl)-2-(tetradecenyl)-3-(hydrido)diazobuta-1,3-diene]di(butoxy)nickel; [1,4-bis(3,5-dibutyl-4-pentylphenyl)-2,3-(dibutyl)diazobuta-1,3-diene]di(heptadecyl)nickel; [1,4-bis(3,5-dimethyl-4-butylphenyl)-2-(pentyl)-3-(hydrido)diazobuta-1,3-diene]di(decyl)nickel; [1,4-bis(3,5-dihexyl-4-pentylphenyl)-2-(butyl)-3-(hydrido)diazobuta-1,3-diene]di(ethoxy)palladium; [1,4-bis(3,5-dipentyl-4-(trimethylsilylmethyl)phenyl)-2-(octyl)-3-(butyl)diazobuta-1,3-diene]di(diethylamino)nickel; [1,4-bis(3,5-diethyl-4-pentylphenyl)-2-(hydrido)-3-(butyl)diazobuta-1,3-diene]di(tolyl)nickel; [1,4-bis(3,5-dibutyl-4-octylphenyl)-2-(butyl)-3-(hydrido)diazobuta-1,3-diene]di(hexyl)nickel; [1,4-bis(3,5-dihexyl-4-butylphenyl)-2-(butyl)-3-(pentyl)diazobuta-1,3-diene]di(benzoxy)nickel; [1,4-bis(3,5-dipropyl-4-butylphenyl)-2-(pentenyl)-3-(ethyl)diazobuta-1,3-diene]di(methoxy)nickel; [1,4-bis(3,5-dihexyl-4-methylphenyl)-2,3-(dihydrido)diazobuta-1,3-diene]di(ethyl)palladium; [1,4-bis(3,5-dihexyl-4-hexylphenyl)-2-(butyl)-3-(hydrido)diazobuta-1,3-diene]di(bromo)palladium; [1,4-bis(3,5-diethyl-4-methylethylaminophenyl)-2-(octyl)-3-(heptenyl)diazobuta-1,3-diene]di(undecyl) palladium; [1,4-bis(3,5-diethyl-4-pentylphenyl)-2-(tridecyl)-3-(butyl)diazobuta-1,3-diene]di(triacontyl)palladium; [1,4-bis(3,5-diethyl-4-butylphenyl)-2,3-(dibutyl)diazobuta-1,3-diene]di(octadecyl)nickel; [1,4-bis(3,5-dibutyl-4-tetradecenylphenyl)-2-(hexyl)-3-(butyl)diazobuta-1,3-diene]di(butyl)nickel; [1,4-bis(3,5-dipentyl-4-hexylphenyl)-2,3-(dihydrido)diazobuta-1,3-diene]di(butyl)nickel; [1,4-bis(3,5-diethyl-4-hexylphenyl)-2-(hexacenyl)-3-(butyl)diazobuta-1,3-diene]di(chloro)nickel; [1,4-bis(3,5-dibutyl-4-tetracosenylphenyl)-2-(heptadecenyl)-3-(butyl)diazobuta-1,3-diene]di(hydrido) palladium; [1,4-bis(3,5-dibutyl-4-nonacosynylphenyl)-2-(pentyl)-3-(octyl)diazobuta-1,3-diene]di(chloro)palladium; [1,4-bis(3,5-dibutyl-4-ethylphenyl)-2-(butyl)-3-(hydrido)diazobuta-1,3-diene]di(ethyl)palladium; [1,4-bis(3,5-diethyl-4-butylphenyl)-2-(butyl)-3-(hexyl)diazobuta-1,3-diene]di(tricosyl)palladium; [1,4-bis(3,5-dipentyl-4-methylphenyl)-2-(methyl)-3-(hydrido)diazobuta-1,3-diene]di(butyl)nickel; [1,4-bis(3,5-diethyl-4-pentylphenyl)-2,3-(dioctyl)diazobuta-1,3-diene]di(ethyl)nickel; [1,4-bis(3,5-dipropyl-4-methylphenyl)-2-(hydrido)-3-(pentyl)diazobuta-1,3-diene]di(ethyl)palladium; [1,4-bis(3,5-dimethyl-4-butylphenyl)-2-(methyl)-3-(hydrido)diazobuta-1,3-diene]di(tolyl)nickel; [1,4-bis(3,5-dibutyl-4-octacosylphenyl)-2-(butyl)-3-(hydrido)diazobuta-1,3-diene]di(octadecyl)nickel; [1,4-bis(3,5-dipropyl-4-pentacosynylphenyl)-2-(ethyl)-3-(octyl)diazobuta-1,3-diene]di(methyl)nickel; [1,4-bis(3,5-dihexyl-4-butylphenyl)-2-(hexyl)-3-(hydrido)diazobuta-1,3-diene]di(hydrido)nickel; [1,4-bis(3,5-dimethyl-4-butylphenyl)-2-(octadecyl)-3-(butyl)diazobuta-1,3-diene]di(allyl)nickel; [1,4-bis(3,5-dibutyl-4-hexadecylphenyl)-2-(hydrido)-3-(butyl)diazobuta-1,3-diene]di(propoxy)nickel; [1,4-bis(3,5-dibutyl-4-octylphenyl)-2-(pentyl)-3-(butyl)diazobuta-1,3-diene]di(pentyl)nickel; [1,4-bis(3,5-diethyl-4-butylphenyl)-2-(butyl)-3-(ethyl)diazobuta-1,3-diene]di(butoxy)nickel; [1,4-bis(3,5-dipentyl-4-hexacosenylphenyl)-2-(butyl)-3-(hydrido)diazobuta-1,3-diene]di(allyl)nickel; [1,4-bis(3,5-dimethyl-4-butylphenyl)-2-(methyl)-3-(hexadecenyl)diazobuta-1,3-diene]di(hydrido)nickel; [1,4-bis(3,5-dibutyl-4-methylphenyl)-2-(octyl)-3-(hydrido)diazobuta-1,3-diene]di(diethylamino)nickel; [1,4-bis(3,5-dibutyl-4-octylphenyl)-2-(hydrido)-3-(heneicosynyl)diazobuta-1,3-diene]di(hydrido)palladium; [1,4-bis(3,5-dipropyl-4-butylphenyl)-2,3-(dibutyl)diazobuta-1,3-diene]di(benzoxy)nickel; [1,4-bis(3,5-dipentyl-4-octacosylphenyl)-2-(octadecynyl)-3-(hydrido)diazobuta-1,3-diene]di(butyl)nickel; [1,4-bis(3,5-dimethyl-4-butylphenyl)-2-(hydrido)-3-(triacontyl)diazobuta-1,3-diene]di(ethyl)palladium; [1,4-bis(3,5-dihexyl-4-butylphenyl)-2-(hexyl)-3-(pentyl)diazobuta-1,3-diene]di(hydride)nickel; [1,4-bis(3,5-dibutyl-4-(trimethylsilylethyl)phenyl)-2-(pentadecyl)-3-(butyl)diazobuta-1,3-diene]di(heptadecyl)nickel; [1,4-bis(3,5-diethyl-4-butylphenyl)-2-(pentyl)-3-(hydrido)diazobuta-1,3-diene]di(docosyl)nickel; [1,4-bis(3,5-dibutyl-4-methylphenyl)-2-(butyl)-3-(hexyl)diazobuta-1,3-diene]di(propyl)nickel; [1,4-bis(3,5-dipropyl-4-butylphenyl)-2-(ethyl)-3-(pentyl)diazobuta-1,3-diene]di(methyl)nickel; [1,4-bis(3,5-dihexyl-4-butylphenyl)-2-(hexyl)-3-(hydrido)diazobuta-1,3-diene]di(ethyl)nickel; [1,4-bis(3,5-dipropyl-4-tricosenylphenyl)-2-(ethyl)3-(hydrido)diazobuta-1,3-diene]di(hydride)palladium; [1,4-bis(3,5-dipropyl-4-butylphenyl)-2-(octyl)-3-(hydrido)diazobuta-1,3-diene]di(ethyl)palladium; [1,4-bis(3,5-dipentyl-4-butylphenyl)-2,3-(dibutyl)diazobuta-1,3-diene]di(benzyl)nickel; [1,4-bis(3,5-dibutyl-4-hexylphenyl)-2-(hexyl)-3-(butyl)diazobuta-1,3-diene]di(pentyl)nickel; [1,4-bis(3,5-dimethyl-4-nonadecynylphenyl)-2-(butyl)-3-(hydrido)diazobuta-1,3-diene]di(ethoxy)nickel; [1,4-bis(3,5-dipentyl-4-hexylphenyl)-2,3-(dibutyl)diazobuta-1,3-diene]di(diethylamino)nickel; [1,4-bis(3,5-dibutyl-4-pentylphenyl)-2-(butyl)-3-(octyl)diazobuta-1,3-diene]di(methyl)palladium; [1,4-bis(3,5-dibutyl-4-hexylphenyl)-2,3-(dihydrido)diazobuta-1,3-diene]di(propyl)nickel; [1,4-bis(3,5-dimethyl-4-octylphenyl)-2-(methyl)-3-(hexyl)diazobuta-1,3-diene]di(dodecyl)nickel; [1,4-bis(3,5-dipentyl-4-hexylphenyl)-2,3-(dibutyl)diazobuta-1,3-diene]di(phenoxy)nickel; [1,4-bis(3,5-dihexyl-4-hexonylphenyl)-2-(hydrido)-3-(butyl)diazobuta-1,3-diene]di(chloro)nickel; [1,4-bis(3,5-dibutyl-4-octylphenyl)-2-(hydrido)-3-(methyl)diazobuta-1,3-diene]di(octacosyl)nickel; [1,4-bis(3,5-diethyl-4-methyldiethylsilylmethyl)phenyl)-2-(pentyl)-3-(octyl)diazobuta-1,3-diene]di(methyl)nickel; [1,4-bis(3,5-dihexyl-4-octylphenyl)-2-(pentacosenyl)-3-(pentyl)diazobuta-1,3-diene]di(butyl)nickel; [1,4-bis(3,5-dihexyl-4-methylphenyl)-2,3-(dihydrido)diazobuta-1,3-diene]di(butyl)palladium; [1,4-bis(3,5-diethyl-4-decenylphenyl)-2-(butyl)-3-(pentadecynyl)diazobuta-1,3-diene]di(tridecyl)nickel; [1,4-bis(3,5-dimethyl-4-octylphenyl)-2-(ethyl)-3-(butyl)diazobuta-1,3-diene]di(hydride)palladium; [1,4-bis(3,5-dibutyl-4-methylphenyl)-2,3-(dibutyl)diazobuta-1,3-diene]di(tricosyl) palladium; [1,4-bis(3,5-dimethyl-4-pentylphenyl)-2-(pentyl)-3-(hydrido)diazobuta-1,3-diene]di(hydrido)nickel; [1,4-bis(3,5-dipropyl-4-hexylphenyl)-2-(octyl)-3-(hexyl)diazobuta-1,3-diene]di(tridecyl)nickel; [1,4-bis(3,5-dipentyl-4-(trimethylsilylethyl)phenyl)-2-(hydrido)-3-(octyl)diazobuta-1,3-diene]di(octyl)nickel; [1,4-bis(3,5-dihexyl-4-octynylphenyl)-2,3-(dibutyl)diazobuta-1, 3-diene]di(dodecyl)palladium; [1,4-bis(3,5-dipentyl-4-octylphenyl)-2-(hydrido)-3-(butyl)diazobuta-1,3-diene]di(ethyl)nickel; [1,4-bis(3,5-diethyl-4-butylphenyl)-2,3-(dibutyl)diazobuta-1,3-diene]di(methyl)nickel; [1,4-bis(3,5-dimethyl-4-tetracosenylphenyl)-2-(pentyl)-3-(octynyl)diazobuta-1,3-diene]di(benzoxy)nickel; [1,4-bis(3,5-dihexyl-4-pentylphenyl)-2-(octacosenyl)-3-(decyl)diazobuta-1,3-diene]di(undecyl)palladium; [1,4-bis(3,5-dibutyl-4-ethylphenyl)-2-(octyl)-3-(heptyl)diazobuta-1,3-diene]di(hexacosyl)palladium; [1,4-bis(3,5-diethyl-4-methylphenyl)-2-(hydrido)-3-(butyl)diazobuta-1,3-diene]di(hexadecyl)nickel; [1,4-bis(3,5-dimethyl-4-hexacosynylphenyl)-2-(hexyl)-3-(butyl)diazobuta-1,3-diene]di(phenethyl)nickel; [1,4-bis(3,5-dibutyl-4-methylphenyl)-2-(octyl)-3-(tetracosyl)diazobuta-1,3-diene]di(tetracosyl)nickel; [1,4-bis(3,5-dipentyl-4-butylphenyl)-2-(ethyl)-3-(hexacosynyl)diazobuta-1,3-diene]di(benzyl)palladium; [1,4-bis(3,5-dibutyl-4-pentylphenyl)-2-(butyl)-3-(pentyl)diazobuta-1,3-diene]di(hexyl)nickel; [1,4-bis(3,5-dibutyl-4-dodecaphosphinophenyl)-2-(pentyl)-3-(decenyl)diazobuta-1,3-diene]di(methyl)nickel; [1,4-bis(3,5-diethyl-4-hexylphenyl)-2-(tetracosynyl)-3-(hexyl)diazobuta-1,3-diene]di(hexyl)nickel; [1,4-bis(3,5-dipropyl-4-butylphenyl)-2-(methyl)-3-(butyl)diazobuta-1,3-diene]di(eicosyl)nickel; [1,4-bis(3,5-diethyl-4-hexylphenyl)-2-(hydrido)-3-(butyl)diazobuta-1,3-diene]di(hydrido)palladium; [1,4-bis(3,5-dihexyl-4-octylphenyl)-2-(octyl)-3-(butyl)diazobuta-1,3-diene]di(tricosyl)nickel; [1,4-bis(3,5-dibutyl-4-propenylphenyl)-2-(tricosyl)-3-(hexyl)diazobuta-1,3-diene]di(ethoxy)nickel; [1,4-bis(3,5-dipropyl-4-pentylphenyl)-2-(pentyl)-3-(butyl)diazobuta-1,3-diene]di(eicosyl)nickel; [1,4-bis(3,5-dimethyl-4-pentylphenyl)-2-(heptadecynyl)-3-(hydrido)diazobuta-1,3-diene]di(butyl)nickel; [1-(4-(triethylsilylmethyl)phenyl)-2-(butyl)-3-(pentadecynyl)-4-(4-butylphenyl)diazobuta-1,3-diene]di(ethyl)palladium; [1-(4-(triethylsilylmethyl)phenyl)-2-(hydrido)-3-(pentacosyl)-4-(4-pentylphenyl)diazobuta-1,3-diene]di(benzoxy)nickel; [1-(4-(triethylsilylmethyl)phenyl)-2-(pentyl)-3-(butyl)-4-(4-octylphenyl)diazobuta-1,3-diene]di(chloro)nickel; [1-(4-(trimethylsilylethyl)phenyl)-2-(hydrido)-3-(butyl)-4-(4-ethylphenyl)diazobuta-1,3-diene]di(hydrido)nickel; [1-(4-butanalylphenyl)-2-(hexyl)-3-(hydrido)-4-(4-methylphenyl)diazobuta-1,3-diene]di(butyl)nickel; [1-(4-butylphenyl)-2-(butyl)-3-(hexyl)-4-(4-ethylphenyl)diazobuta-1,3-diene]di(methyl)nickel; [1-(4-butylphenyl)-2-(butyl)-3-(hexyl)-4-(4-methylphenyl)diazobuta-1,3-diene]di(octadecyl)palladium; [1-(4-butylphenyl)-2-(butyl)-3-(hexynyl)-4-(4-hexylphenyl)diazobuta-1,3-diene]di(pentyl)palladium; [1-(4-butylphenyl)-2-(butyl)-3-(hydrido)-4-(4-heptenylphenyl)diazobuta-1,3-diene]di(octadecyl)nickel; [1-(4-butylphenyl)-2-(butyl)-3-(hydrido)-4-(4-hexylphenyl)diazobuta-1,3-diene]di(ethoxy)nickel; [1-(4-butylphenyl)-2-(butyl)-3-(hydrido)-4-(4-methylphenyl)diazobuta-1,3-diene]di(pentyl)palladium; [1-(4-butylphenyl)-2-(butyl)-3-(hydrido)-4-(4-octylphenyl)diazobuta-1,3-diene]di(tetracosyl)nickel; [1-(4-butylphenyl)-2-(butyl)-3-(hydrido)-4-(4-pentylphenyl)diazobuta-1,3-diene]di(undecyl)palladium; [1-(4-butylphenyl)-2-(butyl)-3-(methyl)-4-(4-octylphenyl)diazobuta-1,3-diene]di(phenyl)nickel; [1-(4-butylphenyl)-2-(butyl)-3-(octyl)-4-(4-ethylphenyl)diazobuta-1,3-diene]di(iodo)palladium; [1-(4-butylphenyl)-2-(butyl)-3-(octyl)-4-(4-pentylphenyl)diazobuta-1,3-diene]di(hydride)nickel; [1-(4-butylphenyl)-2-(butyl)-3-(octyl)-4-(4-eicosenylphenyl)diazobuta-1,3-diene]di(benzoxy)nickel; [1-(4-butylphenyl)-2-(butyl)-3-(pentyl)-4-(4-pentylphenyl)diazobuta-1,3-diene]di(heptyl)nickel; [1-(4-butylphenyl)-2-(butyl)-3-(pentyl)-4-(4-proponylphenyl)diazobuta-1,3-diene]di(tridecyl)palladium; [1-(4-butylphenyl)-2-(butyl)-3-(tetradecenyl)-4-(4-octylphenyl)diazobuta-1,3-diene]di(heptacosyl)nickel; [1-(4-butylphenyl)-2-(butyl)-3-(undecynyl)-4-(4-octylphenyl)diazobuta-1,3-diene]di(hydrido)nickel; [1-(4-butylphenyl)-2-(eicosynyl)-3-(butyl)-4-(4-methylethylaminophenyl)diazobuta-1,3-diene]di(heptacosyl)nickel; [1-(4-butylphenyl)-2-(hexadecenyl)-3-(butyl)-4-(4-pentylphenyl)diazobuta-1,3-diene]di(octacosyl)palladium; [1-(4-butylphenyl)-2-(hexenyl)-3-(hydrido)-4-(4-undecenylphenyl)diazobuta-1,3-diene]di(methoxy)palladium; [1-(4-butylphenyl)-2-(hexyl)-3-(butyl)-4-(4-hexylphenyl)diazobuta-1,3-diene]di(ethyl)nickel; [1-(4-butylphenyl)-2-(hexyl)-3-(hydrido)-4-(4-methylphenyl)diazobuta-1,3-diene]di(hexyl)palladium; [1-(4-butylphenyl)-2-(hexyl)-3-(nonacosenyl)-4-(4-pentylphenyl)diazobuta-1,3-diene]di(hexyl)nickel; [1-(4-butylphenyl)-2-(hexyl)-3-(octyl)-4-(4-octylphenyl)diazobuta-1,3-diene]di(heptyl)nickel; [1-(4-butylphenyl)-2-(hexyl)-3-(triacontenyl)-4-(4-pentacosylphenyl)diazobuta-1,3-diene]di(tetradecyl)palladium; [1-(4-butylphenyl)-2-(hydrido)-3-(butyl)-4-(4-hexacosylphenyl)diazobuta-1,3-diene]di(methyl)palladium; [1-(4-butylphenyl)-2-(hydrido)-3-(butyl)-4-(4-hexylphenyl)diazobuta-1,3-diene]di(tetradecyl)nickel; [1-(4-butylphenyl)-2-(hydrido)-3-(butyl)-4-(4-pentylphenyl)diazobuta-1,3-diene]di(hydrido)nickel; [1-(4-butylphenyl)-2-(hydrido)-3-(butyl)-4-(4-pentylphenyl)diazobuta-1,3-diene]di(octadecyl)nickel; [1-(4-butylphenyl)-2-(hydrido)-3-(butyl)-4-(4-proponylphenyl)diazobuta-1,3-diene]di(decyl)nickel; [1-(4-butylphenyl)-2-(hydrido)-3-(ethyl)-4-(4-ethanalylphenyl)diazobuta-1,3-diene]di(hexenyl)nickel; [1-(4-butylphenyl)-2-(hydrido)-3-(ethyl)-4-(4-hexylphenyl)diazobuta-1,3-diene]di(hydrido)palladium; [1-(4-butylphenyl)-2-(hydrido)-3-(hexyl)-4-(4-hexylphenyl)diazobuta-1,3-diene]di(methyl)nickel;[1-(4-butylphenyl)-2-(hydrido)-3-(hexyl)-4-(4-pentylphenyl)diazobuta-1,3-diene]di(phenyl)nickel; [1-(4-butylphenyl)-2-(hydrido)-3-(methyl)-4-(4-octylphenyl)diazobuta-1,3-diene]di(phenethyl)palladium; [1-(4-butylphenyl)-2-(hydrido)-3-(octyl)-4-(4-methylphenyl)diazobuta-1,3-diene]di(octyl)nickel; [1-(4-butylphenyl)-2-(hydrido)-3-(octyl)-4-(4-undecenylphenyl)diazobuta-1,3-diene]di(butyl)palladium; [1-(4-butylphenyl)-2-(methyl)-3-(butyl)-4-(4-pentylphenyl)diazobuta-1,3-diene]di(nonyl)nickel; [1-(4-butylphenyl)-2-(nonadecenyl)-3-(butyl)-4-(4-pentacosenylphenyl)diazobuta-1,3-diene]di(nonacosyl)palladium; [1-(4-butylphenyl)-2-(nonadecynyl)-3-(butyl)-4-(4-pentylphenyl)diazobuta-1,3-diene]di(nonacosyl)palladium; [1-(4-butylphenyl)-2-(octacosynyl)-3-(butyl)-4-(4-octylphenyl)diazobuta-1,3-diene]di(hydrido)palladium; [1-(4-butylphenyl)-2-(octyl)-3-(ethyl)-4-(4-pentylphenyl)diazobuta-1,3-diene]di(octyl)nickel; [1-(4-butylphenyl)-2-(octyl)-3-(hexyl)-4-(4-octylphenyl)diazobuta-1,3-diene]di(pentyl)nickel; [1-(4-butylphenyl)-2-(octyl)-3-(hydrido)-4-(4-octylphenyl)diazobuta-1,3-diene]di(hydrido)nickel; [1-(4-butylphenyl)-2-(pentacosyl)-3-(butyl)-4-(4-nonacosylphenyl)diazobuta-1,3-diene]di(phenethyl)nickel; [1-(4-butylphenyl)-2-(pentadecenyl)-3-(pentacosyl)-4-(4-hexylphenyl)diazobuta-1,3-diene]di(butyl)nickel; [1-(4-butylphenyl)-2-(pentadecynyl)-3-(hydrido)-4-(4-(trimethylsilylethyl)phenyl)diazobuta-1,3-diene]di(methyl)nickel; [1-(4-butylphenyl)-2-(pentyl)-3-(butyl)-4-(4-nonylphenyl)diazobuta-1,3-diene]di(methyl)nickel; [1-(4-butylphenyl)-2-(pentyl)-3-(hexyl)-4-(4-dodecynylphenyl)diazobuta-1,3-diene]di(nonacosynyl)nickel; [1-(4-butylphenyl)-2-(pentyl)-3-(hexyl)-4-(4-octylphenyl)diazobuta-1,3-diene]di(butyl)nickel; [1-(4-butylphenyl)-2-(pentyl)-3-(hydrido)-4-

(4-hexylphenyl)diazobuta-1,3-diene]di(heptadecyl)palladium; [1-(4-butylphenyl)-2-(pentyl)-3-(octyl)-4-(4-tricosenylphenyl)diazobuta-1,3-diene]di(nonyl)nickel; [1-(4-butylphenyl)-2-(pentyl)-3-(pentadecyl)-4-(4-octylphenyl)diazobuta-1,3-diene]di(butyl)nickel; [1-(4-butylphenyl)-2-(tetracosenyl)-3-(butyl)-4-(4-tricosylphenyl)diazobuta-1,3-diene]di(heptyl)nickel; [1-(4-butylphenyl)-2-(tetradecenyl)-3-(hexyl)-4-(4-octylphenyl)diazobuta-1,3-diene]di(pentacosyl)nickel; [1-(4-butylphenyl)-2-(tridecyl)-3-(octyl)-4-(4-tetradecenylphenyl)diazobuta-1,3-diene]di(diethylamino)nickel; [1-(4-butylphenyl)-2,3-(dibutyl)-4-(4-butenylphenyl)diazobuta-1,3-diene]di(tolyl)nickel; [1-(4-butylphenyl)-2,3-(dibutyl)-4-(4-heptadecynylphenyl)diazobuta-1,3-diene]di(benzyl)nickel; [1-(4-butylphenyl)-2,3-(dibutyl)-4-(4-hexylphenyl)diazobuta-1,3-diene]di(butoxy)palladium; [1-(4-butylphenyl)-2,3-(dibutyl)-4-(4-hexylphenyl)diazobuta-1,3-diene]di(methyl)nickel; [1-(4-butylphenyl)-2,3-(dibutyl)-4-(4-hexylphenyl)diazobuta-1,3-diene]di(tetradecyl)nickel; [1-(4-butylphenyl)-2,3-(dibutyl)-4-(4-octadecenylphenyl)diazobuta-1,3-diene]di(hydrido)nickel; [1-(4-butylphenyl)-2,3-(dibutyl)-4-(4-octylphenyl)diazobuta-1,3-diene]di(ethyl)palladium; [1-(4-butylphenyl)-2,3-(dibutyl)-4-(4-octylphenyl)diazobuta-1,3-diene]di(hexyl)nickel; [1-(4-butylphenyl)-2,3-(dibutyl)-4-(4-octylphenyl)diazobuta-1,3-diene]di(hydrido)nickel; [1-(4-butylphenyl)-2,3-(dibutyl)-4-(4-pentylphenyl)diazobuta-1,3-diene]di(butyl)nickel; [1-(4-butylphenyl)-2,3-(dibutyl)-4-(4-pentylphenyl)diazobuta-1,3-diene]di(chloro)palladium; [1-(4-butylphenyl)-2,3-(dibutyl)-4-(4-pentylphenyl)diazobuta-1,3-diene]di(decyl) palladium; [1-(4-butylphenyl)-2,3-(dibutyl)-4-(4-pentylphenyl)diazobuta-1,3-diene]di(ethyl)palladium; [1-(4-butylphenyl)-2,3-(dibutyl)-4-(4-pentylphenyl)diazobuta-1,3-diene]di(hydrido)nickel; [1-(4-butylphenyl)-2,3-(dibutyl)-4-(4-tetracosynylphenyl)diazobuta-1,3-diene]di(methyl)nickel; [1-(4-butylphenyl)-2,3-(dihydrido)-4-(4-ethylphenyl)diazobuta-1,3-diene]di(heneicosyl)nickel; [1-(4-butylphenyl)-2,3-(dihydrido)-4-(4-octylphenyl)diazobuta-1,3-diene]di(tolyl)nickel; [1-(4-butylphenyl)-2,3-(dihydrido)-4-(4-tricosenylphenyl)diazobuta-1,3-diene]di(hydrido)nickel; [1-(4-butylphenyl)-2,3-(dioctyl)-4-(4-hexylphenyl)diazobuta-1,3-diene]di(methyl)palladium; [1-(4-butylphenyl)-2,3-(dioctyl)-4-(4-octylphenyl)diazobuta-1,3-diene]di(pentyl)nickel; [1-(4-butylphenyl)-2,3-(dipentyl)-4-(4-(trimethylsilylethyl)phenyl)diazobuta-1,3-diene]di(octacosyl)nickel; [1-(4-butylphenyl)-2,3-(dipentyl)-4-(4-hexylphenyl)diazobuta-1,3-diene]di(benzyl)palladium; [1-(4-butynylphenyl)-2-(butyl)-3-(octyl)-4-(4-butanalylphenyl)diazobuta-1,3-diene]di(methyl)nickel; [1-(4-diethylaminophenyl)-2-(hydrido)-3-(nonyl)-4-(4-hexylphenyl)diazobuta-1,3-diene]di(phenethyl)palladium; [1-(4-diethylaminophenyl)-2,3-(dibutyl)-4-(4-butylphenyl)diazobuta-1,3-diene]di(tolyl)nickel; [1-(4-docosenylphenyl)-2-(pentyl)-3-(butyl)-4-(4-butylphenyl)diazobuta-1,3-diene]di(ethyl) nickel; [1-(4-docosylphenyl)-2-(hydrido)-3-(butyl)-4-(4-octylphenyl)diazobuta-1,3-diene]di(phenethyl)nickel; [1-(4-docosynylphenyl)-2-(butyl)-3-(hydrido)-4-(4-butylphenyl)diazobuta-1,3-diene]di(nonyl)nickel; [1-(4-docosynylphenyl)-2-(pentyl)-3-(butyl)-4-(4-butylphenyl)diazobuta-1,3-diene]di(heptyl)nickel; [1-(4-dodecanonylphenyl)-2-(hexyl)-3-(hexadecenyl)-4-(4-pentacosenylphenyl)diazobuta-1,3-diene]di(methyl)palladium; [1-(4-dodecenylphenyl)-2,3-(dibutyl)-4-(4-butylphenyl)diazobuta-1,3-diene]di(dimethylamino)nickel; [1-(4-dodecylphenyl)-2,3-(dihydrido)-4-(4-ethylphenyl)diazobuta-1,3-diene]di(propyl)nickel; [1-(4-dodecynylphenyl)-2-(octyl)-3-(hydrido)-4-(4-pentylphenyl)diazobuta-1,3-diene]di(butyl)nickel; [1-(4-ethanalylphenyl)-2-(hydrido)-3-(ethyl)-4-(4-pentylphenyl)diazobuta-1,3-diene]di(butyl)nickel; [1-(4-ethylphenyl)-2-(butyl)-3-(hexyl)-4-(4-butylphenyl)diazobuta-1,3-diene]di(butyl)palladium; [1-(4-ethylphenyl)-2-(butyl)-3-(hexyl)-4-(4-eicosylphenyl)diazobuta-1,3-diene]di(propenyl)nickel; [1-(4-ethylphenyl)-2-(butyl)-3-(pentyl)-4-(4-butylphenyl)diazobuta-1,3-diene]di(hexadecyl)nickel; [1-(4-ethylphenyl)-2-(docosenyl)-3-(butyl)-4-(4-butylphenyl)diazobuta-1,3-diene]di(bromo)palladium; [1-(4-ethylphenyl)-2-(ethyl)-3-(octyl)-4-(4-pentylphenyl)diazobuta-1,3-diene]di(heptacosyl)nickel; [1-(4-ethylphenyl)-2-(hexyl)-3-(pentyl)-4-(4-dodecaphosphinophenyl)diazobuta-1,3-diene]di(ethoxy)nickel; [1-(4-ethylphenyl)-2-(nonacosenyl)-3-(hexyl)-4-(4-pentylphenyl)diazobuta-1,3-diene]di(nonyl)nickel; [1-(4-ethylphenyl)-2-(nonenyl)-3-(hexyl)-4-(4-hexylphenyl)diazobuta-1,3-diene]di(ethyl)nickel; [1-(4-ethylphenyl)-2-(octyl)-3-(hydrido)-4-(4-octylphenyl)diazobuta-1,3-diene]di(pentyl)palladium; [1-(4-ethylphenyl)-2,3-(dibutyl)-4-(4-butenylphenyl)diazobuta-1,3-diene]di(tolyl)nickel; [1-(4-ethylphenyl)-2,3-(dibutyl)-4-(4-butylphenyl)diazobuta-1,3-diene]di(nonyl)nickel; [1-(4-ethylphenyl)-2,3-(dibutyl)-4-(4-hexylphenyl)diazobuta-1,3-diene]di(nonacosyl)nickel; [1-(4-ethylphenyl)-2,3-(dibutyl)-4-(4-pentylphenyl)diazobuta-1,3-diene]di(ethyl)palladium; [1-(4-ethylphenyl)-2,3-(dihydrido)-4-(4-butylphenyl)diazobuta-1,3-diene]di(ethyl)palladium; [1-(4-heneicosenylphenyl)-2-(pentyl)-3-(hydrido)-4-(4-tricosenylphenyl)diazobuta-1,3-diene]di(propyl)nickel; [1-(4-heneicosynylphenyl)-2-(hydrido)-3-(octyl)-4-(4-hexylphenyl)diazobuta-1,3-diene]di(methyl)nickel; [1-(4-heptadecylphenyl)-2-(butyl)-3-(hydrido)-4-(4-butylphenyl)diazobuta-1,3-diene]di(bromo)nickel; [1-(4-hexacosylphenyl)-2-(butyl)-3-(hydrido)-4-(4-hexylphenyl)diazobuta-1,3-diene]di(nonadecyl)palladium; [1-(4-hexadecynylphenyl)-2-(butyl)-3-(ethyl)-4-(4-(trimethylsilylmethyl)phenyl)diazobuta-1,3-diene]di(benzyl)nickel; [1-(4-hexadecynylphenyl)-2-(butyl)-3-(octyl)-4-(4-butylphenyl)diazobuta-1,3-diene]di(methyl)nickel; [1-(4-hexenylphenyl)-2,3-(dibutyl)-4-(4-tetracosylphenyl)diazobuta-1,3-diene]di(pentacosyl)nickel; [1-(4-hexylphenyl)-2-(butyl)-3-(ethyl)-4-(4-butylphenyl)diazobuta-1,3-diene]di(butyl)nickel; [1-(4-hexylphenyl)-2-(butyl)-3-(methyl)-4-(4-butylphenyl)diazobuta-1,3-diene]di(butyl)palladium; [1-(4-hexylphenyl)-2-(butyl)-3-(octyl)-4-(4-butylphenyl)diazobuta-1,3-diene]di(heptyl)palladium; [1-(4-hexylphenyl)-2-(butyl)-3-(octyl)-4-(4-undecenylphenyl)diazobuta-1,3-diene]di(pentyl)nickel; [1-(4-hexylphenyl)-2-(ethyl)-3-(butyl)-4-(4-butylphenyl)diazobuta-1,3-diene]di(docosyl)palladium; [1-(4-hexylphenyl)-2-(hexyl)-3-(butyl)-4-(4-octylphenyl)diazobuta-1,3-diene]di(nonadecyl)nickel; [1-(4-hexylphenyl)-2-(hexyl)-3-(eicosenyl)-4-(4-pentylphenyl)diazobuta-1,3-diene]di(tridecyl)nickel; [1-(4-hexylphenyl)-2-(hexyl)-3-(pentyl)-4-(4-butylphenyl)diazobuta-1,3-diene]di(dodecyl)nickel; [1-(4-hexylphenyl)-2-(hydrido)-3-(butyl)-4-(4-butylphenyl)diazobuta-1,3-diene]di(hydrido)palladium; [1-(4-hexylphenyl)-2-(hydrido)-3-(butyl)-4-(4-octylphenyl)diazobuta-1,3-diene]di(hydrido)palladium; [1-(4-hexylphenyl)-2-(hydrido)-3-(dodecynyl)-4-(4-butylphenyl)diazobuta-1,3-diene]di(methyl)nickel; [1-(4-hexylphenyl)-2-(hydrido)-3-(octyl)-4-(4-butylphenyl)diazobuta-1,3-diene]di(methyl)nickel; [1-(4-hexylphenyl)-2-(hydrido)-3-(pentyl)-4-(4-hexacosynylphenyl)diazobuta-1,3-diene]di(hydrido)nickel; [1-(4-hexylphenyl)-2-(nonacosynyl)-3-(pentyl)-4-(4-butylphenyl)diazobuta-1,3-diene]di(tridecyl)nickel; [1-(4-hexylphenyl)-2-(nonadecenyl)-3-(butyl)-4-(4-butylphenyl)

diazobuta-1,3-diene]di(ethoxy)nickel; [1-(4-hexylphenyl)-2-(pentacosyl)-3-(docosenyl)-4-(4-butylphenyl)diazobuta-1,3-diene]di(hydrido)palladium; [1-(4-hexylphenyl)-2-(pentyl)-3-(butyl)-4-(4-butylphenyl)diazobuta-1,3-diene]di(hydrido)nickel; [1-(4-hexylphenyl)-2-(propyl)-3-(butyl)-4-(4-butylphenyl)diazobuta-1,3-diene]di(heneicosyl)nickel; [1-(4-hexylphenyl)-2-(tricosyl)-3-(octyl)-4-(4-butylphenyl)diazobuta-1,3-diene]di(ethyl)nickel; [1-(4-hexylphenyl)-2,3-(dibutyl)-4-(4-butylphenyl)diazobuta-1,3-diene]di(heptacosyl)palladium; [1-(4-hexylphenyl)-2,3-(dibutyl)-4-(4-octacosynylphenyl)diazobuta-1,3-diene]di(pentyl)palladium; [1-(4-hexylphenyl)-2,3-(dibutyl)-4-(4-octadecenylphenyl)diazobuta-1,3-diene]di(phenethyl)nickel; [1-(4-hexylphenyl)-2,3-(dihexyl)-4-(4-butylphenyl)diazobuta-1,3-diene]di(phenyl)nickel; [1-(4-hexylphenyl)-2,3-(dihexyl)-4-(4-pentylphenyl)diazobuta-1,3-diene]di(diethylamino)palladium; [1-(4-hexylphenyl)-2,3-(dihydrido)-4-(4-butylphenyl)diazobuta-1,3-diene]di(methylethylamino)nickel; [1-(3,5-dibutylphenyl)-2-(octyl)-3-(butyl)-4-(3,5-di(triethylsilylmethyl)phenyl)diazobuta-1,3-diene]di(methyl)nickel; [1-(3,5-dibutylphenyl)-2-(octyl)-3-(butyl)-4-(3,5-dimethylphenyl)diazobuta-1,3-diene]di(benzoxy)nickel; [1-(3,5-dibutylphenyl)-2-(octyl)-3-(butyl)-4-(3,5-dioctylphenyl)diazobuta-1,3-diene]di(triacontyl)nickel; [1-(3,5-dibutylphenyl)-2-(octyl)-3-(butyl)-4-(3,5-dipentylphenyl)diazobuta-1,3-diene]di(hexadecyl)palladium; [1-(3,5-dibutylphenyl)-2-(octyl)-3-(butyl)-4-(3,5-dipentylphenyl)diazobuta-1,3-diene]di(methyl)nickel; [1-(3,5-dibutylphenyl)-2-(octyl)-3-(hydrido)-4-(3,5-dipentylphenyl)diazobuta-1,3-diene]di(allyl)palladium; [1-(3,5-dibutylphenyl)-2-(octyl)-3-(methyl)-4-(3,5-diethylphenyl)diazobuta-1,3-diene]di(hydrido)nickel; [1-(3,5-dibutylphenyl)-2-(octyl)-3-(octadecyl)-4-(3,5-di(trimethylsilylmethyl)phenyl)diazobuta-1,3-diene]di(methyl)palladium; [1-(3,5-dibutylphenyl)-2-(octyl)-3-(pentyl)-4-(3,5-dioctylphenyl)diazobuta-1,3-diene]di(bromo)nickel; [1-(3,5-dibutylphenyl)-2-(pentyl)-3-(butyl)-4-(3,5-dihexylphenyl)diazobuta-1,3-diene]di(docosyl)nickel; [1-(3,5-dibutylphenyl)-2-(pentyl)-3-(butyl)-4-(3,5-dihexylphenyl)diazobuta-1,3-diene]di(eicosyl)nickel; [1-(3,5-dibutylphenyl)-2-(pentyl)-3-(butyl)-4-(3,5-dipentylphenyl)diazobuta-1,3-diene]di(hydrido)nickel; [1-(3,5-dibutylphenyl)-2-(pentyl)-3-(butyl)-4-(3,5-dipentylphenyl)diazobuta-1,3-diene]di(nonyl)nickel; [1-(3,5-dibutylphenyl)-2-(pentyl)-3-(butyl)-4-(3,5-dipentylphenyl)diazobuta-1,3-diene]di(propoxy)nickel; [1-(3,5-dibutylphenyl)-2-(pentyl)-3-(eicosynyl)-4-(3,5-dihexylphenyl)diazobuta-1,3-diene]di(pentacosyl)nickel; [1-(3,5-dibutylphenyl)-2-(pentyl)-3-(hydrido)-4-(3,5-dihexylphenyl)diazobuta-1,3-diene]di(pentadecyl)palladium; [1-(3,5-dibutylphenyl)-2-(pentyl)-3-(pentacosynyl)-4-(3,5-dipentylphenyl)diazobuta-1,3-diene]di(nonacosyl)nickel; [1-(3,5-dibutylphenyl)-2-(pentyl)-3-(pentadecenyl)-4-(3,5-dimethylphenyl)diazobuta-1,3-diene]di(triacontyl)palladium; [1-(3,5-dibutylphenyl)-2-(tetracosenyl)-3-(butyl)-4-(3,5-diethylphenyl)diazobuta-1,3-diene]di(hydrido)nickel; [1-(3,5-dibutylphenyl)-2-(tridecenyl)-3-(hydrido)-4-(3,5-dioctylphenyl)diazobuta-1,3-diene]di(tetracosyl)palladium; [1-(3,5-dibutylphenyl)-2,3-(dibutyl)-4-(3,5-diheneicosenylphenyl)diazobuta-1,3-diene]di(hydrido)nickel; [1-(3,5-dibutylphenyl)-2,3-(dibutyl)-4-(3,5-dihexacosynylphenyl)diazobuta-1,3-diene]di(heneicosyl)palladium; [1-(3,5-dibutylphenyl)-2,3-(dibutyl)-4-(3,5-dihexonylphenyl)diazobuta-1,3-diene]di(dimethylamino)nickel; [1-(3,5-dibutylphenyl)-2,3-(dibutyl)-4-(3,5-dihexylphenyl)diazobuta-1,3-diene]di(propoxy)nickel; [1-(3,5-dibutylphenyl)-2,3-(dibutyl)-4-(3,5-dimethylethylaminophenyl)diazobuta-1,3-diene]di(hydrido)nickel; [1-(3,5-dibutylphenyl)-2,3-(dibutyl)-4-(3,5-dinonenylphenyl)diazobuta-1,3-diene]di(phenyl)nickel; [1-(3,5-dibutylphenyl)-2,3-(dibutyl)-4-(3,5-dioctylphenyl)diazobuta-1,3-diene]di(propoxy)nickel; [1-(3,5-dibutylphenyl)-2,3-(dibutyl)-4-(3,5-dipropanylphenyl)diazobuta-1,3-diene]di(phenyl)nickel; [1-(3,5-dibutylphenyl)-2,3-(dibutyl)-4-(3,5-ditetracosylphenyl)diazobuta-1,3-diene]di(hydrido)nickel; [1-(3,5-dibutylphenyl)-2,3-(dibutyl)-4-(3,5-ditriacontynylphenyl)diazobuta-1,3-diene]di(dodecyl)nickel; [1-(3,5-dibutylphenyl)-2,3-(dihydrido)-4-(3,5-dihexylphenyl)diazobuta-1,3-diene]di(hydrido)nickel; [1-(3,5-dibutylphenyl)-2,3-(dihydrido)-4-(3,5-dihexylphenyl)diazobuta-1,3-diene]di(hydrido)nickel; [1-(3,5-dibutylphenyl)-2,3-(dihydrido)-4-(3,5-dioctylphenyl)diazobuta-1,3-diene]di(methoxy)nickel; [1-(3,5-dibutylphenyl)-2,3-(dihydrido)-4-(3,5-dipentylphenyl)diazobuta-1,3-diene]di(tetracosyl)palladium; [1-(3,5-dibutylphenyl)-2,3-(dihydrido)-4-(3,5-diundecenylphenyl)diazobuta-1,3-diene]di(heptyl)palladium; [1-(3,5-didecylphenyl)-2-(butyl)-3-(pentyl)-4-(3,5-dipentylphenyl)diazobuta-1,3-diene]di(decyl)nickel; [1-(3,5-didecynylphenyl)-2-(butyl)-3-(octyl)-4-(3,5-diethylphenyl)diazobuta-1,3-diene]di(hydrido)palladium; [1-(3,5-didecynylphenyl)-2-(pentyl)-3-(butyl)-4-(3,5-dibutylphenyl)diazobuta-1,3-diene]di(pentadecyl)palladium; [1-(3,5-didiethylaminophenyl)-2-(ethyl)-3-(pentyl)-4-(3,5-dipentylphenyl)diazobuta-1,3-diene]di(ethyl)nickel; [1-(3,5-didocosynylphenyl)-2,3-(dihexyl)-4-(3,5-dibutylphenyl)diazobuta-1,3-diene]di(pentacosyl)palladium; [1-(3,5-didodecaminophenyl)-2-(hydrido)-3-(hexyl)-4-(3,5-dipentenylphenyl)diazobuta-1,3-diene]di(ethyl)nickel; [1-(3,5-didodecanonylphenyl)-2-(methyl)-3-(decynyl)-4-(3,5-dibutylphenyl)diazobuta-1,3-diene]di(docosyl)nickel; [1-(3,5-didodecylphenyl)-2,3-(dibutyl)-4-(3,5-dibutylphenyl)diazobuta-1,3-diene]di(methyl)nickel; [1-(3,5-dieicosylphenyl)-2-(octyl)-3-(hydrido)-4-(3,5-dibutylphenyl)diazobuta-1,3-diene]di(undecyl)nickel; [1-(3,5-diethylphenyl)-2-(butyl)-3-(heptyl)-4-(3,5-dibutylphenyl)diazobuta-1,3-diene]di(nonynyl)palladium; [1-(3,5-diethylphenyl)-2-(butyl)-3-(octadecenyl)-4-(3,5-dibutylphenyl)diazobuta-1,3-diene]di(methyl)nickel; [1-(3,5-diethylphenyl)-2-(butyl)-3-(octyl)-4-(3,5-dipentylphenyl)diazobuta-1,3-diene]di(octacosyl)palladium; [1-(3,5-diethylphenyl)-2-(butyl)-3-(pentyl)-4-(3,5-dibutanalylphenyl)diazobuta-1,3-diene]di(docosyl)nickel; [1-(3,5-diethylphenyl)-2-(butyl)-3-(pentyl)-4-(3,5-dinonenylphenyl)diazobuta-1,3-diene]di(butyl)nickel; [1-(3,5-diethylphenyl)-2-(hydrido)-3-(hexyl)-4-(3,5-dibutylphenyl)diazobuta-1,3-diene]di(ethyl)palladium; [1-(3,5-diethylphenyl)-2-(hydrido)-3-(pentyl)-4-(3,5-dipropenylphenyl)diazobuta-1,3-diene]di(methyl)nickel; [1-(3,5-diethylphenyl)-2-(methyl)-3-(butyl)-4-(3,5-dibutylphenyl)diazobuta-1,3-diene]di(hydrido)nickel; [1-(3,5-diethylphenyl)-2-(octyl)-3-(butyl)-4-(3,5-dimethyldiethylsilylmethyl)phenyl)diazobuta-1,3-diene]di(allyl)nickel; [1-(3,5-diethylphenyl)-2-(pentadecenyl)-3-(hydrido)-4-(3,5-dihexylphenyl)diazobuta-1,3-diene]di(hydrido)nickel; [1-(3,5-diethylphenyl)-2-(triacontyl)-3-(hexyl)-4-(3,5-dihexylphenyl)diazobuta-1,3-diene]di(tolyl)palladium; [1-(3,5-diethylphenyl)-2,3-(dibutyl)-4-(3,5-dibutylphenyl)diazobuta-1,3-diene]di(benzoxy)nickel; [1-(3,5-diethylphenyl)-2,3-(dibutyl)-4-(3,5-dihexylphenyl)diazobuta-1,3-diene]di(phenethyl)palladium; [1-(3,5-diethylphenyl)-2,3-(dibutyl)-4-(3,5-dinonadecylphenyl)diazobuta-1,3-diene]di(hexadecyl)nickel; [1-(3,5- diethylphenyl)-2,3-(dibutyl)-4-(3,5-dioctylphenyl) diazobuta-1,3-diene]di(methyl)nickel; [1-(3,5-diheptacosylphenyl)-2-(pentyl)-3-(hydrido)-4-(3,5-dibutylphenyl)diazobuta-1,3-diene]di(butyl)nickel; [1-(3,5-diheptadecenylphenyl)-2-(octyl)-3-(butyl)-4-(3,5-dibutylphenyl)diazobuta-1,3-diene]di(nonadecyl)nickel; [1-(3,5-dihexadecynylphenyl)-2,3-(dibutyl)-4-(3,5-ditriacontylphenyl)diazobuta-1,3-diene]di(methylethylamino)nickel; [1-(3,5-dihexenylphenyl)-2-(hydrido)-3-(pentyl)-4-(3,5-dipentenylphenyl)diazobuta-1,3-diene]di(triacontyl)nickel; [1-(3,5-dihexylphenyl)-2-(butyl)-3-(ethyl)-4-(3,5-dibutylphenyl)diazobuta-1,3-diene]di(octadecyl)palladium; [1-(3,5-dihexylphenyl)-2-(butyl)-3-(hexyl)-4-(3,5-dioctylphenyl)diazobuta-1,3-diene]di(docosyl)nickel; [1-(3,5-dihexylphenyl)-2-(butyl)-3-(hydrido)-4-(3,5-dibutylphenyl)diazobuta-1,3-diene]di(methyl)nickel; [1-(3,5-dihexylphenyl)-2-(butyl)-3-(hydrido)-4-(3,5-dimethylphenyl)diazobuta-1,3-diene]di(pentyl)nickel; [1-(3,5-dihexylphenyl)-2-(butyl)-3-(methyl)-4-(3,5-dibutylphenyl)diazobuta-1,3-diene]di(methyl)nickel; [1-(3,5-dihexylphenyl)-2-(butyl)-3-(pentyl)-4-(3,5-dioctylphenyl)diazobuta-1,3-diene]di(methyl)palladium; [1-(3,5-dihexylphenyl)-2-(decynyl)-3-(ethyl)-4-(3,5-dimethylphenyl)diazobuta-1,3-diene]di(butyl)nickel; [1-(3,5-dihexylphenyl)-2-(ethyl)-3-(hexyl)-4-(3,5-dibutylphenyl)diazobuta-1,3-diene]di(methyl)palladium; [1-(3,5-dihexylphenyl)-2-(ethyl)-3-(octadecynyl)-4-(3,5-ditridecynylphenyl)diazobuta-1,3-diene]di(docosyl)palladium; [1-(3,5-dihexylphenyl)-2-(heneicosynyl)-3-(butyl)-4-(3,5-dioctylphenyl)diazobuta-1,3-diene]di(octacosyl)nickel; [1-(3,5-dihexylphenyl)-2-(heptadecyl)-3-(tetracosynyl)-4-(3,5-dibutanalylphenyl)diazobuta-1,3-diene]di(propyl)nickel; [1-(3,5-dihexylphenyl)-2-(heptenyl)-3-(hydrido)-4-(3,5-dibutylphenyl)diazobuta-1,3-diene]di(pentyl)palladium; [1-(3,5-dihexylphenyl)-2-(hexyl)-3-(butyl)-4-(3,5-dibutylphenyl)diazobuta-1,3-diene]di(tetradecyl)nickel; [1-(3,5-dihexylphenyl)-2-(hexyl)-3-(pentyl)-4-(3,5-dibutylphenyl)diazobuta-1,3-diene]di(hydride)nickel; [1-(3,5-dihexylphenyl)-2-(hexyl)-3-(tetracosynyl)-4-(3,5-dioctylphenyl)diazobuta-1,3-diene]di(hydrido)palladium; [1-(3,5-dihexylphenyl)-2-(hydrido)-3-(butyl)-4-(3,5-dibutylphenyl)diazobuta-1,3-diene]di(ethoxy)nickel; [1-(3,5-dihexylphenyl)-2-(hydrido)-3-(butyl)4-(3,5-dibutylphenyl)diazobuta-1,3-diene]di(heneicosyl)nickel; [1-(3,5-dihexylphenyl)-2-(hydrido)-3-(butyl)-4-(3,5-diethylphenyl)diazobuta-1,3-diene]di(phenyl)nickel; [1-(3,5-dihexylphenyl)-2-(hydrido)-3-(octyl)-4-(3,5-diethanalylphenyl)diazobuta-1,3-diene]di(phenoxy)nickel; [1-(3,5-dihexylphenyl)-2-(methyl)-3-(hydrido)-4-(3,5-dibutylphenyl)diazobuta-1,3-diene]di(pentacosyl)nickel; [1-(3,5-dihexylphenyl)-2-(methyl)-3-(hydrido)-4-(3,5-dibutylphenyl)diazobuta-1,3-diene]di(pentyl)nickel; [1-(3,5-dihexylphenyl)-2-(methyl)-3-(hydrido)-4-(3,5-dioctylphenyl)diazobuta-1,3-diene]di(pentacosyl)nickel; [1-(3,5-dihexylphenyl)-2-(methyl)-3-(octyl)-4-(3,5-dibutylphenyl)diazobuta-1,3-diene]di(hexyl)nickel; [1-(3,5-dihexylphenyl)-2-(methyl)-3-(pentyl)-4-(3,5-dimethylphenyl)diazobuta-1,3-diene]di(tridecyl)nickel; [1-(3,5-dihexylphenyl)-2-(octyl)-3-(butyl)-4-(3,5-didecynylphenyl)diazobuta-1,3-diene]di(hydrido)palladium; [1-(3,5-dihexylphenyl)-2-(octyl)-3-(pentyl)-4-(3,5-dibutylphenyl)diazobuta-1,3-diene]di(methyl)nickel; [1-(3,5-dihexylphenyl)-2-(pentyl)-3-(butyl)-4-(3,5-dibutylphenyl)diazobuta-1,3-diene]di(methyl)nickel; [1-(3,5-dihexylphenyl)-2-(pentyl)-3-(butyl)-4-(3,5-ditetracosylphenyl)diazobuta-1,3-diene]di(heptyl)nickel; [1-(3,5-dihexylphenyl)-2-(pentyl)-3-(octyl)-4-(3,5-dibutylphenyl)diazobuta-1,3-diene]di(butyl)nickel; [1-(3,5-dihexylphenyl)-2-(pentyl)-3-(octyl)-4-(3,5-dibutylphenyl)diazobuta-1,3-diene]di(hydrido)palladium; [1-(3,5-dihexylphenyl)-2-(triacontyl)-3-(hydrido)-4-(3,5-dibutylphenyl)diazobuta-1,3-diene]di(methylethylamino)nickel; [1-(3,5-dihexylphenyl)-2,3-(dibutyl)-4-(3,5-dibutylphenyl)diazobuta-1,3-diene]di(phenoxy)nickel; [1-(3,5-dihexylphenyl)-2,3-(dibutyl)-4-(3,5-diethylphenyl)diazobuta-1,3-diene]di(ethyl)nickel; [1-(3,5-dihexylphenyl)-2,3-(dioctyl)-4-(3,5-dimethylphenyl)diazobuta-1,3-diene]di(heneicosyl)nickel; [1-(3,5-dihexylphenyl)-2,3-(dipentyl)-4-(3,5-dibutylphenyl)diazobuta-1,3-diene]di(tetracosyl)nickel; [1-(3,5-dimethyldiethylsilylmethyl)phenyl)-2-(hydrido)-3-(octyl)-4-(3,5-dipentylphenyl)diazobuta-1,3-diene]di(ethyl)nickel; [1-(3,5-dimethylphenyl)-2-(butyl)-3-(octyl)-4-(3,5-dioctylphenyl)diazobuta-1,3-diene]di(bromo)palladium; [1-(3,5-dimethylphenyl)-2-(butyl)-3-(tetradecyl)-4-(3,5-dipentylphenyl)diazobuta-1,3-diene]di(chloro)nickel; [1-(3,5-dimethylphenyl)-2-(heptadecyl)-3-(butyl)-4-(3,5-diethylphenyl)diazobuta-1,3-diene]di(benzyl)nickel; [1-(3,5-dimethylphenyl)-2-(hexyl)-3-(octyl)-4-(3,5-dihexenylphenyl)diazobuta-1,3-diene]di(bromo)palladium; [1-(3,5-dimethylphenyl)-2-(hexyl)-3-(pentyl)-4-(3,5-dibutylphenyl)diazobuta-1,3-diene]di(triacontynyl)nickel; [1-(3,5-dimethylphenyl)-2-(hydrido)-3-(hexyl)-4-(3,5-dipentylphenyl)diazobuta-1,3-diene]di(diethylamino)nickel; [1-(3,5-dimethylphenyl)-2-(octyl)-3-(butyl)-4-(3,5-dibutylphenyl)diazobuta-1,3-diene]di(heneicosenyl)nickel; [1-(3,5-dimethylphenyl)-2-(octyl)-3-(pentyl)-4-(3,5-dibutylphenyl)diazobuta-1,3-diene]di(triacontyl)nickel; [1-(3,5-dimethylphenyl)-2-(pentyl)-3-(hexyl)-4-(3,5-dibutylphenyl)diazobuta-1,3-diene]di(tricosyl)nickel; [1-(3,5-dimethylphenyl)-2-(tricosyl)-3-(butyl)-4-(3,5-dihexylphenyl)diazobuta-1,3-diene]di(allyl)nickel; [1-(3,5-dimethylphenyl)-2,3-(dibutyl)-4-(3,5-dibutylphenyl)diazobuta-1,3-diene]di(phenethyl)palladium; [1-(3,5-dinonacosenylphenyl)-2-(butyl)-3-(hexyl)-4-(3,5-dihexylphenyl)diazobuta-1,3-diene]di(methoxy)nickel; [1-(3,5-dinonacosynylphenyl)-2-(methyl)-3-(hexyl)-4-(3,5-dipentynylphenyl)diazobuta-1,3-diene]di(dodecynyl)nickel; [1-(3,5-dinonacosynylphenyl)-2-(octyl)-3-(tetracosenyl)-4-(3,5-dibutylphenyl)diazobuta-1,3-diene]di(chloro)nickel; [1-(3,5-dinonadecenylphenyl)-2-(butyl)-3-(octyl)-4-(3,5-diheptadecynylphenyl)diazobuta-1,3-diene]di(heneicosyl)nickel; [1-(3,5-dinonenylphenyl)-2-(pentyl)-3-(pentadecyl)-4-(3,5-dibutylphenyl)diazobuta-1,3-diene]di(tridecyl)nickel; [1-(3,5-dinonynylphenyl)-2-(butyl)-3-(hydrido)-4-(3,5-didodecenylphenyl)diazobuta-1,3-diene]di(nonyl)nickel; [1-(3,5-dioctacosynylphenyl)-2-(butyl)-3-(hydrido)-4-(3,5-dibutylphenyl)diazobuta-1,3-diene]di(heptyl)palladium; [1-(3,5-dioctacosynylphenyl)-2-(hydrido)-3-(hexyl)-4-(3,5-dibutylphenyl)diazobuta-1,3-diene]di(nonyl)nickel; [1-(3,5-dioctadecylphenyl)-2-(ethyl)-3-(octyl)-4-(3,5-dihexylphenyl)diazobuta-1,3-diene]di(ethyl)nickel; [1-(3,5-dioctadecylphenyl)-2-(pentyl)-3-(hydrido)-4-(3,5-didodecanonylphenyl)diazobuta-1,3-diene]di(ethyl)palladium; [1-(3,5-dioctylphenyl)-2-(butyl)-3-(heptacosynyl)-4-(3,5-dihexylphenyl)diazobuta-1,3-diene]di(methyl)palladium; [1-(3,5-dioctylphenyl)-2-(butyl)-3-(hydrido)-4-(3,5-dibutylphenyl)diazobuta-1,3-diene]di(ethoxy)nickel; [1-(3,5-dioctylphenyl)-2-(butyl)-3-(hydrido)-4-(3,5-didocosylphenyl)diazobuta-1,3-diene]di(pentadecyl)palladium; [1-(3,5-dioctylphenyl)-2-(butyl)-3-(hydrido)-4-(3,5-dihexylphenyl)diazobuta-1,3-diene]di(methylethylamino)nickel; [1-(3,5-dioctylphenyl)-2-(butyl)-

3-(hydrido)-4-(3,5-dipentylphenyl)diazobuta-1,3-diene]di(decyl)palladium; [1-(3,5-dioctylphenyl)-2-(butyl)-3-(methyl)-4-(3,5-dihexadecenylphenyl)diazobuta-1,3-diene]di(docosenyl)nickel; [1-(3,5-dioctylphenyl)-2-(butyl)-3-(nonynyl)-4-(3,5-dibutylphenyl)diazobuta-1,3-diene]di(methoxy)nickel; [1-(3,5-dioctylphenyl)-2-(butyl)-3-(octyl)-4-(3,5-dibutylphenyl)diazobuta-1,3-diene]di(methyl)palladium; [1-(3,5-dioctylphenyl)-2-(butyl)-3-(octyl)-4-(3,5-dihexylphenyl)diazobuta-1,3-diene]di(hydrido)nickel; [1-(3,5-dioctylphenyl)-2-(butyl)-3-(pentyl)-4-(3,5-dimethylphenyl)diazobuta-1,3-diene]di(tolyl)palladium; [1-(3,5-dioctylphenyl)-2-(butyl)-3-(propyl)-4-(3,5-dibutylphenyl)diazobuta-1,3-diene]di(phenethyl)palladium; [1-(3,5-dioctylphenyl)-2-(butyl)-3-(tetracosyl)-4-(3,5-dibutylphenyl)diazobuta-1,3-diene]di(phenyl)palladium; [1-(3,5-dioctylphenyl)-2-(dodecynyl)-3-(butyl)-4-(3,5-dihexylphenyl)diazobuta-1,3-diene]di(nonacosyl)nickel; [1-(3,5-dioctylphenyl)-2-(ethyl)-3-(hydrido)-4-(3,5-dihexylphenyl)diazobuta-1,3-diene]di(triacontyl)palladium; [1-(3,5-dioctylphenyl)-2-(ethyl)-3-(hydrido)-4-(3,5-dipentacosenylphenyl)diazobuta-1,3-diene]di(hydrido)nickel; [1-(3,5-dioctylphenyl)-2-(heptacosenyl)-3-(butyl)-4-(3,5-dibutylphenyl)diazobuta-1,3-diene]di(nonacosyl)nickel; [1-(3,5-dioctylphenyl)-2-(heptadecenyl)-3-(butyl)-4-(3,5-dibutylphenyl)diazobuta-1,3-diene]di(heptadecyl)nickel; [1-(3,5-dioctylphenyl)-2-(hexyl)-3-(butyl)-4-(3,5-dihexylphenyl)diazobuta-1,3-diene]di(decenyl)nickel; [1-(3,5-dioctylphenyl)-2-(hexyl)-3-(butyl)-4-(3,5-dipentylphenyl)diazobuta-1,3-diene]di(ethyl)nickel; [1-(3,5-dioctylphenyl)-2-(hexyl)-3-(pentyl)-4-(3,5-dibutylphenyl)diazobuta-1,3-diene]di(ethyl)nickel; [1-(3,5-dioctylphenyl)-2-(hydrido)-3-(butyl)-4-(3,5-dipentylphenyl)diazobuta-1,3-diene]di(methyl)nickel; [1-(3,5-dioctylphenyl)-2-(hydrido)-3-(heptacosenyl)-4-(3,5-dibutylphenyl)diazobuta-1,3-diene]di(nonacosyl)nickel; [1-(3,5-dioctylphenyl)-2-(hydrido)-3-(hexyl)-4-(3,5-dibutylphenyl)diazobuta-1,3-diene]di(methyl)palladium; [1-(3,5-dioctylphenyl)-2-(hydrido)-3-(methyl)-4-(3,5-didecylphenyl)diazobuta-1,3-diene]di(octadecyl)nickel; [1-(3,5-dioctylphenyl)-2-(methyl)-3-(butyl)-4-(3,5-dipentadecynylphenyl)diazobuta-1,3-diene]di(eicosyl)nickel; [1-(3,5-dioctylphenyl)-2-(nonenyl)-3-(butyl)-4-(3,5-dibutylphenyl)diazobuta-1,3-diene]di(butoxy)nickel; [1-(3,5-dioctylphenyl)-2-(octyl)-3-(butyl)-4-(3,5-dibutylphenyl)diazobuta-1,3-diene]di(butyl)nickel; [1-(3,5-dioctylphenyl)-2-(octyl)-3-(hydrido)-4-(3,5-dipentylphenyl)diazobuta-1,3-diene]di(docosyl)nickel; [1-(3,5-dioctylphenyl)-2-(octyl)-3-(octacosenyl)-4-(3,5-dibutylphenyl)diazobuta-1,3-diene]di(butyl)nickel; [1-(3,5-dioctylphenyl)-2-(pentyl)-3-(hydrido)-4-(3,5-dibutylphenyl)diazobuta-1,3-diene]di(hydrido)palladium; [1-(3,5-dioctylphenyl)-2-(tetracosynyl)-3-(octyl)-4-(3,5-dibutylphenyl)diazobuta-1,3-diene]di(nonacosyl)nickel; [1-(3,5-dioctylphenyl)-2-(undecenyl)-3-(butyl)-4-(3,5-dibutylphenyl)diazobuta-1,3-diene]di(octyl)nickel; [1-(3,5-dioctylphenyl)-2,3-(dibutyl)-4-(3,5-dibutylphenyl)diazobuta-1,3-diene]di(ethyl)palladium; [1-(3,5-dioctylphenyl)-2,3-(dibutyl)-4-(3,5-dibutylphenyl)diazobuta-1,3-diene]di(hexyl)nickel; [1-(3,5-dioctylphenyl)-2,3-(dibutyl)-4-(3,5-dibutylphenyl)diazobuta-1,3-diene]di(methoxy)palladium; [1-(3,5-dioctylphenyl)-2,3-(dibutyl)-4-(3,5-dibutylphenyl)diazobuta-1,3-diene]di(triacontyl)palladium; [1-(3,5-dioctylphenyl)-2,3-(dibutyl)-4-(3,5-dipentylphenyl)diazobuta-1,3-diene]di(butyl)nickel; [1-(3,5-dioctylphenyl)-2,3-(dihydrido)-4-(3,5-dibutylphenyl)diazobuta-1,3-diene]di(hexyl)nickel; [1-(3,5-dioctynylphenyl)-2-(pentyl)-3-(octyl)-4-(3,5-dibutylphenyl)diazobuta-1,3-diene]di(heptenyl)nickel; [1-(3,5-dipentacosynylphenyl)-2-(hydrido)-3-(propenyl)-4-(3,5-dipentylpheny)diazobuta-1,3-diene]di(nonacosyl)palladium; [1-(3,5-dipentacosynylphenyl)-2,3-(dihexyl)-4-(3,5-dioctylphenyl)diazobuta-1,3-diene]di(tetradecenyl)nickel; [1-(3,5-dipentadecylphenyl)-2-(hexyl)-3-(hydrido)-4-(3,5-dihexylphenyl)diazobuta-1,3-diene]di(hydrido)nickel; [1-(3,5-dipentadecylphenyl)-2-(pentyl)-3-(butyl)-4-(3,5-dihexylphenyl)diazobuta-1,3-diene]di(ethyl)palladium; [1-(3,5-dipentonylphenyl)-2,3-(dibutyl)-4-(3,5-dibutylphenyl)diazobuta-1,3-diene]di(nonyl)nickel; [1-(3,5-dipentylphenyl)-2-(butyl)-3-(decenyl)-4-(3,5-dibutylphenyl)diazobuta-1,3-diene]di(tridecyl)nickel; [1-(3,5-dipentylphenyl)-2-(butyl)-3-(hydrido)-4-(3,5-dibutylphenyl)diazobuta-1,3-diene]di(hydrido)nickel; [1-(3,5-dipentylphenyl)-2-(butyl)-3-(hydrido)-4-(3,5-dihexylphenyl)diazobuta-1,3-diene]di(pentadecyl)nickel; [1-(3,5-dipentylphenyl)-2-(butyl)-3-(octacosenyl)-4-(3,5-dihexylphenyl)diazobuta-1,3-diene]di(ethyl)palladium; [1-(3,5-dipentylphenyl)-2-(butyl)-3-(octyl)-4-(3,5-dibutylphenyl)diazobuta-1,3-diene]di(ethyl)nickel; [1-(3,5-dipentylphenyl)-2-(butyl)-3-(pentacosyl)-4-(3,5-dibutylphenyl)diazobuta-1,3-diene]di(butyl)nickel; [1-(3,5-dipentylphenyl)-2-(hexyl)-3-(butyl)-4-(3,5-dibutylphenyl)diazobuta-1,3-diene]di(butyl)nickel; [1-(3,5-dipentylphenyl)-2-(hexyl)-3-(butyl)-4-(3,5-dibutylphenyl)diazobuta-1,3-diene]di(hydrido)nickel; [1-(3,5-dipentylphenyl)-2-(hydrido)-3-(butyl)-4-(3,5-dibutylphenyl)diazobuta-1,3-diene]di(diethylamino)nickel; [1-(3,5-dipentylphenyl)-2-(hydrido)-3-(octyl)-4-(3,5-didecylphenyl)diazobuta-1,3-diene]di(hydrido)nickel; [1-(3,5-dipentylphenyl)-2-(hydrido)-3-(pentadecenyl)-4-(3,5-dihexylphenyl)diazobuta-1,3-diene]di(heptyl)nickel; [1-(3,5-dipentylphenyl)-2-(hydrido)-3-(pentyl)-4-(3,5-dibutylphenyl)diazobuta-1,3-diene]di(phenoxy)nickel; [1-(3,5-dipentylphenyl)-2-(methyl)-3-(butyl)-4-(3,5-diundecylphenyl)diazobuta-1,3-diene]di(hydrido)nickel; [1-(3,5-dipentylphenyl)-2-(octyl)-3-(butyl)-4-(3,5-diethylphenyl)diazobuta-1,3-diene]di(heptacosyl)nickel; [1-(3,5-dipentylphenyl)-2-(octyl)-3-(hexyl)-4-(3,5-dibutonylphenyl)diazobuta-1,3-diene]di(tetracosyl)palladium; [1-(3,5-dipentylphenyl)-2-(pentadecyl)-3-(butyl)-4-(3,5-dibutylphenyl)diazobuta-1,3-diene]di(methyl)palladium; [1-(3,5-dipentylphenyl)-2-(pentyl)-3-(butyl)-4-(3,5-dinonynyl)diazobuta-1,3-diene]di(heptacosyl)nickel; [1-(3,5-dipentylphenyl)-2-(pentyl)-3-(hydrido)-4-(3,5-dioctylphenyl)diazobuta-1,3-diene]di(allyl)nickel; [1-(3,5-dipentylphenyl)-2-(pentyl)-3-(octyl)-4-(3,5-dibutylphenyl)diazobuta-1,3-diene]di(butyl)palladium; [1-(3,5-dipentylphenyl)-2,3-(dibutyl)-4-(3,5-dibutylphenyl)diazobuta-1,3-diene]di(diethylamino)palladium; [1-(3,5-dipentylphenyl)-2,3-(dibutyl)-4-(3,5-dibutylphenyl)diazobuta-1,3-diene]di(docosyl)nickel; [1-(3,5-dipentylphenyl)-2,3-(dibutyl)-4-(3,5-dibutylphenyl)diazobuta-1,3-diene]di(hydrido)palladium; [1-(3,5-dipentylphenyl)-2,3-(dibutyl)-4-(3,5-dibutylphenyl)diazobuta-1,3-diene]di(propyl)nickel; [1-(3,5-dipentylphenyl)-2,3-(dipentyl)-4-(3,5-dibutylphenyl)diazobuta-1,3-diene]di(hydrido)palladium; [1-(3,5-dipropynylphenyl)-2-(nonadecyl)-3-(butyl)-4-(3,5-diethylphenyl)diazobuta-1,3-diene]di(methyl)nickel; [1-(3,5-dipropynylphenyl)-2-(pentyl)-3-(hydrido)-4-(3,5-diethylphenyl)diazobuta-1,3-diene]di(phenethyl)nickel; [1-(3,5-ditetracosenylphenyl)-2-(hydrido)-3-(butyl)-4-(3,5-dibutylphenyl)diazobuta-1,3-diene]di(nonadecyl)palladium; [1-(3,5-ditetracosynylphenyl)-2-(pentyl)-3-(butyl)-4-(3,5-dipentynylphenyl)diazobuta-1,3-diene]di (heneicosyl)palladium; [1-(3,5-ditricosylphenyl)-2-(butyl)-3-(pentyl)-4-(3,5-dipentylphenyl)diazobuta-1,3-diene]di(hydrido)nickel; [1-(3,5-ditricosylphenyl)-2-(ethyl)-3-(octadecenyl)-4-(3,5-dibutylphenyl)diazobuta-1,3-diene]di(decyl)nickel; [1-(3,5-ditricosylphenyl)-2,3-(dibutyl)-4-(3,5-dibutylphenyl)diazobuta-1,3-diene]di(hydrido)nickel; [1-(3,5-ditricosynylphenyl)diazobuta-1,3-diene]-2-(hydrido)-3-(octyl)-4-(3,5-dihexylphenyl)diazobuta-1,3-diene]di(hydrido)palladium; [1-(3,5-ditridecenylphenyl)-2-(butyl)-3-(pentyl)-4-(3,5-dipentylphenyl)diazobuta-1,3-diene]di(benzoxy)nickel; [1-(3,5-diundecylphenyl)-2-(hydrido)-3-(pentyl)-4-(3,5-dibutylphenyl)diazobuta-1,3-diene]di(methyl)nickel; [1-(3,4,5-tributylphenyl)-2-(butyl)-3-(ethyl)-4-(3,4,5-tripentylphenyl)diazobuta-1,3-diene]di(hexadecyl)nickel; [1-(3,4,5-tributylphenyl)-2-(butyl)-3-(heptenyl)-4-(3,4,5-tripentylphenyl)diazobuta-1,3-diene]di(hydrido)nickel; [1-(3,4,5-tributylphenyl)-2-(butyl)-3-(hexyl)-4-(3,4,5-trihexylphenyl)diazobuta-1,3-diene]di(heptacosyl)nickel; [1-(3,4,5-tributylphenyl)-2-(butyl)-3-(hexyl)-4-(3,4,5-tripentylphenyl)diazobuta-1,3-diene]di(ethyl)nickel; [1-(3,4,5-tributylphenyl)-2-(butyl)-3-(hexyl)-4-(3,4,5-tripropylphenyl)diazobuta-1,3-diene]di(ethyl)nickel; [1-(3,4,5-tributylphenyl)-2-(butyl)-3-(hydrido)-4-(3,4,5-trimethylphenyl)diazobuta-1,3-diene]di(pentadecyl)nickel; [1-(3,4,5-tributylphenyl)-2-(butyl)-3-(hydrido)-4-(3,4,5-tripentylphenyl)diazobuta-1,3-diene]di(hydrido)palladium; [1-(3,4,5-tributylphenyl)-2-(butyl)-3-(hydrido)-4-(3,4,5-tripropylphenyl)diazobuta-1,3-diene]di(heptacosyl)nickel; [1-(3,4,5-tributylphenyl)-2-(butyl)-3-(hydrido)-4-(3,4,5-tripropylphenyl)diazobuta-1,3-diene]di(hexyl)nickel; [1-(3,4,5-tributylphenyl)-2-(butyl)-3-(methyl)-4-(3,4,5-triethylphenyl)diazobuta-1,3-diene]di(docosyl)nickel; [1-(3,4,5-tributylphenyl)-2-(butyl)-3-(methyl)-4-(3,4,5-tripentylphenyl)diazobuta-1,3-diene]di(ethyl)nickel; [1-(3,4,5-tributylphenyl)-2-(butyl)-3-(methyl)-4-(3,4,5-tripropylphenyl)diazobuta-1,3-diene]di(butoxy)palladium; [1-(3,4,5-tributylphenyl)-2-(butyl)-3-(pentyl)-4-(3,4,5-tripentylphenyl)diazobuta-1,3-diene]di(benzyl)nickel; [1-(3,4,5-tributylphenyl)-2-(butyl)-3-(pentyl)-4-(3,4,5-tripentylphenyl)diazobuta-1,3-diene]di(undecyl)palladium; [1-(3,4,5-tributylphenyl)-2-(decyl)-3-(pentyl)-4-(3,4,5-triethylphenyl)diazobuta-1,3-diene]di(butyl)nickel; [1-(3,4,5-tributylphenyl)-2-(decynyl)-3-(hydrido)-4-(3,4,5-tripropylphenyl)diazobuta-1,3-diene]di(hydrido)nickel; [1-(3,4,5-tributylphenyl)-2-(docosenyl)-3-(octyl)-4-(3,4,5-trimethylphenyl)diazobuta-1,3-diene]di(dimethylamino)nickel; [1-(3,4,5-tributylphenyl)-2-(eicosynyl)-3-(hexyl)-4-(3,4,5-trihexylphenyl)diazobuta-1,3-diene]di(hydrido)nickel; [1-(3,4,5-tributylphenyl)-2-(ethyl)-3-(butyl)-4-(3,4,5-trimethylphenyl)diazobuta-1,3-diene]di(tridecyl)nickel; [1-(3,4,5-tributylphenyl)-2-(ethyl)-3-(butyl)-4-(3,4,5-tripropylphenyl)diazobuta-1,3-diene]di(iodo)palladium; [1-(3,4,5-tributylphenyl)-2-(heptadecynyl)-3-(ethyl)-4-(3,4,5-trimethylphenyl)diazobuta-1,3-diene]di(tridecyl)nickel; [1-(3,4,5-trihexylphenyl)-2,3-(dibutyl)-4-(3,4,5-tributylphenyl)diazobuta-1,3-diene]di(heptyl)nickel; [1-(3,4,5-trihexylphenyl)-2,3-(dibutyl)-4-(3,4,5-trimethylphenyl)diazobuta-1,3-diene]di(ethyl)palladium; [1-(3,4,5-trihexylphenyl)-2,3-(dibutyl)-4-(3,4,5-trimethylphenyl)diazobuta-1,3-diene]di(nonadecyl)nickel; [1-(3,4,5-trihexylphenyl)-2,3-(dibutyl)-4-(3,4,5-tripropylphenyl)diazobuta-1,3-diene]di(methyl)nickel; [1-(3,4,5-trihexylphenyl)-2,3-(diethyl)-4-(3,4,5-trimethylphenyl)diazobuta-1,3-diene]di(eicosyl)palladium; [1-(3,4,5-trihexylphenyl)-2,3-(dihydrido)-4-(3,4,5-triethylphenyl)diazobuta-1,3-diene]di(tetracosyl)nickel; [1-(3,4,5-trihexylphenyl)-2,3-(dihydrido)-4-(3,4,5-trimethylphenyl)diazobuta-1,3-diene]di(triacontyl)nickel; [1-(3,4,5-trihexylphenyl)-2,3-(dihydrido)-4-(3,4,5-tripentonylphenyl)diazobuta-1,3-diene]di(phenethyl)nickel; [1-(3,4,5-trihexylphenyl)-2,3-(dioctyl)-4-(3,4,5-tributylphenyl)diazobuta-1,3-diene]di(ethyl)nickel; [1-(3,4,5-trihexylphenyl)-2,3-(dipentyl)-4-(3,4,5-tripentylphenyl)diazobuta-1,3-diene]di(ethyl)nickel; [1-(3,4,5-trimethylphenyl)-2-(butyl)-3-(ethyl)-4-(3,4,5-tributylphenyl)diazobuta-1,3-diene]di(butyl)palladium; [1-(3,4,5-trimethylphenyl)-2-(butyl)-3-(ethyl)-4-(3,4,5-tripentylphenyl)diazobuta-1,3-diene]di(tetradecynyl)nickel; [1-(3,4,5-trimethylphenyl)-2-(butyl)-3-(hexadecyl)-4-(3,4,5-trihexylphenyl)diazobuta-1,3-diene]di(butyl)palladium; [1-(3,4,5-trimethylphenyl)-2-(butyl)-3-(hexyl)-4-(3,4,5-trihexylphenyl)diazobuta-1,3-diene]di(butyl)nickel; [1-(3,4,5-trimethylphenyl)-2-(butyl)-3-(hydrido)-4-(3,4,5-tributylphenyl)diazobuta-1,3-diene]di(tetradecyl)palladium; [1-(3,4,5-trimethylphenyl)-2-(butyl)-3-(hydrido)-4-(3,4,5-trihexylphenyl)diazobuta-1,3-diene]di(dodecynyl)palladium; [1-(3,4,5-trimethylphenyl)-2-(butyl)-3-(hydrido)-4-(3,4,5-trihexylphenyl)diazobuta-1,3-diene]di(ethyl)palladium; [1-(3,4,5-trimethylphenyl)-2-(butyl)-3-(hydrido)-4-(3,4,5-tripentylphenyl)diazobuta-1,3-diene]di(tetradecyl)palladium; [1-(3,4,5-trimethylphenyl)-2-(butyl)-3-(octyl)-4-(3,4,5-tributylphenyl)diazobuta-1,3-diene]di(undecyl)nickel; [1-(3,4,5-trimethylphenyl)-2-(butyl)-3-(octyl)-4-(3,4,5-trihexylphenyl)diazobuta-1,3-diene]di(methyl)palladium; [1-(3,4,5-trimethylphenyl)-2-(butyl)-3-(octyl)-4-(3,4,5-tripropylphenyl)diazobuta-1,3-diene]di(butoxy)palladium; [1-(3,4,5-trimethylphenyl)-2-(ethyl)-3-(hydrido)-4-(3,4,5-tributylphenyl)diazobuta-1,3-diene]di(heptadecyl)nickel; [1-(3,4,5-trimethylphenyl)-2-(hexenyl)-3-(butyl)-4-(3,4,5-tributylphenyl)diazobuta-1,3-diene]di(pentadecyl)nickel; [1-(3,4,5-trimethylphenyl)-2-(hexyl)-3-(butyl)-4-(3,4,5-tributylphenyl)diazobuta-1,3-diene]di(propyl)nickel; [1-(3,4,5-trimethylphenyl)-2-(hexyl)-3-(hydrido)-4-(3,4,5-trihexylphenyl)diazobuta-1,3-diene]di(ethyl)palladium; [1-(3,4,5-trimethylphenyl)-2-(hexyl)-3-(hydrido)-4-(3,4,5-trihexylphenyl)diazobuta-1,3-diene]di(hydrido)nickel; [1-(3,4,5-trimethylphenyl)-2-(hexyl)-3-(hydrido)-4-(3,4,5-tripentylphenyl)diazobuta-1,3-diene]di(butoxy)nickel; [1-(3,4,5-trimethylphenyl)-2-(hydrido)-3-(butyl)-4-(3,4,5-tributylphenyl)diazobuta-1,3-diene]di(hydrido)nickel; [1-(3,4,5-trimethylphenyl)-2-(hydrido)-3-(heptyl)-4-(3,4,5-tributylphenyl)diazobuta-1,3-diene]di(nonynyl)nickel; [1-(3,4,5-trimethylphenyl)-2-(hydrido)-3-(nonacosyl)-4-(3,4,5-tributylphenyl)diazobuta-1,3-diene]di(ethoxy)nickel; [1-(3,4,5-trimethylphenyl)-2-(hydrido)-3-(octyl)-4-(3,4,5-tributylphenyl)diazobuta-1,3-diene]di(bromo)nickel; [1-(3,4,5-trimethylphenyl)-2-(hydrido)-3-(octyl)-4-(3,4,5-tributylphenyl)diazobuta-1,3-diene]di(hydrido)palladium; [1-(3,4,5-trimethylphenyl)-2-(methyl)-3-(butyl)-4-(3,4,5-tripentylphenyl)diazobuta-1,3-diene]di(tolyl)palladium; [1-(3,4,5-trimethylphenyl)-2-(methyl)-3-(butyl)-4-(3,4,5-tripropylphenyl)diazobuta-1,3-diene]di(butyl)nickel; [1-(3,4,5-trimethylphenyl)-2-(octyl)-3-(butyl)-4-(3,4,5-tributylphenyl)diazobuta-1,3-diene]di(butyl)palladium; [1-(3,4,5-trimethylphenyl)-2-(octyl)-3-(heptacosyl)-4-(3,4,5-tripropylphenyl)diazobuta-1,3-diene]di(propyl) palladium; [1-(3,4,5-trimethylphenyl)-2-(octynyl)-3-(butyl)-4-(3,4,5-trihexylphenyl)diazobuta-1,3-diene]di(tetradecyl)nickel; [1-(3,4,5-trimethylphenyl)-2-(pentyl)-3-(butyl)-4-(3,4,5-tributylphenyl)diazobuta-1,3-diene]di(tolyl)palladium; [1-(3,4,5-trimethylphenyl)-2-(pentyl)-3-(hexyl)-4-(3,4,5-tripropylphenyl)diazobuta-1,3-diene]di(hydrido) nickel; [1-(3,4,5-trimethylphenyl)-2-(pentyl)-3-(methyl)-4-(3,4,5-tributylphenyl)diazobuta-1,3- diene]di(hydrido)nickel; [1-(3,4,5-trimethylphenyl)-2-(tricosenyl)-3-(butyl)-4-(3,4,5-tributylphenyl)diazobuta-1,3-diene]di(butyl)nickel; [1-(3,4,5-trimethylphenyl)-2,3-(dibutyl)-4-(3,4,5-tributylphenyl)diazobuta-1,3-diene]di(butoxy)nickel; [1-(3,4,5-trimethylphenyl)-2,3-(dibutyl)-4-(3,4,5-triethylphenyl)diazobuta-1,3-diene]di(diethylamino)palladium; [1-(3,4,5-trimethylphenyl)-2,3-(dibutyl)-4-(3,4,5-tripentylphenyl)diazobuta-1,3-diene]di(heneicosyl)nickel; [1-(3,4,5-trimethylphenyl)-2,3-(dibutyl)-4-(3,4,5-tripentylphenyl)diazobuta-1,3-diene]di(tetracosyl)palladium; [1-(3,4,5-trimethylphenyl)-2,3-(dihexyl)-4-(3,4,5-trihexylphenyl)diazobuta-1,3-diene]di(decyl)palladium; [1-(3,4,5-trimethylphenyl)-2,3-(dihexyl)-4-(3,4,5-tripropylphenyl)diazobuta-1,3-diene]di(octadecyl)palladium; [1-(3,4,5-trimethylphenyl)-2,3-(dihydrido)-4-(3,4,5-tripentylphenyl)diazobuta-1,3-diene]di(bromo)nickel; [1-(3,4,5-trimethylphenyl)-2,3-(dihydrido)-4-(3,4,5-tripropylphenyl)diazobuta-1,3-diene]di(phenethyl)nickel; [1-(3,4,5-trimethylphenyl)-2,3-(dimethyl)-4-(3,4,5-tributylphenyl)diazobuta-1,3-diene]di(phenyl)nickel; [1-(3,4,5-tripentylphenyl)-2-(butyl)-3-(hydrido)-4-(3,4,5-tributylphenyl)diazobuta-1,3-diene]di(ethyl)palladium; [1-(3,4,5-tripentylphenyl)-2-(butyl)-3-(hydrido)-4-(3,4,5-tributylphenyl)diazobuta-1,3-diene]di(methyl)palladium; [1-(3,4,5-tripentylphenyl)-2-(butyl)-3-(hydrido)-4-(3,4,5-tributylphenyl)diazobuta-1,3-diene]di(nonenyl)palladium; [1-(3,4,5-tripentylphenyl)-2-(butyl)-3-(hydrido)-4-(3,4,5-triethylphenyl)diazobuta-1,3-diene]di(tridecyl)nickel; [1-(3,4,5-tripentylphenyl)-2-(butyl)-3-(octadecyl)-4-(3,4,5-trihexylphenyl)diazobuta-1,3-diene]di(methyl)nickel; [1-(3,4,5-tripentylphenyl)-2-(eicosyl)-3-(hexyl)-4-(3,4,5-tripropylphenyl)diazobuta-1,3-diene]di(hydride)nickel; [1-(3,4,5-tripentylphenyl)-2-(ethyl)-3-(nonynyl)-4-(3,4,5-tripropylphenyl)diazobuta-1,3-diene]di(dodecynyl)nickel; [1-(3,4,5-tripentylphenyl)-2-(ethyl)-3-(pentyl)-4-(3,4,5-trimethylphenyl)diazobuta-1,3-diene]di(methyl)nickel; [1-(3,4,5-tripentylphenyl)-2-(ethyl)-3-(propenyl)-4-(3,4,5-triethylphenyl)diazobuta-1,3-diene]di(pentyl)nickel; [1-(3,4,5-tripentylphenyl)-2-(hexenyl)-3-(butyl)-4-(3,4,5-tributylphenyl)diazobuta-1,3-diene]di(hydrido)nickel; [1-(3,4,5-tripentylphenyl)-2-(hexyl)-3-(butyl)-4-(3,4,5-tributylphenyl)diazobuta-1,3-diene]di(nonyl)nickel; [1-(3,4,5-tripentylphenyl)-2-(hexyl)-3-(butyl)-4-(3,4,5-tributylphenyl)diazobuta-1,3-diene]di(phenethyl)nickel; [1-(3,4,5-tripentylphenyl)-2-(hexyl)-3-(butyl)-4-(3,4,5-trimethylphenyl)diazobuta-1,3-diene]di(benzoxy)nickel; [1-(3,4,5-tripentylphenyl)-2-(hexyl)-3-(hydrido)-4-(3,4,5-tripropylphenyl)diazobuta-1,3-diene]di(dodecyl)nickel; [1-(3,4,5-tripentylphenyl)-2-(hexyl)-3-(methyl)-4-(3,4,5-tripropylphenyl)diazobuta-1,3-diene]di(tricosyl)palladium; [1-(3,4,5-tripentylphenyl)-2-(hydrido)-3-(butyl)-4-(3,4,5-tributylphenyl)diazobuta-1,3-diene]di(butyl)nickel; [1-(3,4,5-tripentylphenyl)-2-(methyl)-3-(butyl)-4-(3,4,5-trihexylphenyl)diazobuta-1,3-diene]di(ethyl)nickel; [1-(3,4,5-tripentylphenyl)-2-(methyl)-3-(pentyl)-4-(3,4,5-trimethylphenyl)diazobuta-1,3-diene]di(decyl)nickel; [1-(3,4,5-tripentylphenyl)-2-(nonacosyl)-3-(hydrido)-4-(3,4,5-tripropylphenyl)diazobuta-1,3-diene]di(propyl) nickel; [1-(3,4,5-tripentylphenyl)-2-(octacosynyl)-3-(octyl)-4-(3,4,5-trihexylphenyl)diazobuta-1,3-diene]di(tricosyl)nickel; [1-(3,4,5-tripentylphenyl)-2-(pentacosyl)-3-(butyl)-4-(3,4,5-triethylphenyl)diazobuta-1,3-diene]di(hydrido)nickel; [1-(3,4,5-tripentylphenyl)-2-(pentadecynyl)-3-(octyl)-4-(3,4,5-tributylphenyl)diazobuta-1,3-diene]di(ethyl)nickel; [1-(3,4,5-tripentylphenyl)-2-(pentyl)-3-(butyl)-4-(3,4,5-triethylphenyl)diazobuta-1,3-diene]di(hexadecyl)nickel; [1-(3,4,5-tripentylphenyl)-2,3-(dibutyl)-4-(3,4,5-triethylphenyl)diazobuta-1,3-diene]di(methylethylamino)palladium; [1-(3,4,5-tripentylphenyl)-2,3-(dibutyl)-4-(3,4,5-tripropylphenyl)diazobuta-1,3-diene]di(ethyl)palladium; [1-(3,4,5-tripropanalylphenyl)-2-(hexyl)-3-(butyl)-4-(3,4,5-tributylphenyl)diazobuta-1,3-diene]di(hydrido)nickel; [1-(3,4,5-tripropanalylphenyl)-2-(hydrido)-3-(butyl)-4-(3,4,5-tributylphenyl)diazobuta-1,3-diene]di(pentyl)palladium; [1-(3,4,5-tripropanalylphenyl)-2-(hydrido)-3-(butyl)-4-(3,4,5-triethylphenyl)diazobuta-1,3-diene]di(phenethyl)nickel; [1-(3,4,5-triproponylphenyl)-2-(butyl)-3-(hexyl)-4-(3,4,5-tripropylphenyl)diazobuta-1,3-diene]di(ethyl)nickel; [1-(3,4,5-triproponylphenyl)-2-(hydrido)-3-(butenyl)-4-(3,4,5-tributylphenyl)diazobuta-1,3-diene]di(methyl)nickel; [1-(3,4,5-triproponylphenyl)-2-(pentacosyl)-3-(octyl)-4-(3,4,5-trihexylphenyl)diazobuta-1,3-diene]di(pentadecyl)palladium; [1-(3,4,5-triproponylphenyl)-2-(pentyl)-3-(hydrido)-4-(3,4,5-tributylphenyl)diazobuta-1,3-diene]di(ethyl)nickel; [1-(3,4,5-tripropylphenyl)-2-(butyl)-3-(docosenyl)-4-(3,4,5-tributylphenyl)diazobuta-1,3-diene]di(propoxy)palladium; [1-(3,4,5-tripropylphenyl)-2-(butyl)-3-(docosyl)-4-(3,4,5-trihexylphenyl)diazobuta-1,3-diene]di(tetradecyl)palladium; [1-(3,4,5-tripropylphenyl)-2-(butyl)-3-(heneicosynyl)-4-(3,4,5-trihexylphenyl)diazobuta-1,3-diene]di(dimethylamino)nickel; [1-(3,4,5-tripropylphenyl)-2-(butyl)-3-(hydrido)-4-(3,4,5-tributylphenyl)diazobuta-1,3-diene]di(bromo)palladium; [1-(3,4,5-tripropylphenyl)-2-(butyl)-3-(hydrido)-4-(3,4,5-tributylphenyl)diazobuta-1,3-diene]di(diethylamino)nickel; [1-(3,4,5-tripropylphenyl)-2-(butyl)-3-(hydrido)-4-(3,4,5-trihexylphenyl)diazobuta-1,3-diene]di(hydrido)nickel; [1-(3,4,5-tripropylphenyl)-2-(butyl)-3-(octyl)-4-(3,4,5-tributylphenyl)diazobuta-1,3-diene]di(methyl) nickel; [1-(3,4,5-tripropylphenyl)-2-(butyl)-3-(octyl)-4-(3,4,5-trihexylphenyl)diazobuta-1,3-diene]di(chloro)palladium; [1-(3,4,5-tripropylphenyl)-2-(butyl)-3-(octyl)-4-(3,4,5-trihexylphenyl)diazobuta-1,3-diene]di(heneicosyl)nickel; [1-(3,4,5-tripropylphenyl)-2-(butyl)-3-(pentyl)-4-(3,4,5-tributylphenyl)diazobuta-1,3-diene]di(hydrido)nickel; [1-(3,4,5-tripropylphenyl)-2-(butyl)-3-(pentyl)-4-(3,4,5-trihexylphenyl)diazobuta-1,3-diene]di(methyl)nickel; [1-(3,4,5-tripropylphenyl)-2-(butynyl)-3-(pentyl)-4-(3,4,5-tripentylphenyl)diazobuta-1,3-diene]di(phenyl)nickel; [1-(3,4,5-tripropylphenyl)-2-(dodecyl)-3-(hexyl)-4-(3,4,5-trimethylphenyl)diazobuta-1,3-diene]di(ethoxy)nickel; [1-(3,4,5-tripropylphenyl)-2-(eicosyl)-3-(pentyl)-4-(3,4,5-trihexylphenyl)diazobuta-1,3-diene]di(tetradecyl)nickel; [1-(3,4,5-tripropylphenyl)-2-(hexyl)-3-(butyl)-4-(3,4,5-tributylphenyl)diazobuta-1,3-diene]di(butyl)palladium; [1-(3,4,5-tripropylphenyl)-2-(hexyl)-3-(hydrido)-4-(3,4,5-trimethylphenyl)diazobuta-1,3-diene]di(methyl)nickel; [1-(3,4,5-tripropylphenyl)-2-(hexyl)-3-(hydrido)-4-(3,4,5-trimethylphenyl)diazobuta-1,3-diene]di(phenethyl)nickel; [1-(3,4,5-tripropylphenyl)-2-(hexyl)-3-(pentyl)-4-(3,4,5-triethylphenyl)diazobuta-1,3-diene]di(hexacosyl)nickel; [1-(3,4,5-tripropylphenyl)-2-(hydrido)-3-(butyl)-4-(3,4,5-triethylphenyl)diazobuta-1,3-diene]di(hydrido)nickel; [1-(3,4,5-tripropylphenyl)-2-(hydrido)-3-(butyl)-4-(3,4,5-tripentylphenyl)diazobuta-1,3-diene]di(ethyl)nickel; [1-(3,4,5-tripropylphenyl)-2-(hydrido)-3-(butyl)-4-(3,4,5-tripentylphenyl)diazobuta-1,3-diene]di(hydrido)nickel; [1-(3,4,5-tripropylphenyl)-2-(hydrido)-3-(nonyl)-4-(3,4,5-tributylphenyl)diazobuta-1,3-diene]di(hexacosyl)palladium; [1-(3,4,5-tripropylphenyl)-2-(hydrido)-3-(octyl)-4-(3,4,5-tributylphenyl)diazobuta-1,3-diene]di(hydride)palladium; [1-(3,4,5-tripropylphenyl)-2-(hydrido)-3-(octyl)-4-(3,4,5-triethylphenyl)diazobuta-1,3-diene]di(dimethylamino)nickel; [1-(3,4,5-tripropylphenyl)-2-(octyl)-3-(butyl)-4-(3,4,5-trimethylphenyl)diazobuta-1,3- diene]di(hexacosynyl)nickel; [1-(3,4,5-tripropylphenyl)-2-(octyl)-3-(ethyl)-4-(3,4,5-tributylphenyl)diazobuta-1,3-diene]di(phenethyl)palladium; [1-(3,4,5-tripropylphenyl)-2-(octyl)-3-(ethyl)-4-(3,4,5-triethylphenyl)diazobuta-1,3-diene]di(bromo)nickel; [1-(3,4,5-tripropylphenyl)-2-(octynyl)-3-(hexyl)-4-(3,4,5-tripentylphenyl)diazobuta-1,3-diene]di(hydrido)palladium; [1-(3,4,5-tripropylphenyl)-2-(pentyl)-3-(butyl)-4-(3,4,5-triethylphenyl)diazobuta-1,3-diene]di(heptyl)nickel; [1-(3,4,5-tripropylphenyl)-2-(pentyl)-3-(butyl)-4-(3,4,5-tripentylphenyl)diazobuta-1,3-diene]di(methyl)nickel; [1-(3,4,5-tripropylphenyl)-2-(pentyl)-3-(hexyl)-4-(3,4,5-triethylphenyl)diazobuta-1,3-diene]di(benzyl)palladium; [1-(3,4,5-tripropylphenyl)-2-(pentyl)-3-(triacontynyl)-4-(3,4,5-trihexylphenyl) diazobuta-1,3-diene]di(hydrido)palladium; [1-(3,4,5-tripropylphenyl)-2-(tetradecynyl)-3-(ethyl)-4-(3,4,5-tributylphenyl)diazobuta-1,3-diene]di(undecyl)nickel; [1-(3,4,5-tripropylphenyl)-2,3-(dibutyl)-4-(3,4,5-tributylphenyl)diazobuta-1,3-diene]di(ethyl)nickel; [1-(3,4,5-tripropylphenyl)-2,3-(dibutyl)-4-(3,4,5-tributylphenyl) diazobuta-1,3-diene]di(ethyl)nickel; [1-(3,4,5-tripropylphenyl)-2,3-(dibutyl)-4-(3,4,5-tributylphenyl) diazobuta-1,3-diene]di(hexadecyl)nickel; [1-(3,4,5-tripropylphenyl)-2,3-(dibutyl)-4-(3,4,5-tributylphenyl) diazobuta-1,3-diene]di(nonyl)nickel; [1-(3,4,5-tripropylphenyl)-2,3-(dibutyl)-4-(3,4,5-trimethylphenyl) diazobuta-1,3-diene]di(methyl)nickel; [1-(3,4,5-tripropylphenyl)-2,3-(dibutyl)-4-(3,4,5-trimethylphenyl) diazobuta-1,3-diene]di(phenyl)nickel; [1-(3,4,5-tripropylphenyl)-2,3-(dibutyl)-4-(3,4,5-tripentylphenyl) diazobuta-1,3-diene]di(pentacosyl) nickel; [1-(3,4,5-tripropylphenyl)-2,3-(dihydrido)-4-(3,4,5-tributylphenyl) diazobuta-1,3-diene]di(allyl)nickel;; ; [1-(4-(triethylsilylmethyl)phenyl)-2-(pentyl)-3-(butyl)-4-(3-octylphenyl)diazobuta-1,3-diene]di(tricosyl)nickel; [1-(4-(trimethylsilylethyl)phenyl)-2-(tridecenyl)-3-(hydrido)-4-(3-ethylphenyl)diazobuta-1,3-diene]di(phenethyl)nickel; [1-(4-butanalylphenyl)-2-(pentyl)-3-(butyl)-4-(3-octylphenyl) diazobuta-1,3-diene]di(ethyl)nickel; [1-(4-butylphenyl)-2-(butenyl)-3-(octacosynyl)-4-(3-butylphenyl)diazobuta-1,3-diene]di(ethyl)palladium; [1-(4-butylphenyl)-2-(butyl)-3-(hexyl)-4-(3-butylphenyl)diazobuta-1,3-diene]di(heneicosyl)nickel; [1-(4-butylphenyl)-2-(butyl)-3-(hexyl)-4-butylphenyl)diazobuta-1,3-diene]di(hydrido) palladium; [1-(4-butylphenyl)-2-(butyl)-3-(hexyl)-4-(3-ethylphenyl)diazobuta-1,3-diene]di(hydrido)palladium; [1-(4-butylphenyl)-2-(butyl)-3-(hexyl)-4-(3-octylphenyl) diazobuta-1,3-diene]di(pentyl)nickel; [1-(4-butylphenyl)-2-(butyl)-3-(hydrido)-4-(3-butylphenyl)diazobuta-1,3-diene] di(hydrido)palladium; [1-(4-butylphenyl)-2-(butyl)-3-(hydrido)-4-(3-butylphenyl)diazobuta-1,3-diene]di (methylethylamino)nickel; [1-(4-butylphenyl)-2-(butyl)-3-(hydrido)-4-(3-heneicosynylphenyl)diazobuta-1,3-diene]di (propyl)nickel; [1-(4-butylphenyl)-2-(butyl)-3-(hydrido)-4-(3-propylphenyl)diazobuta-1,3-diene]di(bromo)nickel; [1-(4-butylphenyl)-2-(butyl)-3-(methyl)-4-(3-heptacosenylphenyl)diazobuta-1,3-diene]di(iodo)nickel; [1-(4-butylphenyl)-2-(butyl)-3-(pentyl)-4-(3-ethylphenyl) diazobuta-1,3-diene]di(butoxy)palladium; [1-(4-butylphenyl)-2-(butyl)-3-(pentyl)-4-(3-heptenylphenyl) diazobuta-1,3-diene]di(hydrido)nickel; [1-(4-butylphenyl)-2-(butyl)-3-(pentyl)-4-(3-hexylphenyl)diazobuta-1,3-diene] di(undecynyl)nickel; [1-(4-butylphenyl)-2-(butyl)-3-(pentyl)-4-(3-methylphenyl)diazobuta-1,3-diene]di (hydrido)nickel; [1-(4-butylphenyl)-2-(butyl)-3-(pentyl)-4-(3-octylphenyl)diazobuta-1,3-diene]di(hydrido)palladium; [1-(4-butylphenyl)-2-(butyl)-3-(pentyl)-4-(3-pentylphenyl) diazobuta-1,3-diene]di(hydrido)nickel; [1-(4-butylphenyl)-2-(docosyl)-3-(octadecynyl)-4-(3-pentylphenyl)diazobuta-1,3-diene]di(methyl)palladium; [1-(4-butylphenyl)-2-(docosyl)-3-(pentyl)-4-(3-tricosylphenyl)diazobuta-1,3-diene]di(dodecyl)nickel; [1-(4-butylphenyl)-2-(eicosyl)-3-(hexyl)-4-(3-octylphenyl)diazobuta-1,3-diene]di(eicosyl) palladium; [1-(4-butylphenyl)-2-(ethyl)-3-(butyl)-4-(3-butylphenyl)diazobuta-1,3-diene]di(ethyl)nickel; [1-(4-butylphenyl)-2-(ethyl)-3-(butyl)-4-(3-pentylphenyl) diazobuta-1,3-diene]di(methyl)palladium; [1-(4-butylphenyl)-2-(ethyl)-3-(hydrido)-4-(3-hexacosynylphenyl)diazobuta-1,3-diene]di(methyl) palladium; [1-(4-butylphenyl)-2-(ethyl)-3-(octacosynyl)-4-(3-butylphenyl)diazobuta-1,3-diene]di(hydrido)nickel; [1-(4-butylphenyl)-2-(heneicosynyl)-3-(butyl)-4-(3-butylphenyl)diazobuta-1,3-diene]di(nonadecyl)nickel; [1-(4-butylphenyl)-2-(hexacosenyl)-3-(ethyl)-4-(3-butylphenyl)diazobuta-1,3-diene]di(nonadecyl)nickel; [1-(4-butylphenyl)-2-(hexacosenyl)-3-(hydrido)-4-(3-(trimethylsilylmethyl)phenyl)diazobuta-1,3-diene]di (phenyl)nickel; [1-(4-butylphenyl)-2-(hexacosynyl)-3-(methyl)-4-(3-dodecylphenyl)diazobuta-1,3-diene]di (hexacosyl)nickel; [1-(4-butylphenyl)-2-(hexadecynyl)-3-(hydrido)-4-(3-butylphenyl)diazobuta-1,3-diene]di (hexacosyl)palladium; [1-(4-butylphenyl)-2-(hexyl)-3-(butyl)-4-butylphenyl)diazobuta-1,3-diene]di(ethyl) nickel; [1-(4-butylphenyl)-2-(hexyl)-3-(butyl)-4-(3-tridecynylphenyl)diazobuta-1,3-diene]di(iodo)nickel; [1-(4-butylphenyl)-2-(hexyl)-3-(hydrido)-4-(3-ethylphenyl) diazobuta-1,3-diene]di(propoxy)nickel; [1-(4-butylphenyl)-2-(hexyl)-3-(hydrido)-4-(3-octylphenyl)diazobuta-1,3-diene]di(butyl)nickel; [1-(4-butylphenyl)-2-(hexyl)-3-(hydrido)-4-(3-undecenylphenyl)diazobuta-1,3-diene]di (tolyl)nickel; [1-(4-butylphenyl)-2-(hexyl)-3-(nonenyl)-4-(3-octylphenyl)diazobuta-1,3-diene]di(propyl)nickel; [1-(4-butylphenyl)-2-(hexyl)-3-(pentyl)-4-(3-butylphenyl) diazobuta-1,3-diene]di(nonacosyl)nickel; [1-(4-butylphenyl)-2-(hexyl)-3-(pentyl)-4-(3-butylphenyl) diazobuta-1,3-diene]di(tetracosyl)nickel; [1-(4-butylphenyl)-2-(hydrido)-3-(butyl)-4-(3-ethylphenyl) diazobuta-1,3-diene]di(propyl)nickel; [1-(4-butylphenyl)-2-(hydrido)-3-(butyl)-4-(3-hexylphenyl)diazobuta-1,3-diene] di(hydrido)nickel; [1-(4-butylphenyl)-2-(hydrido)-3-(butyl)-4-(3-hexylphenyl)diazobuta-1,3-diene]di(methyl) nickel; [1-(4-butylphenyl)-2-(hydrido)-3-(butyl)-4-(3-octacosenylphenyl)diazobuta-1,3-diene]di(pentadecyl) palladium; [1-(4-butylphenyl)-2-(hydrido)-3-(butyl)-4-(3-octylphenyl)diazobuta-1,3-diene]di(butyl)nickel; [1-(4-butylphenyl)-2-(hydrido)-3-(butyl)-4-(3-octylphenyl) diazobuta-1,3-diene]di(iodo)palladium; [1-(4-butylphenyl)-2-(hydrido)-3-(butyl)-4-(3-pentadecylphenyl)diazobuta-1,3-diene]di(hydrido)nickel; [1-(4-butylphenyl)-2-(hydrido)-3-(butyl)-4-(3-pentylphenyl)diazobuta-1,3-diene]di (tridecyl)nickel; [1-(4-butylphenyl)-2-(hydrido)-3-(eicosynyl)-4-(3-methylphenyl)diazobuta-1,3-diene]di (hydrido)palladium; [1-(4-butylphenyl)-2-(hydrido)-3-(hexyl)-4-(3-pentylphenyl)diazobuta-1,3-diene]di(butyl) nickel; [1-(4-butylphenyl)-2-(hydrido)-3-(octyl)-4-(3-butylphenyl)diazobuta-1,3-diene]di(nonyl)nickel; [1-(4-butylphenyl)-2-(hydrido)-3-(octyl)-4-(3-pentylphenyl) diazobuta-1,3-diene]di(triacontyl)palladium; [1-(4-butylphenyl)-2-(hydrido)-3-(pentadecenyl)-4-(3-octylphenyl)diazobuta-1,3-diene]di(ethyl)nickel; [1-(4-butylphenyl)-2-(hydrido)-3-(pentyl)-4-(3-docosynylphenyl) diazobuta-1,3-diene]di(hydrido)nickel; [1-(4-butylphenyl)-2-(hydrido)-3-(pentyl)-4-(3-pentenylphenyl)diazobuta-1,3-diene]di(methyl)nickel; [1-(4-butylphenyl)-2-(methyl)-3-

(butyl)-4-(3-butylphenyl)diazobuta-1,3-diene]di(methylethylamino)nickel; [1-(4-butylphenyl)-2-(methyl)-3-(butyl)-4-(3-pentylphenyl)diazobuta-1,3-diene]di(hydride)nickel; [1-(4-butylphenyl)-2-(methyl)-3-(hydrido)-4-(3-butylphenyl)diazobuta-1,3-diene]di(docosyl)nickel; [1-(4-butylphenyl)-2-(methyl)-3-(pentyl)-4-(3-hexylphenyl)diazobuta-1,3-diene]di(nonyl)nickel; [1-(4-butylphenyl)-2-(methyl)-3-(undecynyl)-4-(3-hexylphenyl)diazobuta-1,3-diene]di(octadecyl)palladium; [1-(4-butylphenyl)-2-(nonadecenyl)-3-(butyl)-4-(3-butylphenyl)diazobuta-1,3-diene]di(hydrido)nickel; [1-(4-butylphenyl)-2-(nonadecynyl)-3-(pentyl)-4-(3-hexylphenyl)diazobuta-1,3-diene]di(methyl)palladium; [1-(4-butylphenyl)-2-(nonadecynyl)-3-(pentyl)-4-(3-octylphenyl)diazobuta-1,3-diene]di(pentyl)nickel; [1-(4-butylphenyl)-2-(nonenyl)-3-(tridecenyl)-4-(3-butylphenyl)diazobuta-1,3-diene]di(ethyl)nickel; [1-(4-butylphenyl)-2-(octyl)-3-(butyl)-4-(3-butylphenyl)diazobuta-1,3-diene]di(ethyl)palladium; [1-(4-butylphenyl)-2-(octyl)-3-(butyl)-4-(3-butylphenyl)diazobuta-1,3-diene]di(hydrido)nickel; [1-(4-butylphenyl)-2-(octyl)-3-(butyl)-4-(3-butylphenyl)diazobuta-1,3-diene]di(hydrido)nickel; [1-(4-butylphenyl)-2-(octyl)-3-(butyl)-4-(3-hexylphenyl)diazobuta-1,3-diene]di(octadecyl)nickel; [1-(4-butylphenyl)-2-(octyl)-3-(butyl)-4-(3-pentylphenyl)diazobuta-1,3-diene]di(tricosyl)palladium; [1-(4-butylphenyl)-2-(octyl)-3-(hydrido)-4-(3-octylphenyl)diazobuta-1,3-diene]di(dimethylamino)nickel; [1-(4-butylphenyl)-2-(octyl)-3-(methyl)-4-(3-butylphenyl)diazobuta-1,3-diene]di(dodecyl)nickel; [1-(4-butylphenyl)-2-(octyl)-3-(pentyl)-4-(3-butonylphenyl)diazobuta-1,3-diene]di(dimethylamino)nickel; [1-(4-butylphenyl)-2-(pentacosyl)-3-(butyl)-4-(3-octylphenyl)diazobuta-1,3-diene]di(hydrido)nickel; [1-(4-butylphenyl)-2-(pentyl)-3-(butyl)-4-(3-hexadecynylphenyl)diazobuta-1,3-diene]di(pentacosyl)nickel; [1-(4-butylphenyl)-2-(pentyl)-3-(butyl)-4-(3-hexylphenyl)diazobuta-1,3-diene]di(docosyl)palladium; [1-(4-butylphenyl)-2-(pentyl)-3-(butyl)-4-(3-hexylphenyl)diazobuta-1,3-diene]di(octacosyl)palladium; [1-(4-butylphenyl)-2-(pentyl)-3-(butyl)-4-(3-octylphenyl)diazobuta-1,3-diene]di(pentacosyl)palladium; [1-(4-butylphenyl)-2-(pentyl)-3-(hexacosyl)-4-(3-butylphenyl)diazobuta-1,3-diene]di(methoxy)nickel; [1-(4-butylphenyl)-2-(pentyl)-3-(hexyl)-4-(3-hexylphenyl)diazobuta-1,3-diene]di(heptacosyl)nickel; [1-(4-butylphenyl)-2-(pentyl)-3-(hexyl)-4-(3-octylphenyl)diazobuta-1,3-diene]di(ethyl)nickel; [-(4-butylphenyl)-2-(pentyl)-3-(hydrido)-4-(3-butylphenyl)diazobuta-1,3-diene]di(ethyl)nickel; [1-(4-butylphenyl)-2-(pentyl)-3-(hydrido)-4-(3-butylphenyl)diazobuta-1,3-diene]di(heptacosyl)palladium; [1-(4-butylphenyl)-2-(pentyl)-3-(hydrido)-4-(3-butylphenyl)diazobuta-1,3-diene]di(hydrido)palladium; [1-(4-butylphenyl)-2-(pentyl)-3-(hydrido)-4-(3-heptynylphenyl)diazobuta-1,3-diene]di(butyl)nickel; [1-(4-butylphenyl)-2-(pentyl)-3-(hydrido)-4-(3-octylphenyl)diazobuta-1,3-diene]di(hydrido)nickel; [-(4-butylphenyl)-2-(pentyl)-3-(hydrido)-4-(3-octylphenyl)diazobuta-1,3-diene]di(methyl)nickel; [1-(4-butylphenyl)-2-(pentyl)-3-(octyl)-4-(3-butylphenyl)diazobuta-1,3-diene]di(butyl)palladium; [1-(4-butylphenyl)-2-(tetracosyl)-3-(hydrido)-4-(3-pentadecylphenyl)diazobuta-1,3-diene]di(octyl)nickel; [1-(4-butylphenyl)-2-(tetracosynyl)-3-(hydrido)-4-(3-butylphenyl)diazobuta-1,3-diene]di(methyl)palladium; [1-(4-butylphenyl)-2-(triacontyl)-3-(pentyl)-4-(3-butylphenyl)diazobuta-1,3-diene]di(ethyl)nickel; [1-(4-butylphenyl)-2,3-(tridecenyl)-3-(octenyl)-4-(3-butylphenyl)diazobuta-1,3-diene]di(ethyl)nickel; [1-(4-butylphenyl)-2,3-(dibutyl)-4-(3-butylphenyl)diazobuta-1,3-diene]di(heptacosyl)palladium; [1-(4-butylphenyl)-2,3-(dibutyl)-4-(3-butylphenyl)diazobuta-1,3-diene]di(hydrido)nickel; [1-(4-butylphenyl)-2,3-(dibutyl)-4-(3-butylphenyl)diazobuta-1,3-diene]di(octadecynyl)nickel; [1-(4-butylphenyl)-2,3-(dibutyl)-4-(3-butylphenyl)diazobuta-1,3-diene]di(phenyl)nickel; [1-(4-butylphenyl)-2,3-(dibutyl)-4-(3-butylphenyl)diazobuta-1,3-diene]di(undecyl)nickel; [1-(4-butylphenyl)-2,3-(dibutyl)-4-(3-heneicosynylphenyl)diazobuta-1,3-diene]di(methyl)nickel; [1-(4-butylphenyl)-2,3-(dibutyl)-4-(3-heptadecylphenyl)diazobuta-1,3-diene]di(butyl)palladium; [1-(4-butylphenyl)-2,3-(dibutyl)-4-(3-hexylphenyl)diazobuta-1,3-diene]di(ethyl)nickel; [1-(4-butylphenyl)-2,3-(dibutyl)-4-(3-methylphenyl)diazobuta-1,3-diene]di(hexenyl)nickel; [1-(4-butylphenyl)-2,3-(dibutyl)-4-(3-methylphenyl)diazobuta-1,3-diene]di(methyl)nickel; [1-(4-butylphenyl)-2,3-(dibutyl)-4-(3-octylphenyl)diazobuta-1,3-diene]di(bromo)nickel; [1-(4-butylphenyl)-2,3-(dibutyl)-4-(3-octylphenyl)diazobuta-1,3-diene]di(heneicosyl)palladium; [1-(4-butylphenyl)-2,3-(dibutyl)-4-(3-octylphenyl)diazobuta-1,3-diene]di(propyl)nickel; [1-(4-butylphenyl)-2,3-(dibutyl)-4-(3-octylphenyl)diazobuta-1,3-diene]di(tetradecyl)nickel; [1-(4-butylphenyl)-2,3-(dibutyl)-4-(3-pentylphenyl)diazobuta-1,3-diene]di(nonacosyl)palladium; [1-(4-butylphenyl)-2,3-(dibutyl)-4-(3-pentynylphenyl)diazobuta-1,3-diene]di(tridecyl)nickel; [1-(4-butylphenyl)-2,3-(dibutyl)-4-(3-propynylphenyl)diazobuta-1,3-diene]di(butyl)palladium; [1-(4-butylphenyl)-2,3-(dibutyl)-4-(3-tetracosynylphenyl)diazobuta-1,3-diene]di(methyl)nickel; [1-(4-butylphenyl)-2,3-(diethyl)-4-(3-butylphenyl)diazobuta-1,3-diene]di(nonyl)nickel; [1-(4-butylphenyl)-2,3-(dihexyl)-4-(3-triocosanalylphenyl)diazobuta-1,3-diene]di(hexadecyl)palladium; [1-(4-butylphenyl)-2,3-(dihydrido)-4-(3-hexylphenyl)diazobuta-1,3-diene]di(methyl)nickel; [1-(4-butylphenyl)-2,3-(dihydrido)-4-(3-methylphenyl)diazobuta-1,3-diene]di(hexadecyl)palladium; [1-(4-butylphenyl)-2,3-(dioctyl)-4-(3-octylphenyl)diazobuta-1,3-diene]di(tolyl)nickel; [1-(4-butylphenyl)-2,3-(dipentyl)-4-(3-octylphenyl)diazobuta-1,3-diene]di(benzoxy)nickel; [1-(4-decylphenyl)-2-(octyl)-3-(ethyl)-4-(3-pentylphenyl)diazobuta-1,3-diene]di(heptacosyl)nickel; [1-(4-docosenylphenyl)-2-(butyl)-3-(octyl)-4-(3-butylphenyl)diazobuta-1,3-diene]di(octadecyl)nickel; [1-(4-docosenylphenyl)-2-(hydrido)-3-(butyl)-4-(3-butylphenyl)diazobuta-1,3-diene]di(undecyl)nickel; [1-(4-docosenylphenyl)-2-(hydrido)-3-(butyl)-4-(3-pentylphenyl)diazobuta-1,3-diene]di(ethyl)nickel; [1-(4-dodecaminophenyl)-2-(hydrido)-3-(hexyl)-4-(3-methylphenyl)diazobuta-1,3-diene]di(hydrido)nickel; [1-(4-dodecaminophenyl)-2,3-(dibutyl)-4-(3-octynylphenyl)diazobuta-1,3-diene]di(methylethylamino)nickel; [1-(4-dodecanonylphenyl)-2-(methyl)-3-(hydrido)-4-(3-pentacosylphenyl)diazobuta-1,3-diene]di(hexyl)palladium; [1-(4-ethylphenyl)-2-(butyl)-3-(hexyl)-4-(3-butylphenyl)diazobuta-1,3-diene]di(hexadecyl)nickel; [1-(4-ethylphenyl)-2-(butyl)-3-(octyl)-4-(3-butylphenyl)diazobuta-1,3-diene]di(ethyl)nickel; [1-(4-ethylphenyl)-2-(butyl)-3-(octyl)-4-(3-methylphenyl)diazobuta-1,3-diene]di(hydrido)palladium; [1-(4-ethylphenyl)-2-(heptacosenyl)-3-(pentyl)-4-(3-hexylphenyl)diazobuta-1,3-diene]di(hydrido)nickel; [1-(4-ethylphenyl)-2-(heptenyl)-3-(butyl)-4-(3-triacontynylphenyl)diazobuta-1,3-diene]di(nonadecyl)nickel; [1-(4-ethylphenyl)-2-(hexyl)-3-(pentyl)-4-(3-butylphenyl)diazobuta-1,3-diene]di(docosyl)nickel; [1-(4-ethylphenyl)-2,3-(diethyl)-4-(3-ethylphenyl)diazobuta-1,3-diene]di(hexadecyl)nickel; [1-(4-ethylphenyl)-2,3-(dibutyl)-4-(3-proponylphenyl)diazobuta-1,3-diene]di(octacosyl)nickel; [1-(4-ethylphenyl)-2,3-(dihydrido)-4-(3-nonadecenylphenyl)diazobuta-1,3-diene]di(eicosyl)palladium; [1-(4-ethylphenyl)-2,3-(dipentyl)-4-(3-ethylphenyl)diazobuta-1,3-diene]di(butyl)nickel; [1-(4-heneicosenylphenyl)-2-(butyl)-3-(hexyl)-4-(3-methylphenyl)diazobuta-1,3-diene]di(ethyl) nickel; [1-(4-heneicosylphenyl)-2-(nonenyl)-3-(butyl)-4-(3-pentylphenyl)diazobuta-1,3-diene]di(ethyl)palladium; [1-(4-heptacosylphenyl)-2-(hydrido)-3-(butyl)-4-(3-octylphenyl)diazobuta-1,3-diene]di(dodecyl)nickel; [1-(4-heptadecylphenyl)-2-(butyl)-3-(hexyl)-4-(3-pentylphenyl)diazobuta-1,3-diene]di(hydride)nickel; [1-(4-heptadecylphenyl)-2-(heptynyl)-3-(heneicosynyl)-4-(3-pentylphenyl)diazobuta-1,3-diene]di(hydrido)nickel; [1-(4-heptadecylphenyl)-2-(hydrido)-3-(pentyl)-4-(3-butylphenyl)diazobuta-1,3-diene]di(methyl)nickel; [1-(4-heptadecynylphenyl)-2-(ethyl)-3-(hydrido)-4-(3-butylphenyl)diazobuta-1,3-diene]di(heneicosyl)nickel; [1-(4-heptylphenyl)-2-(butyl)-3-(octyl)-4-(3-hexylphenyl)diazobuta-1,3-diene]di(hydrido)nickel; [1-(4-hexacosenylphenyl)-2-(methyl)-3-(hydrido)-4-(3-butylphenyl)diazobuta-1,3-diene]di(ethyl)nickel; [1-(4-hexacosenylphenyl)-2-(heptacosenyl)-3-(butyl)-4-(3-butylphenyl)diazobuta-1,3-diene]di(butoxy)nickel; [1-(4-hexacosylphenyl)-2-(hydrido)-3-(pentyl)-4-(3-butylphenyl)diazobuta-1,3-diene]di(hydrido)nickel; [1-(4-hexacosylphenyl)-2,3-(dihydrido)-4-(3-pentylphenyl)diazobuta-1,3-diene]di(methyl) palladium; [1-(4-hexacosynylphenyl)-2-(hexyl)-3-(octyl)-4-(3-hexylphenyl)diazobuta-1,3-diene]di(ethyl)palladium; [1-(4-hexacosynylphenyl)-2,3-(dibutyl)-4-(3-eicosylphenyl)diazobuta-1,3-diene]di(ethyl)nickel; [1-(4-hexadecylphenyl)-2-(hydrido)-3-(triacontenyl)-4-(3-octylphenyl)diazobuta-1,3-diene]di(nonyl)nickel; [1-(4-hexenylphenyl)-2-(ethyl)-3-(tricosyl)-4-(3-pentadecylphenyl)diazobuta-1,3-diene]di(hydrido) palladium; [1-(4-hexenylphenyl)-2-(octyl)-3-(butyl)-4-(3-heneicosynylphenyl)diazobuta-1,3-diene]di(ethyl)nickel; [1-(4-hexonylphenyl)-2,3-(dibutyl)-4-(3-hexylphenyl)diazobuta-1,3-diene]di(heptacosyl)nickel; [1-(4-hexylphenyl)-2-(butyl)-3-(decyl)-4-(3-ethylphenyl)diazobuta-1,3-diene] di(butoxy)nickel; [1-(4-hexylphenyl)-2-(butyl)-3-(hydrido)-4-3-butylphenyl)diazobuta-1,3-diene]di(dimethylamino) nickel; [1-(4-hexylphenyl)-2-(butyl)-3-(hydrido)-4-(3-hexylphenyl)diazobuta-1,3-diene]di(hydrido)palladium; [1-(4-hexylphenyl)-2-(butyl)-3-(nonadecyl)-4-(3-butylphenyl)diazobuta-1,3-diene]di(nonyl)nickel; [1-(4-hexylphenyl)-2-(butyl)-3-(pentyl)-4-(3-butylphenyl)diazobuta-1,3-diene]di(bromo)palladium; [1-(4-hexylphenyl)-2-(butyl)-3-(pentyl)-4-(3-butylphenyl)diazobuta-1,3-diene]di(ethoxy)nickel; [1-(4-hexylphenyl)-2-(butyl)-3-(undecenyl)-4-(3-butylphenyl)diazobuta-1,3-diene]di(dimethylamino)nickel; [1-(4-hexylphenyl)-2-(decenyl)-3-(triacontyl)-4-(3-butylphenyl)diazobuta-1,3-diene]di(allyl)nickel; [1-(4-hexylphenyl)-2-(ethyl)-3-(methyl)-4-(3-hexylphenyl)diazobuta-1,3-diene]di(hydrido)nickel; [1-(4-hexylphenyl)-2-(ethyl)-3-(octyl)-4-(3-hexynylphenyl)diazobuta-1,3-diene]di(ethyl)palladium; [1-(4-hexylphenyl)-2-(hexyl)-3-(butyl)-4-(3-pentylphenyl)diazobuta-1,3-diene]di(methyl)nickel; [1-(4-hexylphenyl)-2-(hexyl)-3-(pentacosenyl)-4-(3-butylphenyl)diazobuta-1,3-diene]di(hydride)nickel; [1-(4-hexylphenyl)-2-(hydrido)-3-(butyl)-4-(3-octylphenyl)diazobuta-1,3-diene]di(propoxy)nickel; [1-(4-hexylphenyl)-2-(hydrido)-3-(butyl)-4-(3-tetracosenylphenyl)diazobuta-1,3-diene]di(hexadecyl) nickel; [1-(4-hexylphenyl)-2-(hydrido)-3-(methyl)-4-(3-octylphenyl)diazobuta-1,3-diene]di(ethyl)nickel; [1-(4-hexylphenyl)-2-(hydrido)-3-(octyl)-4-(3-methylphenyl)diazobuta-1,3-diene]di(methyl)palladium; [1-(4-hexylphenyl)-2-(methyl)-3-(ethyl)-4-(3-methylphenyl) diazobuta-1,3-diene]di(dimethylamino)nickel; [1-(4-hexylphenyl)-2-(methyl)-3-(hydrido)-4-(3-hexylphenyl) diazobuta-1,3-diene]di(tricosyl)nickel; [1-(4-hexylphenyl)-2-(methyl)-3-(pentyl)-4-(3-octylphenyl)diazobuta-1,3-diene]di(benzoxy)nickel; [1-(4-hexylphenyl)-2-(pentyl)-3-(butyl)-4-(3-butylphenyl)diazobuta-1,3-diene]di(propyl) nickel; [1-(4-hexylphenyl)-2-(pentyl)-3-(butyl)-4-(3-hexylphenyl)diazobuta-1,3-diene]di(pentyl)nickel; [1-(4-hexylphenyl)-2-(pentyl)-3-(hydrido)-4-(3-ethylphenyl) diazobuta-1,3-diene]di(allyl)nickel; [1-(4-hexylphenyl)-2-(tetracosenyl)-3-(pentyl)-4-(3-hexylphenyl)diazobuta-1,3-diene]di(methyl)nickel; [1-(4-hexylphenyl)-2,3-(dibutyl)-4-(3-butylphenyl)diazobuta-1,3-diene]di(hydrido)nickel; [1-(4-hexylphenyl)-2,3-(dibutyl)-4-(3-ethanalylphenyl) diazobuta-1,3-diene]di(dimethylamino)nickel; [1-(4-hexylphenyl)-2,3-(dibutyl)-4-(3-octylphenyl)diazobuta-1,3-diene]di(triacontyl) palladium; [1-(4-hexylphenyl)-2,3-(dibutyl)-4-(3-undecylphenyl)diazobuta-1,3-diene]di(ethyl) nickel; [1-(4-hexylphenyl)-2,3-(dihydrido)-4-(3-hexylphenyl)diazobuta-1,3-diene]di(dodecyl)palladium; [1-(4-hexylphenyl)-2,3-(dihydrido)-4-(3-nonacosylphenyl) diazobuta-1,3-diene]di(butoxy)nickel; [1-(4-hexynylphenyl)-2-(hexyl)-3-(butyl)-4-(3-heptadecynylphenyl)diazobuta-1,3-diene]di(octynyl)nickel; [1-(4-methylethylaminophenyl)-2-(heptacosynyl)-3-(octyl)-4-(3-butylphenyl)diazobuta-1,3-diene]di(tolyl)nickel; [1-(4-methylphenyl)-2-(butyl)-3-(hydrido)-4-(3-butylphenyl)diazobuta-1,3-diene]di(methyl)nickel; [1-(4-methylphenyl)-2-(butyl)-3-(hydrido)-4-(3-pentadecynylphenyl)diazobuta-1,3-diene]di(butyl)palladium; [1-(4-methylphenyl)-2-(butyl)-3-(undecynyl)-4-(3-octylphenyl)diazobuta-1,3-diene]di(methyl)nickel; [1-(4-methylphenyl)-2-(dodecyl)-3-(methyl)-4-(3-methylethylaminophenyl)diazobuta-1,3-diene]di(decyl)nickel; [1-(4-methylphenyl)-2-(dodecynyl)-3-(hexyl)-4-(3-hexylphenyl)diazobuta-1,3-diene]di(docosyl)nickel; [1-(4-methylphenyl)-2-(hexyl)-3-(heneicosenyl)-4-(3-triacontynylphenyl)diazobuta-1,3-diene]di(butyl)palladium; [1-(4-methylphenyl)-2-(hexyl)-3-(hydrido)-4-(3-butylphenyl)diazobuta-1,3-diene]di(dimethylamino)palladium; [1-(4-methylphenyl)-2-(hydrido)-3-(butyl)-4-(3-butylphenyl)diazobuta-1,3-diene]di(ethoxy)nickel; [1-(4-methylphenyl)-2-(hydrido)-3-(butyl)-4-(3-octylphenyl)diazobuta-1,3-diene]di(triacontyl) nickel; [1-(4-methylphenyl)-2-(hydrido)-3-(pentyl)-4-(3-butylphenyl)diazobuta-1,3-diene]di(butyl)nickel; [1-(4-methylphenyl)-2-(nonadecyl)-3-(hexyl)-4-(3-butylphenyl) diazobuta-1,3-diene]di(ethyl)nickel; [1-(4-methylphenyl)-2-(octyl)-3-(butyl)-4-(3-butylphenyl)diazobuta-1,3-diene]di(triacontyl)nickel; [1-(4-methylphenyl)-2-(octyl)-3-(butyl)-4-(3-hexacosylphenyl)diazobuta-1,3-diene]di(tricosyl) nickel; [1-(4-methylphenyl)-2-(octyl)-3-(butyl)-4-(3-pentonylphenyl)diazobuta-1,3-diene]di(butyl)nickel; [1-(4-methylphenyl)-2-(octyl)-3-(hydrido)-4-(3-methylphenyl) diazobuta-1,3-diene]di(methyl)nickel; [1-(4-methylphenyl)-2-(pentyl)-3-(hexyl)-4-(3-butylphenyl)diazobuta-1,3-diene] di(heneicosyl)nickel; [1-(4-methylphenyl)-2-(pentyl)-3-(tetradecynyl)-4-(3-hexylphenyl)diazobuta-1,3-diene]di(hydrido)nickel; [1-(4-methylphenyl)-2,3-(dibutyl)-4-(3-methylphenyl)diazobuta-1,3-diene]di(ethoxy)nickel; [1-(4-methylphenyl)-2,3-(dipentyl)-4-(3-hexylphenyl)diazobuta-1,3-diene]di(hydrido)palladium; [1-(4-nonacosylphenyl)-2,3-(dipentyl)-4-(3-butylphenyl)diazobuta-1,3-diene]di (methyl)palladium; [1-(4-nonacosynylphenyl)-2-(pentenyl)-3-(hydrido)-4-(3-butylphenyl)diazobuta-1,3-diene]di (eicosyl)nickel; [1-(4-octacosenylphenyl)-2-(ethyl)-3-(methyl)-4-(3-butylphenyl)diazobuta-1,3-diene]di(hydrido) nickel; [1-(4-octylphenyl)-2-(butyl)-3-(ethyl)-4-(3- hexylphenyl)diazobuta-1,3-diene]di(hydrido)nickel; [1-(4-octylphenyl)-2-(butyl)-3-(hexyl)-4-(3-butylphenyl) diazobuta-1,3-diene]di(hexadecyl)palladium; [1-(4-octylphenyl)-2-(butyl)-3-(hexyl)-4-(3-ethylphenyl) diazobuta-1,3-diene]di(methyl)nickel; [1-(4-octylphenyl)-2-(butyl)-3-(hexyl)-4-(3-hexylphenyl)diazobuta-1,3-diene]di (methyl)nickel; [1-(4-octylphenyl)-2-(butyl)-3-(hexyl)-4-(3-pentylphenyl)diazobuta-1,3-diene]di(phenyl)palladium; [1-(4-octylphenyl)-2-(butyl)-3-(hydrido)-4-(3-butylphenyl) diazobuta-1,3-diene]di(butyl)palladium; [1-(4-octylphenyl)-2-(butyl)-3-(hydrido)-4-(3-hexylphenyl)diazobuta-1,3-diene]di(hydrido)nickel; [1-(4-octylphenyl)-2-(butyl)-3-(hydrido)-4-(3-pentylphenyl)diazobuta-1,3-diene]di(nonyl)nickel; [1-(4-octylphenyl)-2-(butyl)-3-(methyl)-4-(3-butylphenyl)diazobuta-1,3-diene]di(ethyl)nickel; [1-(4-octylphenyl)-2-(butyl)-3-(nonynyl)-4-(3-butylphenyl) diazobuta-1,3-diene]di(propoxy)nickel; [1-(4-octylphenyl)-2-(butyl)-3-(octyl)-4-(3-butylphenyl)diazobuta-1,3-diene]di (butyl)nickel; [1-(4-octylphenyl)-2-(butyl)-3-(pentyl)-4-(3-butylphenyl)diazobuta-1,3-diene]di(hydrido)palladium; [1-(4-octylphenyl)-2-(butyl)-3-(pentyl)-4-(3-hexylphenyl) diazobuta-1,3-diene]di(benzoxy)nickel; [1-(4-octylphenyl)-2-(butyl)-3-(pentyl)-4-(3-pentylphenyl)diazobuta-1,3-diene]di(benzyl)nickel; [1-(4-octylphenyl)-2-(ethyl)-3-(methyl)-4-(3-pentylphenyl)diazobuta-1,3-diene]di(methyl) nickel; [1-(4-octylphenyl)-2-(ethyl)-3-(pentyl)-4-(3-hexylphenyl)diazobuta-1,3-diene]di(ethyl)nickel; [1-(4-octylphenyl)-2-(ethyl)-3-(pentyl)-4-(3-tetradecenylphenyl) diazobuta-1,3-diene]di(methyl)palladium; [1-(4-octylphenyl)-2-(hexyl)-3-(hydrido)-4-(3-butylphenyl) diazobuta-1,3-diene]di(hydrido)nickel; [1-(4-octylphenyl)-2-(hexyl)-3-(octyl)-4-(3-octadecenylphenyl)diazobuta-1,3-diene]di(hexadecyl)nickel; [1-(4-octylphenyl)-2-(hydrido)-3-(butyl)-4-(3-butylphenyl)diazobuta-1,3-diene]di(butyl) nickel; [1-(4-octylphenyl)-2-(hydrido)-3-(butyl)-4-(3-butylphenyl)diazobuta-1,3-diene]di(hydrido)palladium; [1-(4-octylphenyl)-2-(hydrido)-3-(butyl)-4-(3-ethylphenyl) diazobuta-1,3-diene]di(heptadecynyl)palladium; [1-(4-octylphenyl)-2-(hydrido)-3-(butyl)-4-(3-octylphenyl) diazobuta-1,3-diene]di(butoxy)nickel; [1-(4-octylphenyl)-2-(hydrido)-3-(octyl)-4-(3-octylphenyl)diazobuta-1,3-diene] di(hydrido)nickel; [1-(4-octylphenyl)-2-(methyl)-3-(hydrido)-4-(3-butylphenyl)diazobuta-1,3-diene]di(ethoxy) palladium; [1-(4-octylphenyl)-2-(octyl)-3-(hydrido)-4-(3-hexylphenyl)diazobuta-1,3-diene]di(ethyl)nickel; [1-(4-octylphenyl)-2-(octyl)-3-(hydrido)-4-(3-pentylphenyl) diazobuta-1,3-diene]di(methylethylamino)nickel; [1-(4-octylphenyl)-2-(octyl)-3-(nonenyl)-4-(3-ethylphenyl) diazobuta-1,3-diene]di(tridecyl)nickel; [1-(4-octylphenyl)-2-(pentyl)-3-(ethyl)-4-(3-octylphenyl)diazobuta-1,3-diene] di(butyl)nickel; [1-(4-octylpenyl)-2-(pentyl)-3-(hydrido)-4-(3-methylphenyl)diazobuta-1,3-diene]di(diethylamino) nickel; [1-(4-octylphenyl)-2-(pentyl)-3-(hydrido)-4-(3-tricosylphenyl)diazobuta-1,3-diene]di(hydrido)nickel; [1-(4-octylphenyl)-2-(pentyl)-3-(octacosynyl)-4-(3-butylphenyl)diazobuta-1,3-diene]di(hexadecyl)nickel; [1-(4-octylphenyl)-2-(pentyl)-3-(octyl)-4-(3-butylphenyl) diazobuta-1,3-diene]di(pentyl)palladium; [1-(4-octylphenyl)-2-(triacontenyl)-3-(decynyl)-4-(3-butylphenyl)diazobuta-1,3-diene]di(tricosyl)nickel; [1-(4-octylphenyl)-2-(tricosyl)-3-(octyl)-4-(3-butylphenyl) diazobuta-1,3-diene]di(methylethylamino)nickel; [1-(4-octylphenyl)-2,3-(dibutyl)-4-(3-butylphenyl)diazobuta-1,3-diene]di(butyl)nickel; [1-(4-octylphenyl)-2,3-(dibutyl)-4-(3-heptadecynylphenyl)diazobuta-1,3-diene]di(tetracosyl) nickel; [1-(4-octylphenyl)-2,3-(dibutyl)-4-(3-octylphenyl) diazobuta-1,3-diene]di(nonadecyl)nickel; [1-(4-octylphenyl)-2,3-(dibutyl)-4-(3-pentylphenyl)diazobuta-1,3-diene]di(octyl)palladium; [1-(4-octylphenyl)-2,3-(dihydrido)-4-(3-butylphenyl)diazobuta-1,3-diene]di (ethoxy)nickel; [1-(4-octylphenyl)-2,3-(dihydrido)-4-(3-methylphenyl)diazobuta-1,3-diene]di(butoxy)palladium; [1-(4-octylphenyl)-2,3-(dihydrido)-4-(3-octylphenyl) diazobuta-1,3-diene]di(eicosyl)palladium; [1-(4-octylphenyl)-2,3-(dihydrido)-4-(3-pentylphenyl)diazobuta-1,3-diene]di(nonyl)nickel; [1-(4-octylphenyl)-2,3-(dihydrido)-4-(3-pentylphenyl)diazobuta-1,3-diene]di (tridecyl)nickel; [1-(4-pentacosenylphenyl)-2-(ethyl)-3-(nonacosyl)-4-(3-hexylphenyl)diazobuta-1,3-diene]di (methyl)palladium; [1-(4-pentacosylphenyl)-2,3-(dibutyl)-4-(3-butylphenyl)diazobuta-1,3-diene]di(ethyl)nickel; [1-(4-pentacosynylphenyl)-2,3-(dibutyl)-4-(3-butylphenyl) diazobuta-1,3-diene]di(dodecyl)nickel; [1-(4-pentadecenylphenyl)-2-(propynyl)-3-(hydrido)-4-(3-butylphenyl)diazobuta-1,3-diene]di(tridecenyl)nickel; [1-(4-pentadecylphenyl)-2-(docosynyl)-3-(butyl)-4-(3-octylphenyl)diazobuta-1,3-diene]di(hydrido)nickel; [1-(4-pentylphenyl)-2-(butyl)-3-(decenyl)-4-(3-hexylphenyl) diazobuta-1,3-diene]di(butyl)nickel; [1-(4-pentylphenyl)-2-(butyl)-3-(ethyl)-4-(3-ethylphenyl)diazobuta-1,3-diene]di (hexyl)nickel; [1-(4-pentylphenyl)-2-(butyl)-3-(hydrido)-4-(3-butylphenyl)diazobuta-1,3-diene]di(nonenyl)palladium; [1-(4-pentylphenyl)-2-(butyl)-3-(hydrido)-4-(3-octylphenyl)diazobuta-1,3-diene]di(hydrido)nickel; [1-(4-pentylphenyl)-2-(butyl)-3-(hydrido)-4-(3-octylphenyl)diazobuta-1,3-diene]di(octadecyl)nickel; [1-(4-pentylphenyl)-2-(butyl)-3-(octadecynyl)-4-(3-butylphenyl)diazobuta-1,3-diene]di (nonadecenyl)palladium; [1-(4-pentylphenyl)-2-(butyl)-3-(octyl)-4-(3-octylphenyl)diazobuta-1,3-diene]di (diethylamino)nickel; [1-(4-pentylphenyl)-2-(butyl)-3-(pentyl)-4-(3-butylphenyl)diazobuta-1,3-diene]di(hydrido) nickel; [1-(4-pentylphenyl)-2-(butyl)-3-(pentyl)-4-(3-dodecaphosphinophenyl)diazobuta-1,3-diene]di(hydrido) nickel; [1-(4-pentylphenyl)-2-(butyl)-3-(pentyl)-4-(3-hexylphenyl)diazobuta-1,3-diene]di(eicosyl)palladium; [1-(4-pentylphenyl)-2-(butyl)-3-(propynyl)-4-(3-pentylphenyl) diazobuta-1,3-diene]di(dimethylamino)nickel; [1-(4-pentylphenyl)-2-(butyl)-3-(tetracosenyl)-4-(3-butylphenyl) diazobuta-1,3-diene]di(heptacosyl)palladium; [1-(4-pentylphenyl)-2-(butynyl)-3-(hexyl)-4-(3-butylphenyl) diazobuta-1,3-diene]di(hexyl)nickel; [1-(4-pentylphenyl)-2-(ethyl)-3-(octadecynyl)-4-(3-pentylphenyl)diazobuta-1,3-diene]di(decyl)nickel; [1-(4-pentylphenyl)-2-(ethyl)-3-(octyl)-4-(3-butylphenyl)diazobuta-1,3-diene]di(methyl) nickel; [1-(4-pentylphenyl)-2-(hexyl)-3-(hydrido)-4-(3-butylphenyl)diazobuta-1,3-diene]di(octadecyl)nickel; [1-(4-pentylphenyl)-2-(hexyl)-3-(methyl)-4-(3-octacosenylphenyl)diazobuta-1,3-diene]di(hydrido)nickel; [1-(4-pentylphenyl)-2-(hexyl)-3-(pentyl)-4-(3-butylphenyl) diazobuta-1,3-diene]di(methyl)nickel; [1-(4-pentylphenyl)-2-(hexyl)-3-(pentyl)-4-(3-octylphenyl)diazobuta-1,3-diene] di(hydrido)nickel; [1-(4-pentylphenyl)-2-(hydrido)-3-(butyl)-4-(3-butylphenyl)diazobuta-1,3-diene]di (dimethylamino)nickel; [1-(4-pentylphenyl)-2-(hydrido)-3-(butyl)-4-(3-octylphenyl)diazobuta-1,3-diene]di(hydrido) nickel; [1-(4-pentylphenyl)-2-(hydrido)-3-(hexyl)-4-(3-butylphenyl)diazobuta-1,3-diene]di(heptyl)nickel; [1-(4-pentylphenyl)-2-(hydrido)-3-(hexyl)-4-(3-butylphenyl) diazobuta-1,3-diene]di(methyl)palladium; [1-(4-pentylphenyl)-2-(methyl)-3-(octyl)-4-(3-nonacosylphenyl) diazobuta-1,3-diene]di(triacontyl)nickel; [1-(4-pentylphenyl)-2-(nonenyl)-3-(butyl)-4-(3-butylphenyl) diazobuta-1,3-diene]di(hexadecyl)nickel; [1-(4-pentylphenyl)-2-(octyl)-3-(butyl)-4-(3-hexylphenyl)

diazobuta-1,3-diene]di(hydrido)nickel; [1-(4-pentylphenyl)-2-(octyl)-3-(butyl)-4-(3-propynylphenyl)diazobuta-1,3-diene]di(diethylamino)nickel; [1-(4-pentylphenyl)-2-(octynyl)-3-(pentadecenyl)-4-(3-butylphenyl)diazobuta-1,3-diene]di(octacosyl)nickel; [1-(4-pentylphenyl)-2-(pentyl)-3-(butyl)-4-(3-butylphenyl)diazobuta-1,3-diene]di(heneicosyl)nickel; [1-(4-pentylphenyl)-2-(pentyl)-3-(hydrido)-4-(3-octylphenyl)diazobuta-1,3-diene]di(hydrido)palladium; [1-(4-pentylphenyl)-2,3-(dibutyl)-4-(3-butylphenyl)diazobuta-1,3-diene]di(butyl)nickel; [1-(4-pentylphenyl)-2,3-(dibutyl)-4-(3-butylphenyl)diazobuta-1,3-diene]di(hydrido)nickel; [1-(4-pentylphenyl)-2,3-(dibutyl)-4-(3-hexylphenyl)diazobuta-1,3-diene]di(tricosyl)nickel; [1-(4-pentylphenyl)-2,3-(dibutyl)-4-(3-pentylphenyl)diazobuta-1,3-diene]di(pentadecyl)nickel; [1-(4-pentylphenyl)-2,3-(dihydrido)-4-(3-pentylphenyl)diazobuta-1,3-diene]di(methyl)palladium; [1-(4-pentylphenyl)-2,3-(dipentyl)-4-(3-butylphenyl)diazobuta-1,3-diene]di(ethyl)palladium; [1-(4-pentylphenyl)-2,3-(dipentyl)-4-(3-dodecaphosphinophenyl)diazobuta-1,3-diene]di(hexadecyl)nickel; [1-(4-propenylphenyl)-2-(hydrido)-3-(butyl)-4-(3-hexylphenyl)diazobuta-1,3-diene]di(hydrido)nickel; [1-(4-proponylphenyl)-2-(methyl)-3-(butyl)-4-(3-butylphenyl)diazobuta-1,3-diene]di(octacosyl)palladium; [1-(4-proponylphenyl)-2,3-(dihydrido)-4-(3-butylphenyl)diazobuta-1,3-diene]di(octyl)nickel; [1-(4-propylphenyl)-2-(butyl)-3-(hydrido)-4-(3-hexylphenyl)diazobuta-1,3-diene]di(pentyl)nickel; [1-(4-tetracosynylphenyl)-2-(octyl)-3-(pentyl)-4-(3-butylphenyl)diazobuta-1,3-diene]di(pentenyl)nickel; [1-(4-tetradecylphenyl)-2-(butyl)-3-(hydrido)-4-(3-hexacosylphenyl)diazobuta-1,3-diene]di(ethyl)palladium; [1-(4-triacontenylphenyl)-2-(hydrido)-3-(hexyl)-4-(3-butylphenyl)diazobuta-1,3-diene]di(tricosyl)nickel; [1-(4-triacontynylphenyl)-2,3-(dibutyl)-4-(3-butylphenyl)diazobuta-1,3-diene]di(hexadecyl)nickel; [1-(4-tricosylphenyl)-2-(butyl)-3-(hydrido)-4-(3-pentylphenyl)diazobuta-1,3-diene]di(hydrido)nickel; [1-(4-tricosynylphenyl)-2-(hexadecynyl)-3-(hydrido)-4-(3-butylphenyl)diazobuta-1,3-diene]di(butoxy)palladium; [1-(4-tridecenylphenyl)-2-(butyl)-3-(octyl)-4-(3-butylphenyl)diazobuta-1,3-diene]di(nonyl)nickel; [1-(4-tridecenylphenyl)-2,3-(dibutyl)-4-(3-pentylphenyl)diazobuta-1,3-diene]di(methoxy)nickel; [1-(4-triocosanalylphenyl)-2-(hexyl)-3-(butyl)-4-(3-butylphenyl)diazobuta-1,3-diene]di(butoxy)nickel; [1-(4-undecenylphenyl)-2-(hexyl)-3-(pentyl)-4-(3-pentylphenyl)diazobuta-1,3-diene]di(hydrido)nickel; [1-(3-(triethylsilylmethyl)phenyl)-2-(butyl)-3-(octyl)-4-(3-hexylphenyl)diazobuta-1,3-diene]di(methyl)nickel; [1-(3-(trimethylsilylmethyl)phenyl)-2-(octyl)-3-(pentadecenyl)-4-(3-methylphenyl)diazobuta-1,3-diene]di(butyl)nickel; [1-(3-butanalylphenyl)-2-(butyl)-3-(hydrido)-4-(3-butylphenyl)diazobuta-1,3-diene]di(phenoxy)nickel; [1-(3-butonylphenyl)-2-(hydrido)-3-(pentacosenyl)-4-(3-octylphenyl)diazobuta-1,3-diene]di(hexacosyl)nickel; [1-(3-butylphenyl)-2-(butyl)-3-(hexyl)-4-(3-ethylphenyl)diazobuta-1,3-diene]di(pentadecyl)nickel; [1-(3-butylphenyl)-2-(butyl)-3-(hexyl)-4-(3-heneicosenylphenyl)diazobuta-1,3-diene]di(docosyl)nickel; [1-(3-butylphenyl)-2-(butyl)-3-(hexyl)-4-(3-propylphenyl)diazobuta-1,3-diene]di(tetradecyl)nickel; [1-(3-butylphenyl)-2-(butyl)-3-(hydrido)-4-(3-ethylphenyl)diazobuta-1,3-diene]di(ethyl)nickel; [1-(3-butylphenyl)-2-(butyl)-3-(hydrido)-4-(3-hexylphenyl)diazobuta-1,3-diene]di(hydrido)nickel; [1-(3-butylphenyl)-2-(butyl)-3-(hydrido)-4-(3-hexylphenyl)diazobuta-1,3-diene]di(methyl)nickel; [1-(3-butylphenyl)-2-(butyl)-3-(hydrido)-4-(3-methylphenyl)diazobuta-1,3-diene]di(pentadecyl)nickel; [1-(3-butylphenyl)-2-(butyl)-3-(hydrido)-4-(3-pentylphenyl)diazobuta-1,3-diene]di(ethyl)nickel; [1-(3-butylphenyl)-2-(butyl)-3-(hydrido)-4-(3-tetracosenylphenyl)diazobuta-1,3-diene]di(butoxy)nickel; [1-(3-butylphenyl)-2-(butyl)-3-(hydrido)-4-(3-undecylphenyl)diazobuta-1,3-diene]di(ethyl)nickel; [1-(3-butylphenyl)-2-(butyl)-3-(nonacosenyl)-4-(3-hexylphenyl)diazobuta-1,3-diene]di(benzyl)nickel; [1-(3-butylphenyl)-2-(butyl)-3-(octyl)-4-(3-methylphenyl)diazobuta-1,3-diene]di(hydrido)nickel; [1-(3-butylphenyl)-2-(butyl)-3-(pentyl)-4-(3-heptadecylphenyl)diazobuta-1,3-diene]di(methyl)nickel; [1-(3-butylphenyl)-2-(butyl)-3-(pentyl)-4-(3-hexylphenyl)diazobuta-1,3-diene]di(propoxy)nickel; [1-(3-butylphenyl)-2-(butyl)-3-(pentyl)-4-(3-methylphenyl)diazobuta-1,3-diene]di(heneicosyl)palladium; [1-(3-butylphenyl)-2-(butyl)-3-(pentyl)-4-(3-octylphenyl)diazobuta-1,3-diene]di(propyl)nickel; [1-(3-butylphenyl)-2-(butyl)-3-(pentyl)-4-(3-pentylphenyl)diazobuta-1,3-diene]di(methyl)nickel; [1-(3-butylphenyl)-2-(butyl)-3-(tetracosyl)-4-(3-pentylphenyl)diazobuta-1,3-diene]di(ethyl)nickel; [1-(3-butylphenyl)-2-(docosynyl)-3-(hexyl)-4-(3-hexylphenyl)diazobuta-1,3-diene]di(ethyl)nickel; [1-(3-butylphenyl)-2-(heneicosenyl)-3-(hexacosenyl)-4-(3-decylphenyl)diazobuta-1,3-diene]di(docosyl)nickel; [1-(3-butylphenyl)-2-(heneicosynyl)-3-(octyl)-4-(3-dodecynylphenyl)diazobuta-1,3-diene]di(eicosyl)nickel; [1-(3-butylphenyl)-2-(hexadecyl)-3-(butyl)-4-(3-pentadecylphenyl)diazobuta-1,3-diene]di(benzyl)palladium; [1-(3-butylphenyl)-2-(hexyl)-3-(butyl)-4-(3-hexylphenyl)diazobuta-1,3-diene]di(butyl)nickel; [1-(3-butylphenyl)-2-(hexyl)-3-(butyl)-4-(3-tricosylphenyl)diazobuta-1,3-diene]di(propoxy)nickel; [1-(3-butylphenyl)-2-(hexyl)-3-(dodecynyl)-4-(3-ethylphenyl)diazobuta-1,3-diene]di(bromo)nickel; [1-(3-butylphenyl)-2-(hexyl)-3-(nonynyl)-4-(3-(trimethylsilylmethyl)phenyl)diazobuta-1,3-diene]di(hexyl)palladium; [1-(3-butylphenyl)-2-(hexynyl)-3-(methyl)-4-(3-pentylphenyl)diazobuta-1,3-diene]di(methyl)nickel; [1-(3-butylphenyl)-2-(hydrido)-3-(butyl)-4-(3-hexylphenyl)diazobuta-1,3-diene]di(bromo)nickel; [1-(3-butylphenyl)-2-(hydrido)-3-(butyl)-4-(3-hexylphenyl)diazobuta-1,3-diene]di(heptyl)nickel; [1-(3-butylphenyl)-2-(hydrido)-3-(butyl)-4-(3-octylphenyl)diazobuta-1,3-diene]di(heneicosyl)nickel; [1-(3-butylphenyl)-2-(hydrido)-3-(butyl)-4-(3-pentenylphenyl)diazobuta-1,3-diene]di(tetradecyl)palladium; [1-(3-butylphenyl)-2-(hydrido)-3-(butyl)-4-(3-pentylphenyl)diazobuta-1,3-diene]di(hexyl)palladium; [1-(3-butylphenyl)-2-(hydrido)-3-(hexyl)-4-(3-octylphenyl)diazobuta-1,3-diene]di(hydrido)nickel; [1-(3-butylphenyl)-2-(hydrido)-3-(octyl)-4-(3-octacosenylphenyl)diazobuta-1,3-diene]di(ethyl)nickel; [1-(3-butylphenyl)-2-(hydrido)-3-(octyl)-4-(3-octacosenylphenyl)diazobuta-1,3-diene]di(ethyl)nickel; [1-(3-butylphenyl)-2-(hydrido)-3-(octyl)-4-(3-octacosynylphenyl)diazobuta-1,3-diene]di(butoxy)palladium; [1-(3-butylphenyl)-2-(hydrido)-3-(octyl)-4-(3-octylphenyl)diazobuta-1,3-diene]di(methyl)nickel; [1-(3-butylphenyl)-2-(hydrido)-3-(octyl)-4-(3-pentylphenyl)diazobuta-1,3-diene]di(nonadecyl)palladium; [1-(3-butylphenyl)-2-(hydrido)-3-(pentadecynyl)-4-(3-pentylphenyl)diazobuta-1,3-diene]di(tridecynyl)palladium; [1-(3-butylphenyl)-2-(hydrido)-3-(pentyl)-4-(3-methylphenyl)diazobuta-1,3-diene]di(hydrido)nickel; [1-(3-butylphenyl)-2-(hydrido)-3-(pentyl)-4-(3-methylphenyl)diazobuta-1,3-diene]di(methyl)nickel; [1-(3-butylphenyl)-2-(hydrido)-3-(pentyl)-4-(3-octylphenyl)diazobuta-1,3-diene]di(butyl)palladium; [1-(3-butylphenyl)-2-(nonadecenyl)-3-(octyl)-4-(3-ethanalylphenyl)diazobuta-1,3-diene]di(tridecyl)palladium; [1-(3-butylphenyl)-2-(nonadecynyl)-3-(butyl)-4-(3-hexacosylphenyl)diazobuta-1,3-diene]di(allyl)nickel; [1-

(3-butylphenyl)-2-(nonyl)-3-(butyl)-4-(3-ethylphenyl)diazobuta-1,3-diene]di(undecyl)nickel; [1-(3-butylphenyl)-2-(octacosyl)-3-(hydrido)-4-(3-pentadecylphenyl)diazobuta-1,3-diene]di(nonyl)palladium; [1-(3-butylphenyl)-2-(octyl)-3-(butyl)-4-(3-nonadecynylphenyl)diazobuta-1,3-diene]di(heptyl)palladium; [1-(3-butylphenyl)-2-(pentacosyl)-3-(pentyl)-4-(3-hexylphenyl)diazobuta-1,3-diene]di(butyl)palladium; [1-(3-butylphenyl)-2-(pentyl)-3-(butyl)-4-(3-hexylphenyl)diazobuta-1,3-diene]di(butoxy)nickel; [1-(3-butylphenyl)-2-(pentyl)-3-(butyl)-4-(3-methylphenyl)diazobuta-1,3-diene]di(octyl)nickel; [1-(3-butylphenyl)-2-(pentyl)-3-(butyl)-4-(3-triacontynylphenyl)diazobuta-1,3-diene]di(docosyl)palladium; [1-(3-butylphenyl)-2-(pentyl)-3-(ethyl)-4-(3-pentadecylphenyl)diazobuta-1,3-diene]di(hydrido)nickel; [1-(3-butylphenyl)-2-(pentyl)-3-(heptadecyl)-4-(3-pentadecylphenyl)diazobuta-1,3-diene]di(ethyl)nickel; [1-(3-butylphenyl)-2-(pentyl)-3-(hydrido)-4-(3-ethylphenyl)diazobuta-1,3-diene]di(hexacosyl)palladium; [1-(3-butylphenyl)-2-(pentyl)-3-(hydrido)-4-(3-octylphenyl)diazobuta-1,3-diene]di(hydrido)nickel; [1-(3-butylphenyl)-2-(pentyl)-3-(hydrido)-4-(3-tetracosynylphenyl)diazobuta-1,3-diene]di(methyl)palladium; [1-(3-butylphenyl)-2-(tetradecynyl)-3-(pentyl)-4-(3-octylphenyl)diazobuta-1,3-diene]di(methyl)nickel; [1-(3-butylphenyl)-2,3-(dibutyl)-4-(3-hexylphenyl)diazobuta-1,3-diene]di(ethyl)palladium; [1-(3-butylphenyl)-2,3-(dibutyl)-4-(3-hexylphenyl)diazobuta-1,3-diene]di(ethyl)palladium; [1-(3-butylphenyl)-2,3-(dibutyl)-4-(3-hexylphenyl)diazobuta-1,3-diene]di(hydrido)nickel; [1-(3-butylphenyl)-2,3-(dibutyl)-4-(3-hexylphenyl)diazobuta-1,3-diene]di(tolyl)nickel; [1-(3-butylphenyl)-2,3-(dibutyl)-4-(3-octacosynylphenyl)diazobuta-1,3-diene]di(hexyl)palladium; [1-(3-butylphenyl)-2,3-(dibutyl)-4-(3-octylphenyl)diazobuta-1,3-diene]di(pentyl)nickel; [1-(3-butylphenyl)-2,3-(dibutyl)-4-(3-octylphenyl)diazobuta-1,3-diene]di(tetradecyl)palladium; [1-(3-butylphenyl)-2,3-(dibutyl)-4-(3-pentylphenyl)diazobuta-1,3-diene]di(benzoxy)nickel; [1-(3-butylphenyl)-2,3-(dibutyl)-4-(3-proponylphenyl)diazobuta-1,3-diene]di(tolyl)palladium; [1-(3-butylphenyl)-2,3-(dihydrido)-4-(3-pentylphenyl)diazobuta-1,3-diene]di(ethyl)palladium; [1-(3-butylphenyl)-2,3-(dioctyl)-4-(3-methylphenyl)diazobuta-1,3-diene]di(octyl)nickel; [1-(3-butylphenyl)-2,3-(dioctyl)-4-(3-undecylphenyl)diazobuta-1,3-diene]di(tridecyl)nickel; [1-(3-butylphenyl)-2,3-(dipentyl)-4-(3-pentylphenyl)diazobuta-1,3-diene]di(methyl)nickel; [1-(3-docosenylphenyl)-2-(butyl)-3-(octyl)-4-(3-pentylphenyl)diazobuta-1,3-diene]di(tridecyl)nickel; [1-(3-docosenylphenyl)-2,3-(dibutyl)-4-(3-butylphenyl)diazobuta-1,3-diene]di(benzoxy)nickel; [1-(3-docosenylphenyl)-2,3-(dibutyl)-4-(3-hexylphenyl)diazobuta-1,3-diene]di(undecynyl)nickel; [1-(3-docosynylphenyl)-2-(heptadecenyl)-3-(methyl)-4-(3-octylphenyl)diazobuta-1,3-diene]di(dodecyl)nickel; [1-(3-dodecaminophenyl)-2-(butyl)-3-(hydrido)-4-(3-butylphenyl)diazobuta-1,3-diene]di(octadecyl)nickel; [1-(3-dodecaminophenyl)-2-(ethyl)-3-(pentyl)-4-(3-octylphenyl)diazobuta-1,3-diene]di(ethyl)nickel; [1-(3-dodecaminophenyl)-2-(octacosyl)-3-(hydrido)-4-(3-butylphenyl)diazobuta-1,3-diene]di(hexyl)nickel; [1-(3-dodecaphosphinophenyl)-2-(pentyl)-3-(octyl)-4-(3-butylphenyl)diazobuta-1,3-diene]di(methyl)nickel; [1-(3-dodecynylphenyl)-2,3-(dibutyl)-4-(3-hexylphenyl)diazobuta-1,3-diene]di(ethoxy)nickel; [1-(3-eicosenylphenyl)-2,3-(dipentyl)-4-(3-methylphenyl)diazobuta-1,3-diene]di(phenyl)nickel; [1-(3-ethanalylphenyl)-2-(butyl)-3-(hydrido)-4-(3-pentylphenyl)diazobuta-1,3-diene]di(methyl)nickel; [1-(3-ethylphenyl)-2-(butyl)-3-(butynyl)-4-(3-butylphenyl)diazobuta-1,3-diene]di(methyl)nickel; [1-(3-ethylphenyl)-2-(butyl)-3-(hydrido)-4-(3-butylphenyl)diazobuta-1,3-diene]di(benzoxy)palladium; [1-(3-ethylphenyl)-2-(butyl)-3-(hydrido)-4-(3-hexylphenyl)diazobuta-1,3-diene]di(phenethyl)palladium; [1-(3-ethylphenyl)-2-(butyl)-3-(methyl)-4-(3-hexylphenyl)diazobuta-1,3-diene]di(hydride)nickel; [1-(3-ethylphenyl)-2-(butyl)-3-(propyl)-4-(3-nonadecynylphenyl)diazobuta-1,3-diene]di(tetradecyl)nickel; [1-(3-ethylphenyl)-2-(docosynyl)-3-(hydrido)-4-(3-butylphenyl)diazobuta-1,3-diene]di(heptyl)nickel; [1-(3-ethylphenyl)-2-(hexacosynyl)-3-(butyl)-4-(3-butylphenyl)diazobuta-1,3-diene]di(phenethyl)nickel; [1-(3-ethylphenyl)-2-(hydrido)-3-(ethyl)-4-(3-pentylphenyl)diazobuta-1,3-diene]di(bromo)palladium; [1-(3-ethylphenyl)-2-(hydrido)-3-(pentyl)-4-(3-butylphenyl)diazobuta-1,3-diene]di(butyl)palladium; [1-(3-ethylphenyl)-2-(methyl)-3-(butenyl)-4-(3-butylphenyl)diazobuta-1,3-diene]di(methyl)palladium; [1-(3-ethylphenyl)-2-(octyl)-3-(ethyl)-4-(3-hexylphenyl)diazobuta-1,3-diene]di(dimethylamino)nickel; [1-(3-ethylphenyl)-2-(pentyl)-3-(hydrido)-4-(3-octylphenyl)diazobuta-1,3-diene]di(tetracosynyl)palladium; [1-(3-ethylphenyl)-2-(pentyl)-3-(methyl)-4-(3-butynylphenyl)diazobuta-1,3-diene]di(butyl)palladium; [1-(3-ethylphenyl)-2,3-(dihydrido)-4-(3-hexylphenyl)diazobuta-1,3-diene]di(benzyl)nickel; [1-(3-heneicosylphenyl)-2-(butyl)-3-(triacontenyl)-4-(3-hexylphenyl)diazobuta-1,3-diene]di(hydrido)palladium; [1-(3-heneicosylphenyl)-2-(pentyl)-3-(octyl)-4-(3-butylphenyl)diazobuta-1,3-diene]di(butyl)nickel; [1-(3-heptacosylphenyl)-2-(hexyl)-3-(hydrido)-4-(3-butylphenyl)diazobuta-1,3-diene]di(methoxy)nickel; [1-(3-heptacosynylphenyl)-2,3-(dibutyl)-4-(3-octacosynylphenyl)diazobuta-1,3-diene]di(methoxy)nickel; [1-(3-heptadecenylphenyl)-2-(hydrido)-3-(methyl)-4-(3-butylphenyl)diazobuta-1,3-diene]di(nonyl)nickel; [1-(3-heptenylphenyl)-2-(hydrido)-3-(pentyl)-4-(3-ethylphenyl)diazobuta-1,3-diene]di(heptacosyl)nickel; [1-(3-heptynylphenyl)-2-(butyl)-3-(octadecynyl)-4-(3-butylphenyl)diazobuta-1,3-diene]di(ethyl)palladium; [1-(3-heptynylphenyl)-2-(undecenyl)-3-(hydrido)-4-(3-octylphenyl)diazobuta-1,3-diene]di(butyl)nickel; [1-(3-hexacosenylphenyl)-2-(butyl)-3-(hydrido)-4-(3-butylphenyl)diazobuta-1,3-diene]di(butyl)nickel; [1-(3-hexacosenylphenyl)-2-(heptadecyl)-3-(butyl)-4-(3-butylphenyl)diazobuta-1,3-diene]di(butyl)palladium; [1-(3-hexacosenylphenyl)-2-(hydrido)-3-(butyl)-4-(3-(trimethylsilylmethyl)phenyl)diazobuta-1,3diene]di(phenethyl)palladium; [1-(3-hexacosenylphenyl)-2,3-(dibutyl)-4-(3-butylphenyl)diazobuta-1,3-diene]di(hydrido)nickel; [1-(3-hexylphenyl)-2-(butyl)-3-(hexyl)-4-(3-butylphenyl)diazobuta-1,3-diene]di(hexyl)nickel; [1-(3-hexylphenyl)-2-(butyl)-3-(hexyl)-4-(3-pentylphenyl)diazobuta-1,3-diene]di(butyl)nickel; [1-(3-hexylphenyl)-2-(butyl)-3-(hexyl)-4-(3-pentylphenyl)diazobuta-1,3-diene]di(methyl)palladium; [1-(3-hexylphenyl)-2-(butyl)-3-(hydrido)-4-(3-butylphenyl)diazobuta-1,3-diene]di(methyl)nickel; [1-(3-hexylphenyl)-2-(butyl)-3-(hydrido)-4-(3-ethylphenyl)diazobuta-1,3-diene]di(ethyl)palladium; [1-(3-hexylphenyl)-2-(butyl)-3-(octyl)-4-(3-heneicosylphenyl)diazobuta-1,3-diene]di(triacontyl)nickel; [1-(3-hexylphenyl)-2-(butyl)-3-(pentyl)-4-(3-ethylphenyl)diazobuta-1,3-diene]di(dodecenyl)nickel; [1-(3-hexylphenyl)-2-(heptyl)-3-(octyl)-4-(3-butylphenyl)diazobuta-1,3-diene]di(hydrido)nickel; [1-(3-hexylphenyl)-2-(hexyl)-3-(butyl)-4-(3-hexacosynylphenyl)diazobuta-1,3- diene]di(butyl)palladium; [1-(3-hexylphenyl)-2-(hexyl)-3-(butyl)-4-(3-pentylphenyl)diazobuta-1,3-diene]di(ethyl)nickel; [1-(3-hexylphenyl)-2-(hydrido)-3-(butyl)-4-(3-hexacosynylphenyl)diazobuta-1,3-diene]di(docosyl)nickel; [1-(3-hexylphenyl)-2-(hydrido)-3-(butyl)-4-(3-pentylphenyl)diazobuta-1,3-diene]di(nonacosyl)nickel; [1-(3-hexylphenyl)-2-(hydrido)-3-(pentyl)-4-(3-tetracosynylphenyl)diazobuta-1,3-diene]di(tolyl)nickel; [1-(3-hexylphenyl)-2-(methyl)-3-(hexyl)-4-(3-butylphenyl)diazobuta-1,3-diene]di(tricosyl)nickel; [1-(3-hexylphenyl)-2-(octacosyl)-3-(ethyl)-4-(3-pentylphenyl)diazobuta-1,3-diene]di(chloro)palladium; [1-(3-hexylphenyl)-2-(octyl)-3-(butyl)-4-(3-butylphenyl)diazobuta-1,3-diene]di(hexacosyl)nickel; [1-(3-hexylphenyl)-2-(pentacosyl)-3-(hexyl)-4-(3-octylphenyl)diazobuta-1,3-diene]di(pentadecyl)nickel; [1-(3-hexylphenyl)-2-(pentyl)-3-(hexyl)-4-(3-octylphenyl)diazobuta-1,3-diene]di(methyl)nickel; [1-(3-hexylphenyl)-2-(pentyl)-3-(octacosynyl)-4-(3-butylphenyl)diazobuta-1,3-diene]di(ethyl)palladium; [1-(3-hexylphenyl)-2-(pentyl)-3-(octyl)-4-(3-butylphenyl)diazobuta-1,3-diene]di(benzoxy)palladium; [1-(3-hexylphenyl)-2-(undecyl)-3-(pentyl)-4-(3-butylphenyl)diazobuta-1,3-diene]di(ethoxy)nickel; [1-(3-hexylphenyl)-2,3-(dibutyl)-4-(3-butylphenyl)diazobuta-1,3-diene]di(bromo)nickel; [1-(3-hexylphenyl)-2,3-(dibutyl)-4-(3-butylphenyl)diazobuta-1,3-diene]di(heptyl)palladium; [1-(3-methylphenyl)-2-(butenyl)-3-(hexyl)-4-(3-nonacosylphenyl)diazobuta-1,3-diene]di(methyl)palladium; [1-(3-methylphenyl)-2-(butyl)-3-(heptenyl)-4-(3-pentacosylphenyl)diazobuta-1,3-diene]di(dimethylamino)nickel; [1-(3-methylphenyl)-2-(butyl)-3-(hexyl)-4-(3-butylphenyl)diazobuta-1,3-diene]di(tricosyl)nickel; [1-(3-methylphenyl)-2-(butyl)-3-(hexyl)-4-(3-octylphenyl)diazobuta-1,3-diene]di(propoxy)palladium; [1-(3-methylphenyl)-2-(butyl)-3-(hydrido)-4-(3-octylphenyl)diazobuta-1,3-diene]di(hydride)nickel; [1-(3-methylphenyl)-2-(butyl)-3-(nonacosyl)-4-(3-butylphenyl)diazobuta-1,3-diene]di(methyl)nickel; [1-(3-methylphenyl)-2-(eicosyl)-3-(butyl)-4-(3-butylphenyl)diazobuta-1,3-diene]di(pentyl)nickel; [1-(3-methylphenyl)-2-(hexadecynyl)-3-(butyl)-4-(3-dodecylphenyl)diazobuta-1,3-diene]di(butoxy)nickel; [1-(3-methylphenyl)-2-(hexyl)-3-(butyl)-4-(3-heptenylphenyl)diazobuta-1,3-diene]di(octacosyl)nickel; [1-(3-methylphenyl)-2-(hexyl)-3-(butyl)-4-(3-pentylphenyl)diazobuta-1,3-diene]di(ethyl)palladium; [1-(3-methylphenyl)-2-(hexyl)-3-(hydrido)-4-(3-ethylphenyl)diazobuta-1,3-diene]di(ethyl)nickel; [1-(3-methylphenyl)-2-(hydrido)-3-(butyl)-4-(3-butenylphenyl)diazobuta-1,3-diene]di(hydrido)nickel; [1-(3-methylphenyl)-2-(hydrido)-3-(butyl)-4-(3-butylphenyl)diazobuta-1,3-diene]di(hydrido)nickel; [1-(3-methylphenyl)-2-(pentyl)-3-(pentynyl)-4-(3-octylphenyl)diazobuta-1,3-diene]di(hydrido)nickel; [1-(3-methylphenyl)-2-(propyl)-3-(octyl)-4-(3-butylphenyl)diazobuta-1,3-diene]di(tricosyl)nickel; [1-(3-methylphenyl)-2,3-(dibutyl)-4-(3-octylphenyl)diazobuta-1,3-diene]di(hydrido)nickel; [1-(3-nonacosynylphenyl)-2-(dodecyl)-3-(heneicosenyl)-4-(3-hexylphenyl)diazobuta-1,3-diene]di(benzoxy)palladium; [1-(3-nonacosynylphenyl)-2-(hexyl)-3-(butyl)-4-(3-tetracosynylphenyl)diazobuta-1,3-diene]di(methyl)nickel; [1-(3-nonadecynylphenyl)-2-(butyl)-3-(hydrido)-4-(3-methylphenyl)diazobuta-1,3-diene]di(hydrido)nickel; [1-(3-nonadecynylphenyl)-2,3-(dibutyl)-4-(3-butylphenyl)diazobuta-1,3-diene]di(benzoxy)nickel; [1-(3-nonylphenyl)-2-(pentyl)-3-(butyl)-4-(3-pentylphenyl)diazobuta-1,3-diene]di(phenethyl)palladium; [1-(3-nonynylphenyl)-2-(butyl)-3-(hexyl)-4-(3-hexylphenyl)diazobuta-1,3-diene]di(methylethylamino)nickel; [1-(3-nonynylphenyl)-2-(pentyl)-3-(ethyl)-4-(3-hexylphenyl)diazobuta-1,3-diene]di(ethyl)palladium; [1-(3-octacosynylphenyl)-2-(pentyl)-3-(hydrido)-4-(3-tricosylphenyl)diazobuta-1,3-diene]di(benzoxy)nickel; [1-(3-octadecenylphenyl)-2,3-(dihydrido)-4-(3-methylphenyl)diazobuta-1,3-diene]di(nonyl)palladium; [1-(3-octadecylphenyl)-2-(hydrido)-3-(hexyl)-4-(3-ethylphenyl)diazobuta-1,3-diene]di(pentadecyl)nickel; [1-(3-octadecylphenyl)-2-(octyl)-3-(butyl)-4-(3-methylphenyl)diazobuta-1,3-diene]di(hydrido)palladium; [1-(3-octylphenyl)-2-(butyl)-3-(hexadecenyl)-4-(3-butylphenyl)diazobuta-1,3-diene]di(hydrido)palladium; [1-(3-octylphenyl)-2-(butyl)-3-(hydrido)-4-(3-butylphenyl)diazobuta-1,3-diene]di(hydrido)nickel; [1-(3-octylphenyl)-2-(butyl)-3-(hydrido)-4-(3-butylphenyl)diazobuta-1,3-diene]di(hydrido)palladium; [1-(3-octylphenyl)-2-(butyl)-3-(hydrido)-4-(3-hexylphenyl)diazobuta-1,3-diene]di(methyl)palladium; [1-(3-octylphenyl)-2-(butyl)-3-(octyl)-4-(3-heptadecylphenyl)diazobuta-1,3-diene]di(iodo)nickel; [1-(3-octylphenyl)-2-(butyl)-3-(octyl)-4-(3-pentylphenyl)diazobuta-1,3-diene]di(heptyl)nickel; [1-(3-octylphenyl)-2-(butyl)-3-(pentadecynyl)-4-(3-pentylphenyl)diazobuta-1,3-diene]di(tetracosyl)nickel; [1-(3-octylphenyl)-2-(butyl)-3-(pentyl)-4-(3-butylphenyl)diazobuta-1,3-diene]di(tricosyl)nickel; [1-(3-octylphenyl)-2-(butyl)-3-(pentyl)-4-(3-methylphenyl)diazobuta-1,3-diene]di(methyl)nickel; [1-(3-octylphenyl)-2-(hexadecenyl)-3-(butyl)-4-(3-methylphenyl)diazobuta-1,3-diene]di(dimethylamino)palladium; [1-(3-octylphenyl)-2-(hexyl)-3-(butyl)-4-(3-nonenylphenyl)diazobuta-1,3-diene]di(propyl)nickel; [1-(3-octylphenyl)-2-(hexyl)-3-(octyl)-4-(3-butylphenyl)diazobuta-1,3-diene]di(hexadecyl)nickel; [1-(3-octylphenyl)-2-(hydrido)-3-(hexyl)-4-(3-butylphenyl)diazobuta-1,3-diene]di(hydrido)nickel; [1-(3-octylphenyl)-2-(hydrido)-3-(methyl)-4-(3-methylphenyl)diazobuta-1,3-diene]di(benzoxy)nickel; [1-(3-octylphenyl)-2-(hydrido)-3-(octyl)-4-(3-ethanalylphenyl)diazobuta-1,3-diene]di(decyl)nickel; [1-(3-octylphenyl)-2-(hydrido)-3-(pentyl)-4(3-butylphenyl)diazobuta-1,3-diene]di(decyl)palladium; [1-(3-octylphenyl)-2-(hydrido)-3-(pentyl)-4-(3-nonylphenyl)diazobuta-1,3-diene]di(ethyl)nickel; [1-(3-octylphenyl)-2-(octyl)-3-(butyl)-4-(3-butylphenyl)diazobuta-1,3-diene]di(dodecyl)palladium; [1-(3-octylphenyl)-2-(octyl)-3-(butyl)-4-(3-octadecenylphenyl)diazobuta-1,3-diene]di(tridecyl)nickel; [1-(3-octylphenyl)-2-(octyl)-3-(hydrido)-4-(3-butylphenyl)diazobuta-1,3-diene]di(allyl)nickel; [1-(3-octylphenyl)-2-(pentenyl)-3-(butyl)-4-(3-pentylphenyl)diazobuta-1,3-diene]di(undecyl)palladium; [1-(3-octylphenyl)-2-(pentyl)-3-(hexyl)-4-(3-pentylphenyl)diazobuta-1,3-diene]di(nonyl)palladium; [1-(3-octylphenyl)-2-(pentyl)-3-(hydrido)-4-(3-butylphenyl)diazobuta-1,3-diene]di(triacontyl)nickel; [1-(3-octylphenyl)-2-(pentyl)-3-(hydrido)-4-(3-ethylphenyl)diazobuta-1,3-diene]di(diethylamino)palladium; [1-(3-octylphenyl)-2-(triacontyl)-3-(octacosyl)-4-(3-methylphenyl)diazobuta-1,3-diene]di(ethyl)nickel; [1-(3-octylphenyl)-2,3-(dibutyl)-4-(3-butylphenyl)diazobuta-1,3-diene]di(hydrido)nickel; [1-(3-octylphenyl)-2,3-(dibutyl)-4-(3-butylphenyl)diazobuta-1,3-diene]di(hydrido)palladium; [1-(3-octylphenyl)-2,3-(dibutyl)-4-(3-eicosynylphenyl)diazobuta-1,3-diene]di(ethyl)nickel; [1-(3-octylphenyl)-2,3-(dibutyl)-4-(3-ethylphenyl)diazobuta-1,3-diene]di(ethyl)nickel; [1-(3-octylphenyl)-2,3-(dibutyl)-4-(3-ethylphenyl)diazobuta-1,3-diene]di(pentyl)nickel; [1-(3-octylphenyl)-2,3-(dibutyl)-4-(3-hexylphenyl)diazobuta-1,3-diene]di(ethyl)nickel; [1-(3-octylphenyl)-2,3-(dihydrido)-4-(3-tridecylphenyl)diazobuta-1,3-diene]di(phenoxy)nickel; [1-(3-octylphenyl)-2,3-(dioctyl)-4-(3-butylphenyl)diazobuta-1, 3-diene]di(decyl)nickel; [1-(3-octynylphenyl)-2-(heptyl)-3-(ethyl)-4-(3-butylphenyl)diazobuta-1,3-diene]di(methyl)palladium; [1-(3-pentacosylphenyl)-2-(methyl)-3-(butyl)-4-(3-octylphenyl)diazobuta-1,3-diene]di(phenyl)palladium; [1-(3-pentadecynylphenyl)-2-(hexyl)-3-(hydrido)-4-(3-butylphenyl)diazobuta-1,3-diene]di(hexyl)nickel; [1-(3-pentylphenyl)-2-(butyl)-3-(hexenyl)-4-(3-hexylphenyl)diazobuta-1,3-diene]di(heptynyl)nickel; [1-(3-pentylphenyl)-2-(butyl)-3-(hexyl)-4-(3-tricosenylphenyl)diazobuta-1,3-diene]di(heptacosyl)nickel; [1-(3-pentylphenyl)-2-(butyl)-3-(hydrido)-4-(3-butylphenyl)diazobuta-1,3-diene]di(heptadecyl)palladium; [1-(3-pentylphenyl)-2-(butyl)-3-(hydrido)-4-(3-butylphenyl)diazobuta-1,3-diene]di(hydrido) nickel; [1-(3-pentylphenyl)-2-(butyl)-3-(octyl)-4-(3-ethylphenyl)diazobuta-1,3-diene]di(tricosyl)palladium; [1-(3-pentylphenyl)-2-(eicosynyl)-3-(octyl)-4-(3-butylphenyl)diazobuta-1,3-diene]di(methylethylamino)nickel; [1-(3-pentylphenyl)-2-(hydrido)-3-(butyl)-4-(3-ethylphenyl)diazobuta-1,3-diene]di(benzyl)nickel; [1-(3-pentylphenyl)-2-(hydrido)-3-(butyl)-4-(3-ethylphenyl)diazobuta-1,3-diene]di(methylethylamino)nickel; [1-(3-pentylphenyl)-2-(hydrido)-3-(butyl)-4-(3-hexadecynylphenyl)diazobuta-1,3-diene]di(methyl)palladium; [1-(3-pentylphenyl)-2-(hydrido)-3-(butyl)-4-(3-hexylphenyl)diazobuta-1,3-diene]di(tridecyl)nickel; [1-(3-pentylphenyl)-2-(hydrido)-3-(butyl)-4-(3-octylphenyl)diazobuta-1,3-diene]di(tricosynyl)nickel; [1-(3-pentylphenyl)-2-(hydrido)-3-(pentacosynyl)-4-(3-nonacosynylphenyl)diazobuta-1,3-diene]di(pentyl)nickel; [1-(3-pentylphenyl)-2-(hydrido)-3-(pentyl)-4-(3-butylphenyl)diazobuta-1,3-diene]di(tetradecyl)nickel; [1-(3-pentylphenyl)-2-(hydrido)-3-(pentyl)-4-(3-butylphenyl)diazobuta-1,3-diene]di(undecyl)nickel; [1-(3-pentylphenyl)-2-(methyl)-3-(hexyl)-4-(3-octylphenyl)diazobuta-1,3-diene]di(butyl)nickel; [1-(3-pentylphenyl)-2-(methyl)-3-(pentyl)-4-(3-butylphenyl)diazobuta-1,3-diene]di(methyl)nickel; [1-(3-pentylphenyl)-2-(nonenyl)-3-(butyl)-4-(3-butylphenyl)diazobuta-1,3-diene]di(hydrido)nickel; [1-(3-pentylphenyl)-2-(octyl)-3-(hexyl)-4-(3-octylphenyl)diazobuta-1,3-diene]di(docosyl)nickel; [1-(3-pentylphenyl)-2-(pentyl)-3-(butyl)-4-(3-methylphenyl)diazobuta-1,3-diene]di(hydrido)palladium; [1-(3-pentylphenyl)-2-(pentyl)-3-(butyl)-4-(3-octylphenyl)diazobuta-1,3-diene]di(pentadecyl)nickel; [1-(3-pentylphenyl)-2-(pentyl)-3-(hydrido)-4-(3-hexylphenyl)diazobuta-1,3-diene]di(heptadecyl)nickel; [1-(3-pentylphenyl)-2-(pentyl)-3-(octyl)-4-(3-heneicosylphenyl)diazobuta-1,3-diene]di(tetracosyl)nickel; [1-(3-pentylphenyl)-2,3-(dibutyl)-4-(3-butylphenyl)diazobuta-1,3-diene]di(nonyl)nickel; [1-(3-pentylphenyl)-2,3-(dibutyl)-4-(3-hexylphenyl)diazobuta-1,3-diene]di(heneicosyl)nickel; [1-(3-pentylphenyl)-2,3-(dibutyl)-4-(3-hexylphenyl)diazobuta-1,3-diene]di(methyl)nickel; [1-(3-pentylphenyl)-2,3-(dihydrido)-4-(3-butylphenyl)diazobuta-1,3-diene]di(hydrido)palladium; [1-(3-pentylphenyl)-2,3-(dihydrido)-4-(3-methylphenyl)diazobuta-1,3-diene]di(ethyl)nickel; [1-(3-pentylphenyl)-2,3-(dipentyl)-4-(3-butylphenyl)diazobuta-1,3-diene]di(heneicosyl)palladium; [1-(3-pentylphenyl)-2,3-(dipentyl)-4-(3-hexylphenyl)diazobuta-1,3-diene]di(heptyl)nickel; [1-(3-propenylphenyl)-2-(butyl)-3-(hydrido)-4-(3-octylphenyl)diazobuta-1,3-diene]di(docosyl)palladium; [1-(3-propynylphenyl)-2-(butyl)-3-(hydrido)-4-(3-octylphenyl)diazobuta-1,3-diene]di(hydrido)nickel; [1-(3-propynylphenyl)-2-(butyl)-3-(hydrido)-4-(3-triacontenylphenyl)diazobuta-1,3-diene]di(ethoxy)nickel; [1-(3-tetracosylphenyl)-2-(butyl)-3-(hydrido)-4-(3-ethylphenyl)diazobuta-1,3-diene]di(ethoxy)nickel; [1-(3-tricosenylphenyl)-2,3-(dihydrido)-4-(3-butylphenyl)diazobuta-1,3-diene]di(ethyl)nickel; [1-(3-tricosylphenyl)-2-(butyl)-3-(octyl)-4-(3-octylphenyl)diazobuta-1,3-diene]di(tolyl)nickel; [1-(3-tricosylphenyl)-2,3-(dipentyl)-4-(3-dodecenylphenyl)diazobuta-1,3-diene]di(heptacosyl)nickel; [1-(3-tricosynylphenyl)-2-(butyl)-3-(tetradecyl)-4-(3-butylphenyl)diazobuta-1,3-diene]di(hexyl)palladium; [1-(3-tridecenylphenyl)-2-(butyl)-3-(ethyl)-4-(3-butylphenyl)diazobuta-1,3-diene]di(hydrido)nickel; [1-(3-tridecenylphenyl)-2,3-(dihydrido)-4-(3-butylphenyl)diazobuta-1,3-diene]di(methoxy)palladium; [1-(3-tridecylphenyl)-2,3-(dibutyl)-4-(3-butylphenyl)diazobuta-1,3-diene]di(dimethylamino)nickel; [1-(3-tridecylphenyl)-2,3-(dibutyl)-4-(3-butylphenyl)diazobuta-1,3-diene]di(ethyl)palladium; [1-(3-undecynylphenyl)-2-(hexyl)-3-(butyl)-4-(3-nonacosylphenyl)diazobuta-1,3-diene]di(octacosyl)palladium; [1-(3-undecynylphenyl)-2-(hydrido)-3-(pentyl)-4-(3-butylphenyl)diazobuta-1,3-diene]di(ethyl)nickel; [1,4-bis(3-octadecynyl-5-hexylphenyl)-2-(butyl)-3-(ethyl)diazobuta-1,3-diene]di(hydrido)nickel; [1,4-bis(3-pentyl-5-butylphenyl)-2-(nonadecynyl)-3-(butyl)diazobuta-1,3-diene]di(bromo)nickel; [1,4-bis(3-pentyl-5-hexylphenyl)-2-(pentyl)-3-(pentacosyl)diazobuta-1,3-diene]di(eicosyl)nickel; [1,4-bis(3-methyldiethylsilylmethyl)-5-heptacosenylphenyl)-2,3-(dibutyl))diazobuta-1,3-diene]di(ethyl)palladium; [1,4-bis(3-butyl-5-pentylphenyl)-2-(ethyl)-3-(hydrido)diazobuta-1,3-diene]di(methyl)nickel; [1,4-bis(3-pentyl-5-butylphenyl)-2-(pentyl)-3-(butyl)diazobuta-1,3-diene]di(methoxy)nickel; [1,4-bis(3-butyl-5-heneicosenylphenyl)-2-(hydrido)-3-(hexyl)diazobuta-1,3-diene]di(butyl)nickel; [1,4-bis(3-pentyl-5-methylphenyl)-2,3-(dibutyl))diazobuta-1,3-diene]di(nonynyl)palladium; [1,4-bis(3-octyl-5-ethylphenyl)-2-(pentyl)-3-(octyl)diazobuta-1,3-diene]di(bromo)nickel; [1,4-bis(3-butyl-5-hexylphenyl)-2-(hydrido)-3-(butyl)diazobuta-1,3-diene]di(hexyl)nickel; [1,4-bis(3-hexacosenyl-5-butylphenyl)-2-(butyl)-3-(methyl)diazobuta-1,3-diene]di(undecyl)palladium; [1,4-bis(3-hexyl-5-butylphenyl)-2,3-(dihexyl))diazobuta-1,3-diene]di(butyl)palladium; [1,4-bis(3-pentyl-5-butylphenyl)-2-(heptadecyl)-3-(hexyl)diazobuta-1,3-diene]di(hexadecyl)nickel; [1,4-bis(3-octyl-5-hexylphenyl)-2-(hydrido)-3-(octyl)diazobuta-1,3-diene]di(butoxy)nickel; [1,4-bis(3-hexyl-5-methylphenyl)-2,3-(dioctyl))diazobuta-1,3-diene]di(hydrido)nickel; [1,4-bis(3-hexyl-5-butylphenyl)-2-(hexyl)-3-(pentyl)diazobuta-1,3-diene]di(ethoxy)nickel; [1,4-bis(3-dodecanonyl-5-butylphenyl)-2-(hydrido)-3-(hexyl)diazobuta-1,3-diene]di(allyl)palladium; [1,4-bis(3-pentyl-5-butylphenyl)-2-(methyl)-3-(butyl)diazobuta-1,3-diene]di(hexacosyl)nickel; [1,4-bis(3-pentyl-5-butylphenyl)-2-(hydrido)-3-(octyl)diazobuta-1,3-diene]di(butyl)palladium; [1,4-bis(3-nonacosyl-5-butylphenyl)-2,3-(dibutyl))diazobuta-1,3-diene]di(tricosyl)nickel; [1,4-bis(3-pentyl-5-butylphenyl)-2-(hydrido)-3-(octyl)diazobuta-1,3-diene]di(phenoxy)nickel; [1,4-bis(3-eicosynyl-5-pentylphenyl)-2-(methyl)-3-(butyl)diazobuta-1,3-diene]di(butyl)nickel; [1,4-bis(3-octylamino-5-octylphenyl)-2,3-(dibutyl))diazobuta-1,3-diene]di(octacosyl)nickel; [1,4-bis(3-pentyl-5-butylphenyl)-2-(butyl)-3-(hydrido)diazobuta-1,3-diene]di(nonyl)palladium; [1,4-bis(3-butyl-5-octylphenyl)-2,3-(dipentyl))diazobuta-1,3-diene]di(bromo)nickel; [1,4-bis(3-butyl-5-ethylphenyl)-2-(butyl)-3-(hydrido)diazobuta-1,3-diene]di(octadecyl)palladium; [1,4-bis(3-pentyl-5-butylphenyl)-2-(butyl)-3-(octyl)diazobuta-1,3-diene]di(butyl)nickel; [1,4-bis(3-nonynyl-5-butylphenyl)-2-(butyl)-3-(pentyl)diazobuta-1,3-diene]di(ethyl)palladium; [1,4-bis(3-butyl-5-hexylphenyl)-2,3-(dihydrido))diazobuta-1,3-diene]di(butyl)nickel; [1,4-bis(3-butyl-5-heptacosenylphenyl)-2-(pentyl)-3-(octyl)diazobuta-1,3- diene]di(methylethylamino)palladium; [1,4-bis(3-butyl-5-octylphenyl)-2-(butyl)-3-(hydrido)diazobuta-1,3-diene]di(eicosyl)nickel; [1,4-bis(3-butyl-5-octynylphenyl)-2-(propenyl)-3-(ethyl)diazobuta-1,3-diene]di(dodecyl)nickel; [1,4-bis(3-butyl-5-hexylphenyl)-2-(ethyl)-3-(hydrido)diazobuta-1,3-diene]di(butoxy)nickel; [1,4-bis(3-hexyl-5-butylphenyl)-2,3-(dibutyl))diazobuta-1,3-diene]di(pentacosyl)nickel; [1,4-bis(3-nonacosyl-5-butylphenyl)-2-(butyl)-3-(hexyl)diazobuta-1,3-diene]di(octyl)nickel; [1,4-bis(3-butyl-5-pentadecynylphenyl)-2-(hydrido)-3-(butyl)diazobuta-1,3-diene]di(benzyl)nickel; [1,4-bis(3-hexadecynyl-5-butylphenyl)-2,3-(dibutyl))diazobuta-1,3-diene]di(allyl)nickel; [1,4-bis(3-hexyl-5-butylphenyl)-2,3-(dihydrido))diazobuta-1,3-diene]di(octenyl)nickel; [1,4-bis(3-butyl-5-(triethylsilylmethyl)phenyl)-2-(butyl)-3-(hydrido)diazobuta-1,3-diene]di(tridecyl)nickel; [1,4-bis(3-butyl-5-octylphenyl)-2,3-(dibutyl))diazobuta-1,3-diene]di(heptadecyl)nickel; [1,4-bis(3-heptynyl-5-butylphenyl)-2-(pentyl)-3-(octacosynyl)diazobuta-1,3-diene]di(hexadecynyl)nickel; [1,4-bis(3-ethyl-5-eicosynylphenyl)-2-(hydrido)-3-(pentyl)diazobuta-1,3-diene]di(methylethylamino)palladium; [1,4-bis(3-butyl-5-pentylphenyl)-2,3-(dibutyl))diazobuta-1,3-diene]di(ethoxy)nickel; [1,4-bis(3-pentyl-5-octylphenyl)-2-(nonacosynyl)-3-(heptynyl)diazobuta-1,3-diene]di(nonadecyl)nickel; [1,4-bis(3-butyl-5-heptacosylphenyl)-2-(octyl)-3-(butyl)diazobuta-1,3-diene]di(hydrido)palladium; [1,4-bis(3-hexyl-5-methylphenyl)-2-(pentyl)-3-(hydrido)diazobuta-1,3-diene]di(tetracosyl)nickel; [1,4-bis(3-butyl-5-eicosenylphenyl)-2-(hexyl)-3-(octyl)diazobuta-1,3-diene]di(nonacosyl)palladium; [1,4-bis(3-pentyl-5-octylphenyl)-2,3-(dihydrido))diazobuta-1,3-diene]di(propyl)nickel; [1,4-bis(3-pentyl-5-butylphenyl)-2-(octyl)-3-(butyl)diazobuta-1,3-diene]di(nonyl)nickel; [1,4-bis(3-eicosynyl-5-hexylphenyl)-2-(pentyl)-3-(ethyl)diazobuta-1,3-diene]di(ethyl)palladium; [1,4-bis(3-ethyl-5-hexylphenyl)-2-(hexyl)-3-(methyl)diazobuta-1,3-diene]di(methyl)nickel; [1,4-bis(3-butyl-5-octylphenyl)-2-(pentacosenyl)-3-(pentyl)diazobuta-1,3-diene]di(methyl)palladium; [1,4-bis(3-pentyl-5-butylphenyl)-2-(hexyl)-3-(butyl)diazobuta-1,3-diene]di(tolyl)palladium; [1,4-bis(3-octyl-5-pentylphenyl)-2-(hydrido)-3-(octyl)diazobuta-1,3-diene]di(butyl)palladium; [1,4-bis(3-pentyl-5-butylphenyl)-2,3-(dibutyl))diazobuta-1,3-diene]di(pentyl)nickel; [1,4-bis(3-butyl-5-pentylphenyl)-2-(octyl)-3-(pentyl)diazobuta-1,3-diene]di(butyl)palladium; [1,4-bis(3-hexyl-5-butylphenyl)-2-(hexyl)-3-(butyl)diazobuta-1,3-diene]di(hydrido)nickel; [1,4-bis(3-ethyl-5-butylphenyl)-2-(pentyl)-3-(heptacosynyl)diazobuta-1,3-diene]di(hexadecyl)nickel; [1,4-bis(3-pentenyl-5-butylphenyl)-2-(methyl)-3-(butyl)diazobuta-1,3-diene]di(propyl)nickel; [1,4-bis(3-methyl-5-butylphenyl)-2-(butyl)-3-(pentyl)diazobuta-1,3-diene]di(hydrido)nickel; [1,4-bis(3-butyl-5-hexylphenyl)-2-(ethyl)-3-(butyl)diazobuta-1,3-diene]di(phenyl)nickel; [1,4-bis(3-hexenyl-5-tetradecylphenyl)-2-(hydrido)-3-(butyl)diazobuta-1,3-diene]di(benzyl)palladium; [1,4-bis(3-butyl-5-octylphenyl)-2-(hydrido)-3-(methyl)diazobuta-1,3-diene]di(hydrido)nickel; [1,4-bis(3-(trimethylsilylmethyl)-5-decenylphenyl)-2-(hydrido)-3-(methyl)diazobuta-1,3-diene]di(tetracosyl)nickel; [1,4-bis(3-octadecenyl-5-butylphenyl)-2-(butyl)-3-(pentyl)diazobuta-1,3-diene]di(tricosyl)nickel; [1,4-bis(3-butyl-5-pentylphenyl)-2-(hydrido)-3-(butyl)diazobuta-1,3-diene]di(butyl)nickel; [1,4-bis(3-butyl-5-(triethylsilylmethyl)phenyl)-2-(hexyl)-3-(butyl)diazobuta-1,3-diene]di(decyl)nickel; [1,4-bis(3-pentyl-5-tridecenylphenyl)-2-(methyl)-3-(docosyl)diazobuta-1,3-diene]di(octacosyl)nickel; [1,4-bis(3-ethyl-5-pentylphenyl)-2-(methyl)-3-(butyl)diazobuta-1,3-diene]di(methyl)nickel; [1,4-bis(3-butyl-5-hexylphenyl)-2-(ethyl)-3-(hexyl)diazobuta-1,3-diene]di(propyl)nickel; [1,4-bis(3-hexyl-5-butylphenyl)-2-(hexyl)-3-(octyl)diazobuta-1,3-diene]di(butyl)nickel; [1,4-bis(3-nonenyl-5-butylphenyl)-2,3-(dibutyl))diazobuta-1,3-diene]di(ethyl)palladium; [1,4-bis(3-pentyl-5-tridecenylphenyl)-2-(butyl)-3-(hydrido)diazobuta-1,3-diene]di(phenyl)nickel; [1,4-bis(3-pentyl-5-butylphenyl)-2,3-(dibutyl))diazobuta-1,3-diene]di(bromo)nickel; [1,4-bis(3-tricosynyl-5-pentacosenylphenyl)-2-(hexyl)-3-(butyl)diazobuta-1,3-diene]di(heneicosyl)nickel; [1,4-bis(3-docosenyl-5-pentylphenyl)-2-(hydrido)-3-(heptyl)diazobuta-1,3-diene]di(hexyl)nickel; [1,4-bis(3-butyl-5-pentylphenyl)-2-(pentyl)-3-(octyl)diazobuta-1,3-diene]di(benzyl)nickel; [1,4-bis(3-hexyl-5-pentylphenyl)-2-(hydrido)-3-(pentyl)diazobuta-1,3-diene]di(ethyl)palladium; [1,4-bis(3-butyl-5-methylphenyl)-2-(hydrido)-3-(octyl)diazobuta-1,3-diene]di(allyl)palladium; [1,4-bis(3-ethyl-5-octylphenyl)-2-(butyl)-3-(pentyl)diazobuta-1,3-diene]di(hydrido)nickel; [1,4-bis(3-pentyl-5-ethylphenyl)-2-(ethyl)-3-(hydrido)diazobuta-1,3-diene]di(nonyl)nickel; [1,4-bis(3-hexyl-5-undecenylphenyl)-2-(octadecenyl)-3-(hydrido)diazobuta-1,3-diene]di(nonacosyl)nickel; [1,4-bis(3-butyl-5-butenylphenyl)-2,3-(dioctyl))diazobuta-1,3-diene]di(nonacosyl)nickel; [1,4-bis(3-butyl-5-octylphenyl)-2-(butyl)-3-(octyl)diazobuta-1,3-diene]di(methylethylamino)palladium; [1,4-bis(3-heptadecyl-5-(triethylsilylmethyl)phenyl)-2-(butyl)-3-(hydrido)diazobuta-1,3-diene]di(ethyl)nickel; [1,4-bis(3-pentyl-5-butylphenyl)-2-(methyl)-3-(butyl)diazobuta-1,3-diene]di(methyl)palladium; [1,4-bis(3-heptenyl-5-butenylphenyl)-2,3-(dibutyl))diazobuta-1,3-diene]di(octacosyl)nickel; [1,4-bis(3-octyl-5-pentylphenyl)-2-(pentyl)-3-(ethyl)diazobuta-1,3-diene]di(tridecyl)nickel; [1,4-bis(3-tetradecyl-5-methylphenyl)-2-(butyl)-3-(ethyl)diazobuta-1,3-diene]di(octyl)nickel; [1,4-bis(3-butyl-5-methyldiethylsilylmethyl)phenyl)-2-(pentyl)-3-(hydrido)diazobuta-1,3-diene]di(methyl)nickel; [1,4-bis(3-butyl-5-ethylphenyl)-2-(methyl)-3-(hexyl)diazobuta-1,3-diene]di(ethyl)palladium; [1,4-bis(3-propanalyl-5-butylphenyl)-2,3-(dibutyl))diazobuta-1,3-diene]di(hydrido)nickel; [1,4-bis(3-(trimethylsilylethyl)-5-octylphenyl)-2-(butyl)-3-(hydrido)diazobuta-1,3-diene]di(hexyl)nickel; [1,4-bis(3-octyl-5-eicosylphenyl)-2-(octyl)-3-(hexyl)diazobuta-1,3-diene]di(methyl)nickel; [1,4-bis(3-ethyl-5-tetradecenylphenyl)-2-(hexyl)-3-(butyl)diazobuta-1,3-diene]di(ethyl)nickel; [1,4-bis(3-butyl-5-pentylphenyl)-2-(dodecenyl)-3-(butyl)diazobuta-1,3-diene]di(hydrido)nickel; [1,4-bis(3-octacosyl-5-butylphenyl)-2-(tetracosynyl)-3-(hexyl)diazobuta-1,3-diene]di(phenyl)palladium; [1,4-bis(3-butyl-5-pentylphenyl)-2-(methyl)-3-(hexyl)diazobuta-1,3-diene]di(tetradecyl)nickel; [1,4-bis(3-pentyl-5-octylphenyl)-2-(hydrido)-3-(pentyl)diazobuta-1,3-diene]di(heptacosyl)nickel; [1,4-bis(3-octyl-5-butylphenyl)-2-(octyl)-3-(hydrido)diazobuta-1,3-diene]di(phenyl)nickel; [1,4-bis(3-pentyl-5-butylphenyl)-2-(hydrido)-3-(butyl)diazobuta-1,3-diene]di(eicosyl)nickel; [1,4-bis(3-butyl-5-octacosylphenyl)-2-(butyl)-3-(hexyl)diazobuta-1,3-diene]di(octyl)nickel; [1,4-bis(3-butyl-5-pentylphenyl)-2,3-(dibutyl))diazobuta-1,3-diene]di(butyl)nickel; [1,4-bis(3-butyl-5-octylphenyl)-2-(butyl)-3-(hexyl)diazobuta-1,3-diene]di(phenethyl)nickel; [1,4-bis(3-octyl-5-butylphenyl)-2-(methyl)-3-(ethyl)diazobuta-1,3-diene]di(octadecyl)nickel; [1,4-bis(3-hexadecenyl-5-octylphenyl)-2-(ethyl)-3-(hydrido)diazobuta-1,3-diene]di(butyl)palladium; [1,4-bis(3-pentyl-5-butylphenyl)-2-(pentyl)-3-(octyl)diazobuta-1,3-diene]di(decyl)nickel; [1,4-bis(3-hexyl-5-decynylphenyl)-2-(hexyl)-3-(hydrido)diazobuta-1,3-diene]di(hexacosyl)

nickel; [1,4-bis(3-octylamino-5-ethylphenyl)-2-(hydrido)-3-(butyl)diazobuta-1,3-diene]di(propyl)nickel; [1,4-bis(3-octyl-5-hexylphenyl)-2-(pentyl)-3-(octyl)diazobuta-1,3-diene]di(pentacosyl)nickel; [1,4-bis(3-pentyl-5-hexylphenyl)-2,3-(dibutyl)diazobuta-1,3-diene]di(hydrido)nickel; [1,4-bis(3-hexonyl-5-butylphenyl)-2-(octyl)-3-(butyl)diazobuta-1,3-diene]di(hydrido)nickel; [1,4-bis(3-butyl-5-pentylphenyl)-2-(pentyl)-3-(butyl)diazobuta-1,3-diene]di(methylethylamino)nickel; [1,4-bis(3-pentyl-5-hexylphenyl)-2-(hexyl)-3-(octyl)diazobuta-1,3-diene]di(methylethylamino)palladium; [1,4-bis(3-butyl-5-hexonylphenyl)-2,3-(dihydrido))diazobuta-1,3-diene]di(tricosyl)nickel; [1,4-bis(3-pentyl-5-octylphenyl)-2-(hydrido)-3-(butyl)diazobuta-1,3-diene]di(butyl)nickel; [1,4-bis(3-octyl-5-methylphenyl)-2-(butyl)-3-(nonynyl)diazobuta-1,3-diene]di(methylethylamino)nickel; [1,4-bis(3-tetracosynyl-5-octylphenyl)-2-(butyl)-3-(hydrido)diazobuta-1,3-diene]di(propoxy)nickel; [1,4-bis(3-butyl-5-tridecenylphenyl)-2-(hexynyl)-3-(hydrido)diazobuta-1,3-diene]di(hydrido)nickel; [1,4-bis(3-ethyl-5-hexylphenyl)-2-(hydrido)-3-(hexadecyl)diazobuta-1,3-diene]di(benzyl)palladium; [1,4-bis(3-hexyl-5-octylphenyl)-2-(octyl)-3-(ethyl)diazobuta-1,3-diene]di(methyl)nickel; [1,4-bis(3-octyl-5-butylphenyl)-2-(hexyl)-3-(pentyl)diazobuta-1,3-diene]di(heptyl)nickel; [1,4-bis(3-butyl-5-hexylphenyl)-2-(butyl)-3-(methyl)diazobuta-1,3-diene]di(propyl)nickel; [1,4-bis(3-pentyl-5-methylphenyl)-2-(butyl)-3-(octyl)diazobuta-1,3-diene]di(propoxy)nickel; [1,4-bis(3-ethyl-5-eicosynylphenyl)-2-(butyl)-3-(octyl)diazobuta-1,3-diene]di(tetradecyl)nickel; [1,4-bis(3-octyl-5-pentylphenyl)-2-(heptacosyl)-3-(hydrido)diazobuta-1,3-diene]di(butyl)nickel; [1,4-bis(3-butyl-5-hexylphenyl)-2,3-(dioctyl))diazobuta-1,3-diene]di(tridecyl)nickel; [1,4-bis(3-heneicosyl-5-butylphenyl)-2-(butyl)-3-(octyl)diazobuta-1,3-diene]di(hydrido)nickel; [1,4-bis(3-pentyl-5-hexylphenyl)-2-(ethyl)-3-(octadecenyl)diazobuta-1,3-diene]di(butyl)nickel; [1,4-bis(3-methyl-5-ethylphenyl)-2-(hydrido)-3-(ethyl)diazobuta-1,3-diene]di(decyl)nickel; [1,4-bis(3-octyl-5-pentylphenyl)-2-(butyl)-3-(octyl)diazobuta-1,3-diene]di(ethyl)palladium; [1,4-bis(3-ethyl-5-butylphenyl)-2,3-(dihydrido))diazobuta-1,3-diene]di(ethyl)palladium; [1,4-bis(3-octacosynyl-5-butylphenyl)-2-(nonadecyl)-3-(butyl)diazobuta-1,3-diene]di(methyl)nickel; [1,4-bis(3-methyl-5-octylphenyl)-2-(heptyl)-3-(pentyl)diazobuta-1,3-diene]di(butoxy)nickel; [1,4-bis(3-butyl-5-pentylphenyl)-2-(hexyl)-3-(butyl)diazobuta-1,3-diene]di(heneicosenyl)nickel; [1,4-bis(3-eicosynyl-5-butylphenyl)-2,3-(dioctyl))diazobuta-1,3-diene]di(hexyl)palladium; [1,4-bis(3-pentyl-5-octacosynylphenyl)-2,3-(dibutyl))diazobuta-1,3-diene]di(tricosyl)nickel; [1,4-bis(3-octyl-5-pentylphenyl)-2-(butyl)-3-(hydrido)diazobuta-1,3-diene]di(methyl)nickel; [1,4-bis(3-ethyl-5-octylphenyl)-2,3-(dihydrido))diazobuta-1,3-diene]di(ethyl)nickel; [1,4-bis(3-butyl-5-hexylphenyl)-2,3-(dibutyl))diazobuta-1,3-diene]di(ethyl)nickel; [1,4-bis(3-octyl-5-butylphenyl)-2-(hydrido)-3-(ethyl)diazobuta-1,3-diene]di(tolyl)palladium; [1,4-bis(3-nonadecyl-5-pentylphenyl)-2-(butyl)-3-(hydrido)diazobuta-1,3-diene]di(hydrido)palladium; [1,4-bis(3-heneicosynyl-5-butylphenyl)-2-(hexyl)-3-(butyl)diazobuta-1,3-diene]di(undecenyl)nickel; [1,4-bis(3-butyl-5-octylphenyl)-2-(butyl)-3-(hydrido)diazobuta-1,3-diene]di(tetracosyl)nickel; [1,4-bis(3-hexyl-5-butylphenyl)-2-(hydrido)-3-(hexyl)diazobuta-1,3-diene]di(eicosyl)palladium; [1,4-bis(3-octyl-5-pentacosylphenyl)-2-(pentyl)-3-(dodecynyl)diazobuta-1,3-diene]di(tridecyl)nickel; [1,4-bis(3-hexyl-5-butylphenyl)-2-(hydrido)diazobuta-1,3-diene]di(tricosyl)nickel; [1,4-bis(3-butyl-5-tricosenyl phenyl)-2-(methyl)-3-(butyl)diazobuta-1,3-diene]di(methylethylamino)nickel; [1,4-bis(3-ethyl-5-butylphenyl)-2-(hydrido)-3-(propenyl)diazobuta-1,3-diene]di(tolyl)nickel; [1,4-bis(3-butyl-5-octylphenyl)-2-(octyl)-3-(hydrido)diazobuta-1,3-diene]di(octyl)nickel; [1,4-bis(3-pentyl-5-butylphenyl)-2-(pentyl)-3-(butyl)diazobuta-1,3-diene]di(butyl)nickel; [1,4-bis(3-butyl-5-ethylphenyl)-2-(butyl)-3-(tridecyl)diazobuta-1,3-diene]di(docosyl)nickel; [1,4-bis(3-butyl-5-pentacosenylphenyl)-2-(hydrido)-3-(butyl)diazobuta-1,3-diene]di(tetracosyl)nickel; [1,4-bis(3-hexyl-5-butylphenyl)-2-(hexadecenyl)-3-(butyl)diazobuta-1,3-diene]di(hydrido)palladium; [1,4-bis(3-tricosynyl-5-pentacosenylphenyl)-2-(nonadecyl)-3-(hydrido)diazobuta-1,3-diene]di(butoxy)nickel; [1,4-bis(3-butyl-5-methylethylaminophenyl)-2-(octyl)-3-(hydrido)diazobuta-1,3-diene]di(butyl)nickel; [1,4-bis(3-pentyl-5-butylphenyl)-2-(methyl)-3-(hydrido)diazobuta-1,3-diene]di(butyl)nickel; [1,4-bis(3-butyl-5-hexylphenyl)-2-(pentyl)-3-(hexyl)diazobuta-1,3-diene]di(triacontenyl)nickel; [1,4-bis(3-butyl-5-methylphenyl)-2-(butyl)-3-(hydrido)diazobuta-1,3-diene]di(decyl)nickel; [1,4-bis(3-butyl-5-ethylphenyl)-2,3-(dihydrido))diazobuta-1,3-diene]di(beptyl)nickel; [1,4-bis(3-butyl-5-pentylphenyl)-2-(butyl)-3-(octacosynyl)diazobuta-1,3-diene]di(iodo)palladium; [1,4-bis(3-octyl-5-hexylphenyl)-2-(hydrido)-3-(pentyl)diazobuta-1,3-diene]di(pentenyl)nickel; [1,4-bis(3-butyl-5-pentylphenyl)-2,3-(dihydrido))diazobuta-1,3-diene]di(allyl)palladium; [1,4-bis(3-pentyl-5-butylphenyl)-2-(hydrido)-3-(octacosenyl)diazobuta-1,3-diene]di(benzoxy)nickel; [1,4-bis(3-butyl-5-hexylphenyl)-2-(ethyl)-3-(nonacosynyl)diazobuta-1,3-diene]di(tridecyl)palladium; [1,4-bis(3-butenyl-5-butonylphenyl)-2-(hexyl)-3-(pentenyl)diazobuta-1,3-diene]di(butyl)nickel; [1,4-bis(3-docosynyl-5-ethylphenyl)-2-(hydrido)-3-(pentyl)diazobuta-1,3-diene]di(methoxy)nickel; [1,4-bis(3-pentyl-5-butylphenyl)-2-(pentyl)-3-(butyl)diazobuta-1,3-diene]di(methyl)nickel; [1,4-bis(3-butyl-5-pentadecynylphenyl)-2-(hydrido)-3-(butyl)diazobuta-1,3-diene]di(octyl)nickel; [1,4-bis(3-tetradecynyl-5-tricosylphenyl)-2,3-(dibutyl))diazobuta-1,3-diene]di(methyl)nickel; [1,4-bis(3-butyl-5-octylphenyl)-2-(butyl)-3-(methyl)diazobuta-1,3-diene]di(tricosyl)nickel; [1,4-bis(3-butyl-5-octylphenyl)-2-(methyl)-3-(octyl)diazobuta-1,3-diene]di(hydrido)nickel; [1,4-bis(3-butyl-5-octylphenyl)-2-(pentyl)-3-(heneicosynyl)diazobuta-1,3-diene]di(decyl)nickel; [1,4-bis(3-butyl-5-docosenylphenyl)-2-(undecenyl)-3-(butyl)diazobuta-1,3-diene]di(phenoxy)palladium; [1,4-bis(3-hexacosyl-5-butylphenyl)-2-(butyl)-3-(hydrido)diazobuta-1,3-diene]di(docosyl)nickel; [1,4-bis(3-butyl-5-ethylphenyl)-2-(hydrido)-3-(butyl)diazobuta-1,3-diene]di(methyl)nickel; [1,4-bis(3-heneicosenyl-5-butylphenyl)-2-(hexenyl)-3-(butyl)diazobuta-1,3-diene]di(pentadecyl)nickel; [1,4-bis(3-butyl-5-nonadecylphenyl)-2-(butyl)-3-(pentyl)diazobuta-1,3-diene]di(phenoxy)nickel; [1,4-bis(3-hexacosynyl-5-hexylphenyl)-2-(hydrido)-3-(heptenyl)diazobuta-1,3-diene]di(phenoxy)palladium; [1,4-bis(3-butyl-5-methylphenyl)-2-(octyl)-3-(butyl)diazobuta-1,3-diene]di(hydrido)nickel; [1,4-bis(3-heneicosyl-5-hexylphenyl)-2-(hydrido)-3-(butyl)diazobuta-1,3-diene]di(hexadecynyl)nickel; [1,4-bis(3-hexyl-5-butylphenyl)-2-(pentyl)-3-(butyl)diazobuta-1,3-diene]di(octacosyl)nickel; [1,4-bis(3-nonynyl-5-pentylphenyl)-2-(methyl)-3-(butyl)diazobuta-1,3-diene]di(ethoxy)palladium; [1,4-bis(3-butyl-5-octylphenyl)-2-(hexyl)-3-(hydrido)diazobuta-1,3-diene]di(nonadecyl)palladium; [1,4-bis(3-butyl-5-(triethylsilylmethyl)phenyl)-2-(octyl)-3-(butyl)diazobuta-1,3-diene]di(octadecyl)palladium; [1,4-bis(3-butyl-5-tetradecylphenyl)-2-(butyl)-3-(hydrido)diazobuta-1,3-diene]di(methyl)nickel; [1,4-bis(3-butyl-5- tridocosanalylphenyl)-2-(ethyl)-3-(butyl)diazobuta-1,3-diene]di(butoxy)nickel; [1,4-bis(3-heptacosynyl-5-octylphenyl)-2,3-(dibutyl))diazobuta-1,3-diene]di(butyl)nickel; [1,4-bis(3-pentyl-5-hexylphenyl)-2,3-(dibutyl))diazobuta-1,3-diene]di(hydride)palladium; [1,4-bis(3-hexyl-5-butylphenyl)-2-(pentyl)-3-(butyl)diazobuta-1,3-diene]di(hydrido)nickel; [1,4-bis(3-heptenyl-5-butenylphenyl)-2-(hydrido)-3-(octyl)diazobuta-1,3-diene]di(ethoxy)nickel; [1,4-bis(3-butyl-5-heptadecylphenyl)-2-(hydrido)-3-(butyl)diazobuta-1,3-diene]di(hexyl)nickel; [1,4-bis(3-butyl-5-tridecenylphenyl)-2-(ethyl)-3-(hexyl)diazobuta-1,3-diene]di(hydride)nickel; [1,4-bis(3-butyl-5-pentylphenyl)-2-(pentyl)-3-(butyl)diazobuta-1,3-diene]di(hydrido)nickel; [1,4-bis(3-butyl-5-pentylphenyl)-2-(butyl)-3-(hexadecyl)diazobuta-1,3-diene]di(hydrido)nickel; [1,4-bis(3-pentyl-5-methylphenyl)-2-(hydrido)-3-(butyl)diazobuta-1,3-diene]di(methyl)nickel; [1,4-bis(3-hexyl-5-butylphenyl)-2-(nonadecynyl)-3-(hydrido)diazobuta-1,3-diene]di(propyl)nickel; [1,4-bis(3-decenyl-5-butylphenyl)-2-(hexyl)-3-(octynyl)diazobuta-1,3-diene]di(ethyl)nickel; [1,4-bis(3-pentyl-5-octylphenyl)-2-(ethyl)-3-(butyl)diazobuta-1,3-diene]di(octyl)nickel; [1,4-bis(3-hexyl-5-butylphenyl)-2-(pentyl)-3-(hexyl)diazobuta-1,3-diene]di(butyl)palladium; [1,4-bis(3-butyl-5-hexylphenyl)-2-(butenyl)-3-(octyl)diazobuta-1,3-diene]di(propynyl)nickel; [1,4-bis(3-methyl-5-octylphenyl)-2,3-(dibutyl))diazobuta-1,3-diene]di(tricosyl)nickel; [1,4-bis(3-heptenyl-5-pentylphenyl)-2-(butyl)-3-(hexyl)diazobuta-1,3-diene]di(butyl)nickel; [1,4-bis(3-pentyl-5-eicosylphenyl)-2-(pentyl)-3-(hydrido)diazobuta-1,3-diene]di(tricosyl)nickel; [1,4-bis(3-hexadecynyl-5-butylphenyl)-2,3-(dihydrido))diazobuta-1,3-diene]di(methyl)palladium; [1,4-bis(3-butyl-5-octylphenyl)-2-(hydrido)-3-(undecyl)diazobuta-1,3-diene]di(dimethylamino)palladium; [1,4-bis(3-hexadecyl-5-octylphenyl)-2-(hexyl)-3-(butyl)diazobuta-1,3-diene]di(heneicosyl)nickel; [1,4-bis(3-hexynyl-5-butylphenyl)-2-(hydrido)-3-(butyl)diazobuta-1,3-diene]di(butyl)nickel; [1,4-bis(3-heptacosyl-5-ethylphenyl)-2-(hexyl)-3-(butyl)diazobuta-1,3-diene]di(ethyl)nickel; [1,4-bis(3-butyl-5-methylphenyl)-2-(octyl)-3-(pentyl)diazobuta-1,3-diene]di(phenoxy)nickel; [1,4-bis(3-hexyl-5-heneicosenylphenyl)-2-(hexyl)-3-(butyl)diazobuta-1,3-diene]di(nonyl)nickel; [1,4-bis(3-hexyl-5-methylphenyl)-2-(decynyl)-3-(hydrido)diazobuta-1,3-diene]di(hydrido)nickel; [1,4-bis(3-pentyl-5-ethylphenyl)-2,3-(dibutyl))diazobuta-1,3-diene]di(pentyl)nickel; [1,4-bis(3-butyl-5-pentylphenyl)-2,3-(dibutyl))diazobuta-1,3-diene]di(pentacosyl)palladium; [1,4-bis(3-butyl-5-octylphenyl)-2-(butyl)-3-(octyl)diazobuta-1,3-diene]di(methoxy)nickel; [1,4-bis(3-pentyl-5-butylphenyl)-2-(butyl)-3-(hexyl)diazobuta-1,3-diene]di(butoxy)nickel; [1,4-bis(3-heptacosyl-5-ethylphenyl)-2-(hexyl)-3-(methyl)diazobuta-1,3-diene]di(tridecyl)palladium; [1,4-bis(3-pentyl-5-heneicosynylphenyl)-2-(decenyl)-3-(butyl)diazobuta-1,3-diene]di(hydrido)nickel; [1,4-bis(3-pentyl-5-butylphenyl)-2,3-(dibutyl))diazobuta-1,3-diene]di(undecyl)nickel; [1,4-bis(3-pentacosyl-5-octylphenyl)-2-(methyl)-3-(hydrido)diazobuta-1,3-diene]di(octyl)nickel; [1,4-bis(3-butyl-5-hexylphenyl)-2-(butyl)-3-(hydrido)diazobuta-1,3-diene]di(hydrido)nickel; [1,4-bis(3-pentyl-5-hexylphenyl)-2-(octyl)-3-(butyl)diazobuta-1,3-diene]di(hydrido)nickel; [1,4-bis(3-butyl-5-eicosylphenyl)-2-(butyl)-3-(hydrido)diazobuta-1,3-diene]di(phenethyl)palladium; [1,4-bis(3-butanalyl-5-pentylphenyl)-2-(hydrido)-3-(butyl)diazobuta-1,3-diene]di(hydrido)nickel; [1,4-bis(3-butyl-5-hexylphenyl)-2,3-(dihydrido))diazobuta-1,3-diene]di(methyl)nickel; [1,4-bis(3-hexyl-5-octylphenyl)-2,3-(dibutyl))diazobuta-1,3-diene]di(hydrido)palladium; [1,4-bis(3-pentyl-5-ethylphenyl)-2-(octyl)-3-(hydrido)diazobuta-1,3-diene]di(ethyl)palladium; [1,4-bis(3-hexyl-5-octylphenyl)-2-(hydrido)-3-(butyl)diazobuta-1,3-diene]di(pentadecyl)nickel; [1,4-bis(3-pentyl-5-ethylphenyl)-2-(octyl)-3-(butyl)diazobuta-1,3-diene]di(butyl)palladium; [1,4-bis(3-octyl-5-butylphenyl)-2-(decyl)-3-(butyl)diazobuta-1,3-diene]di(hexacosyl)nickel; [1,4-bis(3-methyl-5-tetradecylphenyl)-2-(ethyl)-3-(butyl)diazobuta-1,3-diene]di(propoxy)palladium; [1,4-bis(3-ethyl-5-butylphenyl)-2-(butyl)-3-(triacontynyl)diazobuta-1,3-diene]di(butyl)nickel; [1,4-bis(3-butyl-5-pentylphenyl)-2-(ethyl)-3-(hydrido)diazobuta-1,3-diene]di(tricosyl)nickel; [1,4-bis(3-nonadecenyl-5-docosenylphenyl)-2,3-(dibutyl))diazobuta-1,3-diene]di(decenyl)nickel; [1,4-bis(3-octadecyl-5-decylphenyl)-2-(pentacosenyl)-3-(heptacosynyl)diazobuta-1,3-diene]di(dimethylamino)palladium; [1,4-bis(3-heptyl-5-butylphenyl)-2-(octyl)-3-(methyl)diazobuta-1,3-diene]di(hydrido)nickel; [1,4-bis(3-octyl-5-octadecenylphenyl)-2-(hydrido)-3-(butyl)diazobuta-1,3-diene]di(methyl)nickel; [1,4-bis(3-butyl-5-pentylphenyl)-2-(pentenyl)-3-(eicosyl)diazobuta-1,3-diene]di(methyl)nickel; [1,4-bis(3-octyl-5-butylphenyl)-2-(butyl)-3-(octyl)diazobuta-1,3-diene]di(butyl)palladium; [1,4-bis(3-pentyl-5-butylphenyl)-2-(butyl)-3-(methyl)diazobuta-1,3-diene]di(tridecyl)nickel; [1,4-bis(3-octyl-5-butylphenyl)-2-(butyl)-3-(octyl)diazobuta-1,3-diene]di(ethyl)nickel; [1,4-bis(3-hexyl-5-butylphenyl)-2-(pentadecyl)-3-(octyl)diazobuta-1,3-diene]di(tetradecyl)nickel; [1,4-bis(3-butyl-5-nonadecylphenyl)-2-(butyl)-3-(hydrido)diazobuta-1,3-diene]di(tridecyl)nickel; [1,4-bis(3-butyl-5-octylphenyl)-2,3-(dioctyl))diazobuta-1,3-diene]di(nonadecyl)nickel; [1,4-bis(3-pentyl-5-butylphenyl)-2-(hydrido)-3-(butyl)diazobuta-1,3-diene]di(diethylamino)nickel; [1,4-bis(3-heneicosyl-5-butylphenyl)-2-(octyl)-3-(pentyl)diazobuta-1,3-diene]di(methylethylamino)nickel; [1,4-bis(3-butyl-5-octylphenyl)-2-(pentyl)-3-(butyl)diazobuta-1,3-diene]di(methyl)nickel; [1,4-bis(3-hexyl-5-octylphenyl)-2,3-(dibutyl))diazobuta-1,3-diene]di(butyl)palladium; [1,4-bis(3-butyl-5-hexylphenyl)-2-(hexacosyl)-3-(hexyl)diazobuta-1,3-diene]di(hydrido)palladium; [1,4-bis(3-hexyl-5-octylphenyl)-2-(butyl)-3-(ethyl)diazobuta-1,3-diene]di(ethyl)nickel; [1,4-bis(3-ethyl-5-butylphenyl)-2,3-(dihydrido))diazobuta-1,3-diene]di(butyl)palladium; [1,4-bis(3-hexyl-5-nonadecenylphenyl)-2-(hydrido)-3-(hexyl)diazobuta-1,3-diene]di(pentyl)nickel; [1,4-bis(3-ethyl-5-butylphenyl)-2-(butyl)-3-(octyl)diazobuta-1,3-diene]di(hydrido)nickel; [1,4-bis(3-hexyl-5-pentylphenyl)-2,3-(dioctyl))diazobuta-1,3-diene]di(tridecyl)palladium; [1,4-bis(3-eicosenyl-5-methylphenyl)-2-(methyl)-3-(hexyl)diazobuta-1,3-diene]di(butyl)nickel; [1,4-bis(3-butyl-5-pentylpbenyl)-2-(hexyl)-3-(pentyl)diazobuta-1,3-diene]di(hydrido)palladium; [1,4-bis(3-methyl-5-butylphenyl)-2-(hexyl)-3-(butyl)diazobuta-1,3-diene]di(hexadecyl)nickel; [1,4-bis(3-octyl-5-pentylphenyl)-2,3-(dibutyl))diazobuta-1,3-diene]di(dodecyl)nickel; [1,4-bis(3-butyl-5-octylphenyl)-2-(butyl)-3-(hexyl)diazobuta-1,3-diene]di(hydride)nickel; [1,4-bis(3-heneicosynyl-5-butylphenyl)-2-(butyl)-3-(pentyl)diazobuta-1,3-diene]di(hydrido)nickel; [1,4-bis(3-octacosyl-5-butylphenyl)-2-(octyl)-3-(pentyl)diazobuta-1,3-diene]di(methylethylamino)nickel; [1,4-bis(3-ethyl-5-butylphenyl)-2-(hexynyl)-3-(butyl)diazobuta-1,3-diene]di(propoxy)palladium; [1,4-bis(3-pentyl-5-hexylphenyl)-2-(octyl)-3-(hydrido)diazobuta-1,3-diene]di(ethyl)nickel; [1,4-bis(3-butyl-5-hexylphenyl)-2,3-(dibutyl))diazobuta-1,3-diene]di(ethyl)nickel; [1,4-bis(3-butyl-5-hexylphenyl)-2-(butyl)-3-(pentyl)diazobuta-1,3-diene]di(phenoxy)nickel; [1,4-bis(3-nonacosyl-5-hexylphenyl)-2-(octyl)-3-(hexyl)diazobuta-1,3-diene]di(propyl)nickel; [1,4-bis(3-butyl-5- eicosylphenyl)-2-(methyl)-3-(ethyl)diazobuta-1,3-diene]di(propyl)palladium; [1,4-bis(3-butyl-5-octylphenyl)-2-(heptadecynyl)-3-(dodecyl)diazobuta-1,3-diene]di(heneicosyl)nickel; [1,4-bis(3-butyl-5-hexylphenyl)-2-(butyl)-3-(methyl)diazobuta-1,3-diene]di(ethyl)nickel; [1,4-bis(3-hexyl-5-octylphenyl)-2,3-(dioctyl))diazobuta-1,3-diene]di(eicosyl)palladium; [1,4-bis(3-pentyl-5-butylphenyl)-2-(octyl)-3-(hydrido)diazobuta-1,3-diene]di(ethyl)nickel; [1,4-bis(3-heptyl-5-butylphenyl)-2-(butyl)-3-(hydrido)diazobuta-1,3-diene]di(propoxy)nickel; [1,4-bis(3-hexacosynyl-5-hexylphenyl)-2-(nonacosynyl)-3-(hexyl)diazobuta-1,3-diene]di(hydrido)nickel; [1,4-bis(3-pentyl-5-octylphenyl)-2-(hydrido)-3-(octyl)diazobuta-1,3-diene]di(ethyl)palladium; [1,4-bis(3-butyl-5-dodecaminophenyl)-2-(hydrido)-3-(heptadecyl)diazobuta-1,3-diene]di(nonyl)nickel; [1,4-bis(3-octyl-5-heptacosynyl)phenyl)-2-(hexyl)-3-(octyl)diazobuta-1,3-diene]di(hydrido)palladium; [1,4-bis(3-methyl-5-pentylphenyl)-2-(octyl)-3-(hexenyl)diazobuta-1,3-diene]di(hydrido)palladium; [1,4-bis(3-pentyl-5-butylphenyl)-2-(butyl)-3-(hexyl)diazobuta-1,3-diene]di(nonadecyl)nickel; [1,4-bis(3-butynyl-5-octylphenyl)-2-(octyl)-3-(butyl)diazobuta-1,3-diene]di(hexacosyl)nickel; [1,4-bis(3-butyl-5-octylphenyl)-2-(pentyl)-3-(ethyl)diazobuta-1,3-diene]di(nonadecynyl)nickel; [1,4-bis(3-methyl-5-octylphenyl)-2-(octyl)-3-(butyl)diazobuta-1,3-diene]di(octyl)nickel; [1,4-bis(3-butyl-5-dodecynylphenyl)-2-(butyl)-3-(ethyl)diazobuta-1,3-diene]di(heptyl)nickel; [1,4-bis(3-pentyl-5-methylphenyl)-2-(octyl)-3-(octadecyl)diazobuta-1,3-diene]di(ethyl)nickel; [1,4-bis(3-pentyl-5-butylphenyl)-2-(heneicosyl)-3-(hydrido)diazobuta-1,3-diene]di(benzyl)palladium; [1,4-bis(3-pentyl-5-heneicosenylphenyl)-2-(octyl)-3-(butyl)diazobuta-1,3-diene]di(methoxy)nickel; [1,4-bis(3-tetradecyl-5-butylphenyl)-2,3-(dihydrido))diazobuta-1,3-diene]di(hydrido)nickel; [1,4-bis(3-butyl-5-heptadecenylphenyl)-2-(butyl)-3-(octacosenyl)diazobuta-1,3-diene]di(pentadecyl)palladium; [1,4-bis(3-hexyl-5-octylphenyl)-2-(methyl)-3-(octyl)diazobuta-1,3-diene]di(ethyl)nickel; [1,4-bis(3-butyl-5-methylphenyl)-2-(dodecynyl)-3-(butyl)diazobuta-1,3-diene]di(ethyl)nickel; [1,4-bis(3-pentyl-5-heptacosynylphenyl)-2-(octyl)-3-(butyl)diazobuta-1,3-diene]di(hydrido)nickel; [1,4-bis(3-hexyl-5-butylphenyl)-2,3-(dibutyl))diazobuta-1,3-diene]di(ethyl)palladium; [1,4-bis(3-heneicosyl-5-butylphenyl)-2-(hydrido)-3-(octyl)diazobuta-1,3-diene]di(tricosyl)nickel; [1,4-bis(3-butyl-5-ethylphenyl)-2-(hydrido)-3-(pentyl)diazobuta-1,3-diene]di(hexadecyl)nickel; [1,4-bis(3-ethyl-5-butylphenyl)-2-(octyl)-3-(butyl)diazobuta-1,3-diene]di(methyl)nickel; [1,4-bis(3-heneicosynyl-5-butylphenyl)-2-(hexynyl)-3-(hexyl)diazobuta-1,3-diene]di(hydrido)nickel; [1,4-bis(3-hexyl-5-hexynylphenyl)-2-(nonynyl)-3-(hexyl)diazobuta-1,3-diene]di(hexyl)nickel; [1,4-bis(3-heptyl-5-hexylphenyl)-2-(butyl)-3-(hydrido)diazobuta-1,3-diene]di(octadecyl)nickel; [1,4-bis(3-pentyl-5-heptadecylphenyl)-2-(hexyl)-3-(octadecenyl)diazobuta-1,3-diene]di(decynyl)nickel; [1,4-bis(3-pentyl-5-butylphenyl)-2,3-(dibutyl))diazobuta-1,3-diene]di(phenoxy)palladium; [1,4-bis(3-pentyl-5-butylphenyl)-2,3-(dibutyl))diazobuta-1,3-diene]di(phenyl)nickel; [1,4-bis(3-ethyl-5-butylphenyl)-2-(octyl)-3-(hydrido)diazobuta-1,3-diene]di(octadecyl)nickel; [1,4-bis(3-butyl-5-nonynylphenyl)-2-(methyl)-3-(butyl)diazobuta-1,3-diene]di(diethylamino)nickel; [1,4-bis(3-butylphenyl)-2-(octyl)-3-(methyl)diazobuta-1,3-diene]di(phenoxy)nickel; [1,4-bis(3-butylphenyl)-2-(hydrido)-3-(octyl)diazobuta-1,3-diene]di(hexacosyl)nickel; [1,4-bis(3-pentylphenyl)-2-(butyl)-3-(hexyl)diazobuta-1,3-diene]di(hydrido)palladium; [1,4-bis(3-eicosylphenyl)-2-(hydrido)-3-(octenyl)diazobuta-1,3-diene]di(hydrido)nickel; [1,4-bis(3-decenylphenyl)-2-(hexyl)-3-(butyl)diazobuta-1,3-diene]di(phenyl)nickel; [1,4-bis(3-tetracosenylphenyl)-2-(octyl)-3-(ethyl)diazobuta-1,3-diene]di(butyl)nickel; [1,4-bis(3-butylphenyl)-2-(butyl)-3-(heptyl)diazobuta-1,3-diene]di(methoxy)nickel; [1,4-bis(3-octylphenyl)-2,3-(dibutyl))diazobuta-1,3-diene]di(heptacosenyl)nickel; [1,4-bis(3-butylphenyl)-2-(butyl)-3-(pentyl)diazobuta-1,3-diene]di(phenoxy)nickel; [1,4-bis(3-hexylphenyl)-2-(methyl)-3-(tricosyl)diazobuta-1,3-diene]di(heneicosyl)nickel; [1,4-bis(3-hexylphenyl)-2-(butyl)-3-(pentyl)diazobuta-1,3-diene]di(propyl)nickel; [1,4-bis(3-octylphenyl)-2-(hydrido)-3-(hexyl)diazobuta-1,3-diene]di(hexyl)palladium; [1,4-bis(3-butylphenyl)-2-(octenyl)-3-(butyl)diazobuta-1,3-diene]di(nonadecyl)nickel; [1,4-bis(3-hexylphenyl)-2-(butyl)-3-(hexynyl)diazobuta-1,3-diene]di(docosyl)nickel; [1,4-bis(3-butylphenyl)-2-(pentyl)-3-(hydrido)diazobuta-1,3-diene]di(chloro)nickel; [1,4-bis(3-hexylphenyl)-2,3-(dibutyl))diazobuta-1,3-diene]di(heptacosyl)nickel; [1,4-bis(3-butylphenyl)-2-(pentyl)-3-(butyl)diazobuta-1,3-diene]di(hydrido)nickel; [1,4-bis(3-octylphenyl)-2-(octyl)-3-(butyl)diazobuta-1,3-diene]di(decyl)palladium; [1,4-bis(3-nonynylphenyl)-2,3-(dibutyl))diazobuta-1,3-diene]di(octyl)nickel; [1,4-bis(3-ethylphenyl)-2-(hexacosynyl)-3-(butyl)diazobuta-1,3-diene]di(hydrido)nickel; [1,4-bis(3-butylphenyl)-2-(hydrido)-3-(butyl)diazobuta-1,3-diene]di(tetracosyl)nickel; [1,4-bis(3-pentylphenyl)-2-(pentyl)-3-(hydrido)diazobuta-1,3-diene]di(ethyl)nickel; [1,4-bis(3-butylphenyl)-2-(hexyl)-3-(butyl)diazobuta-1,3-diene]di(methyl)nickel; [1,4-bis(3-hexylphenyl)-2,3-(dihydrido))diazobuta-1,3-diene]di(ethoxy)nickel; [1,4-bis(3-pentylphenyl)-2-(hydrido)-3-(nonyl)diazobuta-1,3-diene]di(methyl)nickel; [1,4-bis(3-butylphenyl)-2-(pentyl)-3-(butyl)diazobuta-1,3-diene]di(ethoxy)nickel; [1,4-bis(3-pentylphenyl)-2-(butyl)-3-(undecenyl)diazobuta-1,3-diene]di(nonacosyl)nickel; [1,4-bis(3-butylphenyl)-2-(octyl)-3-(hydrido)diazobuta-1,3-diene]di(nonacosyl)nickel; [1,4-bis(3-butylphenyl)-2-(butyl)-3-(heptadecynyl)diazobuta-1,3-diene]di(octadecynyl)nickel; [1,4-bis(3-butylphenyl)-2-(butyl)-3-(methyl)diazobuta-1,3-diene]di(hydrido)palladium; [1,4-bis(3-butonylphenyl)-2-(hexyl)-3-(octyl)diazobuta-1,3-diene]di(ethyl)nickel; [1,4-bis(3-pentynylphenyl)-2-(pentyl)-3-(butyl)diazobuta-1,3-diene]di(methoxy)nickel; [1,4-bis(3-butylphenyl)-2-(butyl)-3-(pentyl)diazobuta-1,3-diene]di(ethyl)nickel; [1,4-bis(3-octylphenyl)-2-(pentyl)-3-(hydrido)diazobuta-1,3-diene]di(heptenyl)nickel; [1,4-bis(3-methylphenyl)-2-(methyl)-3-(pentyl)diazobuta-1,3-diene]di(methyl)nickel; [1,4-bis(3-pentylphenyl)-2,3-(dibutyl))diazobuta-1,3-diene]di(hydrido)palladium; [1,4-bis(3-butylphenyl)-2,3-(dihydrido))diazobuta-1,3-diene]di(chloro)nickel; [1,4-bis(3-butylphenyl)2-(hexyl)-3-(hydrido)diazobuta-1,3-diene]di(hydrido)nickel; [1,4-bis(3-butylphenyl)-2(tridecenyl)-3-(butyl)diazobuta-1,3-diene]di(hydrido)nickel; [1,4-bis(3-methylphenyl)- 2-(nonyl)-3-(hydrido)diazobuta-1,3-diene]di(nonyl)nickel; [1,4-bis(3-butylphenyl)-2,3-(dibutyl))diazobuta-1,3-diene]di(ethyl)nickel; [1,4-bis(3-octylphenyl)-2-(butyl)-3-(octyl)diazobuta-1,3-diene]di(butyl)nickel; [1,4-bis(3-butylphenyl)-2,3-(dibutyl))diazobuta-1,3-diene]di(propoxy)nickel; [1,4-bis(3-butylphenyl)-2,3-(dibutyl))diazobuta-1,3-diene]di(hydrido)nickel; [1,4-bis(3-butylphenyl)-2-(butyl)-3-(hexyl)diazobuta-1,3-diene]di(ethyl)palladium; [1,4-bis(3-pentylphenyl)-2-(butyl)-3-(hexyl)diazobuta-1,3-diene]di(hydrido)nickel; [1,4-bis(3-methylphenyl)-2-(butyl)-3-(hexyl)diazobuta-1,3-diene]di(heptadecyl)nickel; [1,4-bis(3-butylphenyl)-2-(butyl)-3-(hydrido)diazobuta-1,3-diene]

di(heptyl)nickel; [1,4-bis(3-butylphenyl)-2-(hydrido)-3-(butyl)diazobuta-1,3-diene]di(heneicosyl)nickel; [1,4-bis(3-butylphenyl)-2-(butyl)-3-(hydrido)diazobuta-1,3-diene]di(triacontyl)palladium; [1,4-bis(3-ethylphenyl)-2-(butyl)-3-(octyl)diazobuta-1,3-diene]di(hydrido)nickel; [1,4-bis(3-butylphenyl)-2-(hydrido)-3-(ethyl)diazobuta-1,3-diene]di(allyl)nickel; [1,4-bis(3-hexylphenyl)-2,3-(dibutyl))diazobuta-1,3-diene]di(decyl)palladium; [1,4-bis(3-butylphenyl)-2-(butyl)-3-(hexyl)diazobuta-1,3-diene]di(hydrido)nickel; [1,4-bis(3-butylphenyl)-2,3-(dihexyl))diazobuta-1,3-diene]di(butyl)palladium; [1,4-bis(3-butylphenyl)-2-(hydrido)-3-(butyl)diazobuta-1,3-diene]di(hydrido)nickel; [1,4-bis(3-butylphenyl)-2-(octyl)-3-(ethyl)diazobuta-1,3-diene]di(pentyl)nickel; [1,4-bis(3-butylphenyl)-2-(hydrido)-3-(butyl)diazobuta-1,3-diene]di(docosyl)nickel; [1,4-bis(3-butylphenyl)-2-(tridecenyl)-3-(hexyl)diazobuta-1,3-diene]di(ethyl)palladium; [1,4-bis(3-heptenylphenyl)-2-(pentyl)-3-(undecenyl)diazobuta-1,3-diene]di(bromo)nickel; [1,4-bis(3-nonynylphenyl)-2,3-(dibutyl))diazobuta-1,3-diene]di(butyl)nickel; [1,4-bis(3-butylphenyl)-2-(pentyl)-3-(butyl)diazobuta-1,3-diene]di(heneicosyl)palladium; [1,4-bis(3-butylphenyl)-2-(decyl)-3-(hydrido)diazobuta-1,3-diene]di(butyl)palladium; [1,4-bis(3-ethylphenyl)-2-(butyl)-3-(hexacosynyl)diazobuta-1,3-diene]di(ethyl)nickel; [1,4-bis(3-heptacosylphenyl)-2-(butyl)-3-(pentyl)diazobuta-1,3-diene]di(butyl)nickel; [1,4-bis(3-butylphenyl)-2-(hydrido)-3-(ethyl)diazobuta-1,3-diene]di(octacosyl)nickel; [1,4-bis(3-butylphenyl)-2-(methyl)-3-(octyl)diazobuta-1,3-diene]di(methoxy)nickel; [1,4-bis(3-pentylphenyl)-2-(octyl)-3-(butyl)diazobuta-1,3-diene]di(hydrido)palladium; [1,4-bis(3-nonadecylphenyl)-2-(methyl)-3-(butyl)diazobuta-1,3-diene]di(nonadecyl)nickel; [1,4-bis(3-octylphenyl)-2-(ethyl)-3-(octacosynyl)diazobuta-1,3-diene]di(propyl)nickel; [1,4-bis(3-butylphenyl)-2,3-(dioctyl))diazobuta-1,3-diene]di(octadecyl)nickel; [1,4-bis(3-nonacosynylphenyl)-2-(hexadecynyl)-3-(hydrido)diazobuta-1,3-diene]di(ethyl)nickel; [1,4-bis(3-butylphenyl)-2-(butyl)-3-(hydrido)diazobuta-1,3-diene]di(phenyl)nickel; [1,4-bis(3-ethylphenyl)-2-(hydrido)-3-(butyl)diazobuta-1,3-diene]di(decyl)nickel; [1,4-bis(3-butylphenyl)-2-(ethyl)-3-(heptacosyl)diazobuta-1,3-diene]di(tolyl)palladium; [1,4-bis(3-butylphenyl)-2-(hydrido)-3-(butyl)diazobuta-1,3-diene]di(hexyl)palladium; [1,4-bis(3-ethylphenyl)-2-(butyl)-3-(octyl)dazobuta-1,3-diene]di(methyl)nickel; [1,4-bis(3-butylphenyl)-2-(butyl)-3-(octyl)dazobuta-1,3-diene]di(hydrido)nickel; [1,4-bis(3-methylphenyl)-2-(butyl)-3-(eicosenyl)diazobuta-1,3-diene]di(heptadecyl)nickel; [1,4-bis(3-methylphenyl)-2,3-(dihydrido))diazobuta-1,3-diene]di(benzoxy)nickel; [1,4-bis(3-hexylphenyl)-2-(octyl)-3-(butyl)diazobuta-1,3-diene]di(hydrido)nickel; [1,4-bis(3-pentylphenyl)-2-(hydrido)-3-(butyl)diazobuta-1,3-diene]di(pentadecyl)nickel; [1,4-bis(3-octylphenyl)-2,3-(dibutyl))diazobuta-1,3-diene]di(hexyl)nickel; [1,4-bis(3-butylphenyl)-2-(hydrido)-3-(butyl)diazobuta-1,3-diene]di(triacontyl)nickel; [1,4-bis(3-butylphenyl)-2,3-(dibutyl))diazobuta-1,3-diene]di(methoxy)nickel; [1,4-bis(3-butylphenyl)-2-(methyl)-3-(butyl)diazobuta-1,3-diene]di(nonyl)nickel; [1,4-bis(3-hexadecylphenyl)-2-(pentyl)-3-(butyl)diazobuta-1,3-diene]di(butyl)nickel; [1,4-bis(3-hexylphenyl)-2-(hexacosenyl)-3-(butyl)diazobuta-1,3-diene]di(hydrido)nickel; [1,4-bis(3-butylphenyl)-2-(octyl)-3-(methyl)diazobuta-1,3-diene]di(ethoxy)palladium; [1,4-bis(3-butylphenyl)-2-(hexacosenyl)-3-(butyl)diazobuta-1,3-diene]di(nonyl)nickel; [1,4-bis(3-octylphenyl)-2-(pentyl)-3-(butenyl)diazobuta-1,3-diene]di(propoxy)nickel; [1,4-bis(3-butylphenyl-2-(butyl)-3-(pentyl)diazobuta-1,3-diene]di(butyl)nickel; [1,4-bis(3-(trimethylsilylmethyl)phenyl)-2-(hydrido)-3-(butyl)diazobuta-1,3-diene]di(pentacosyl)palladium; [1,4-bis(3-ethylphenyl)-2-(butyl)-3-(hydrido)diazobuta-1,3-diene]di(tridecyl)nickel; [1,4-bis(3-octylphenyl)-2-(pentyl)-3-(heneicosenyl)diazobuta-1,3-diene]di(methyl)nickel; [1,4-bis(3-butylphenyt)-2,3-(dibutyl))diazobuta-1,3-diene]di(triacontynyl)palladium; [1,4-bis(3-butylphenyl)-2-(butyl)-3-(octyl)diazobuta-1,3-diene]di(hydrido)nickel; [1,4-bis(3-butylphenyl)-2-(octyl)-3-(hydrido)diazobuta-1,3-diene]di(methylethylamino)nickel; [1,4-bis(3-hexylphenyl)-2-(tridecyl)-3-(hydrido)diazobuta-1,3-diene]di(hexadecyl)nickel; [1,4-bis(3-butylphenyl)-2-(octyl)-3-(hexyl)diazobuta-1,3-diene]di(methyl)palladium; [1,4-bis(3-pentylphenyl)-2-(tetracosenyl)-3-(butyl)diazobuta-1,3-diene]di(hydrido)palladium; [1,4-bis(3-butylphenyl)-2-(methyl)-3-(butyl)dazobuta-1,3-diene]di(butyl)palladium; [1,4-bis(3-octadecynylphenyl)-2-(butyl)-3-(hydrido)diazobuta-1,3-diene]di(hydrido)nickel; [1,4-bis(3-octacosenylphenyl)-2-(methyl)-3-(butyl)diazobuta-1,3-diene]di(octacosenyl)nickel; [1,4-bis(3-hexylphenyl)-2-(hydrido)-3-(butyl)diazobuta-1,3-diene]di(heneicosyl)nickel; [1,4-bis(3-butylphenyl)-2-(pentyl)-3-(butyl)diazobuta-1,3-diene]di(diethylamino)nickel; [1,4-bis(3-octylphenyl)-2-(butyl)-3-(hydrido)diazobuta-1,3-diene]di(pentadecyl)nickel; [1,4-bis(3-butylphenyl)-2-(hexyl)-3-(hydrido)diazobuta-1,3-diene]di(iodo)nickel; [1,4-bis(3-butylphenyl)-2-(octyl)-3-(hydrido)diazobuta-1,3-diene]di(allyl)nickel; [1,4-bis(3-octylphenyl)-2-(hydrido)-3-(octyl)diazobuta-1,3-diene]di(methyl)palladium; [1,4-bis(3-octylphenyl)-2-(butyl)-3-(hydrido)diazobuta-1,3-diene]di(hydrido)palladium; [1,4-bis(3-butylphenyl)-2-(pentyl)3-(hexyl)diazobuta-1,3-diene]di(butyl)palladium; [1,4-bis(3-octylphenyl)-2,3-(dibutyl))diazobuta-1,3-diene]di(hydrido)nickel; [1,4-bis(3-ethylphenyl)-2-(heptyl)-3-(hydrido)diazobuta-1,3-diene]di(hydrido)nickel; [1,4-bis(3-butonylphenyl)-2-(octyl)-3-(butyl)diazobuta-1,3-diene]di(hydride)palladium; [1,4-bis(3-butylphenyl)-2-(butyl)-3-(hydrido)diazobuta-1,3-diene]di(propyl)palladium; [1,4-bis(3-butylphenyl)-2-(pentyl)-3-(butyl)diazobuta-1,3-diene]di(bromo)nickel; [1,4-bis(3-butylphenyl)-2-(octacosenyl)-3-(octyl)diazobuta-1,3-diene]di(dimethylamino)nickel; [1,4-bis(3-pentacosynylphenyl)-2-(butyl)-3-(hydrido)diazobuta-1,3-diene]di(eicosyl)nickel; [1,4-bis(3-octylphenyl)-2-(hydrido)-3-(butyl)diazobuta-1,3-diene]di(hexyl)palladium; [1,4-bis(3-ethylphenyl)-2-(butyl)-3-(hydrido)diazobuta-1,3-diene]di(nonyl)nickel; [1,4-bis(3-methylphenyl)-2-(hexadecynyl)-3-(hydrido)diazobuta-1,3-diene]di(eicosyl)nickel; [1,4-bis(3-methylphenyl)-2-(butyl)-3-(tetracosyl)diazobuta-1,3-diene]di(hexadecyl)nickel; [1,4-bis(3-butylphenyl)-2-(pentyl)-3-(butyl)diazobuta-1,3-diene]di(allyl)nickel; [1,4-bis(3-pentylphenyl)-2,3-(dihydrido))diazobuta-1,3-diene]di(hydrido)nickel; [1,4-bis(3-butylphenyl)-2-(hydrido)-3-(octyl)diazobuta-1,3-diene]di(propoxy)nickel; [1,4-bis(3-butylphenyl)-2-(pentyl)-3-(butyl)diazobuta-1,3-diene]di(docosyl)nickel; [1,4-bis(3-pentylphenyl)-2-(hydrido)-3-(methyl)diazobuta-1,3-diene]di(eicosyl)nickel; [1,4-bis(3-butylphenyl)-2-(pentyl)-3-(hydrido)diazobuta-1,3-diene]di(pentadecyl)nickel; [1,4-bis(3-pentylphenyl)-2-(dodecyl)-3-(butyl)diazobuta-1,3-diene]di(ethyl)nickel; [1,4-bis(3-butylphenyl)-2-(heptadecynyl)-3-(methyl)diazobuta-1,3-diene]di(methyl)palladium; [1,4-bis(3-methylphenyl)-2-(methyl)-3-(pentadecenyl)diazobuta-1,3-diene]di(butyl)nickel; [1,4-bis(3-ethanalylphenyl)-2-(octyl)-3-(hydrido)diazobuta-1,3-diene]di(heptacosyl)nickel; [1,4-bis(3-pentylphenyl)-2-(butyl)-3-(tetracosyl)diazobuta-1,3-diene]di(benzoxy)palladium; [1,4-bis(3-hexylphenyl)-2,3-(dioctyl))diazobuta-1,3-diene]di(hydrido)nickel; [1,4-bis(3- methylphenyl)-2-(ethyl)-3-(butyl)diazobuta-1,3-diene]di(heneicosyl)nickel; [1,4-bis(3-hexadecylphenyl)-2-(hydrido)-3-(nonadecynyl)diazobuta-1,3-diene]di(pentadecyl)nickel; [1,4-bis(3-hexadecylphenyl)-2-(hydrido)-3-(pentyl)diazobuta-1,3-diene]di(triacontyl)palladium; [1,4-bis(3-butylphenyl)-2-(triacontyl)-3-(butyl)diazobuta-1,3-diene]di(pentadecyl)nickel; [1,4-bis(3-methylphenyl)-2-(pentyl)-3-(ethyl)diazobuta-1,3-diene]di(methoxy)nickel; [1,4-bis(3-butylphenyl)-2-(butyl)-3-(hydrido)diazobuta-1,3-diene]di(pentacosyl)nickel; [1,4-bis(3-butylphenyl)-2-(octyl)-3-(hydrido)diazobuta-1,3-diene]di(hexyl)palladium; [1,4-bis(3-butylphenyl)-2-(hydrido)-3-(octyl)diazobuta-1,3-diene]di(butoxy)palladium; [1,4-bis(3-butylphenyl)-2-(butyl)-3-(octacosynyl)diazobuta-1,3-diene]di(pentacosyl)nickel; [1,4-bis(3-butylphenyl)-2-(octyl)-3-(heptyl)diazobuta-1,3-diene]di(methylethylamino)nickel; [1,4-bis(3-butylphenyl)-2-(pentyl)-3-(butyl)diazobuta-1,3-diene]di(undecyl)nickel; [1,4-bis(3-methylphenyl)-2-(octyl)-3-(hydrido)diazobuta-1,3-diene]i(hydrido)nickel; [1,4-bis(3-decenylphenyl)-2-(octyl)-3-(butyl)diazobuta-1,3-diene]di(chloro)nickel; [1,4-bis(3-nonacosylphenyl)-2,3-(dihydrido))diazobuta-1,3-diene]di(tolyl)nickel; [1,4-bis(3-butylphenyl)-2,3-(dibutyl))diazobuta-1,3-diene]di(heptyl)nickel; [1,4-bis(3-butylphenyl)-2-(octyl)-3-(butyl)diazobuta-1,3-diene]di(ethyl)nickel; [1,4-bis(3-butylphenyl)-2,3-(dibutyl))diazobuta-1,3-diene]di(ethyl)nickel; [1,4-bis(3-butylphenyl)-2-(methyl)-3-(butyl)diazobuta-1,3-diene]di(ethyl)nickel; [1,4-bis(3-butylphenyl)-2-(hydrido)-3-(octyl)diazobuta-1,3-diene]di(phenethyl)nickel; [1,4-bis(3-hexylphenyl)-2-(methyl)-3-(hydrido)diazobuta-1,3-diene]di(nonadecynyl)nickel; [1,4-bis(3-butylphenyl)-2-(pentacosynyl)-3-(pentyl)diazobuta-1,3-diene]di(propoxy)palladium; [1,4-bis(3-tricosynylphenyl)-2-(hexyl)-3-(hydrido)diazobuta-1,3-diene]di(nonyl)nickel; [1,4-bis(3-butylphenyl)-2-(hexyl)-3-(methyl)diazobuta-1,3-diene]di(hydrido)nickel; [1,4-bis(3-butylphenyl)-2-(butyl)-3-(pentyl)diazobuta-1,3-diene]di(octadecyl)palladium; [1,4-bis(3-butylphenyl)-2,3-(dibutyl))diazobuta-1,3-diene]di(heneicosyl)nickel; [1,4-bis(3-pentylphenyl)-2-(ethyl)-3-(pentyl)diazobuta-1,3-diene]di(hydrido)palladium; [1,4-bis(3-octylphenyl)-2-(methyl)-3-(butyl)diazobuta-1,3-diene]di(ethyl)nickel; [1,4-bis(3-ethylphenyl)-2-(octyl)-3-(hydrido)diazobuta-1,3-diene]di(methoxy)palladium; [1,4-bis(3-butylphenyl)-2-(ethyl)-3-(hydrido)diazobuta-1,3-diene]di(ethyl)nickel; [1,4-bis(3-pentylphenyl)-2-(butyl)-3-(butenyl)diazobuta-1,3-diene]di(tricosyl)palladium; [1,4-bis(3-hexylphenyl)-2-(nonacosyl)-3-(hydrido)diazobuta-1,3-diene]di(decyl)nickel; [1,4-bis(3-butylphenyl)-2-(pentyl)-3-(docosenyl)diazobuta-1,3-diene]di(phenoxy)nickel; [1,4-bis(3-butylphenyl)-2-(butyl)-3-(methyl)diazobuta-1,3-diene]di(chloro)nickel; [1,4-bis(3-pentadecenylphenyl)-2,3-(dibutyl))diazobuta-1,3-diene]di(tolyl)nickel; [1,4-bis(3-butylphenyl)-2,3-(dipentyl))diazobuta-1,3-diene]di(hexyl)palladium; [1,4-bis(3-nonadecylphenyl)-2-(hydrido)-3-(methyl)diazobuta-1,3-diene]di(hydrido)nickel; [1,4-bis(3-heptenylphenyl)-2-(butyl)-3-(hydrido)diazobuta-1,3-diene]di(butyl)nickel; [1,4-bis(3-butylphenyl)-2-(butyl)-3-(hydrido)diazobuta-1,3-diene]di(hydrido)nickel; [1,4-bis(3-butylphenyl)-2,3-(dipentyl))diazobuta-1,3-diene]di(phenoxy)nickel; [1,4-bis(3-heptadecylphenyl)-2-(butyl)-3-(hydrido)diazobuta-1,3-diene]di(butyl)nickel; [1,4-bis(3-hexylphenyl)-2-(hexyl)-3-(pentyl)diazobuta-1,3-diene]di(benzyl)nickel; [1,4-bis(3-butylphenyl)-2-(hexyl)-3-(butyl)diazobuta-1,3-diene]di(phenethyl)palladium; [1,4-bis(3-butylphenyl)-2-(pentyl)-3-(butyl)diazobuta-1,3-diene]di(phenethyl)nickel; [1,4-bis(3-butylphenyl)-2-(hexynyl)-3-(octyl)diazobuta-1,3-diene]di(phenoxy)nickel; [1,4-bis(3-butylphenyl)-2-(butyl)-3-(hydrido)diazobuta-1,3-diene]di(benzoxy)palladium; [1,4-bis(3-pentylphenyl)-2-(butyl)-3-(hydrido)diazobuta-1,3-diene]di(heneicosyl)nickel; [1,4-bis(3-butylphenyl)-2-(butyl)-3-(octyl)diazobuta-1,3-diene]di(ethyl)nickel; [1,4-bis(3-tetradecynylphenyl)-2-(pentenyl)-3-(hydrido)diazobuta-1,3-diene]di(hexyl)nickel; [1,4-bis(3-butylphenyl)-2-(butyl)-3-(hydrido)diazobuta-1,3-diene]di(chloro)palladium; [1,4-bis(3-hexylphenyl)-2-(hexyl)-3-(ethyl)diazobuta-1,3-diene]di(nonadecyl)nickel; [1,4-bis(3-butylphenyl)-2-(ethyl)-3-(pentacosyl)diazobuta-1,3-diene]di(butyl)nickel; [1,4-bis(3-butylphenyl)-2-(hydrido)-3-(butyl)diazobuta-1,3-diene]di(diethylamino)palladium; [1,4-bis(3-pentacosenylphenyl)-2-(octyl)-3-(butyl)diazobuta-1,3-diene]di(tetracosyl)nickel; [1,4-bis(3-butylphenyl)-2,3-(dibutyl))diazobuta-1,3-diene]di(hydrido)nickel; [1,4-bis(3-ethylphenyl)-2,3-(dihydrido))diazobuta-1,3-diene]di(bydrido)nickel; [1,4-bis(3-pentadecynylphenyl)-2-(octyl)-3-(butyl)diazobuta-1,3-diene]di(nonyl)nickel; [1,4-bis(3-methylphenyl)-2-(octyl)-3-(heptacosynyl)diazobuta-1,3-diene]di(phenoxy)nickel; [1,4-bis(3-tricosynylphenyl)-2-(hexyl)-3-(butyl)diazobuta-1,3-diene]di(pbenethyl)palladium; [1,4-bis(3-butylphenyl)-2-(hydrido)-3-(tridecenyl)diazobuta-1,3-diene]di(hexadecyl)nickel; [1,4-bis(3-octacosylphenyl)-2-(hexyl)-3-(hydrido)diazobuta-1,3-diene]di(hydrido)palladium; [1,4-bis(3-hexylphenyl)-2-(ethyl)-3-(butyl)diazobuta-1,3-diene]di(methyl)nickel; [1,4-bis(3-octylphenyl)-2-(ethyl)-3-(methyl)diazobuta-1,3-diene]di(hydrido)nickel; [1,4-bis(3-butylphenyl)-2-(pentyl)-3-(hydrido)diazobuta-1,3-diene]di(decyl)nickel; [1,4-bis(3-pentonylphenyl)-2-(octacosynyl)-3-(butyl)diazobuta-1,3-diene]di(pentadecyl)palladium; [1,4-bis(3-butylphenyl)-2,3-(dihydrido))diazobuta-1,3-diene]di(butyl)nickel; [1,4-bis(3-butylphenyl)-2-(hexyl)-3-(butyl)diazobuta-1,3-diene]di(butyl)palladium; [1,4-bis(3-pentenylphenyl)-2-(hydrido)-3-(methyl)diazobuta-1,3-diene]di(decyl)nickel; [1,4-bis(3-methylphenyl)-2,3-(dibutyl))diazobuta-1,3-diene]di(decyl)nickel; [1,4-bis(3-butylphenyl)-2-(hexyl)-3-(hydrido)diazobuta-1,3-diene]di(methyl)nickel; [1,4-bis(3-pentylphenyl)-2-(octyl)-3-(nonacosynyl)diazobuta-1,3-diene]di(pentadecyl)nickel; [1,4-bis(3-hexylphenyl)-2-(butyl)-3-(methyl)diazobuta-1,3-diene]di(hydrido)nickel; [1,4-bis(3-octylphenyl)-2-(hexacosyl)-3-(butyl)diazobuta-1,3-diene]di(ethyl)nickel; [1,4-bis(3-butylphenyl)-2-(octyl)-3-(butyl)diazobuta-1,3-diene]di(ethoxy)nickel; [1,4-bis(3-octylphenyl)-2-(butyl)-3-(hydrido)diazobuta-1,3-diene]di(methyl)palladium; [1,4-bis(3-hexadecylphenyl)-2-(butyl)-3-(pentyl)diazobuta-1,3-diene]di(ethyl)palladium; [1,4-bis(3-octylphenyl)-2-(hexacosenyl)-3-(heptynyl)diazobuta-1,3-diene]di(butyl)nickel; [1,4-bis(3-hexylphenyl)-2-(hexyl)-3-(tricosynyl)diazobuta-1,3-diene]di(propyl)palladium; [1,4-bis(3-butylphenyl)-2-(butyl)-3-(octyl)diazobuta-1,3-diene]di(tetradecyl)nickel; [1,4-bis(3-undecenylphenyl)-2-(octyl)-3-(pentacosynyl)diazobuta-1,3-diene]di(hydrido)nickel; [1,4-bis(3-octylphenyl)-2-(hydrido)-3-(hexyl)diazobuta-1,3-diene]di(hexacosyl)palladium; [1,4-bis(3-butylphenyl)-2-(tricosenyl)-3-(butyl)diazobuta-1,3-diene]di(ethyl)nickel; [1,4-bis(3-ethylphenyl)-2-(butyl)-3-(heptenyl)diazobuta-1,3-diene]di(methoxy)nickel; [1,4-bis(3-hexylphenyl)-2-(hexacosynyl)-3-(octyl)diazobuta-1,3-diene]di(iodo)nickel; [1,4-bis(3-butylphenyl)-2,3-(dibutyl))diazobuta-1,3-diene]di(ethyl)nickel; [1,4-bis(3-ethylphenyl)-2-(butyl)-3-(hydrido)diazobuta-1,3-diene]di(hexacosenyl)nickel; [1,4-bis(3-pentylphenyl)-2-(octynyl)-3-(octyl)diazobuta-1,3-diene]di(phenyl)nickel; [1,4-bis(3-butylphenyl)-2-(butyl)-3-(methyl)diazobuta-1,3-diene]di(ethoxy)palladium; [1,4-bis(3-octylphenyl)-2,3-(dibutyl))diazobuta-1,3-diene]di (propoxy)palladium; [1,4-bis(3-pentylphenyl)-2-(hexyl)-3-(octyl)diazobuta-1,3-diene]di(ethyl)nickel; [1,4-bis(3-heptadecenylphenyl)-2-(butyl)-3-(hydrido)diazobuta-1,3-diene]di(ethyl)nickel; [1,4-bis(3-ethylphenyl)-2-(ethyl)-3-(hexyl)diazobuta-1,3-diene]di(tetracosyl)nickel; [1,4-bis(3-butylphenyl)-2-(butyl)-3-(hexyl)diazobuta-1,3-diene]di(nonacosyl)palladium; [1,4-bis(3-ethylphenyl)-2-(pentyl)-3-(butyl)diazobuta-1,3-diene]di(heptacosyl)palladium; [1,4-bis(3-butylphenyl)-2-(octadecyl)-3-(hydrido)diazobuta-1,3-diene]di(ethyl)nickel; [1,4-bis(3-butylphenyl)-2-(octyl)-3-(nonenyl)diazobuta-1,3-diene]di(hydrido)nickel; [1,4-bis(3-hexylphenyl)-2-(butyl)-3-(pentyl)diazobuta-1,3-diene]di(heptadecyl)nickel; [1,4-bis(3-butylphenyl)-2-(methyl)-3-(butyl)diazobuta-1,3-diene]di(butyl)nickel; [1,4-bis(3-octynylphenyl)-2-(pentyl)-3-(butyl)diazobuta-1,3-diene]di(tricosyl)nickel; [1,4-bis(3-pentylphenyl)-2,3-(dibutyl))diazobuta-1,3-diene]di(butyl)nickel; [1,4-bis(3-octylphenyl)-2-(hydrido)-3-(ethyl)diazobuta-1,3-diene]di(heneicosyl)palladium; [1,4-bis(3-eicosylphenyl)-2-(octyl)-3-(hexyl)diazobuta-1,3-diene]di(methyl)palladium; [1,4-bis(3-butylphenyl)-2-(hexyl)-3-(octyl)diazobuta-1,3-diene]di(hydrido)nickel; [1,4-bis(3-pentylphenyl)-2-(undecenyl)-3-(butyl)dlazobuta-1,3-diene]di(phenoxy)nickel; [1,4-bis(3-hexylphenyl)-2,3-(dipentyl))diazobuta-1,3-diene]di(ethyl)nickel; [1,4-bis(3-ethylphenyl)-2-(octyl)-3-(ethyl)diazobuta-1,3-diene]di(methyl)nickel; [1,4-bis(3-methylphenyl)-2,3-(dibutyl))diazobuta-1,3-diene]di(propyl)nickel; [1,4-bis(3-methylphenyl)-2,3-(dibutyl))diazobuta-1,3-diene]di(bromo)palladium; [1,4-bis(3-butylphenyl)-2-(hexyl)-3-(butyl)diazobuta-1,3-diene]di(methyl)nickel; [1,4-bis(3-butylphenyl)-2-(propynyl)-3-(tridecenyl)diazobuta-1,3-diene]di(methyl)nickel; [1,4-bis(3-butylphenyl)-2-(hydrido)-3-(butyl)diazobuta-1,3-diene]di(tridecyl)nickel; [1,4-bis(3-hexonylphenyl)-2-(hexyl)-3-(hydrido)diazobuta-1,3-diene]di(heptacosyl)palladium; [1,4-bis(3-ethylphenyl)-2-(hexyl)-3-(pentyl)diazobuta-1,3-diene]di(hydrido)palladium; [1,4-bis(3-pentylphenyl)-2-(hexyl)-3-(ethyl)diazobuta-1,3-diene]di(heptadecyl)nickel; [1,4-bis(3-octylphenyl)-2-(hydrido)-3-(hexyl)diazobuta-1,3-diene]di(ethyl)nickel; [1,4-bis(3-butylphenyl)-2-(hexyl)-3-(butyl)diazobuta-1,3-diene]di(heptacosyl)palladium; [1,4-bis(3-pentylphenyl)-2-(butyl)-3-(octyl)diazobuta-1,3-diene]di(phenethyl)palladium; [1,4-bis(3-butylphenyl)-2-(hexyl)-3-(butyl)diazobuta-1,3-diene]di(phenyl)nickel; [1,4-bis(3-nonadecylphenyl)-2,3-(dibutyl))diazobuta-1,3-diene]di(tolyl)nickel; [1,4-bis(3-butylphenyl)-2-(ethyl)-3-(hexyl)diazobuta-1,3-diene]di(methyl)nickel; [1,4-bis(3-hexylphenyl)-2-(hydrido)-3-(hexyl)diazobuta-1,3-diene]di(methyl)nickel; [1,4-bis(3-butylphenyl)-2-(octacosenyl)-3-(butyl)diazobuta-1,3-diene]di(ethyl)nickel; [1,4-bis(3-butylphenyl)-2-(pentyl)-3-(hexyl)diazobuta-1,3-diene]di(hydrido)palladium; [1,4-bis(3-butylphenyl)-2-(octyl)-3-(butyl)diazobuta-1,3-diene]di(ethoxy)palladium; [1,4-bis(3-hexylphenyl)-2-(hydrido)-3-(hexyl)diazobuta-1,3-diene]di(tricosyl)palladium; [1,4-bis(3-hexylphenyl)-2-(butyl)-3-(tricosynyl)diazobuta-1,3-diene]di(pentyl)nickel; [1,4-bis(3-butylphenyl)-2-(butyl)-3-(hexyl)diazobuta-1,3-diene]di(methyl)nickel; [1,4-bis(3-butylphenyl)-2-(hydrido)-3-(butyl)diazobuta-1,3-diene]di(tetradecyl)palladium; [1,4-bis(3-pentadecylphenyl)-2-(hydrido)-3-(octyl)diazobuta-1,3-diene]di(eicosyl)nickel; [1,4-bis(3-octylphenyl)-2-(hydrido)-3-(butyl)diazobuta-1,3-diene]di(tricosyl)palladium; [1,4-bis(3-butylphenyl)-2-(methyl)-3-(hydrido)diazobuta-1,3-diene]di(tolyl)nickel; [1,4-bis(3-butylphenyl)-2-(butyl)-3-(hexadecynyl)diazobuta-1,3-diene]di(pentyl)nickel; [1,4-bis(3-octylphenyl)-2-(hexyl)-3-(heptyl)diazobuta-1,3-diene]di(heptyl)nickel; [1,4-bis(3-butylphenyl)-2-(hexyl)-3-(hydrido)diazobuta-1,3-diene]di(pentacosyl)palladium; [1,4-bis(3-butylphenyl)-2-(butyl)-3-(ethyl)diazobuta-1,3-diene]di(butyl)nickel; [1,4-bis(3-octadecenylphenyl)-2-(octyl)-3-(butyl)diazobuta-1,3-diene]di(heptacosyl)nickel; [1,4-bis(3-butylphenyl)-2-(pentyl)-3-(butyl)diazobuta-1,3-diene]di(nonyl)nickel; [1,4-bis(3-octylphenyl)-2,3-(dipentyl))diazobuta-1,3-diene]di(butyl)palladium; [1,4-bis(3-butylphenyl)-2,3-(dioctyl))diazobuta-1,3-diene]di(hydrido)nickel; [1,4-bis(3-tridocosanalylphenyl)-2-(butyl)-3-(hydrido)diazobuta-1,3-diene]di(butyl)palladium; [1,4-bis(3-butylphenyl)-2-(butyl)-3-(tetracosyl)diazobuta-1,3-diene]di(hydrido)nickel; [1,4-bis(3-butylphenyl)-2-(hexyl)-3-(butyl)diazobuta-1,3-diene]di(methyl)nickel; [1,4-bis(3-(trimethylsilylethyl)phenyl)-2-(butyl)-3-(octyl)diazobuta-1,3-diene]di(propyl)nickel; [1,4-bis(3-butylphenyl)-2-(butyl)-3-(octyl)diazobuta-1,3-diene]di(octadecyl)palladium; [1,4-bis(3-butylphenyl)-2-(hydrido)-3-(pentyl)diazobuta-1,3-diene]di(heptacosyl)palladium; [1,4-bis(3-dodecanonylphenyl)-2,3-(dibutyl))diazobuta-1,3-diene]di(tetracosenyl)palladium; [1,4-bis(3-butylphenyl)-2-(nonacosyl)-3-(butyl)diazobuta-1,3-diene]di(hydride)nickel; [1,4-bis(3-butylphenyl)-2-(hydrido)-3-(butyl)diazobuta-1,3-diene]di(octacosyl)palladium; [1,4-bis(3-heneicosylphenyl)-2-(hydrido)-3-(tridecenyl)diazobuta-1,3-diene]di(tricosyl)nickel; [1,4-bis(3-butylphenyl)-2-(methyl)-3-(hydrido)diazobuta-1,3-diene]di(ethyl)palladium; [1,4-bis(3-butylphenyl)-2-(pentyl)-3-(butyl)diazobuta-1,3-diene]di(nonacosyl)palladium; [1,4-bis(3-propylphenyl)-2,3-(dipentyl))diazobuta-1,3-diene]di(heptyl)nickel; [1,4-bis(3-hexylphenyl)-2-(hexyl)-3-(octadecyl)diazobuta-1,3-diene]di(propyl)nickel; [1,4-bis(3-butylphenyl)-2,3-(dibutyl))diazobuta-1,3-diene]di(tetracosenyl)nickel; [1,4-bis(3-butylphenyl)-2-(pentyl)-3-(hexyl)diazobuta-1,3-diene]di(propyl)nickel; [1,4-bis(3-hexylphenyl)-2-(hydrido)-3-(octyl)diazobuta-1,3-diene]di(tridecyl)palladium; [1,4-bis(3-butylphenyl)-2-(butyl)-3-(octyl)diazobuta-1,3-diene]di(butyl)nickel; [1,4-bis(3-butylphenyl)-2,3-(dibutyl))diazobuta-1,3-diene]di(tolyl)nickel; [1,4-bis(3-pentylphenyl)-2,3-(dihydrido))diazobuta-1,3-diene]di(dimethylamino)nickel; [1,4-bis(3-hexylphenyl)-2-(tridecenyl)-3-(octyl)diazobuta-1,3-diene]di(tetradecyl)nickel; [1,4-bis(3-butylphenyl)-2-(butyl)-3-(hydrido)diazobuta-1,3-diene]di(benzyl)nickel; [1,4-bis(3-pentylphenyl)-2-(ethyl)-3-(octynyl)diazobuta-1,3-diene]di(dodecyl)nickel; [1,4-bis(3-pentylphenyl)-2-(butyl)-3-(hexyl)diazobuta-1,3-diene]di(octadecyl)palladium; [1,4-bis(3-pentylphenyl)-2-(pentyl)-3-(hydrido)diazobuta-1,3-diene]di(chloro)nickel; [1,4-bis(3-butylphenyl)-2-(butyl)-3-(hydrido)diazobuta-1,3-diene]di(hydrido)nickel; [1,4-bis(3-triacontenylphenyl)-2-(pentadecenyl)-3-(octyl)diazobuta-1,3-diene]di(hexadecyl)nickel; [1,4-bis(3-butylphenyl)-2-(pentadecenyl)-3-(hexyl)diazobuta-1,3-diene]di(eicosyl)nickel; [1,4-bis(3-octylphenyl)-2-(butyl)-3-(methyl)diazobuta-1,3-diene]di(pentyl)nickel.

EXAMPLES

The following examples are presented to illustrate the discussion above. Although the examples may be directed toward certain embodiments of the present invention, they do not limit the invention in any specific way. In these examples, certain abbreviations are used to facilitate the description. These include standard chemical abbreviations for the elements and certain commonly accepted abbreviations, such as: Me=methyl, Et=ethyl, Bu=butyl, Ph=phenyl, MAO=methylalumoxane, DAB=diazabutadiene, DAB(Me)₂=2,3-dimethyldiazabutadiene, COD=cyclooctadiene and DME=ethylene glycol dimethyl ether.

All preparations were performed under an inert nitrogen atmosphere, using standard Schlenk or glovebox techniques, unless mentioned otherwise. Dry solvents (toluene, diethyl ether, pentane, methylene chloride) were purchased as anhydrous solvents and further purified by passing them down an alumina (Fluka) column. Ethylene was purchased from BOC (99.9%). Formic acid (96%), methanol, 4-butylaniline, 2,3-butanedione, sodium sulfate, nickel(II)bromide ethylene glycol dimethylether complex, and dichloro(1,5-cyclooctadiene)palladium(II) were purchased from Aldrich Chemical Company.

Deuterated solvents were dried with CaH and vacuum distilled prior to use. The compounds are illustrated below:

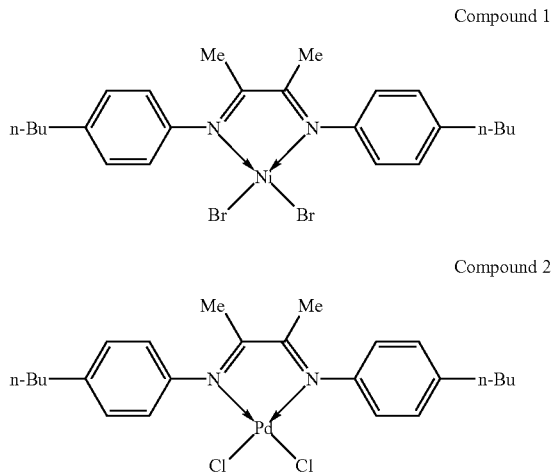

Compound 1

Compound 2

Preparation of the ligand, 4-n-BuPh—N═C(Me)C(Me)═N—Ph-n-Bu. 4-butylaniline (0.106 mol), methanol (15 ml) and formic acid (2 drops) were mixed together at 0°C. The mixture was warmed to room temperature, and 2,3-butanedione (0.053 mol) was slowly added. The reaction mixture was stirred at room temperature for about 20 hours; then the yellow precipitate was filtered and washed with cold methanol. The resulting solid was dissolved in pentane containing $Na_2SO_4$ and stirred overnight. The mixture was warmed to dissolve the product, and the pentane solution was filtered to remove the $Na_2SO_4.xH_2O$. The resulting filtrate was reduced in volume, then cooled to room temperature. After filtration, yellow crystals of 4-n-Bu—Ph—N═C(Me)C(Me)═N—Ph-n-Bu were obtained in a yield of 48%.

Preparation of [(4-CH₃CH₂CH₂CH₂Ph)₂DAB(Me)₂]NiBr₂ (1). CH₂Cl₂ (25 ml)was added to a Schlenk flask containing the α-diimine ligand (4-n-Bu—Ph—N═C(Me)C(Me)═N—Ph-4-n-Bu, 2.53 g, 7.22 mmol) in a dry box. A bright yellow solution formed. (DME)NiBr₂ (2.07 g, 6.72 mmol) was added to this solution. A brown solution formed immediately upon mixing. The reaction mixture was stirred for 20 hours. The solution was filtered and recrystallized from CH₂Cl₂/ether. The brown product was washed with an additional 15 ml of pentane three times and then dried for 1 hour under vacuum. A brown CH₂Cl₂-soluble solid was isolated in 66.4% yield. ¹H NMR indicated that the complex was paramagnetic. Anal. Calcd for (C₂₄H₃₂N₂Br₂Ni): C, 50.83%; H, 5.70%; N, 4.94%. Found: C, 50.58%; H, 5.69%; N, 5.15%. The IR (cm⁻¹, KBr): 1605, ν(C═N); 268, ν(Ni—Br).

Preparation of [(4-CH₃CH₂CH₂CH₂Ph)₂DAB(Me)₂]PdCl₂ (2).

Et₂O (30 ml) was added to a Schlenk flask containing a mixture of the α-diimine ligand (4-n-BuPh—N═C(Me)C(Me)═N—Ph—4-n-Bu, 2.25 g, 6.42 mmol) and (COD)PdCl₂ (0.86 g, 3.0 mmol) in a dry box. The reaction mixture was stirred overnight and then filtered, leaving a yellow solution. The Et₂O solvent was removed under vacuum. The resulting orange powder was then dissolved in 20 ml of CH₂Cl₂. The solution was filtered again and recrystallized from CH₂Cl₂/pentane. The product was washed with an additional 15 ml of pentane three times and then dried for 1 hour under vacuum. An orange powder was isolated in 89.6% yield. This product was soluble in both CH₂Cl₂ and Et₂O. ¹H NMR indicated that the complex was diamagnetic. ¹H NMR (250 MHz, CD₂Cl₂, δ, ppm): 0.96 t (6H, 2×CH₃); 1.35–1.47 m (4H, 2×CH₂); 1.59–1.71 m (4H, 2×CH₂); 2.14 s (6H, 2×N═CCH₃); 2.67 t (4H, 2×CH₂); 7.08 d and 7.30 d (8H, $H_{aryl}$). Anal. Calcd for (C₂₄H₃₂N₂Cl₂Pd): C, 54.60%; H, 6.12%; N, 5.31%. Found: 54.53%; H, 6.18%; N, 5.32%.

Oligomerization Reactions

Oligomerization reactions were run in a 300-mL HastelloyC Parr reactor equipped with a mechanical stirrer. Catalyst was added to the reactor as a solution in toluene (75 ml) under argon. Ethylene was added to the reactor at 100 psig and then vented to maintain an ethylene atmosphere. Methylalumoxane solution (Albemarle, 30 wt % in toluene)was then added to the reactor. Thus, the catalyst was activated in the monomer's presence. The ethylene pressure was brought to the desired value. The aim was to maintain the reactor temperature at room temperature; but in cases where the reaction exotherm was very large, higher reaction temperatures were reached. After the reaction had run for an hour, the reactor was cooled in an acetone/dry ice bath, vented, and quenched with methanol. A sample of the product solution was analyzed by GC/MS after adding nonane as an internal standard. In the case of supported transition metal compounds, silica loaded samples were prepared by adding a solution of the transition metal complex in methylene chloride to silica followed by drying of the silica under vacuum overnight. MAO (0.18 g 30 wt % solution in toluene, Al/M molar=290)was added to the reactor solution prior to adding the supported transition metal compound. The results of the oligomerization reactions are tabulated in Table 2:

TABLE 2

Oligomerization Examples

| Catalyst | Cat (mmol) | $C_2$ (psig) | Rxn Exotherm (° C.) | Final Rxn Temp (° C.) | Activity (mol $C_2$/mol Ni · hr) | K[a] | % α olefin (total)[b] |
|---|---|---|---|---|---|---|---|
| 1 | 0.0032 | 820 | 27–58 | 25 | 926,300 | 0.63 | 86 |
| 1 | 0.0032 | 100 | 27–69 | 30 | 264,500 | 0.63 | 51 |
| 1[c] | 0.0032 | 100 | 27–72 | 30 | 152,900 | 0.59 | 59 |

[a]K is based on $C_{14}/C_{12}$ molar ratio for all isomers.
[b]These numbers are subject to the interpretation of the GC/MS spectra and are calculated from averaging the weight % of alpha olefin from the $C_8$, $C_{10}$ and $C_{12}$ peaks.
[c]1 wt % of 1 loaded on silica.

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

What is claimed is:

1. A composition comprising:
   (1) a metal selected from nickel or palladium connected to a ligand comprising 1,4-diazabutadiene:
      (a) having a phenyl ring connected to the 1 position of the diazabutadiene where the phenyl ring is connected at the 3, 4 or 5 position to at least one hydrocarbyl group having at least three carbon atoms, and
      (b) having a phenyl ring connected to the 4 position of the diazabutadiene where the phenyl ring is connected at the 3, 4 or 5 position to at least one hydrocarbyl group having at least three carbon atoms, and
      (c) where the 2 and 6 positions of both phenyl rings are connected to hydrogen radicals, and
      (d) where the 2 and 3 positions of the diazabutadiene are, each independently, connected to hydrogen or a hydrocarbyl group; and
   (2) an abstractable ligand connected to the metal, that does not contain sulfur atoms.

2. The composition of claim 1 where the 2 and 3 positions of the 1,4-diazabutadiene are, each independently, connected to a hydrogen radical or a $C_1$–$C_{30}$ hydrocarbyl radical.

3. The composition of claim 2 where the 2 and 3 positions of the 1,4-diazabutadiene are, each independently, connected to a $C_1$–$C_{30}$ hydrocarbyl radical and the hydrocarbyl radicals link to form a ring structure comprising one or more, substituted or unsubstituted, aromatic or non-aromatic rings.

4. The composition of claim 1 where the hydrocarbyl radicals connected to the 2 and 3 positions of the 1,4-diazabutadiene are, independently, selected from the group consisting of methyl, ethyl, and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, cyclohexyl, cyclopentyl, cycloheptyl, cyclooctyl, cyclodecyl, cyclododecyl, napthyl, phenyl, tolyl, benzyl, and phenethyl radicals.

5. The composition of claim 1 where the hydrocarbyl radicals connected to the 2 and 3 positions of the 1,4-diazabutadiene are, independently, methyl or ethyl radicals.

6. The composition of claim 3 where the ring structure is 1,8-naphthalene or 2,2'-biphenyl.

7. The composition of claim 1 where at least one of the $C_3$–$C_{30}$ hydrocarbyl radicals connected to the phenyl ring at the 3, 4 or 5 position is the same at least one of the $C_3$–$C_{30}$ hydrocarbyl radicals connected to the other phenyl ring at the 3, 4 or 5 position.

8. The composition of claim 7 where the hydrocarbyl radicals are selected from the group consisting of all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl radicals.

9. The composition of claim 1 where a hydrocarbyl radical having at least 3 carbon atoms connects to at least one phenyl ring at the 4 position.

10. The composition of claim 9 where the hydrocarbyl radical is selected from the group consisting of all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl radicals.

11. The composition of claim 1 where a butyl radical is connected to at least one phenyl ring at the 4 position.

12. The composition of claim 1 where at least one phenyl ring has only one 3, 4 or 5 position connected to a hydrogen radical.

13. The composition of claim 1 where at least one phenyl ring has at least 2 hydrocarbyl radicals connected to the 3, 4 or 5 position where the hydrocarbyl radicals are, independently, selected from the group consisting of all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl radicals.

14. The composition of claim 13 where the hydrocarbyl radicals are selected from butyl, pentyl, hexyl or octyl radicals.

15. The composition of claim 1 where the abstractable ligand is one of hydride, organic radicals, or organic-radical-substituted organometalloid radicals.

16. A composition comprising a ligand represented by the following structure:

where
(a) Pn is a Group-15 element wherein a nickel or palladium atom is connected to one or both Group 15 elements;
(b) H is hydrogen;
(c) $R^7$ and $R^8$ are independently hydrogen or $C_1$–$C_{30}$ hydrocarbyl radicals, or both are $C_1$–$C_{30}$ hydrocarbyl radicals that link to form a ring structure comprising one or more aromatic or non-aromatic rings;
(d) $R^1$, $R^2$, or $R^3$ are, independently, hydrogen or a hydrocarbyl radical having at least three carbon atoms and where at least one of $R^1$, $R^2$, or $R^3$ is hydrocarbyl radical having at least three carbon atoms;
(e) $R^4$, $R^5$, and $R^6$ are, independently, hydrogen or a hydrocarbyl radical having at least three carbon atoms and where at least one of $R^4$, $R^5$, and $R^6$ is a hydrocarbyl radical having at least three carbon atoms; and
(f) an abstractable ligand that does not contain sulfur atoms connected to the nickel or palladium atom.

17. The composition of claim 16 where one or more saturated or unsaturated cyclic structures are formed by independently joining two or more adjacent non-hydrogen $R^1$, $R^2$, or $R^3$ and/or two or more adjacent non-hydrogen $R^4$, $R^5$, or $R^6$.

18. The composition of claim 16 where at least one of $R^1$, $R^2$, or $R^3$ is a $C_3$–$C_{30}$ hydrocarbyl radical.

19. The composition of claim 16 where at least one of $R^4$, $R^5$, or $R^6$ is a $C_3$–$C_{30}$ hydrocarbyl radical.

20. The composition of claim 16 where at least one of $R^1$, $R^2$, or $R^3$ is a $C_3$–$C_{30}$ hydrocarbyl radical, at least one of $R^4$, $R^5$, or $R^6$ is a $C_3$–$C_{30}$ hydrocarbyl radical and the radicals are selected from the group consisting of all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl radicals.

21. The composition of claim 16 where:
(a) $R^1$ and $R^4$ are each independently a $C_3$–$C_{30}$ hydrocarbyl radical, and $R^2$, $R^3$, $R^5$, and $R^6$ are each independently hydrogen or a $C_1$–$C_{30}$ hydrocarbyl radical; or
(b) $R^1$ and $R^5$ are each independently a $C_3$–$C_{30}$ hydrocarbyl radical, and $R^2$, $R^3$, $R^4$, and $R^6$ are each independently hydrogen or a $C_1$–$C_{30}$ hydrocarbyl radical; or
(c) $R^2$ and $R^5$ are each independently a $C_3$–$C_{30}$ hydrocarbyl radical, and $R^1$, $R^3$, $R^4$, and $R^6$ each independently hydrogen or a $C_1$–$C_{30}$ hydrocarbyl radical.

22. The composition of claim 16 where
(a) $R^2$ and $R^5$ are each independently a $C_3$–$C_{30}$ hydrocarbyl radical; and
(b) $R^1$, $R^3$, $R^4$ and $R^6$ each independently a hydrogen or a $C_1$–$C_{30}$ hydrocarbyl radical.

23. The composition of claim 16 where Pn is independently selected from nitrogen, phosphorus, arsenic, or antimony.

24. The composition of claim 16 where Pn is nitrogen.

25. The composition of claim 16 where a nickel or palladium atom is connected to both Group-15 atoms.

26. A composition comprising the composition of claim 25 and an abstractable ligand connected to the nickel or palladium.

27. The composition of claim 17 where a nickel or palladium atom is connected to one or both Group-15 atoms.

28. The composition of claim 18 where a nickel or palladium atom is connected to one or both Group-15 atoms.

29. The composition of claim 19 where a nickel or palladium atom is connected to one or both Group-15 atoms.

30. The composition of claim 20 where a nickel or palladium atom is connected to one or both Group-15 atoms.

31. The composition of claim 21 where a nickel or palladium atom is connected to one or both Group-15 atoms.

32. The composition of claim 22 where a nickel or palladium atom is connected to one or both Group-15 atoms.

33. The composition of claim 23 where a nickel or palladium atom is connected to one or both Group-15 atoms.

34. The composition of claim 24 where a nickel or palladium atom is connected to one or both Group-15 atoms.

35. The composition of claim 1 wherein the metal is nickel.

36. A composition represented by the following structure:

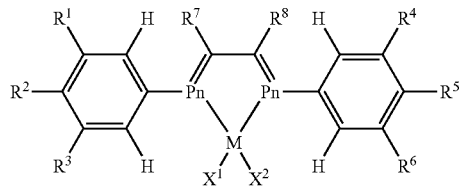

where
(a) Pn is a Group-15 element;
(b) H is hydrogen;
(c) $R^7$ and $R^8$ are independently hydrogen or $C_1$–$C_{30}$ hydrocarbyl radicals, or both are $C_1$–$C_{30}$ hydrocarbyl radicals that link to form a ring structure comprising one or more aromatic or non-aromatic rings;
(d) $R^1$, $R^2$, or $R^3$ are, independently, hydrogen or a hydrocarbyl radical having at least three carbon atoms and where at least one of $R^1$, $R^2$, or $R^3$ is hydrocarbyl radical having at least three carbon atoms;
(e) $R^4$, $R^5$, and $R^6$ are, independently, hydrogen or a hydrocarbyl radical having at least three carbon atoms and where at least one of $R^4$, $R^5$, and $R^6$ is a hydrocarbyl radical having at least three carbon atoms;
(f) M is nickel or palladium;
(g) $X^1$ and $X^2$ are, independently, a hydride radical, a hydrocarbyl radical, a halocarbyl radical, or a hydrocarbyl-substituted organometalloid radical; or $X^1$ and $X^2$ may join and bind to the metal atom to form a metallacycle ring containing from 2–30 carbon atoms, and wherein $X^1$ and $X^2$ do not contain sulfur atoms.

37. The composition of claim 36 wherein $X^1$ and $X^2$ are, independently, selected from the group consisting of halogens, alkoxides, aryloxides, amides and phosphides.

38. The composition of claim 36 where one or more saturated or unsaturated cyclic structures are formed by independently joining two or more adjacent non-hydrogen $R^1$, $R^2$, or $R^3$ and/or two or more adjacent non-hydrogen $R^4$, $R^5$, or $R^6$.

39. The composition of claim 36 where at least one of $R^1$, $R^2$, or $R^3$ is a $C_3$–$C_{30}$ hydrocarbyl radical.

40. The composition of claim 36 where at least one of $R^4$, $R^5$, or $R^6$ is a $C_3$–$C_{30}$ hydrocarbyl radical.

41. The composition of claim 36 where at least one of $R^1$, $R^2$, or $R^3$ is a $C_3$–$C_{30}$ hydrocarbyl radical, at least one of $R^4$, $R^5$, or $R^6$ is a $C_3$–$C_{30}$ hydrocarbyl radical and the radicals are selected from the group consisting of all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl radicals.

42. The composition of claim 36 where $R^1$ and $R^4$ are each independently a $C_3$–$C_{30}$ hydrocarbyl radical, and $R^2$, $R^3$, $R^5$, and $R^6$ are each independently hydrogen or a $C_1$–$C_{30}$ hydrocarbyl radical.

43. The composition of claim 36 where $R^1$ and $R^5$ are each independently a $C_3$–$C_{30}$ hydrocarbyl radical, and $R^2$, $R^3$, $R^4$, and $R^6$ are each independently hydrogen or a $C_1$–$C_{30}$ hydrocarbyl radical.

44. The composition of claim 36 where $R^2$ and $R^5$ are each independently a $C_3$–$C_{30}$ hydrocarbyl radical, and $R^1$, $R^3$, $R^4$, and $R^6$ each independently hydrogen or a $C_1$–$C_{30}$ hydrocarbyl radical.

45. The composition of claim 36 where Pn is independently selected from nitrogen, phosphorus, arsenic, or antimony.

46. The composition of claim 36 where Pn is nitrogen.

47. The composition of claim 36 wherein:
M is nickel;
Pn is N;
at least one of $R^1$, $R^2$, or $R^3$ is a hydrocarbyl radical selected from the group consisting of all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl radicals;
at least one of $R^4$, $R^5$, or $R^6$ is a hydrocarbyl radical selected from the group consisting of all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl radicals;
and $X^1$ and $X^2$ are, independently, selected from the group consisting of halogens, alkoxides, aryloxides, amides and phosphides.

48. A composition represented by the formula:

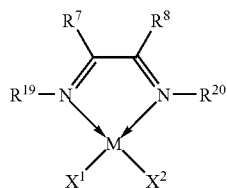

wherein:

| $R^{19}$ and $R^{20}$ are independently selected from the group consisting of | $R^7$ and $R^8$ are independently selected from the group consisting of | $X^1$ and $X^2$ are independently selected from the group consisting of |
|---|---|---|
| 3,4,5-tributylphenyl | Hydrogen | chloride |
| 3,4,5-tridecylphenyl | Methyl | bromide |
| 3,4,5-tridodecylphenyl | Ethyl | iodide |
| 3,4,5-triheptylphenyl | Propyl | methyl |
| 3,4,5-trihexylphenyl | Butyl | ethyl |
| 3,4,5-trinonylphenyl | Pentyl | propyl |
| 3,4,5-trioctylphenyl | Hexyl | butyl |
| 3,4,5-tripentylphenyl | Heptyl | pentyl |
| 3,4,5-tripropylphenyl | Octyl | hexyl |
| 3,4,5-tripropylphenyl | Nonyl | heptyl |
| 3,4,5-triundecylphenyl | Decyl | octyl |
| 3,4-dibutylphenyl | Undecyl | nonyl |
| 3,4-didecylphenyl | Dodecyl | decyl |
| 3,4-didodecylphenyl | Tridecyl | undecyl |
| 3,4-diheptylphenyl | Tetradecyl | dodecyl |
| 3,4-dihexylphenyl | Octacosyl | tridecyl |
| 3,4-dinonylphenyl | Nonacosyl | tetradecyl |
| 3,4-dioctylphenyl | Triacontyl | pentadecyl |
| 3,4-dipentylphenyl | Cyclohexyl | hexadecyl |
| 3,4-dipropylphenyl | Cyclopentyl | heptadecyl |
| 3,4-dipropylphenyl | Cycloheptyl | octadecyl |
| 3,4-diundecylphenyl | Cyclooctyl | nonadecyl |
| 3,5-dibutylphenyl | Cyclodecyl | eicosyl |
| 3,5-dibutylphenyl | Cyclododecyl | heneicosyl |
| 3,5-didecylphenyl | Napthyl | docosyl |
| 3,5-didodecylphenyl | Phenyl | tricosyl |
| 3,5-diheptylphenyl | Tolyl | tetracosyl |
| 4-undecylphenyl | Benzyl | pentacosyl |
| 3,5-dihexylphenyl | Phenethyl | hexacosyl |
| 3,5-dinonylphenyl | $R^7$ joined to $R^8$ | heptacosyl |
| 3,5-dioctylphenyl | 1,8-naphthalene | octacosyl |
| 3,5-dipentylphenyl | 2,2'-biphenyl | nonacosyl |
| 3,5-dipropylphenyl | | triacontyl |
| 3,5-diundecylphenyl | | hydride |
| 3-butylphenyl | | phenyl |
| 3-decylphenyl | | benzyl |
| 3-dodecylphenyl | | phenethyl |
| 3-heptylphenyl | | tolyl |
| 3-hexylphenyl | | methoxy |
| 3-nonylphenyl | | ethoxy |
| 3-octylphenyl | | propoxy |
| 3-pentylphenyl | | butoxy |
| 3-propylphenyl | | dimethylamido |
| 3-propylphenyl | | diethylamido |
| 3-undecylphenyl | | methylethylamido |
| 4-butylphenyl | | phenoxy |
| 4-decylphenyl | | benzoxy |
| 4-dodecylphenyl | | allyl |
| 4-heptylphenyl | | |
| 4-hexylphenyl | | |
| 4-nonylphenyl | | |
| 4-octylphenyl | | |
| 4-pentylphenyl | | |
| 4-propylphenyl | | | and M is nickel or palladium, and wherein $X^1$ and $X^2$ do not contain sulfur atoms.

49. The composition of claim 48 where $R^{19}$ and $R^{20}$ are the same.

50. The composition of claim 48 where M is nickel.

51. A composition represented by the formula:

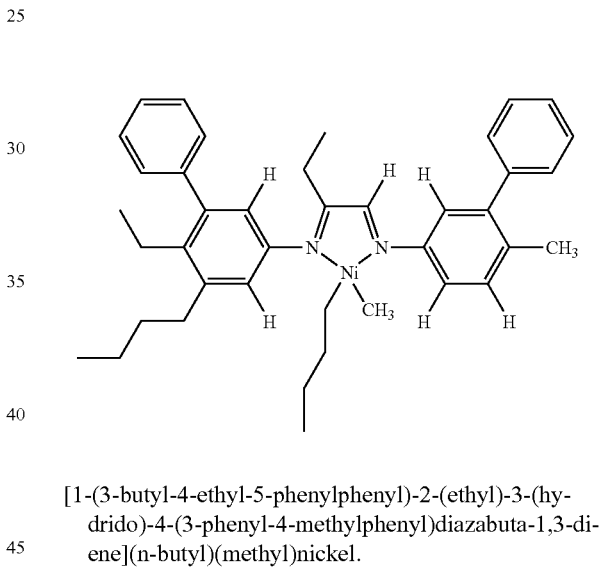

[1-(3-butyl-4-ethyl-5-phenylphenyl)-2-(ethyl)-3-(hydrido)-4-(3-phenyl-4-methylphenyl)diazabuta-1,3-diene](n-butyl)(methyl)nickel.

52. A composition represented by the formula:

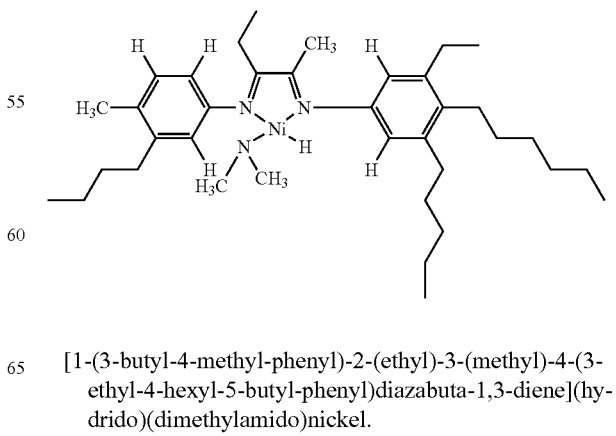

[1-(3-butyl-4-methyl-phenyl)-2-(ethyl)-3-(methyl)-4-(3-ethyl-4-hexyl-5-butyl-phenyl)diazabuta-1,3-diene](hydrido)(dimethylamido)nickel.

53. A composition represented by the formula:

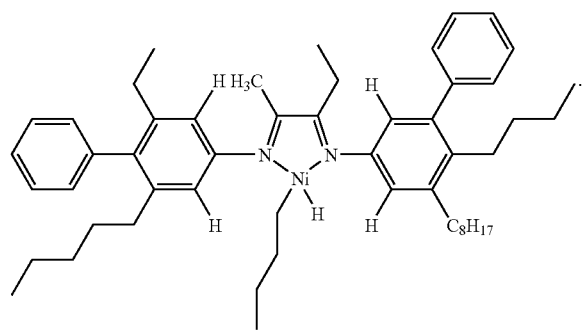

[1-(3-ethyl-4-phenyl-5-butyl-phenyl)-2-(methyl)-3-(ethyl)-4-(3-phenyl-4-butyl-5-octylphenyl)diazabuta-1,3-diene](hydrido)(n-butyl)nickel.

54. A composition represented by the formula:

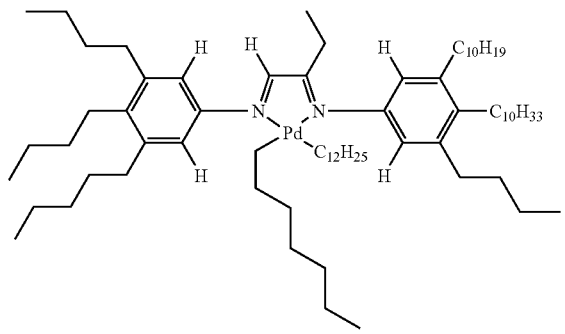

[1-(3,4,5-tributylphenyl)-2-(hydrido)-3-(ethyl)-4-(3-decenyl-4-hexadecyl-5-butylphenyl)diazabuta-1,3-diene](heptyl)(dodecyl)palladium.

55. A composition represented by the formula:

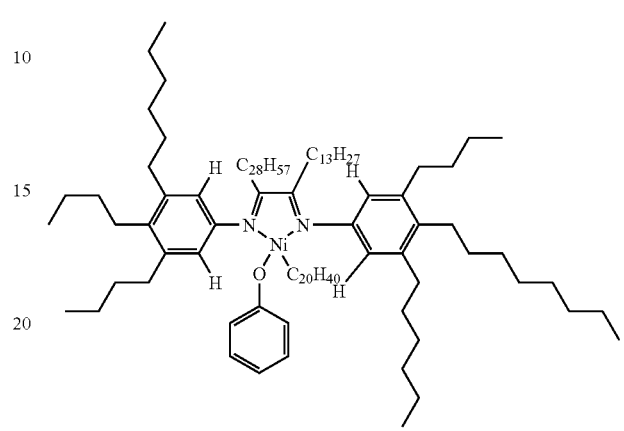

[1-(3,4-dibutyl-5-hexylphenyl)-2-(octacosyl)-3-(tridecyl)-4-(3-butyl-4-octyl-5-hexyl-phenyl)diazabuta-1,3-diene](phenoxy)(eicosenyl)nickel.

56. The composition of claim 48 wherein $X^1$ and $X^2$ are bromine.

57. The composition of claim 48 where $X^1$ and $X^2$ are chlorine.

* * * * *